US011041015B2

(12) United States Patent
Ouzounov et al.

(10) Patent No.: US 11,041,015 B2
(45) Date of Patent: Jun. 22, 2021

(54) RECOMBINANT COLLAGEN AND ELASTIN MOLECULES AND USES THEREOF

(71) Applicant: Geltor, Inc., San Leandro, CA (US)

(72) Inventors: Nikolay Ouzounov, Alameda, CA (US); Alexander Lorestani, Oakland, CA (US); Monica Bhatia, San Ramon, CA (US)

(73) Assignee: GELTOR, INC., San Leandro, CA (US)

( * ) Notice: Subject to any disclaimer, the term of this patent is extended or adjusted under 35 U.S.C. 154(b) by 0 days.

(21) Appl. No.: 16/839,047

(22) Filed: Apr. 2, 2020

(65) Prior Publication Data

US 2020/0247876 A1 Aug. 6, 2020

Related U.S. Application Data

(63) Continuation of application No. 16/144,914, filed on Sep. 27, 2018.

(60) Provisional application No. 62/657,591, filed on Apr. 13, 2018, provisional application No. 62/564,964, filed on Sep. 28, 2017.

(51) Int. Cl.

| | |
|---|---|
| ***C07K 14/78*** | (2006.01) |
| ***A61K 38/39*** | (2006.01) |
| ***A61K 8/65*** | (2006.01) |
| ***A61Q 17/04*** | (2006.01) |
| ***A61Q 19/08*** | (2006.01) |

(52) U.S. Cl.

CPC ................ *C07K 14/78* (2013.01); *A61K 8/65* (2013.01); *A61K 38/39* (2013.01); *A61Q 17/04* (2013.01); *A61Q 19/08* (2013.01)

(58) Field of Classification Search

CPC ................................ C07K 14/78; A61K 38/39

See application file for complete search history.

(56) References Cited

U.S. PATENT DOCUMENTS

| | | | |
|---|---|---|---|
| 4,515,893 | A | 5/1985 | Kung et al. |
| 4,816,397 | A | 3/1989 | Boss et al. |
| 4,816,567 | A | 3/1989 | Cabilly et al. |
| 4,946,778 | A | 8/1990 | Ladner et al. |
| 5,091,313 | A | 2/1992 | Chang |
| 5,602,183 | A | 2/1997 | Martin et al. |
| 5,622,700 | A | 4/1997 | Jardieu et al. |
| 5,672,347 | A | 9/1997 | Aggarwal et al. |
| 5,693,762 | A | 12/1997 | Queen et al. |
| 5,714,338 | A | 2/1998 | Wai Fei et al. |
| 5,721,108 | A | 2/1998 | Robinson et al. |
| 5,725,856 | A | 3/1998 | Hudziak et al. |
| 5,736,137 | A | 4/1998 | Anderson et al. |
| 6,413,742 | B1 | 7/2002 | Olsen et al. |
| 6,428,978 | B1 | 8/2002 | Olsen et al. |
| 6,617,431 | B1 | 9/2003 | Gruber et al. |
| 6,653,450 | B1 | 11/2003 | Berg et al. |
| 6,682,760 | B2 | 1/2004 | Noff et al. |
| 6,903,200 | B1 | 6/2005 | Chou et al. |
| 6,992,172 | B1 | 1/2006 | Chang et al. |
| 7,495,076 | B2 | 2/2009 | Gu et al. |
| 7,700,126 | B2 | 4/2010 | Ng et al. |
| 7,754,447 | B2 | 7/2010 | Glover et al. |
| 7,759,090 | B2 | 7/2010 | Chou et al. |
| 7,803,577 | B2 | 9/2010 | Weiss |
| 7,932,053 | B2 | 4/2011 | Bank et al. |
| 7,932,353 | B2 | 4/2011 | Van Es et al. |
| 8,252,553 | B2 | 8/2012 | Hook et al. |
| 8,507,652 | B2 | 8/2013 | Da Cruz |
| 8,618,250 | B2 | 12/2013 | Russell et al. |
| 8,759,487 | B2 | 6/2014 | Shoseyov et al. |
| 8,889,626 | B2 | 11/2014 | Lin et al. |
| 8,956,632 | B2 | 2/2015 | Boutros |
| 9,040,484 | B2 | 5/2015 | Marinkovich et al. |
| 9,072,724 | B2 | 7/2015 | Hausmanns et al. |
| 9,156,950 | B2 | 10/2015 | Garralda et al. |
| 9,328,154 | B2 | 5/2016 | Chilkoti |
| 9,382,310 | B2 | 7/2016 | Mirochnitchenko et al. |
| 9,591,853 | B2 | 3/2017 | Belgorodsky et al. |
| 9,675,635 | B2 | 6/2017 | Minatelli et al. |
| 9,676,837 | B2 | 6/2017 | Viswanathan et al. |
| 9,725,498 | B2 | 8/2017 | Russell et al. |
| 9,962,582 | B2 | 5/2018 | Antku |
| 10,053,501 | B2 | 8/2018 | Ramshaw et al. |

(Continued)

FOREIGN PATENT DOCUMENTS

| | | | |
|---|---|---|---|
| EP | 0036776 | A2 | 9/1981 |
| EP | 0535446 | A1 | 4/1993 |

(Continued)

OTHER PUBLICATIONS

Sewing et al.; Jellyfish collagen matrices conserve the chondrogenic phenotype in two- and threedimensional collagen matrices; Journal of Tissue Engineering and Regenerative Medicine; 11, 916-925; published online Jan. 29, 2015 (Year: 2015).*
Amino acid sequence of SEQ ID No. 572 in US20130237486A1, pp. 1-2, accessed Jul. 15, 2020 at URL: http://seqdata.uspto.gov/?pageRequest=viewSequence&DocID=US20130237486A1&seqID=572. United States Patent and Trademark Office Publication Site for Issued and Published Sequences (PSIPS).
Co-pending U.S. Appl. No. 16/462,196, filed May 17, 2019.
U.S. Appl. No. 16/839,035 Office Action dated Jul. 24, 2020.
Drumm et al. Genetic Variation and Clinical Heterogeneity in Cystic Fibrosis. Annu Rev Pathol. 2012; 7: 267-282. Published online Oct. 17, 2011. doi: 10.1146/annurev-pathol-011811-120900.

(Continued)

*Primary Examiner* — Antonio Galisteo Gonzalez
(74) *Attorney, Agent, or Firm* — Wilson Sonsini Goodrich & Rosati

(57) ABSTRACT

This disclosure provides non-naturally occurring collagen and elastin molecules. The non-naturally occurring collagens and elastins include truncated collagens, truncated elastins, as well as fusion proteins thereof. The non-naturally occurring collagen and elastin are useful in foods, cosmetics and many other products and uses.

19 Claims, 5 Drawing Sheets

Specification includes a Sequence Listing.

(56) References Cited

U.S. PATENT DOCUMENTS

| | | | |
|---|---|---|---|
| 10,155,793 | B2 | 12/2018 | Ramshaw et al. |
| 10,232,008 | B1 | 3/2019 | Moran |
| 10,358,464 | B2 | 7/2019 | Hook et al. |
| 2013/0078209 | A1 | 3/2013 | Yu et al. |
| 2013/0237486 | A1 | 9/2013 | Bella |
| 2014/0309401 | A1 | 10/2014 | Hayashida et al. |
| 2015/0150764 | A1 | 6/2015 | Pinsky |
| 2016/0130315 | A1 | 5/2016 | Kim et al. |
| 2016/0215018 | A1 | 7/2016 | Yang et al. |
| 2018/0282776 | A1 | 10/2018 | Douchin et al. |
| 2019/0106702 | A1 | 4/2019 | Ouzounov |
| 2019/0153068 | A1 | 5/2019 | Ouzounov et al. |
| 2019/0276515 | A1 | 9/2019 | Bruno-Bonnet et al. |
| 2020/0009184 | A1 | 1/2020 | Akthakul et al. |

FOREIGN PATENT DOCUMENTS

| | | | |
|---|---|---|---|
| EP | 0420937 | B1 | 11/1994 |
| EP | 1323820 | A2 | 7/2003 |
| EP | 2941277 | B1 | 9/2018 |
| EP | 3395860 | A1 | 10/2018 |
| JP | 2013095708 | A | 5/2013 |
| WO | WO-9304173 | A1 | 3/1993 |
| WO | WO-9404690 | A1 | 3/1994 |
| WO | WO-9519181 | A1 | 7/1995 |
| WO | WO-9523865 | A1 | 9/1995 |
| WO | WO-9630046 | A1 | 10/1996 |
| WO | WO-9640210 | A1 | 12/1996 |
| WO | WO-9726912 | A2 | 7/1997 |
| WO | WO-9738710 | A1 | 10/1997 |
| WO | WO-9806248 | A2 | 2/1998 |
| WO | WO-9823761 | A1 | 6/1998 |
| WO | WO-9845331 | A2 | 10/1998 |
| WO | WO-9851793 | A1 | 11/1998 |
| WO | WO-9903886 | A1 | 1/1999 |
| WO | WO-0009018 | A1 | 2/2000 |
| WO | WO-0075348 | A1 | 12/2000 |
| WO | WO-0140309 | A2 | 6/2001 |
| WO | WO-2004056312 | A2 | 7/2004 |
| WO | WO-2005021772 | A1 | 3/2005 |
| WO | WO-2015012682 | A2 | 1/2015 |
| WO | WO-2015012683 | A1 | 1/2015 |
| WO | WO-2016004334 | A1 | 1/2016 |
| WO | WO-2017083398 | A1 | 5/2017 |
| WO | WO-2017125585 | A2 | 7/2017 |
| WO | WO-2017156418 | A1 | 9/2017 |
| WO | WO-2017160636 | A1 | 9/2017 |
| WO | WO-2017125585 | A9 | 10/2017 |
| WO | WO-2017172994 | A1 | 10/2017 |
| WO | WO-2017206326 | A1 | 12/2017 |
| WO | WO-2018014453 | A1 | 1/2018 |
| WO | WO-2018041684 | A1 | 3/2018 |
| WO | WO-2018078276 | A1 | 5/2018 |
| WO | WO-2018119530 | A1 | 7/2018 |
| WO | WO-2019023555 | A1 | 1/2019 |
| WO | WO-2019046943 | A1 | 3/2019 |
| WO | WO-2019068018 | A2 | 4/2019 |
| WO | WO-2019077312 | A1 | 4/2019 |
| WO | WO-2019099561 | A1 | 5/2019 |
| WO | WO-2019166418 | A1 | 9/2019 |
| WO | WO-2020205848 | A1 | 10/2020 |
| WO | WO-2020210440 | A1 | 10/2020 |

OTHER PUBLICATIONS

Dulbecco's Modified Eagle Medium (DMEM). Product Information. Product Code: AT068. HiMedia Laboratories Pvt Ltd., Mumbai, India. 2011. 2 pages.

GenBank Accession No. CAA08789. Version No. CAA08789.1. fibrillar collagen, partial [Podocoryna carnea]. Record created Mar. 9, 1999. 2 pages. Retrieved Apr. 28, 2020 at URL: <https://www.ncbi.nlm.nih.gov/protein/4379341?report=genbank&log$=protalign&blast_rank=1&RID=T1N9ZEUW014>.

GenBank Accession No. XP_016874317. Version No. XP_016874317.1. collagen alpha-1(II) chain isoform X1 [*Homo sapiens*]. Record created Jun. 6, 2016. 3 pages. Accessed Jun. 18, 2020 at URL: <https://www.ncbi.nlm.nih.gov/protein/XP_016874317.1?report=genbank&log$=protalign&blast_rank=11&RID=ER8N7H11014.

Hong et al., Fibrillar Type I Collagen Enhances the Differentiation and Proliferation of Myofibroblasts by Lowering alpha2beta1 Integrin Expression in Cardiac Fibrosis. Biomed Res Int. 2017; 2017: 1790808. Published online Jan. 30, 2017. doi: 10.1155/2017/1790808. 11 pages.

Luo et al. Collagen-like peptides and peptide-polymer conjugates in the design of assembled materials. Eur Polym J. Oct. 2013; 49(10): 2998-3009. doi: 10.1016/j.eurpolymj.2013.05.013. Available online Jun. 4, 2013.

Shigemura et al. Effect of Prolyl-hydroxyproline (Pro-Hyp), a food-derived collagen peptide in human blood, on growth of fibroblasts from mouse skin. J Agric Food Chem. Jan. 28, 2009;57(2):444-9. doi: 10.1021/jf802785h.

U.S. Appl. No. 16/144,914 Office Action dated Jul. 10, 2020.

Water, from http://www.biology-online.org/dictionary/Water, accessed Apr. 24, 2014, 3 pages.

What Is Sorbic Acid? From https://www.healthline.com/health/food-nutrition/what-is-sorbic-acid, accessed Sep. 9, 2019, 3 pages.

Yampolsky et al. The Exchangeability of Amino Acids in Proteins. Genetics. Aug. 2005; 170(4): 1459-1472. doi: 10.1534/genetics.104.039107.

U.S. Appl. No. 16/839,044 Office Action dated Aug. 7, 2020.

Anonymous, "ColF1—Fibrillar collagen—Podocoryna camera (Hydrozoan)—colF1 gene & protein" (Jan. 1, 1998), XP055541622, Retrieved from the Internet: URL:https://www.uniportorg/uniport/076966#entry_information [retrieved on Jan. 14, 2019].

Bornert, Olivier et al. "Analysis of the functional consequences of targeted exon deletion in COL7A1 reveals prospects for dystrophic epidermolysis bullosa therapy", Molecular Therapy. Jul. 1, 2016;24(7):1302-11.

Bornhorst JA, Falke JJ. [16] Purification of proteins using polyhistidine affinity tags. In Methods in enzymology Jan. 1, 2000 (vol. 326, pp. 245-254). Academic Press.

Cayley, D. Scott, et al., "Biophysical characterization of changes in amounts and activity of *Escherichia coli* cell and compartment water and turgor pressure in response to osmotic stress", Biophysical Journal, (Apr. 2000), 78(4):1748-1764.

Chandrakasan et al. Preparation of intact monomeric collagen from rat tail tendon and skin and the structure of the nonhelical ends in solution. J Biol Chem. Oct. 10, 1976;251(19):6062-7.

Chou, M-Y, et al., "Genomic organization and characterization of the human type XXI collagen (COL21A1) gene", Genomics. Mar. 1, 2002;79(3):395-401.

Co-pending U.S. Appl. No. 16/839,035, filed Apr. 2, 2020.

Co-pending U.S. Appl. No. 16/839,042, filed Apr. 2, 2020.

Co-pending U.S. Appl. No. 16/839,044, filed Apr. 2, 2020.

Co-pending U.S. Appl. No. 16/844,226, filed Apr. 9, 2020.

Dinh et al. Using superfolder green fluorescent protein for periplasmic protein localization studies. J Bacteriol 193(18):4984-4987 (Sep. 2011). Epub Jul. 15, 2011. doi: 10.1128/JB.00315-11.

Fleischmajer et al. Rotary shadowing of collagen monomers, oligomers, and fibrils during tendon fibrillogenesis. J Histochem Cytochem. Jan. 1991;39(1):51-8.

GenBank Accession No. AJ009690. Version No. AJ009690.1. Podocoryne carnea mRNA for fibrillar collagen, partial. Record created Jul. 30, 1988. 2 pages. Retrieved Mar. 26, 2020 at URL:<https://www.ncbi.nlm.nih.gov/nucleotide/3355656?report=genbank&log$=nuclalign&blast_rank=1&RID=TSYP7CMV014>.

Gortz, H.-D. et al., "Changes in Fine Structure and Polypeptide Pattern during Development of Holospora obtuse, a bacterium Infecting the macronucleus of Paramecium caudatum", Journal of Bacteriology, (Oct. 1, 1990), 172(10):5664-5669, XP055373233, Retrieved from the Internet: URL: https://www.ncbi.nlm.nih.gov/pmc/articles/PMC526880/pdf/jbacter00164-0156.pdf, [retrieved May 16, 2017].

(56) References Cited

OTHER PUBLICATIONS

Gumpert et al. Characteristic properties and biological significance of stable protoplast type L-forms. In Protoplasts, Lecture Proceedings of the 6th International Protoplast Symposium: Basel. Experientia 1983, 46(suppl):227-241.
Haworth, R.S. et al., "Uncoupler resistance in *E. coli* Tuv and Cuv is due to the exclusion of uncoupler by the outer membrane", Biochim Biophys Acta., (Aug. 9, 1990), 1019(1):67-72, XP023349580, ISBN: 0005-2728, DOI: 10.1016/0005-2728(90)90125-N [retrieved on Aug. 9, 1990]. Abstract only.
Hoischen et al. Lipid and fatty acid composition of cytoplasmic membranes from Streptomyces hygroscopicus and its stable protoplast-type L form. J Bacteriol 179(11):3430-3436 (Jun. 1997).
International Preliminary Report on Patentability, dated Oct. 2, 2018, for International Patent Application No. PCT/US2017/024857.
International Search Report and Written Opinion of the Searching Authority for International Patent Application No. PCT/US2017/024857, dated May 31, 2017.
International Search Report and Written Opinion of the Searching Authority for International Patent Application No. PCT/US2018/053601, dated Apr. 10, 2019.
Joly et al. Chapter 20: Practical Applications for Periplasmic Protein Accumulation, in The Periplasm, ed. Ehrmann, M., ASM Press, Washington D.C., pp. 345-360 (2007).
Krapf et al. Deciphering the aggregation mechanism of bacteria (*Shewanella oneidensis* MR1) in the presence of polyethyleneimine: Effects of the exopolymeric superstructure and polymer molecular weight. Colloids Surf B Biointerfaces. Mar. 1, 2016;139:285-93. doi: 10.1016/j.colsurfb.2015.12.015. Epub Dec. 8, 2015.
Paul-Dauphin et al. Bias and precision in visual analogue scales: a randomized controlled trial. Am J Epidemiol. Nov. 15, 1999;150(10):1117-27.
Pilizota, Teuta and J. W. Shaevitz, "Fast, Multiphase Volume Adaptation to Hyperosmotic Shock by *Escherichia coli*", PLoS ONE, (Apr. 2012), 7(4): e35205. https://doi.org/10.1371/journal.pone.0035205.
Ramshaw, John A. M., et al., "Gly-XY tripeptide frequencies in collagen: a context for host-guest triple-helical peptides", Journal of structural biology. Jan. 1, 1998;122(1-2):86-91.
Schmid, V. et al., "The extracellular matrix (mesoglea) of hydrozoan jellyfish and its ability to support cell adhesion and spreading", In Hydrobiologia Jun. 1, 1991 (vol. 216, No. 1, pp. 3-10). Kluwer Academic Publishers.
Tomaro-Duchesneau et al. Microencapsulation for the Therapeutic Delivery of Drugs, Live Mammalian and Bacterial Cells, and Other Biopharmaceutics: Current Status and Future Directions. J Pharm (Cairo) 2013:103527 (2013). Published online Dec. 4, 2012. doi: 10.1155/2013/103527.
Grosso et al. PGAIPG, a Repeated Hexapeptide of Bovine Tropoelastin, Is a Ligand for the 67-kDa Bovine Elastin Receptor.Matrix.Mar. 1993;13(2):157-64.doi: 10.1016/s0934-8832(11)80074-0.
Kuzan et al. An Estimation of the Biological Properties of Fish Collagen in an Experimental In Vitro Study. Adv Clin Exp Med. May-Jun. 2015;24(3):385-92.doi: 10.17219/acem/31704.
PCT/US2020/025934 International Search Report and Written Opinion dated Jul. 2, 2020.
PCT/US2020/027399 International Search Report and Written Opinion dated Jun. 26, 2020.
Rodriguez et al. Collagen: A Review on Its Sources and Potential Cosmetic Applications. J Cosmet Dermatol. Feb. 2018;17(1):20-26. doi: 10.1111/jocd.12450. Epub Nov. 16, 2017.
Zhuang et al. Effects of Collagen and Collagen Hydrolysate From Jellyfish (*Rhopilema esculentum*) on Mice Skin Photoaging Induced by UV Irradiation. J Food Sci. Aug. 2009;74(6):H183-8.doi: 10.1111/j.1750-3841.2009.01236.x.
Lucas et al. A molecular, morphometric and mechanical comparison of the structural elements of byssus from Mytilus edulis and Mytilus galloprovincialis. J Exp Biol. Jun. 2002;205(Pt 12):1807-17.
Phosphate buffered saline. Protocols Online (Oct. 3, 2016). Retrieved Aug. 7, 2020 from URL: https://www.protocolsonline.com/recipes/phosphate-buffered-saline-pbs/. 3 pages.
Protease cleavage of SEQ ID No. 61 in WO 2019/068018A2, from ExPASy—PeptideCutter, SIB Swiss Institute of Bioinformatics, accessed Oct. 15, 2020 at URL: https://web.expasy.org/cgi-bin/peptide_cutter/peptidecutter.p1, pp. 1-2.
Shin et al. Enhancement of the Tumor Penetration of Monoclonal Antibody by Fusion of a Neuropilin-Targeting Peptide Improves the Antitumor Efficacy. Mol Cancer Ther 13(3):651-661, with supplementary information pp. 1-27 (Mar. 2014).
U.S. Appl. No. 16/839,042 Final Office Action dated Dec. 3, 2020.
U.S. Appl. No. 16/839,044 Final Office Action dated Dec. 10, 2020.
U.S. Appl. No. 16/839,042 Office Action dated Aug. 24, 2020.
U.S. Appl. No. 16/844,226 Office Action dated Oct. 29, 2020.
Peptidecutter of SEQ ID No. 4 in Chou et al., from https://web.expasy.org/cgi-bin/peptide_cutter/peptidecutter.ol, pp. 1-8, accessed Jan. 29, 2021.
Teale et al., Ultraviolet fluorescence of the aromatic amino acids. Biochem J. 65(3):476-482 (1957).
Turczynski et al., Targeted Exon Skipping Restores Type VII Collagen Expression and Anchoring Fibril Formation in an In Vivo RDEB Model. Journal of Investigative Dermatology 136: 2387-2395 (2016).
U.S. Appl. No. 16/144,914 Final Office Action dated Feb. 5, 2021.
U.S. Appl. No. 16/839,042 Notice of Allowance dated Feb. 8, 2021.
U.S. Appl. No. 16/844,226 Final Office Action dated Feb. 4, 2021.
Woodley et al., Intravenously Injected Recombinant Human Type VII Collagen Homes to Skin Wounds and Restores Skin Integrity of Dystrophic Epidermolysis Bullosa. Journal of Investigative Dermatology 133: 1910-1913 (2013).

* cited by examiner

RECOMBINANT COLLAGEN AND ELASTIN MOLECULES AND USES THEREOF

CROSS-REFERENCE

This application is a continuation application of U.S. patent application Ser. No. 16/144,914, filed Sep. 27, 2018, which application claims priority from U.S. Provisional Patent Application No. 62/564,964, filed Sep. 28, 2017, and U.S. Provisional Patent Application No. 62/657,591, filed Apr. 13, 2018, the disclosures of which are incorporated by reference herein in their entirety.

SEQUENCE LISTING

The instant application contains a Sequence Listing which has been submitted electronically in ASCII format and is hereby incorporated by reference in its entirety. Said ASCII copy, created on Nov. 21, 2018, is named 57607702SL.txt and is 320,570 bytes in size.

FIELD

The present disclosure relates to non-naturally occurring full-length and truncated collagen molecules and full-length and truncated elastin molecules and uses thereof.

BACKGROUND

Collagens and similar proteins are the most abundant proteins in the biosphere. Collagens and elastins are structural proteins found in the skin, connective tissue and bone of animals and other tissues. In humans, the amount of collagen present in the body is approximately one third of the total proteins and accounts for about three fourths of the dry weight of skin. Elastin is a highly elastic protein found in connective tissue and other types of tissue.

The structure of collagen is a triple helix in which three polypeptide strands together form a helical coil. The individual polypeptide strands are composed of repeating triplet amino acid sequences designated as GLY-X-Y. X and Y can be any amino acid and the third amino acid is glycine. The amino acids proline and hydroxyproline are found in high concentrations in collagen. The most common triplet is proline-hydroxyproline-glycine (Gly-Pro-Hyp) accounting for approximately 10.5% of the triplets in collagen.

Gelatin is a product obtained by partial hydrolysis of collagen. Typically, gelatin is produced by acid hydrolysis, alkaline hydrolysis, and enzymatic hydrolysis or by exposing collagen to heat in an aqueous solution (e.g., boiling the bones and skins of animal, boiling fish scales, etc.).

Gelatin is used in many products including cosmetics, foods, pharmaceuticals, medical devices, photographic films, adhesives, binders and many others. The physical and chemical properties of gelatin are tuned to the particular application. These physical/chemical properties include gel strength, melting point temperature, viscosity, color, turbidity, pH, isoelectric point and others.

Elastin is an elastic protein that is crucial for the proper functioning of arteries, lung, tendons, ligament, skin and other tissue. Elastin provides the tissues with the ability to stretch and return to its original shape. The protein tropoelastin is the building block of elastin. In contrast to collagen that include a family of genes, there is one tropoelastin gene in humans. When expressed, the single elastin gene is spliced to produce different forms of the tropoelastin protein. Many tropoelastin molecules associate together to form elastin.

L-form bacteria, or L-forms, are bacterial strains derived from parent species (N-forms) that are able to grow as cell wall-deficient (spheroplast type) or as cell wall-less (protoplast type) cells. See, Madoff S (Ed): The Bacterial L-Forms. New York: Marcel Dekker Inc., 1986; Mattmann LH (Ed): Cell Wall Deficient Forms. Boca Raton: CRC Press; 1993; and Gumpert J, Taubeneck U: Characteristic properties and biological significance of stable protoplast type L-forms. In Protoplasts, Lecture Proceedings of the 6th International Protoplast Symposium: Basel. Experientia 1983, 46(suppl): 227-241.

Protoplast type L-forms have been cultivated in the cell wall-less state and represent genetically stable mutants showing extreme pleiotropic changes, including the inability to form cell walls, capsules, flagella, pili, spores and mesosomes, altered colony and cell morphology, qualitative and quantitative changes in the lipid and protein components of the cytoplasmic membrane, the absence of extracellular proteolytic activities, resistance against bacteriophages and the incapability to propagate outside laboratory conditions. See, Gumpert and Taubeneck (supra); and Hoischen et al., Lipid and fatty acid composition of cytoplasmic membranes from *Streptomyces* hygroscopic and its stable protoplast type L-form. J Bacteriol 1997, 179:3430-3436.

SUMMARY

In one aspect, a non-naturally occurring collagen produced by a host cell is provided. The non-naturally occurring collagen is jellyfish (Hydrozoan) collagen, human collagen, *Chondrosia reniformis* (kidney sponge) collagen, or *Rhincodon typus* (whale shark) collagen. In an embodiment, the non-naturally occurring collagen is a full-length or a truncated collagen. In one embodiment, the collagen is truncated by an internal truncation of between 50 amino acids and 500 amino acids. In another embodiment, the truncation is at the C-terminal end or the N-terminal end of the collagen polypeptide. The non-naturally occurring collagens are SEQ ID NO: 10, SEQ ID NO: 12, SEQ ID NO: 14, SEQ ID NO: 16, SEQ ID NO: 18, SEQ ID NO: 20, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 89 SEQ ID NO: 91, SEQ ID NO: 92, SEQ ID NO: 94, SEQ ID NO: 96, SEQ ID NO: 102, SEQ ID NO: 104, SEQ ID NO: 106, SEQ ID NO: 108, SEQ ID NO:110, or SEQ ID NO: 112.

In another aspect, the non-naturally occurring collagen further comprises amino acid sequences including a secretion tag, a histidine tag, a green fluorescent protein tag, a protease cleavage site, a Beta-lactamase and/or GEK amino acid trimer repeats and/or GDK amino acid trimer repeats. When the non-naturally occurring collagen comprises one or more amino acid trimer repeats of the sequence glycine-glutamic acid-lysine (GEK) and/or glycine-aspartic acid-lysine (GDK), the number of GEK and/or GDK trimer repeats can range from 2 to 50 trimer repeats (SEQ ID NOS: 130-131, respectively). In one aspect, the secretion tag is DsbA, PelB, OmpA, TolB, MalE, lpp, TorA, or HylA, or a hybrid secretion tag that comprises a portion of one secretion tag fused to a portion of a second secretion tag. An exemplary secretion tag is DsbA.

In one aspect, provided are compositions that comprise between 0.005% and 30% w/w non-naturally occurring collagen. The compositions can further comprise at least one additional ingredient comprising a topical carrier or a preservative.

Compositions comprising non-naturally occurring collagen are in one aspect topical compositions for applying to skin. The topical compositions are used for decreasing skin damage or promoting the repair of damaged skin.

One aspect provides methods for decreasing skin damage or promoting the repair of damaged skin. The method comprises applying the composition comprising elastin to the skin of a subject. The method increases the viability of the fibroblast cells or keratinocytes of the skin of the subject. In another aspect the application of the composition increases the synthesis of procollagen by the fibroblast cells of the subject's skin. In another aspect the topical application of the composition protects skin or keratinocytes against UV damage. In yet another embodiment, thymine-thymine (TT) dimer formation is decreased by the collagens or elastins disclosed herein.

Another aspect provided herein are methods of increasing the viability of skin cells. The method comprises applying collagen or elastin molecules to the skin or skin cell. The collagen or elastin as provided increases the viability of keratinocytes and/or fibroblasts is increased upon exposure to UV radiation, urban dust or other damaging stimuli.

In another aspect provided herein are methods for decreasing the production of inflammatory cytokines in a skin cell. In one embodiment the skin cell is a keratinocyte. The method comprises applying a collagen or elastin molecule to a skin cell. The production of inflammatory cytokines including TNFα, IL-1α, IL-1β, IL-3, IL-6, IL-7, IL-8, IL-10, IL-18, and IL-1RA.

In another aspect, provided are methods of protecting skin cells against the effect of exposure to urban dust. The method comprises the step of applying the collagen or elastin disclosed herein to the skin cell. The exposure of skin cell to collagen or elastin increases the viability of the skin cell. In an embodiment, the skin cell is a keratinocyte or a fibroblast.

In one aspect, a non-naturally occurring elastin produced by a host cell is provided. The non-naturally occurring elastin is jellyfish elastin, human elastin, *Chondrosia reniformis* (kidney sponge) elastin, or *Rhincodon typus* elastin. In an embodiment, the non-naturally occurring elastin is a full-length or truncated elastin. In one embodiment, the elastin is truncated by an internal truncation of between 50 amino acids and 500 amino acids. In another embodiment, the truncation is at the C-terminal end or the N-terminal end of the elastin polypeptide. The non-naturally occurring elastins are SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55 SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 98, or SEQ ID NO: 110.

In another aspect, the non-naturally occurring elastin further comprises amino acid sequences including a secretion tag, a histidine tag, a green fluorescent protein tag, a protease cleavage site, a Beta-lactamase and/or GEK amino acid trimer repeats and/or GDK amino acid trimer repeats. When the non-naturally occurring collagen comprises one or more amino acid trimer repeats of the sequence glycine-glutamic acid-lysine (GEK) and/or glycine-aspartic acid-lysine (GDK), the number of GEK and/or GDK trimer repeats can range from 2 to 50 trimer repeats (SEQ ID NOS: 130-131, respectively). In one aspect, the secretion tag is DsbA, PelB, OmpA, TolB, MalE, lpp, TorA, or HylA, or a hybrid secretion tag that comprises a portion of one secretion tag fused to a portion of a second secretion tag. An exemplary secretion tag is DsbA.

In another embodiment, compositions that comprise between 0.005% and 30% w/w non-naturally occurring elastin are provided. The compositions can further comprise at least one additional ingredient comprising a topical carrier or a preservative.

Compositions comprising non-naturally occurring elastin are in one aspect topical compositions for applying to skin. The topical compositions are used for decreasing skin damage or promoting the repair of damaged skin.

One embodiment provides methods for decreasing skin damage or promoting the repair of damaged skin. The method comprises applying the composition comprising elastin to the skin of a subject. The method increases the viability of the fibroblast cells of the skin of the subject. In another aspect the application of the composition increases the synthesis of procollagen by the fibroblast cells of the subject's skin. In another aspect the topical application of the compositions protects skin or keratinocytes against UV damage. In yet another embodiment, thymine-thymine (TT) dimer formation is decreased by the collagens or elastins disclosed herein.

Another embodiment provides polynucleotides that encode a non-naturally occurring collagen or a non-naturally occurring elastin. The polynucleotides encode collagen or elastin from jellyfish, human, *Chondrosia reniformis* (kidney sponge), or *Rhincodon typus*. The encoded collagen or elastin may be full length or truncated. In one embodiment, the collagen or elastin is truncated by an internal truncation of between 50 amino acids and 500 amino acids.

In one embodiment polynucleotides that encode fusion proteins comprising a secretion tag, a histidine tag, a green fluorescent protein tag, a protease cleavage site, a Beta-lactamase along and/or GEK amino acid trimer repeat and/or GDK amino acid trimer repeats together with collagen or elastin are provided. The non-naturally occurring collagen or elastin may comprise one or more amino acid trimer repeats of the sequence glycine-glutamic acid-lysine (GEK) and/or glycine-aspartic acid-lysine (GDK), the number of GEK and/or GDK trimer repeats can range from 2 to 50 trimer repeats (SEQ ID NOS: 130-131, respectively). In one aspect, the secretion tag is DsbA, PelB, OmpA, TolB, MalE, lpp, TorA, or HylA, or a hybrid secretion tag that comprises a portion of one secretion tag fused to a portion of a second secretion tag. An exemplary embodiment secretion tag is DsbA.

The polynucleotides and vectors can be used to transform host cells and express the polynucleotides. Polynucleotides encoding a non-naturally occurring collagen, wherein the polynucleotide is SEQ ID NO: 9, SEQ ID NO: 11, SEQ ID NO: 13, SEQ ID NO: 15, SEQ ID NO: 17, SEQ ID NO: 19 SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 90, SEQ ID NO: 93, SEQ ID NO: 95, SEQ ID NO: 97, SEQ ID NO: 103, SEQ ID NO: 105, SEQ ID NO: 107, SEQ ID NO: 109, SEQ ID NO:111, SEQ ID NO: 113, or SEQ ID NO:105 are provided. Polynucleotides encoding a non-naturally occurring elastin, wherein the polynucleotide is SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, and SEQ ID NO: 72, SEQ ID NO: 99, or SEQ ID NO:101 provided.

Host cells that express the polynucleotides of the invention are disclosed. Host cells can be any host cell including bacterial cells, yeast cells, fungal cells, insect cells, mammalian cells, plant cells and any other cells used to express exogenous polynucleotides.

Bacterial host cells in which the cells have been modified to inhibit cell division and the periplasmic space is increased are provided. An exemplary host cell is *E. coli.*

One embodiment provides a method of producing a non-naturally occurring collagen or a non-naturally occurring elastin. The method comprises the steps of inoculating a culture medium with a recombinant host cell comprising polynucleotides that encode the collagen or elastin, cultivating the host cell, and isolating the non-naturally occurring collagen or the non-naturally occurring elastin from the host cell.

DESCRIPTION

Figure 1:
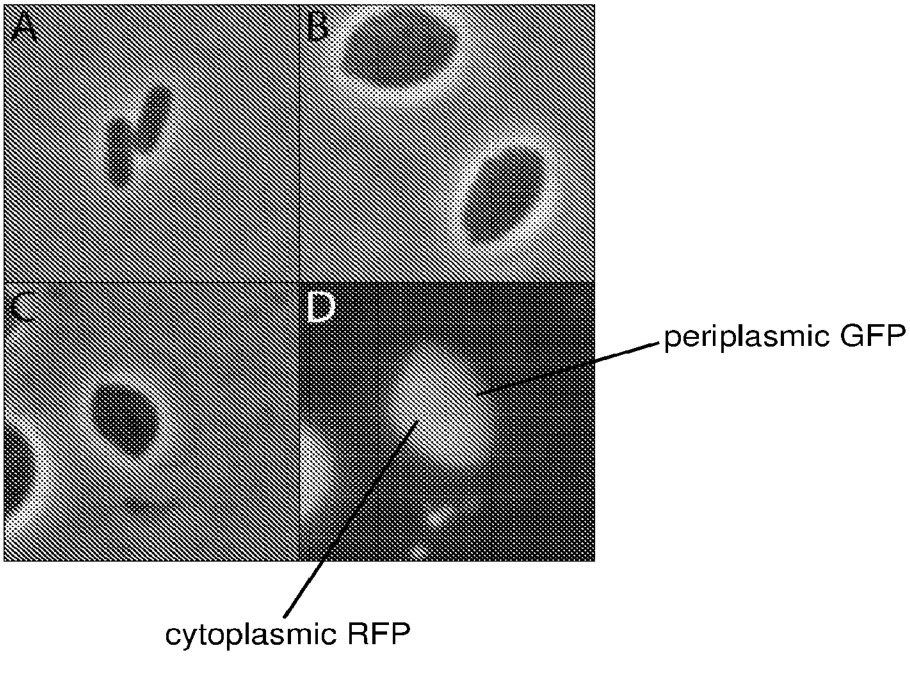
FIG. 1 depicts the physiological state difference between switched and unswitched cells. A) Unswitched *Escherichia coli* cells. B) Same *Escherichia coli* population as figure A but has undergone the physiological switch. C) Phase contrast of switched *Escherichia coli* cell containing cytoplasmic RFP and periplasmic GFP. D) Fluorescent imaging of cell in figure C illustrates targeted protein localization.
Figure 2:
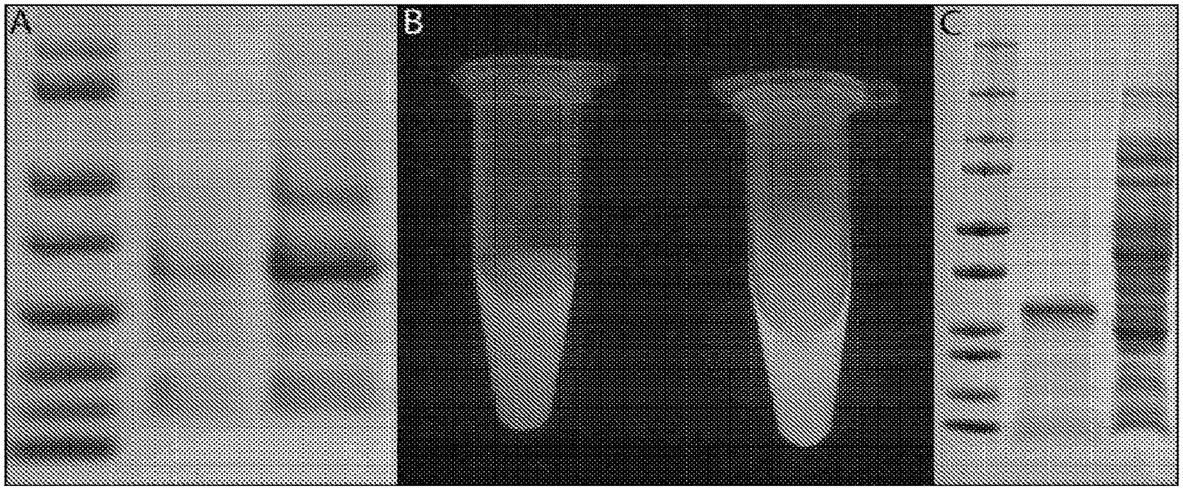
FIG. 2 depicts enhanced protein production in switched cells. A-B) Target protein for T7 inducible protein production is periplasmic expressed GFP, produced in *Escherichia coli* BL21. The same population of cells was used and induced at OD 1.1. A) Protein ladder (lane 1), IPTG induced protein production (lane 2), IPTG induced protein production with physiological switch (lane 3). B) Two vials of the cell GFP induced cultures with IPTG only on left and IPTG+Switch on right. C) Expression of a 22 kDa collagen using switched cells showing protein ladder (lane 1), supernatant after protein production (lane 2), cell pellet (lane 3).
Figure 3:
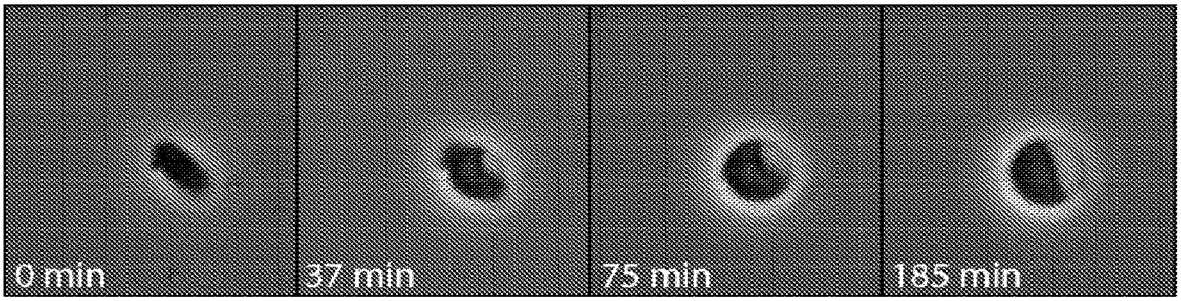
FIG. 3 depicts a time-lapse of *Escherichia coli* cell switching over time.
Figure 4:
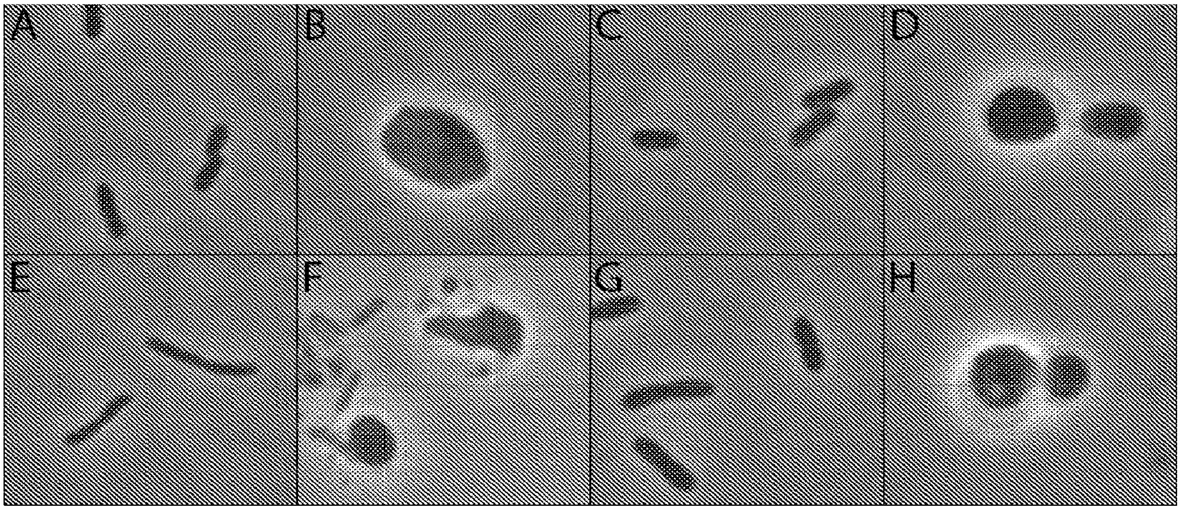
FIG. 4 illustrates other organisms undergoing the physiological switch. A) *Agrobacterium tumefaciens* normal physiology. B) *Agrobacterium tumefaciens* switched physiology. C) *Pseudomonas aeruginosa* PAO1 normal physiology. D) *Pseudomonas aeruginosa* PAO1 switched physiology. E) *Brevundimonas diminuta* normal physiology. F) *Brevundimonas diminuta* switched physiology. G) *Agrobacterium tumefaciens* normal physiology. H) *Agrobacterium tumefaciens* switched physiology.

In the following description, certain specific details are set forth in order to provide a thorough understanding of various embodiments of the disclosure. However, one skilled in the art will understand that the disclosure may be practiced without these details.

As used herein the term "about" refers to ±10%.

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this disclosure may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "collagen" or "collagen-like" as used herein refers to a monomeric polypeptide that can associate with one or more collagen or collagen-like polypeptides to form a quaternary structure. Collagen can be treated with acid, base or heat to prepare gelatin. The quaternary structure of natural collagen is a triple helix typically composed of three polypeptides. Of the three polypeptides that form natural collagen, two are usually identical and are designated as the alpha chain. The third polypeptide is designated as the beta chain. Thus a typical natural collagen can be designated as AAB, wherein the collagen is composed of two alpha ("A") strands and one beta ("B") strand. The term "procollagen" as used herein refers to polypeptides produced by cells that can be processed to naturally occurring collagen.

The terms "elastin" as used herein refers to a polypeptide that is elastic and functions to stretch or contract and return to its original shape. Elastin is found naturally in connective tissue.

The term "expression vector" or "vector" as used herein refers to a nucleic acid assembly which is capable of directing the expression of the exogenous gene. The expression vector may include a promoter which is operably linked to the exogenous gene, restriction endonuclease sites, nucleic acids that encode one or more selection markers, and other nucleic acids useful in the practice of recombinant technologies.

The term "fibroblast" as used herein refers to a cell that synthesizes procollagen and other structural proteins. Fibroblasts are widely distributed in the body and found in skin, connective tissue and other tissues.

The term "fluorescent protein" is a protein that is commonly used in genetic engineering technologies used as a reporter of expression of an exogenous polynucleotide. The protein when exposed to ultraviolet or blue light fluoresces and emits a bright visible light. Proteins that emit green light is green fluorescent protein (GFP) and proteins that emit red light is red fluorescent protein (RFP).

The term "gelatin" as used herein refers to collagen that has been further processed by exposure to acid, base or heat. While not wishing to be bound by theory or mechanism, treatment of collagen with acid, base or heat is thought to denature the collagen polypeptides. Aqueous denatured collagen solutions form reversible gels used in foods, cosmetics, pharmaceuticals, industrial products, medical products, laboratory culture growth media, and many other applications.

The term "gene" as used herein refers to a polynucleotide that encodes a specific protein, and which may refer to the coding region alone or may include regulatory sequences preceding (5' non-coding sequences) and following (3' non-coding sequences) the coding sequence.

The term "histidine tag" is a 2-30 contiguous series of histidine residues on a recombinant polypeptide.

The term "host cell" is a cell that is engineered to express an introduced exogenous polynucleotide.

The term "keratinocyte" is a cell that produces keratins found in the epidermal layer of the skin.

The term "lactamase" as used herein refer to enzymes that hydrolyze antibiotics that contain a lactam (cyclic amide) moiety. "Beta-lactamase" or "β-lactamase" are enzymes that hydrolyze antibiotics that contain a β-lactam moiety.

The term "non-naturally occurring" as used herein refers to collagen or elastin that is not normally found in nature. The non-naturally occurring collagen or elastin are recombinantly prepared. The non-naturally occurring collagen or elastin is a recombinant collagen or recombinant elastin. The non-naturally occurring collagen is in one embodiment a truncated collagen. Other non-naturally occurring collagen polypeptides include chimeric collagens. A chimeric collagen is a polypeptide wherein one portion of a collagen polypeptide is contiguous with a portion of a second collagen polypeptide. For example, a collagen molecule comprising a portion of a jellyfish collagen contiguous with a portion of a human collagen is a chimeric collagen. In another embodiment, the non-naturally occurring collagen comprises a fusion polypeptide that includes additional amino acids such as a secretion tag, histidine tag, green fluorescent protein, protease cleavage site, GEK repeats, GDK repeats, and/or beta-lactamase. The non-naturally occurring elastin in one embodiment a truncated elastin. Other non-naturally occurring elastin polypeptides include chimeric elastins. A chimeric elastin is a polypeptide wherein one portion of an elastin polypeptide is contiguous with a portion of a second elastin polypeptide. For example, a collagen molecule comprising a portion of a jellyfish elastin contiguous with a portion of a human elastin is a chimeric elastin. In another embodiment, the non-naturally occurring elastin comprises a fusion polypeptide that includes additional amino acids such as a secretion tag, histidine tag, green fluorescent protein, protease cleavage site and/or beta-lactamase. The chimeric gelatin or the chimeric elastin can comprise additional amino acids such as a secretion tag, histidine tag, green fluorescent protein, protease cleavage site, GEK repeats, GDK repeats, and/or beta-lactamase.

The term "protease cleavage site" is an amino acid sequence that is cleaved by a specific protease.

The term "secretion tag" or "signal peptide" refers to an amino acid sequence that recruits the host cell's cellular machinery to transport an expressed protein to a particular location or cellular organelle of the host cell.

The term "truncated collagen" refers to a monomeric polypeptide that is smaller than a full-length collagen wherein one or more portions of the full-length collagen is not present. Collagen polypeptides are truncated at the C-terminal end, the N-terminal end, or truncated by removal of internal portion(s) of the full-length collagen polypeptide.

The term "truncated elastin" refers to a monomeric polypeptide that is smaller than a full-length elastin wherein one or more portions of the full-length elastin is not present. Elastin polypeptides are truncated at the C-terminal end, the N-terminal end, or truncated by removal of internal portion (s) of the full-length elastin polypeptide.

In co-owned application PCT/US17/24857, incorporated by reference, an expression system that uses modified bacterial cells (switched cells) in which cell division is inhibited and growth of the periplasmic space is greatly enhanced was disclosed. In this expression system, the expressed proteins are targeted to the periplasmic space. Recombinant protein production in these switched cells is dramatically increased compared with that in non-switched cells. Structurally, the cells comprise both inner and outer membranes but lack a functional peptidoglycan cell wall, while the cell shape is spherical and increases in volume over time. Notably, while the periplasmic space normally comprises only 10-20% of the total cell volume, the periplasmic compartment of the switched state described herein can comprise more than 20%, 30%, 40% or 50% and up to 60%, 70%, 80% or 90% of the total cell volume.

The modified bacterial cells of PCT/US17/24857 are derived from Gram-negative bacteria, e.g. selected from: gammaproteobacteria and alphaproteobacteria. In some embodiments, the bacterium is selected from: *Escherichia coli, Vibrio natriegens, Pseudomonas fluorescens, Caulobacter crescentus, Agrobacterium tumefaciens*, and *Brevundimonas diminuta*. In specific embodiments, the bacterium is *Escherichia coli*, e.g. strain BL21(DE3).

In another aspect, the host bacterial cells have an enlarged periplasmic space in a culture medium comprising a magnesium salt, wherein the concentration of magnesium ions in the medium is at least about 3, 4, 5 or 6 mM. In further embodiments, the concentration of magnesium ions in the medium is at least about 7, 8, 9 or 10 mM. In some embodiments, the concentration of magnesium ions in the medium is between about 5 mM and 25 mM, between about 6 mM and/or about 20, 15 or 10 mM. In some embodiments, the magnesium salt is selected from: magnesium sulfate and magnesium chloride.

In other embodiments, the culture medium further comprises an osmotic stabilizer, including, e.g. sugars (e.g., arabinose, glucose, sucrose, glycerol, sorbitol, mannitol, fructose, galactose, saccharose, maltotrioseerythritol, ribitol, pentaerythritol, arabitol, galactitol, xylitol, iditol, maltotriose, and the like), betaines (e.g., trimethylglycine), proline, sodium chloride, wherein the concentration of the osmotic stabilizer in the medium is at least about 4%, 5%, 6%, or 7% (w/v). In further embodiments, the concentration of osmotic stabilizer is at least about 8%, 9%, or 10% (w/v). In some embodiments, the concentration of the osmotic stabilizer in the medium is between about 5% to about 20% (w/v).

In some embodiments, the cell culture may further comprise ammonium chloride, ammonium sulfate, calcium chloride, amino acids, iron(II) sulfate, magnesium sulfate, peptone, potassium phosphate, sodium chloride, sodium phosphate, and yeast extract.

The host bacterial cell may be cultured continuously or discontinuously; in a batch process, a fed-batch process or a repeated fed-batch process.

In some embodiments, the antibiotic is selected from: β-lactam antibiotics (e.g. penicillins, cephalosporins, carbapenems, and monobactams), phosphonic acid antibiotics, polypeptide antibiotics, and glycopeptide antibiotics. In particular embodiments, the antibiotic is selected from alafosfalin, amoxicillin, ampicillin, aztreonam, bacitracin, carbenicillin, cefamandole, cefotaxime, cefsulodin, cephalothin, fosmidomycin, methicillin, nafcillin, oxacillin, penicillin g, penicillin v, fosfomycin, primaxin, and vancomycin.

Without being bound by theory, the cell morphology that promotes recombinant protein production and inhibits cell division appears to be driven by the removal of the cell wall under the media conditions stated above. In some embodiments, the methods for removal/inhibition of cell wall synthesis can be through the use of antibiotics that inhibit peptidoglycan synthesis (such as ampicillin, carbenicillin, penicillins or fosfomycin), or other methods known in the art.

When having an appropriate periplasmic targeting signal sequence, recombinantly produced polypeptides can be secreted into the periplasmic space of bacterial cells. Joly, J. C. and Laird, M. W., in The Periplasm ed. Ehrmann, M., ASM Press, Washington D.C., (2007) 345-360. In the chemically oxidizing environment of the periplasm the formation of disulfide bonds and thereby the functionally correct folding of polypeptides is favored.

In general, the signal sequence may be a component of the expression vector, or it may be a part of the exogenous gene that is inserted into the vector. The signal sequence selected should be one that is recognized and processed (i.e., cleaved by a signal peptidase) by the host cell. For bacterial host cells that do not recognize and process the native signal sequence of the exogenous gene, the signal sequence is substituted by any commonly known bacterial signal sequence. In some embodiments, recombinantly produced polypeptides can be targeted to the periplasmic space using the DsbA signal sequence. Dinh and Bernhardt, J Bacteriol, September 2011, 4984-4987.

In one aspect, t a non-naturally occurring collagen or elastin is produced by a host cell is provided. The non-naturally occurring collagen or elastin is jellyfish collagen or elastin, t, human collagen or elastin, or *Chondrosia reniformis* (kidney sponge) collagen or elastin, or *Rhincodon typus* collagen or elastin. The non-naturally occurring collagen or elastin is a truncated collagen. The truncation is an internal truncation, a truncation at the N-terminal portion of the collagen or elastin, or a truncation at the C-terminal portion of the collagen or elastin. The collagen or elastin is truncated by a truncation of between 50 amino acids and 1000 amino acids, between, 50 amino acids and 950 amino acids, between 50 amino acids and 900 amino acids, between 50 amino acids and 850 amino acids, between 50 amino acids and 800 amino acids, between 50 amino acids and 850 amino acids, between 50 amino acids and 800 amino acids, between 50 amino acids and 750 amino acids, between 50 amino acids and 700 amino acids, between 50 amino acids and 650 amino acids, between 50 amino acids and 600 amino acids, between 50 amino acids and 650 amino acids, between 50 amino acids and 500 amino acids, between 50 amino acids and 450 amino acids, between 50 amino acids and 400 amino acids, between 50 amino acids and 350 amino acids, between 50 amino acids and 300 amino acids, between 50 amino acids and 250 amino acids, between 50 amino acids and 200 amino acids, between 50 amino acids and 150 amino acids, or between 50 amino acids and 100 amino acids. In another embodiment, the collagen or elastin is truncated by 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900, 950, or 1000 amino acids. The non-naturally occurring collagen or elastin are encoded by a portion of a polynucleotide sequence or the entire polynucleotide sequence disclosed herein.

The non-naturally occurring collagen or elastin further comprises amino acid sequences including a secretion tag. The secretion tag directs the collagen or elastin to the periplasmic space of the host cell. In particular embodiments, the signal peptide is derived from DsbA, PelB, OmpA, TolB, MalE, lpp, TorA, or HylA, or a hybrid secretion tag that comprises a portion of one secretion tag fused to a portion of a second secretion tag. In one aspect the secretion tag is attached to the non-naturally occurring collagen or elastin. In another aspect the secretion tag is cleaved from the non-naturally occurring collagen or elastin.

The non-naturally occurring collagen or the non-naturally occurring elastin o further comprises a histidine tag. The histidine tag or polyhistidine tag is a sequence of 2 to 20 histidine residues (SEQ ID NO: 117) that are attached to the collagen or elastin. The histidine tag comprises 2 to 20 histidine residues (SEQ ID NO: 117), 5 to 15 histidine residues (SEQ ID NO: 118), 5 to 18 histidine residues (SEQ ID NO: 119), 5 to 16 histidine residues (SEQ ID NO: 120), 5 to 15 histidine residues (SEQ ID NO: 118), 5 to 14 histidine residues (SEQ ID NO: 121), 5 to 13 histidine residues (SEQ ID NO: 122), 5 to 12 histidine residues (SEQ ID NO: 123), 5 to 11 (SEQ ID NO: 124), 5 to 10 histidine residues (SEQ ID NO: 125), 6 to 12 histidine residues (SEQ ID NO: 126), 6 to 11 histidine residues (SEQ ID NO: 127), or 7 to 10 histidine residues (SEQ ID NO: 128). The histidine tags are useful in purification of proteins by chromatographic methods utilizing nickel based chromatographic media. Exemplary fluorescent proteins include green fluorescent protein (GFP) or red fluorescent protein (RFP). Fluorescent proteins are well known in the art. In one embodiment the non-naturally occurring collagen or the on-naturally occurring elastin comprises a GFP and/or RFP. In one embodiment a superfolder GFP is fused to the on-naturally occurring collagen or elastin. The superfolder GFP is a GFP that folds properly even when fused to a poorly folded polypeptide. In one aspect the histidine tag is attached to the non-naturally occurring collagen or elastin. In another aspect the histidine tag is cleaved from the non-naturally occurring collagen or elastin.

The non-naturally occurring collagen or non-naturally occurring elastin further comprises a protease cleavage site. The protease cleavage site is useful to cleave the recombinantly produced collagen or elastin to remove portions of the polypeptide. The portions of the polypeptide that may be removed include the secretion tag, the histidine tag, the fluorescent protein tag and/or the Beta-lactamase. The proteases comprise endoproteases, exoproteases, serine proteases, cysteine proteases, threonine proteases, aspartic proteases, glutamic proteases, and metalloproteases. Exemplary protease cleavage sites include amino acids that are cleaved by Thrombin, TEV protease, Factor Xa, Enteropeptidase, and Rhinovirus 3C Protease. In one aspect the cleavage tag is attached to the non-naturally occurring collagen or elastin. In another aspect the cleavage tag is removed by an appropriate protease from the non-naturally occurring collagen or elastin.

The non-naturally occurring collagen or non-naturally occurring elastin further comprises an enzyme that is a Beta-lactamase. The beta-lactamase is useful as a selection marker. In one aspect the beta-lactamase is attached to the non-naturally occurring collagen or elastin. In another aspect the beta-lactamase is cleaved from the non-naturally occurring collagen or elastin.

The non-naturally occurring collagen or non-naturally occurring elastin further comprises GEK amino acid trimer repeats and/or GDK amino acid trimer repeats. The GEK and the GDK trimer repeats facilitate the gelling of the collagen and/or the gelatin. In one embodiment, the non-naturally occurring collagen or the non-naturally occurring elastin comprises 2-50 GEK and/or 2-50 GDK trimer repeats (SEQ ID NOS: 130-131, respectively), 2-40 GEK and/or 2-40 GDK trimer repeats (SEQ ID NOS: 132-133, respectively), 2-30 GEK and/or 2-30 GDK trimer repeats (SEQ ID NOS: 134-135, respectively), 2-20 GEK and/or 2-20 GDK trimer repeats (SEQ ID NOS: 136-137, respectively), 2-15 GEK and/or 2-15 GDK trimer repeats (SEQ ID NOS: 138-139, respectively). 2-10 GEK and/or 2-10 GDK trimer repeats (SEQ ID NOS: 140-141, respectively), 2-9 GEK and/or 2-9 GDK trimer repeats (SEQ ID NOS: 142-143, respectively), 2-8 GEK and/or 2-8 GDK trimer repeats (SEQ ID NOS: 144-145, respectively), 2-7 GEK and/or 2-7 GDK trimer repeats (SEQ ID NOS: 146-147, respectively), 2-6 GEK and/or 2-6 GDK trimer repeats (SEQ ID NOS: 148-149, respectively), 2-5 GEK and/or 2-5 GDK trimer repeats (SEQ ID NOS: 150-151, respectively), or 2-4 GEK and/or 2-4 GDK trimer repeats (SEQ ID NOS: 152-153, respectively). In one aspect the GEK trimer repeat or the GDK trimer repeat is attached to the non-naturally occurring collagen or elastin. In another aspect the GEK trimer repeat or the GDK trimer repeat is cleaved from the non-naturally occurring collagen or elastin.

Provided herein are compositions that comprise between 0.005% and 30% w/w non-naturally occurring collagen and/or non-naturally occurring elastin. The composition comprises between 0.005% and 20% w/w non-naturally occurring collagen and/or non-naturally occurring elastin, between 0.005% and 10% w/w non-naturally occurring collagen and/or non-naturally occurring elastin, between 0.005% and 5% w/w non-naturally occurring collagen and/or non-naturally occurring elastin, between 0.005% and 2% w/w non-naturally occurring collagen and/or non-naturally occurring elastin, between 0.005% and 1% w/w non-naturally occurring collagen and/or non-naturally occurring elastin, between 0.005% and 0.5% w/w non-naturally occurring collagen and/or non-naturally occurring elastin, and between 0.005% and 0.2% w/w non-naturally occurring collagen and/or non-naturally occurring elastin.

The compositions that comprise the between non-naturally occurring collagen and/or non-naturally occurring elastin are personal care products. In some embodiments the compositions are formulated for topical administration. The compositions can contain other cosmetic ingredients suitable for human use. The personal care products are useful for preventing or treating ultraviolet radiation damage to human skin or hair. The personal care products are applied to skin or hair. The compositions include, for example, masks, skin cleaners such as soap, cleansing creams, cleansing lotions, cleansing milks, cleansing pads, facial washes, hair shampoo, hair conditioner and body shampoos.

The compositions that comprise the non-naturally occurring collagen and/or non-naturally occurring elastin can further comprise at least one additional ingredient comprising a topical carrier or a preservative. The topical carrier comprises a topical carrier selected from the group consisting of liposome, biodegradable microcapsule, lotion, spray, aerosol, dusting powder, biodegradable polymer, mineral oil, triglyceride oil, silicone oil, glycerin, glycerin monostearate, alcohols, emulsifying agents, liquid petroleum, white petrolatum, propylene glycol, polyoxyethylene, polyoxypropylene, wax, sorbitan monostearate, polysorbate, cetyl ester wax, cetearyl alcohol, 2-octyldodecanol, benzyl alcohol, cyclomethicone, cyclopentasiloxane, and water. The preservative comprises a preservative selected from the group consisting of tocopherol, diiodomethyl-p-tolylsulfone, 2-Bromo-2-nitropropane-1,3-diol, cis isomer 1-(3-chloroallyl)-3,5,7-triaza-1-azoniaadamantane chloride, glutaraldehyde, 4,4-dimethyl oxazolidine, 7-Ethylbicyclooxazolidine, methyl paraben, sorbic acid, Germaben II, rosemary extract, and EDTA Provided are methods of decreasing skin damage, promoting the repair of damaged skin, protecting skin against UV damage, protecting skin cells against the effects of exposure to urban dust. The method comprises the step of applying the composition comprising the non-naturally occurring collagen and/or non-naturally occurring elastin to the skin of a subject. Without being bound to a particular theory or mechanism, the collagen and/or the elastin in the composition decrease skin damage by protecting against UV damage, and/or promotes the repair of damaged skin by increasing the viability of cells and/or increasing procollagen synthesis when applied to skin, and/or promotes the viability of skin cells. The collagens and elastins in one aspect decrease the formation of thymine-thymine (TT) dimer formation.

One aspect provides polynucleotides that encode a non-naturally occurring collagen or a non-naturally occurring elastin. The polynucleotides encode collagen or elastin from jellyfish, human, *Chondrosia reniformis* (kidney sponge), or *Rhincodon typus*. The polynucleotides encode for collagen or elastin that is full length or truncated.

Another aspect provides polynucleotides that encode collagen or elastin fusion proteins. The elastin or collagen fusion proteins comprise a secretion tag, a histidine tag, a fluorescent protein tag, a protease cleavage site, a Beta-lactamase along and/or GEK amino acid trimer repeats and/or GDK amino acid trimer repeats together with collagen or elastin.

The polynucleotides are in one aspect vectors used to transform host cells and express the polynucleotides. The polynucleotides further comprise nucleic acids that encode enzymes that permit the host organism to grow in the presence of a selection agent. The selection agents include certain sugars including galactose containing sugars or antibiotics including ampicillin, hygromycin, G418 and others. Enzymes that are used to confer resistance to the selection agent include β-galactosidase or a β-lactamase.

In one aspect host cells that express the polynucleotides of the invention are provided. Host cells can be any host cell including gram negative bacterial cells, gram positive bacterial cells, yeast cells, insect cells, mammalian cells, plant cells or any other cells used to express exogenous polynucleotides. An exemplary gram-negative host cell is *E. coli.*

Bacterial host cells in which the cells have been modified to inhibit cell division and the periplasmic space is increased are taught. As discussed herein and taught in example 1, Beta-lactam antibiotics are useful as a switch to convert wild-type bacterial cells to a modified bacterial cell in which cell replication is inhibited and the periplasmic space is increased. Exemplary Beta-lactam antibiotics including penicillins, cephalosporins, carbapenems, and monobactams.

The switched form of bacteria (L-form) are cultivated in culture media that include certain salts and other nutrients. Salts and media compositions that support the physiological switch physiology that have been tested are M63 salt media, M9 salt media, PYE media, and Luria-Bertani (LB) media. Any necessary supplements besides carbon, nitrogen, and inorganic phosphate sources may also be included at appropriate concentrations introduced alone or as a mixture with another supplement or medium such as a complex nitrogen source. In certain embodiments, the medium further comprises one or more ingredients selected from: ammonium chloride, ammonium sulfate, calcium chloride, casamino acids, iron(II) sulfate, magnesium sulfate, peptone, potassium phosphate, sodium chloride, sodium phosphate, and yeast extract.

Beta-lactamases are enzymes that confer resistance to lactam antibiotics in prokaryotic cells. Typically when Beta-lactamases are expressed in bacterial host cells, the expressed Beta-lactamase protein also includes targeting sequences (secretion tag) that direct the Beta-lactamase protein to the periplasmic space. Beta-lactamases are not functional unless they are transported to the periplasmic space.

Beta-lactamase targeted to the periplasmic without the use of an independent secretion tag that targets the enzyme to the periplasmic space are provided. By creating a fusion protein in which a periplasmic secretion tag added to the N-terminus of a protein such as GFP, collagen, or GFP/collagen chimeras, the functionality of the Beta-lactamase lacking a native secretion tag can be used to select for full translation and secretion of the N-terminal fusion proteins. Using this approach, we have used a DsbA-GFP-Collagen-Beta-lactamase fusion to select for truncation products in the target collagens that favor translation and secretion.

Another embodiment provides methods of producing a non-naturally occurring collagen or a non-naturally occurring elastin. The method comprises the steps of inoculating a culture medium with a recombinant host cell comprising polynucleotides that encode the collagen or elastin, cultivating the host cell, and isolating the non-naturally occurring collagen or the non-naturally occurring elastin from the host cell.

A process for fermentative preparation of a protein is provided. The process comprises the steps of:

a) culturing a recombinant Gram-negative bacterial cell in a medium comprising a magnesium salt, wherein the concentration of magnesium ions in the medium is at least about 6 mM, and wherein the bacterial cell comprises an exogenous gene encoding the protein;
b) adding an antibiotic to the medium, wherein the antibiotic inhibits peptidoglycan biogenesis in the bacterial cell; and
c) harvesting the protein from the medium.

The bacteria may be cultured continuously—as described, for example, in WO 05/021772—or discontinuously in a batch process (batch cultivation) or in a fed-batch or repeated fed-batch process for the purpose of producing the target protein. In some embodiments, protein production is conducted on a large-scale. Various large-scale fermentation procedures are available for production of recombinant proteins. Large-scale fermentations have at least 1,000 liters of capacity, preferably about 1,000 to 100,000 liters of capacity. These fermentors use agitator impellers to distribute oxygen and nutrients, especially glucose (the preferred carbon/energy source). Small-scale fermentation refers generally to fermentation in a fermentor that is no more than approximately 20 liters in volumetric capacity.

For accumulation of the target protein, the host cell is cultured under conditions sufficient for accumulation of the target protein. Such conditions include, e.g., temperature, nutrient, and cell-density conditions that permit protein expression and accumulation by the cell. Moreover, such conditions are those under which the cell can perform basic cellular functions of transcription, translation, and passage of proteins from one cellular compartment to another for the secreted proteins, as are known to those skilled in the art.

The bacterial cells are cultured at suitable temperatures. For *E. coli* growth, for example, the typical temperature ranges from about 20° C. to about 39° C. In one embodiment, the temperature is from about 20° C. to about 37° C. In another embodiment, the temperature is at about 30° C. In one embodiment, the host cells, in the non-switched state or switched state are cultivated at one temperature and switched to a different temperature to induce protein production. The host cells are cultivated first at one temperature to propagate the cells, then to induce protein production the cell are cultivated at a lower temperature. The first temperature is 23°, 24°, 25°, 26°, 27°, 28°, 29°, 30°, 31°, 32°, 33°, 34°, 35°, 36°, or 37° C. The second temperature is 20°, 21°, 22°, 23°, 24°, 25°, 26°, 27°, 28°, 29°, 30°, 31°, 32°, 33°, 34°, 35° or 36° C. The cultivation at the second temperature is conducted between 1 hour and 100 hours, between 5 hours and 90 hours, between 5 hours and 80 hours, between 5 hours and 80 hours, between 5 hours and 70 hours, between 10 hours and 70 hours, between 15 hours and 70 hours, between 15 hours and 65 hours, between 15 hours and 60 hours, between 20 hours and 60 hours, between 20 hours and 55 hours, between 20 hours and 50 hours, between 24 hours and 50 hours, between 24 hours and 48 hours, between 30 hours and 50 hours, between 30 hours and 45 hours, or between 30 hours and 40 hours.

The pH of the culture medium may be any pH from about 5-9, depending mainly on the host organism. For *E. coli*, the pH is from about 6.8 to about 7.4, or about 7.0.

For induction of gene expression, typically the cells are cultured until a certain optical density is achieved, e.g., an OD600 of about 1.1, at which point induction is initiated (e.g., by addition of an inducer, by depletion of a repressor, suppressor, or medium component, etc.) to induce expression of the exogenous gene encoding the target protein. In some embodiments, expression of the exogenous gene is inducible by an inducer selected from, e.g. isopropyl-β-d-1-thiogalactopyranoside, lactose, arabinose, maltose, tetracycline, anhydrotetracycline, vavlycin, xylose, copper, zinc, and the like. The induction of gene expression can also be accomplished by decreasing the dissolved oxygen levels during fermentation. The dissolved oxygen levels of the fermentation during cell propagation is between 10% and 30%. To induce gene expression the dissolved oxygen level is reduced to below 10%, 9%, 8%, 7%, 6%, 5%, 4%, 3%, 2%, 1%, or 0%. In host cells, in either the physiological state or the switched state, protein production can be induced by lowering the temperature of the fermentation as disclosed herein.

After product accumulation, the cells are vortexed and centrifuged in order to induce lysis and release of recombinant proteins. The majority of the proteins is found in the supernatant but any remaining membrane bound proteins can be released using detergents (such as triton X-100).

In a subsequent step, the target protein, as a soluble or insoluble product released from the cellular matrix, is recovered in a manner that minimizes co-recovery of cellular debris with the product. The recovery may be done by any means, but in one embodiment, can comprise histidine tag purification through a nickel column.

See, e.g., Purification of Proteins Using Polyhistidine Affinity Tags, Methods Enzymology. 2000; 326: 245-254.

EXAMPLES

Example 1: Expression System

Materials and methods:
Strains:
Tested Physiological Switch and Protein Production:
*E. coli* BL21(DE3)—From NEB, product #c2527
*E. coli* K12 NCM3722—From The *Coli* Genetic Stock Center, CGSC #12355
Tested Physiological Switch:
Gammaproteobacteria:
*Vibrio natriegens*—From ATCC, product #14048
*Pseudomonas fluorescens*—From ATCC, product #31948
*Pseudomonas aeruginosa* PAO1—From ATCC, product #BAA-47
Alphaproteobacteria:
*Caulobacter crescentus*—From ATCC, product #19089
*Agrobacterium tumefaciens/Rhizobium radiobacter*—From ATCC, product #33970
*Brevundimonas diminuta*—From ATCC, product #13184
Media Compositions:
1 liter 5×m63 salts:
10 g (NH4)2SO4—From P212121, product #7783-20-2
68 g KH2PO4—From P212121, product #7778-77-0
2.5 mg FeSO4.7H2O—From Sigma Aldrich, product #F7002
Bring volume up to 1 liter with milliQ water
Adjust to pH 7 with KOH (From P212121, product #1310-58-3)
Autoclave mixture
1 Liter of 1M MgSO4:
246.5 g MgSO4.7$H_2O$—From P212121, (Sigma Aldrich, product #10034-99-8)
Bring volume up to 1 liter with milliQ water.
Autoclave mixture.
1 Liter of Switch Media 1:
133.4 mL 5× m63 salts
10 mL 1M MgSO4
38.6 g Glucose—From P212121, product #50-99-7
66.6 g Sucrose—From P212121, product #57-50-1
8.33 g LB mix—From P212121, product #1b-miller
Bring volume up to 1 liter with milliQ water.
Filter sterilize mixture through a 0.22 μM pore vacuum filter (Sigma Aldrich, product #CLS430517).
1 Liter of Switch Media 2:
133.4 mL 5× m63 salts
10 mL 1M MgSO4
38.6 g Glucose—From P212121, product #50-99-7
66.6 g Sucrose—From P212121, product #57-50-1
10 g Yeast Extract—From FisherSci.com, product #160287A1
Bring volume up to 1 liter with milliQ water.
Filter sterilize mixture through a 0.22 μM pore vacuum filter (Sigma Aldrich, product #CLS430517).
For Bioreactor Growth:
5 liter of bioreactor media MGZ12:
1) Autoclave 1 L of Glucose at concentration of 500 g/L in DI water. (VWR, product #97061-170).
2) Autoclave 1 L of Sucrose at concentration of 500 g/L in DI water. (Geneseesci.com, product #62-112).
3) Autoclave in 3946 mL of DI water:
20 g (NH4)2HPO4. (VWR, product #97061-932).
66.5 g KH2PO4. (VWR, product #97062-348).
22.5 g H3C6H507. (VWR, product #BDH9228-2.5KG).
2.95 g MgSO4.7$H_2O$. (VWR, product #97062-134).
10 mL Trace Metals (Teknova), 1000×. (Teknova, product #T1001).
After autoclaving add 400 mL of (1) to (3), 65 mL of 10M NaOH (VWR, product #97064-480) to (3), and 666 mL of (2) to (3).
A feed of 500 g/L of glucose can be used during fermentation run as needed.
At induction add:
50 mL of 1M MgSO4.7$H_2O$ to a 5 L bioreactor
1 to 10 mM concentration of IPTG. (carbosynth.com, product #EI05931).
Add Fosfomycin (50 μg/mL or higher) and Carbenicillin (100 μg/mL or higher).
Physiological Switch:

The physiological switch is optimally flipped at an OD 600 of 1 to 1.1 for *E. coli* for growth in shake flasks at volumes up to 1 L. For the other species tested, cultures were grown in switch media and subcultured once cultures reached maximal OD 600. In all cases the physiological switch is flipped through the addition of 100-200 ug/mL Carbenicillin (From P212121, product #4800-94-6) and 50-100 ug/mL Fosfomycin (From P212121, product #26016-99-9). The majority of the population is in the switched state within a few hours. To confirm that cells underwent a physiological switch, cells were imaged on a Nikon Ti-E with perfect focus system, Nikon CFI60 Plan Apo 100X NA 1.45 objective, Prior automated filter wheels and stage, LED-CFP/YFP/mCherry and LED-DA/FI/TX filter sets (Semrock), a Lumencor Sola II SE LED illumination system, and a Hamamatsu Flash 4.0 V2 CMOS camera.

Image Analysis of Physiological Switch:

Images were analyzed using ImageJ to measure dimensions. In the switched state, the spherical outline of the outer membrane is treated as a sphere to calculate total volume (V=(4/3)πr3). The cytoplasmic volume is calculated as an ellipsoid that exists within the sphere (V=(4/3)π*(longest radius)*(short radius)2). To calculate the periplasmic volume, the cytoplasmic volume is subtracted from the total volume of the cell.

Protein Expression and Quantification:

*E. coli* BL21(DE3) (NEB product #c2527) containing pET28a (emd Millipore product #69864) and its derivatives carrying GFP or collagen derivatives were grown in a shaking incubator at 37° C. overnight in switch media containing 50 mg/mL kanamycin (p212121 product

#2251180). Next day, subcultures are started with a 1:10 dilution of the overnight culture into fresh switch media containing 50 mg/mL kanamycin. The culture is then physiologically switched and protein production is induced simultaneously at an OD 600 of 1 to 1.1 (Read on a Molecular Devices Spectramax M2 microplate reader). The physiologically switch and protein production are flipped through the addition of 100 ug/mL Carbenicillin, 50 ug/mL Fosfomycin, and 100 ug/mL IPTG (p212121 product #367-93-1). Protein expression is continued in the switched state from between 8 hours to overnight at room temperature (approximately 22° C.) on an orbital shaker. In order to quantify total protein levels, Quick Start™ Bradford Protein Assay was used on mixed portion of culture and standard curves are quantitated on a Molecular Devices Spectramax M2 microplate reader. In order to quantitate the relative intensity of target protein production relative to the rest of the protein population the mixed portion of the cultures were run on Mini-PROTEAN® TGX™ Gels and stained with Bio-Safe™ Coomassie Stain.

Induction of Protein Production:

Standard procedures have been followed to induce protein production in the physiological state. We have been using the strain BL21(DE3) containing the plasmid pET28a driving the IPTG/lactose inducible production of recombinant proteins and targeting them to the periplasmic space using the DsbA signal sequence. Using the GFP protein, targeted to the periplasmic space as described above, we have demonstrated the ability to gain and increase of 5-fold in protein production when compared to un-switched cell populations induced at the same optical density, for the same amount of time (figures). The induction was optimal at an OD600 of 1.1 and induction was continued for 10 hours at which point the protein produced was measured at about 200 mg/mL.

Example 2: Production of Full-Length Collagen

Full length jellyfish collagen was produced using the expression system discussed in Example 1 herein. The wild-type, full length amino acid sequence of *Podocoryna carnea* (jellyfish or Hydrozoan) collagen is provided in SEQ ID NO: 1.

(SEQ ID NO: 1)

```
GPQGVVGADGKDGTPGEKGEQGRTGAAGKQGSPGADGARGPLGSIGQQGA
RGEPGDPGSPGLRGDTGLAGVKGVAGPSGRPGQPGANGLPGVNGRGGLRG
KPGAKGIAGSDGEAGESGAPGQSGPTGPRGQRGPSGEDGNPGLQGLPGSD
GEPGEEGQPGRSGQPGQQGPRGSPGEVGPRGSKGPSGDRGDRGERGVPGQ
TGSAGNVGEDGEQGGKGVDGASGPSGALGARGPPGSRGDTGAVGPPGPTG
RSGLPGNAGQKGPSGEPGSPGKAGSAGEQGPPGKDGSNGEPGSPGKEGER
GLAGPPGPDGRRGETGSPGIAGALGKPGLEGPKGYPGLRGRDGTNGKRGE
QGETGPDGVRGIPGNDGQSGKPGIDGIDGTNGQPGEAGYQGGRGTRGQLG
ETGDVGQNGDRGAPGPDGSKGSAGRPGLR
```

//www.ncbi.nlm.nih.gov/protein/4379341?report=genbank&log$=protalign&blast_rank=1&RID=T1N9ZEUW014

The non-codon optimized polynucleotide sequence encoding the full length jellyfish collagen is disclosed in SEQ ID NO: 2.

(SEQ ID NO: 2)

```
ggaccacaaggtgttgtaggagctgatggcaaagatggaacaccgggaga
gaaaggtgagcaaggacgaaccggagctgcaggaaaacagggaagccctg
gagcagatggagcaagaggccctcttggatcaattggacaacaaggtgct
cgtggagaacctggtgatccaggatctcccggcttaagaggagatactgg
attggctggagtcaaaggagtagcaggaccatctggtcgacctggacaac
ccggtgcaaatggattacctggtgtgaatggcagaggcggtttgagaggc
aaacctggtgctaaaggaattgctggcagtgatggagaagcgggagaatc
tggcgcacctggacagtccggacctaccggtccacgtggtcaacgaggac
caagtggtgaggatggtaatcctggattacagggattgcctggttctgat
ggagagcccggagaggaaggacaacctggaagatctggtcaaccaggaca
gcaaggaccacgtggttcccctggagaggtaggaccaagaggatctaaag
gtccatcaggagatcgtggtgacaggggagagagaggtgttcctggacaa
acaggttcggctggaaatgtaggagaagatggagagcaaggaggcaaagg
tgtcgatggagcgagtggaccaagtggagctcttggtgctcgtggtcccc
caggaagtagaggtgacaccggggcagtgggacctcccggacctactggg
cgatctggtttacctggaaacgcaggacaaaagggaccaagtggtgaacc
aggtagtccaggaaaagcaggatcagctggtgaacagggtcctcctggta
aagacggatcaaatggtgaacctggatctcctggcaaagagggtgaacgt
ggtcttgctggtccaccaggtccagatggcagacgtggtgaaacgggatc
tccaggtatcgctggtgctcttggtaaaccaggtttggaaggacctaaag
gttatccaggattaagaggaagagatggaaccaatggcaaacgaggagaa
caaggagaaactggtcctgatggagtcagaggtattcctggaaatgatgg
acaatctggcaaaccaggtattgatggtattgacggaacaaatggtcaac
caggtgaggctggataccaaggtggtagaggtacacgtggtcagttaggt
gaaactggtgatgtcggacagaatggagatcgaggagctcctggtcctga
tggatctaaaggttctgctggtagaccaggacttcgtgg
```

www.ncbi.nlm.nih.gov/nucleotide/3355656?report=2genbank&log$=nuclalign&blast_rank=1&RID=TSYP7CMV014

Two different codon optimized polynucleotide sequences encoding the wild-type, full-length jellyfish collagen were synthesized. The two polynucleotide sequences were slightly different due to slightly different codon optimization methods. In addition to the non-truncated, full-length jellyfish collagen, the polynucleotides also encoded a secretion tag, a 9 amino acid his tag (SEQ ID NO: 129), a short linker, and a thrombin cleavage site. The DsbA secretion tag is encoded by nucleotides 1-71. The histidine tag comprising 9 histidine residues (SEQ ID NO: 129) is encoded by nucleotides 73-99 and encodes amino acids 25-33. The linker is encoded by nucleotides 100-111. The thrombin cleavage tag is encoded by nucleotides 112-135 and encodes amino acids 38-45. The truncated collagen is encoded by nucleotides 136-1422. The two polynucleotides are disclosed below in SEQ ID NO. 3 and 4

(SEQ ID NO: 3)

```
ATGAAAAAGATTTGGCTGGCGCTGGCTGGTTTAGTTTTAGCGTTTAGCGC
ATCGGCGGCGCAGTATGAAGATCACCATCACCACCACCACCATCACCACT
CTGGCTCGAGCCTGGTGCCGCGCGGCAGCCATATGGGTCCGCAGGGTGTT
GTTGGTGCAGATGGTAAAGACGGTACCCCGGGTGAAAAAGGAGAACAGGG
ACGTACAGGTGCAGCAGGTAAACAGGGCAGCCCGGGTGCCGATGGTGCCC
GTGGCCCGCTGGGTAGCATTGGTCAGCAGGGTGCAAGAGGCGAACCGGGC
GATCCGGGTAGTCCGGGCCTGCGTGGTGATACGGGTCTGGCCGGTGTTAA
AGGCGTTGCAGGTCCTTCAGGTCGTCCAGGTCAACCGGGTGCAAATGGTC
TGCCGGGTGTTAATGGTCGTGGCGGTCTGCGTGGCAAACCGGGAGCAAAA
GGTATTGCAGGTAGCGATGGAGAAGCCGGTGAAAGCGGTGCCCCGGGTCA
GAGTGGTCCGACCGGTCCGCGCGGTCAGCGTGGTCCGTCTGGTGAAGATG
GCAATCCGGGTCTGCAGGGTCTGCCTGGTAGTGATGGCGAACCAGGTGAA
GAAGGTCAGCCGGGTCGTTCAGGCCAGCCGGGCCAGCAGGGCCCGCGTGG
TAGCCCGGGCGAAGTTGGCCCGCGGGGTAGTAAAGGTCCTAGTGGCGATC
GCGGTGATCGTGGTGAACGCGGTGTTCCTGGTCAGACCGGTAGCGCAGGT
AATGTTGGCGAAGATGGTGAACAGGGTGGCAAAGGTGTTGATGGTGCAAG
CGGTCCGAGCGGTGCACTGGGTGCACGTGGTCCTCCGGGCAGCCGTGGTG
ACACCGGTGCAGTTGGTCCGCCTGGCCCGACCGGCCGTAGTGGCTTACCG
GGTAATGCAGGTCAGAAAGGTCCGTCAGGTGAACCTGGCAGCCCTGGTAA
AGCAGGTAGTGCCGGTGAGCAGGGTCCGCCGGGCAAAGATGGTAGTAATG
GTGAGCCGGGTAGCCCTGGCAAAGAAGGTGAACGTGGTCTGGCAGGACCG
CCGGGTCCTGATGGTCGCCGCGGTGAAACGGGTTCACCGGGTATTGCCGG
TGCCCTGGGTAAACCAGGTCTGGAAGGTCCGAAAGGTTATCCTGGTCTGC
GCGGTCGTGATGGTACCAATGGCAAACGTGGCGAACAGGGCGAAACCGGT
CCAGATGGTGTTCGTGGTATTCCGGGTAACGATGGTCAGAGCGGTAAACC
GGGCATTGATGGTATTGATGGCACCAATGGTCAGCCTGGCGAAGCAGGTT
ATCAGGGTGGTCGCGGTACCCGTGGTCAGCTGGGTGAAACAGGTGATGTT
GGTCAGAATGGTGATCGCGGCGCACCGGGTCCGGATGGTAGCAAAGGTAG
CGCCGGTCGTCCGGGTTTACGTtaa
```

(SEQ ID NO: 4)

```
ATGAAAAAGATTTGGCTGGCGCTGGCTGGTTTAGTTTTAGCGTTTAGCGC
ATCGGCGGCGCAGTATGAAGATCACCATCACCACCACCACCATCACCACT
CTGGCTCGAGCCTGGTGCCGCGCGGCAGCCATATGGGTCCGCAGGGTGTT
GTTGGTGCAGATGGTAAAGACGGTACCCCGGGTGAAAAAGGtGAACAGGG
tCGTACcGGTGCAGCAGGTAAACAGGGCAGCCCGGGTGCCGATGGTGCCC
GTGGCCCGCTGGGTAGCATTGGTCAGCAGGGTGCAcgtGGCGAACCGGGC
GATCCGGGTAGcCCGGGCCTGCGTGGTGATACGGGTCTGGCCGGTGTTAA
AGGCGTTGCAGGTCCTTCtGGTCGTCCAGGTCAACCGGGTGCAAATGGTC
```

-continued

```
TGCCGGGTGTTAATGGTCGTGGCGGTCTGCGTGGCAAACCGGGtGCAAAA
GGTATTGCAGGTAGCGATGGcGAAGCCGGTGAAAGCGGTGCCCCGGGTCA
GAGcGGTCCGACCGGTCCGCGCGGTCAGCGTGGTCCGTCTGGTGAAGATG
GCAATCCGGGTCTGCAGGGTCTGCCTGGTagcGATGGCGAACCAGGTGAA
GAAGGTCAGCCGGGTCGTTCtGGCCAGCCGGGCCAGCAGGGCCCGCGTGG
TAGCCCGGGCGAAGTTGGCCCGCGcGGTtcTAAAGGTCCTAGcGGCGATC
GCGGTGATCGTGGTGAACGCGGTGTTCCTGGTCAGACCGGTAGCGCAGGT
AATGTTGGCGAAGATGGTGAACAGGGTGGCAAAGGTGTTGATGGTGCAAG
CGGTCCGAGCGGTGCACTGGGTGCACGTGGTCCTCCGGGCAGCCGTGGTG
ACACCGGTGCAGTTGGTCCGCCTGGCCCGACCGGCCGTAGcGGCctgCCG
GGTAATGCAGGTCAGAAAGGTCCGTCtGGTGAACCTGGCAGCCCTGGTAA
AGCAGGTAGcGCCGGTGAGCAGGGTCCGCCGGGCAAAGATGGTAGcAATG
GTGAGCCGGGTAGCCCTGGCAAAGAAGGTGAACGTGGTCTGGCAGGtCCG
CCGGGTCCTGATGGTCGCCGCGGTGAAACGGGTTCtCCGGGTATTGCCGG
TGCCCTGGGTAAACCAGGTCTGGAAGGTCCGAAAGGTTATCCTGGTCTGC
GCGGTCGTGATGGTACCAATGGCAAACGTGGCGAACAGGGCGAAACCGGT
CCAGATGGTGTTCGTGGTATTCCGGGTAACGATGGTCAGAGCGGTAAACC
GGGCATTGATGGTATTGATGGCACCAATGGTCAGCCTGGCGAAGCAGGTT
ATCAGGGTGGTCGCGGTACCCGTGGTCAGCTGGGTGAAACcGGTGATGTT
GGTCAGAATGGTGATCGCGGCGCACCGGGTCCGGATGGTAGCAAAGGTAG
CGCCGGTCGTCCGGGTctgCGTtaa
```

The amino acid sequence encoded by the polynucleotides of SEQ ID NO: 3 and SEQ ID NO:4 is disclosed in SEQ ID NO:5 below. In SEQ ID NO: 5 the DsbA secretion tag is encoded by nucleotides 1-71 and encodes amino acids 1-24; the histidine tag comprising 9 histidine residues (SEQ ID NO: 129) is encoded by nucleotides 73-99 and encodes amino acids 25-33; the linker is encoded by nucleotides 100-111 and encodes amino acids 34-37; the thrombin cleavage tag is encoded by nucleotides 112-135 and encodes amino acids 38-45; the full-length collagen is encoded by nucleotides 136-1422 and encodes amino acids 46-474.

(SEQ ID NO: 5)

```
MKKIWLALAGLVLAFSASAAQYEDHHHHHHHHHSGSSLVPRGSHMGPQGV
VGADGKDGTPGEKGEQGRTGAAGKQGSPGADGARGPLGSIGQQGARGEPG
DPGSPGLRGDTGLAGVKGVAGPSGRPGQPGANGLPGVNGRGGLRGKPGAK
GIAGSDGEAGESGAPGQSGPTGPRGQRGPSGEDGNPGLQGLPGSDGEPGE
EGQPGRSGQPGQQGPRGSPGEVGPRGSKGPSGDRGDRGERGVPGQTGSAG
NVGEDGEQGGKGVDGASGPSGALGARGPPGSRGDTGAVGPPGPTGRSGLP
GNAGQKGPSGEPGSPGKAGSAGEQGPPGKDGSNGEPGSPGKEGERGLAGP
PGPDGRRGETGSPGIAGALGKPGLEGPKGYPGLRGRDGTNGKRGEQGETG
PDGVRGIPGNDGQSGKPGIDGIDGTNGQPGEAGYQGGRGTRGQLGETGDV
GQNGDRGAPGPDGSKGSAGRPGLR
```

The full length jellyfish collagen without the DsbA secretion tag, the histidine tag, linker and thrombin cleavage site is disclosed in SEQ ID NO: 89.

(SEQ ID NO: 89)

```
GPQGVVGADGKDGTPGEKGEQGRTGAAGKQGSPGADGARGPLGSIGQQGA

RGEPGDPGSPGLRGDTGLAGVKGVAGPSGRPGQPGANGLPGVNGRGGLRG

KPGAKGIAGSDGEAGESGAPGQSGPTGPRGQRGPSGEDGNPGLQGLPGSD

GEPGEEGQPGRSGQPGQQGPRGSPGEVGPRGSKGPSGDRGDRGERGVPGQ

TGSAGNVGEDGEQGGKGVDGASGPSGALGARGPPGSRGDTGAVGPPGPTG

RSGLPGNAGQKGPSGEPGSPGKAGSAGEQGPPGKDGSNGEPGSPGKEGER

GLAGPPGPDGRRGETGSPGIAGALGKPGLEGPKGYPGLRGRDGTNGKRGE

QGETGPDGVRGIPGNDGQSGKPGIDGIDGTNGQPGEAGYQGGRGTRGQLG

ETGDVGQNGDRGAPGPDGSKGSAGRPGLR
```

The polynucleotides of SEQ ID NO: 3 and SEQ ID NO: 4 were synthesized by Gen9 DNA, now Ginkgo Bioworks internal synthesis. Overlaps between the pET28 vector and SEQ ID NO: 3 and SEQ ID NO: 4 were designed to be between 30 and 40 bp long and added using PCR with the enzyme PrimeStar GXL polymerase (www.clontech.com/US/Products/PCR/GC_Rich/PrimeSTAR_GXL_DNA_Polymeras e?sitex=10020:22372:US). The opened pET28a vector and insert DNA (SEQ ID NO: 3 or SEQ ID NO: 4) were then assembled together into the final plasmid using SGI Gibson assembly (us.vwr.com/store/product/17613857/gibson-assembly-hifi-1-step-kit-synthetic-genomics-inc). Sequence of plasmid was then verified through sanger sequencing through Eurofins Genomics (www.eurofinsgenomics.com).

The transformed cells were cultivated in minimal media and frozen in 1.5 aliquots with glycerol at a ratio of 50:50 of cells to glycerol. One vial of this frozen culture was revived in 50 ml of minimal media overnight at 37° C., 200 rpm. Cells were transferred into 300 ml of minimal media and grown for 6-9 hours to reach an OD600 of 5-10.

Minimal media used in this example and throughout this application is prepared as follows. The minimal media (Table 1) was autoclaved in several separate fractions, Salts mix (Ammonium Phosphate dibasic, Potassium phosphate monobasic, Citric acid anhydrous, Magnesium sulfate heptahydrate), the Sucrose at 500 g/L, the Glucose at 55%, the Trace Metals TM5 (table 2), and Sodium Hydroxide 10M. The minimal media was then mixed together at the above concentrations post-autoclaving in the hood.

TABLE 1

Minimal media recipe for shake flask cultures

| chemical | Formula | MW | Conc (g/L) |
|---|---|---|---|
| Ammonium Phosphate dibasic | $(NH_4)_2HPO_4$ | 133 | 4 |
| Potassium phosphate monobasic | $KH_2PO_4$ | 137 | 13.3 |
| Citric acid anhydrous | $H_3C_6H_5O_7$ | 192.14 | 4.5 |
| Magnesium sulfate heptahydrate | $MgSO_4•7H_2O$ | 246 | 0.59 |
| Trace Metals TM5 | | | 2 |
| Glucose | $C_6H_{12}O_6$ | 500 | 40 |
| Sodium Hydroxide 10M | NaOH | 400 | 5.2 |
| Sucrose 500 g/L | $C_{12}H_{22}O_{11}$ | 500 | 66.6 |

TABLE 2

Trace Metals TM5 composition

| chemical | Formula | MW | Conc (g/L) |
|---|---|---|---|
| Ferrous Sulfate Heptahydrate | $FeSO_4•7H_20$ | 278.02 | 27.8 |
| Calcium Chloride | $CaC_{12}•2H_20$ | 147 | 2.94 |
| Manganese Chloride | $MnC_{12}$ | 125.84 | 1.26 |
| Zinc Sulfate | $ZnSO_4•H_20$ | 179.5 | 1.8 |
| Nickel Chloride | $NiC_{12}•6H_20$ | 237.69 | 0.48 |
| Sodium Molybate | $Na_2MoO_4•2H_20$ | 241.95 | 0.48 |
| Sodium Selenite | $Na_2SeO_3$ | 172.94 | 0.35 |
| Boric Acid | $H_3BO_3$ | 61.83 | 0.12 |

The harvested cells were disrupted in a homogenizer at 14,000 psi pressure in 2 passes. Resulting slurry contained the collagen protein along with other proteins.

The collagen was purified by acid treatment of homogenized cell broth. The pH of the homogenized slurry was decreased to 3 using 6M Hydrochloric acid. Acidified cell slurry was incubated overnight at 4° C. with mixing, followed by centrifugation. Supernatant of the acidified slurry was tested on a polyacrylamide gel and found to contain collagen in relatively high abundance compared to starting pellet. The collagen slurry thus obtained was high in salts. To obtain volume and salt reduction, concentration and diafiltration steps were performed using an EMD Millipore Tangential Flow Filtration system with ultrafiltration cassettes of 0.1 $m^2$ each. Total area of filtration was 0.2 $m^2$ using 2 cassettes in parallel. A volume reduction of 5× and a salt reduction of 19× was achieved in the TFF stage. Final collagen slurry was run on an SDS-PAGE gel to confirm presence of the collagen. This slurry was dried using a multi-tray lyophilizer over 3 days to obtain a white, fluffy collagen powder.

The purified collagen was analyzed on an SDS-PAGE gel and a thick and clear band was observed at the expected size of 42 kilodaltons. The purified collagen was also analyzed by mass spectrometry and it was confirmed that the 42 kilodalton protein was jellyfish collagen.

The fermentations were performed at various temperature ranging from 25° to 28° C. For some fermentations, the temperature of the fermentation was maintained at a constant temperature and immediately upon completion of fermentation (OD600 of 5-10) the collagen was purified. For other fermentations, the temperature of the fermentations was maintained for a desired period of time and when cell densities of OD600 of 5-10 were reached, the temperature was reduced to induce protein production. Typically, the temperature was reduced from 28° C. to 25° C. After the fermentation at 25° C. was continued for 40-60 hours, the collagen was isolated.

Additional Full Length Jellyfish Collagens

A full length jellyfish collagen without a His tag, linker, and thrombin cleavage site is disclosed below. Two codon-optimized nucleotide sequence encoding this collagen are provided in SEQ ID NO: 6 and SEQ ID NO: 7. The differences in the nucleotide sequences are due to different codon-optimization strategies but encode the same protein. The amino acid sequence is disclosed in SEQ ID NO: 8. The DsbA secretion tag is encoded by nucleotides 1-72 and encodes amino acids 1-24. The collagen sequence is encoded by nucleotides 73-1359 and encodes amino acids 25-453.

-continued (SEQ ID NO: 6)
ATGAAAAAGATTTGGCTGGCGCTGGCTGGTTTAGTTTTAGCGTTTAGCGC
ATCGGCGGCGCAGTATGAAGATGGTCCGCAGGGTGTTGTTGGTGCAGATG
GTAAAGACGGTACCCCGGGTGAAAAAGGAGAACAGGGACGTACAGGTGCA
GCAGGTAAACAGGGCAGCCCGGGTGCCGATGGTGCCCGTGGCCCGCTGGG
TAGCATTGGTCAGCAGGGTGCAAGAGGCGAACCGGGCGATCCGGGTAGTC
CGGGCCTGCGTGGTGATACGGGTCTGGCCGGTGTTAAAGGCGTTGCAGGT
CCTTCAGGTCGTCCAGGTCAACCGGGTGCAAATGGTCTGCCGGGTGTTAA
TGGTCGTGGCGGTCTGCGTGGCAAACCGGGAGCAAAAGGTATTGCAGGTA
GCGATGGAGAAGCCGGTGAAAGCGGTGCCCCGGGTCAGAGTGGTCCGACC
GGTCCGCGCGGTCAGCGTGGTCCGTCTGGTGAAGATGGCAATCCGGGTCT
GCAGGGTCTGCCTGGTAGTGATGGCGAACCAGGTGAAGAAGGTCAGCCGG
GTCGTTCAGGCCAGCCGGGCCAGCAGGGCCCGCGTGGTAGCCCGGGCGAA
GTTGGCCCGCGGGGTAGTAAAGGTCCTAGTGGCGATCGCGGTGATCGTGG
TGAACGCGGTGTTCCTGGTCAGACCGGTAGCGCAGGTAATGTTGGCGAAG
ATGGTGAACAGGGTGGCAAAGGTGTTGATGGTGCAAGCGGTCCGAGCGGT
GCACTGGGTGCACGTGGTCCTCCGGGCAGCCGTGGTGACACCGGTGCAGT
TGGTCCGCCTGGCCCGACCGGCCGTAGTGGCTTACCGGGTAATGCAGGTC
AGAAAGGTCCGTCAGGTGAACCTGGCAGCCCTGGTAAAGCAGGTAGTGCC
GGTGAGCAGGGTCCGCCGGGCAAAGATGGTAGTAATGGTGAGCCGGGTAG
CCCTGGCAAAGAAGGTGAACGTGGTCTGGCAGGACCGCCGGGTCCTGATG
GTCGCCGCGGTGAAACGGGTTCACCGGGTATTGCCGGTGCCCTGGGTAAA
CCAGGTCTGGAAGGTCCGAAAGGTTATCCTGGTCTGCGCGGTCGTGATGG
TACCAATGGCAAACGTGGCGAACAGGGCGAAACCGGTCCAGATGGTGTTC
GTGGTATTCCGGGTAACGATGGTCAGAGCGGTAAACCGGGCATTGATGGT
ATTGATGGCACCAATGGTCAGCCTGGCGAAGCAGGTTATCAGGGTGGTCG
CGGTACCCGTGGTCAGCTGGGTGAAACAGGTGATGTTGGTCAGAATGGTG
ATCGCGGCGCACCGGGTCCGGATGGTAGCAAAGGTAGCGCCGGTCGTCCG
GGTTTACGTtaa (SEQ ID NO: 7)
ATGAAAAAGATTTGGCTGGCGCTGGCTGGTTTAGTTTTAGCGTTTAGCGC
ATCGGCGGCGCAGTATGAAGATGGTCCGCAGGGTGTTGTTGGTGCAGATG
GTAAAGACGGTACCCCGGGTGAAAAAGGtGAACAGGGtCGTACcGGTGCA
GCAGGTAAACAGGGCAGCCCGGGTGCCGATGGTGCCCGTGGCCCGCTGGG
TAGCATTGGTCAGCAGGGTGCAcgtGGCGAACCGGGCGATCCGGGTAGcC
CGGGCCTGCGTGGTGATACGGGTCTGGCCGGTGTTAAAGGCGTTGCAGGT
CCTTCtGGTCGTCCAGGTCAACCGGGTGCAAATGGTCTGCCGGGTGTTAA
TGGTCGTGGCGGTCTGCGTGGCAAACCGGGtGCAAAAGGTATTGCAGGTA
GCGATGGcGAAGCCGGTGAAAGCGGTGCCCCGGGTCAGAGcGGTCCGACC
GGTCCGCGCGGTCAGCGTGGTCCGTCTGGTGAAGATGGCAATCCGGGTCT
GCAGGGTCTGCCTGGTagcGATGGCGAACCAGGTGAAGAAGGTCAGCCGG
GTCGTTCtGGCCAGCCGGGCCAGCAGGGCCCGCGTGGTAGCCCGGGCGAA
GTTGGCCCGCGcGGTtcTAAAGGTCCTAGcGGCGATCGCGGTGATCGTGG
TGAACGCGGTGTTCCTGGTCAGACCGGTAGCGCAGGTAATGTTGGCGAAG
ATGGTGAACAGGGTGGCAAAGGTGTTGATGGTGCAAGCGGTCCGAGCGGT
GCACTGGGTGCACGTGGTCCTCCGGGCAGCCGTGGTGACACCGGTGCAGT
TGGTCCGCCTGGCCCGACCGGCCGTAGcGGCctgCCGGGTAATGCAGGTC
AGAAAGGTCCGTCtGGTGAACCTGGCAGCCCTGGTAAAGCAGGTAGcGCC
GGTGAGCAGGGTCCGCCGGGCAAAGATGGTAGcAATGGTGAGCCGGGTAG
CCCTGGCAAAGAAGGTGAACGTGGTCTGGCAGGtCCGCCGGGTCCTGATG
GTCGCCGCGGTGAAACGGGTTCtCCGGGTATTGCCGGTGCCCTGGGTAAA
CCAGGTCTGGAAGGTCCGAAAGGTTATCCTGGTCTGCGCGGTCGTGATGG
TACCAATGGCAAACGTGGCGAACAGGGCGAAACCGGTCCAGATGGTGTTC
GTGGTATTCCGGGTAACGATGGTCAGAGCGGTAAACCGGGCATTGATGGT
ATTGATGGCACCAATGGTCAGCCTGGCGAAGCAGGTTATCAGGGTGGTCG
CGGTACCCGTGGTCAGCTGGGTGAAACcGGTGATGTTGGTCAGAATGGTG
ATCGCGGCGCACCGGGTCCGGATGGTAGCAAAGGTAGCGCCGGTCGTCCG
GGTctgCGTtaa (SEQ ID NO: 8)
MKKIWLALAGLVLAFSASAAQYEDGPQGVVGADGKDGTPGEKGEQGRTGA
AGKQGSPGADGARGPLGSIGQQGARGEPGDPGSPGLRGDTGLAGVKGVAG
PSGRPGQPGANGLPGVNGRGGLRGKPGAKGIAGSDGEAGESGAPGQSGPT
GPRGQRGPSGEDGNPGLQGLPGSDGEPGEEGQPGRSGQPGQQGPRGSPGE
VGPRGSKGPSGDRGDRGERGVPGQTGSAGNVGEDGEQGGKGVDGASGPSG
ALGARGPPGSRGDTGAVGPPGPTGRSGLPGNAGQKGPSGEPGSPGKAGSA
GEQGPPGKDGSNGEPGSPGKEGERGLAGPPGPDGRRGETGSPGIAGALGK
PGLEGPKGYPGLRGRDGTNGKRGEQGETGPDGVRGIPGNDGQSGKPGIDG
IDGTNGQPGEAGYQGGRGTRGQLGETGDVGQNGDRGAPGPDGSKGSAGRP
GLR

Example 3: Production of Truncated Collagen

A codon optimized DNA sequence, optimized for expression in *E. coli*, encoding a jellyfish collagen with a truncation of 240 internal amino acids was synthesized and expressed. The DNA sequence is shown below in SEQ ID NO: 9. In SEQ ID NO: 9, The DsbA secretion tag is encoded by nucleotides 1-72 and encodes amino acids 1-24 of SEQ ID NO: 10. The histidine tag comprising 9 histidine (SEQ ID NO: 129) residues is encoded by nucleotides 73-99 and encodes amino acids 25-33 of SEQ ID NO: 10. The linker is encoded by nucleotides 100-111 and encodes amino acids 34-37 of SEQ ID NO: 10. The thrombin cleavage site is encoded by nucleotides 112-135 and encodes amino acids 38-45 of SEQ ID NO: 10. The truncated collagen is encoded by nucleotides 136-822 and encodes amino acids 46-274 of SEQ ID NO:

(SEQ ID NO: 9)
ATGAAAAAGATTTGGCTGGCGCTGGCTGGTTTAGTTTTAGCGTTTAGCGC
ATCGGCGGCGCAGTATGAAGATCACCATCACCACCACCACCATCACCACT
CTGGCTCGAGCCTGGTGCCGCGCGGCAGCCATATGGGTCCGCAGGGTGTT
GTTGGTGCAGATGGTAAAGACGGTACCCCGGGTGAAAAAGGAGAACAGGG
ACGTACAGGTGCAGCAGGTAAACAGGGCAGCCCGGGTGCCGATGGTGCCC
GTGGCCCGCTGGGTAGCATTGGTCAGCAGGGTGCAAGAGGCGAACCGGGC
GATCCGGGTAGTCCGGGCCTGCGTGGTGATACGGGTCTGGCCGGTGTTAA
AGGCGTTGCAGGTCCTTCAGGTCGTCCAGGTCAACCGGGTGCAAATGGTC
TGCCGGGTGTTAATGGTCGTGGCGGTCTGGAACGTGGTCTGGCAGGACCG
CCGGGTCCTGATGGTCGCCGCGGTGAAACGGGTTCACCGGGTATTGCCGG
TGCCCTGGGTAAACCAGGTCTGGAAGGTCCGAAAGGTTATCCTGGTCTGC
GCGGTCGTGATGGTACCAATGGCAAACGTGGCGAACAGGGCGAAACCGGT
CCAGATGGTGTTCGTGGTATTCCGGGTAACGATGGTCAGAGCGGTAAACC
GGGCATTGATGGTATTGATGGCACCAATGGTCAGCCTGGCGAAGCAGGTT
ATCAGGGTGGTCGCGGTACCCGTGGTCAGCTGGGTGAAACAGGTGATGTT
GGTCAGAATGGTGATCGCGGCGCACCGGGTCCGGATGGTAGCAAAGGTAG
CGCCGGTCGTCCGGGTTTACGTtaa The truncated collagen is approximately 54% of the full length collagen and is disclosed below in SEQ ID NO:10.

(SEQ ID NO: 10)
MKKIWLALAGLVLAFSASAAQYEDHHHHHHHHHSGSSLVPRGSHMGPQGV
VGADGKDGTPGEKGEQGRTGAAGKQGSPGADGARGPLGSIGQQGARGEPG
DPGSPGLRGDTGLAGVKGVAGPSGRPGQPGANGLPGVNGRGGLERGLAGP
PGPDGRRGETGSPGIAGALGKPGLEGPKGYPGLRGRDGTNGKRGEQGETG
PDGVRGIPGNDGQSGKPGIDGIDGTNGQPGEAGYQGGRGTRGQLGETGDV
GQNGDRGAPGPDGSKGSAGRPGLR

The polynucleotide encoding the truncated jellyfish collagen without the DsbA secretion tag, the histidine tag, linker and thrombin cleavage site is disclosed in SEQ ID NO: 85

(SEQ ID NO: 85)
GTCCGCAGGGTGTTGTTGGTGCAGATGGTAAAGACGGTACCCCGGGTGAA
AAAGGAGAACAGGGACGTACAGGTGCAGCAGGTAAACAGGGCAGCCCGGG
TGCCGATGGTGCCCGTGGCCCGCTGGGTAGCATTGGTCAGCAGGGTGCAA
GAGGCGAACCGGGCGATCCGGGTAGTCCGGGCCTGCGTGGTGATACGGGT
CTGGCCGGTGTTAAAGGCGTTGCAGGTCCTTCAGGTCGTCCAGGTCAACC
GGGTGCAAATGGTCTGCCGGGTGTTAATGGTCGTGGCGGTCTGGAACGTG
GTCTGGCAGGACCGCCGGGTCCTGATGGTCGCCGCGGTGAAACGGGTTCA
CCGGGTATTGCCGGTGCCCTGGGTAAACCAGGTCTGGAAGGTCCGAAAGG
TTATCCTGGTCTGCGCGGTCGTGATGGTACCAATGGCAAACGTGGCGAAC
AGGGCGAAACCGGTCCAGATGGTGTTCGTGGTATTCCGGGTAACGATGGT

-continued
CAGAGCGGTAAACCGGGCATTGATGGTATTGATGGCACCAATGGTCAGCC
TGGCGAAGCAGGTTATCAGGGTGGTCGCGGTACCCGTGGTCAGCTGGGTG
AAACAGGTGATGTTGGTCAGAATGGTGATCGCGGCGCACCGGGTCCGGAT
GGTAGCAAAGGTAGCGCCGGTCGTCCGGGTTTACGTtaa The truncated jellyfish collagen without the DsbA secretion tag, the histidine tag, linker and thrombin cleavage site is disclosed in SEQ ID NO: 86

(SEQ ID NO: 86)
GPQGVVGADGKDGTPGEKGEQGRTGAAGKQGSPGADGARGPLGSIGQQGA
RGEPGDPGSPGLRGDTGLAGVKGVAGPSGRPGQPGANGLPGVNGRGGLER
GLAGPPGPDGRRGETGSPGIAGALGKPGLEGPKGYPGLRGRDGTNGKRGE
QGETGPDGVRGIPGNDGQSGKPGIDGIDGTNGQPGEAGYQGGRGTRGQLG
ETGDVGQNGDRGAPGPDGSKGSAGRPGLR

The polynucleotides of SEQ ID NO: 9 was codon optimized and synthesized by Gen9 DNA, now Ginkgo Bioworks internal synthesis. Overlaps between the pET28 vector and SEQ ID NO: 9 were designed to be between 30 and 40 bp long and added using PCR with the enzyme PrimeStar GXL polymerase (www.clontech.com/US/Products/PCR/GC_Rich/PrimeSTAR_GXL_DNA_Polymeras e?sitex=10020:22372:US). The opened pET28a vector and insert DNA (SEQ ID NO: 9) was then assembled together into the final plasmid using SGI Gibson assembly (us.vwr.com/store/product/17613857/gibson-assembly-hifi-1-step-kit-synthetic-genomics-inc). Sequence of plasmid was then verified through sanger sequencing through Eurofins Genomics (www.eurofinsgenomics.com).

The transformed cells were cultivated in minimal media and frozen in 1.5 aliquots with glycerol at a ratio of 50:50 of cells to glycerol. One vial of this frozen culture was revived in 50 ml of minimal media overnight at 37° C., 200 rpm. Cells were transferred into 300 ml of minimal media and grown for 6-9 hours to reach an OD600 of 5-10.

A bioreactor was prepared with 2.7 L of minimal media+glucose and 300 ml of OD600 of 5-10 culture was added to bring the starting volume to 3 L. Cells were grown at 28° C., pH7 with Dissolved Oxygen maintained at 20% saturation using a cascade containing agitation, air and oxygen. pH was controlled using 28% w/w Ammonium hydroxide solution. Fermentation was run in a fed-batch mode using a DO-stat based feeding algorithm once the initial bolus of 40 g/L was depleted around 13 hours. After 24-26 hours of initial growth, the OD600 reached above 100. At this point, 300 mL of 500 g/L sucrose was added and temperature was reduced to 25 C. High density culture was induced for protein production using 1 mM IPTG. Fermentation was continued for another 20-24 hours and cells were harvested using a bench top centrifuge at 9000 rcf, 15C for 60 minutes. Cell pellet recovered from centrifugation was resuspended in a buffer containing 0.5M NaCl and 0.1M KH2PO4 at pH8 in a weight by weight ratio of 2× buffer to 1× cells.

The harvested cells were disrupted in a homogenizer at 14,000 psi pressure in 2 passes. Resulting slurry contained the collagen protein along with other proteins.

The fermentations were performed at various temperature ranging from 25° to 28° C. For some fermentations, the temperature of the fermentation was maintained at a constant temperature and immediately upon completion of fermentation (OD600 of 5-10) the collagen was purified. For other fermentations, the temperature of the fermentations was maintained for a desired period of time and when cell densities of OD600 of 5-10 were reached, the temperature was reduced to induce protein production. Typically, the temperature was reduced from 28° C. to 25° C. After the fermentation at 25° C. was continued for 40-60 hours, the collagen was isolated.

The collagen was purified by acid treatment of homogenized cell broth. Additionally, acid treatment was also performed on non-homogenized whole cells recovered from the bioreactor after centrifugation and resuspension in the buffer described above. The pH of either the homogenized slurry of the resuspended whole cells was decreased to 3 using 6M Hydrochloric acid. Acidified cell slurry was incubated overnight at 4° C. with mixing, followed by centrifugation. Supernatant of the acidified slurry was tested on a polyacrylamide gel and found to contain collagen in relatively high abundance compared to starting pellet. The collagen slurry thus obtained was high in salts. To obtain volume and salt reduction, concentration and diafiltration steps were performed using an EMD Millipore Tangential Flow Filtration system with ultrafiltration cassettes of 0.1 $m^2$ each. Total area of filtration was 0.2 $m^2$ using 2 cassettes in parallel. A volume reduction of 5× and a salt reduction of 19× was achieved in the TFF stage. Final collagen slurry was run on an SDS-PAGE gel to confirm presence of the collagen. This slurry was dried using a multi-tray lyophilizer over 3 days to obtain a white, fluffy collagen powder.

The purified truncated collagen obtained from homogenized cell broth or non-homogenized cells were analyzed on an SDS-PAGE gel and a thick and clear band was observed at the expected size of 27 kilodaltons. The purified collagen was also analyzed by mass spectrometry and it was confirmed that the 27 kilodalton protein was jellyfish collagen.

An alternative purification method of the full length and truncated collagens is provided below.

The fermentation broth was mixed with 0.3-0.5% w/v of Poly Ethyl Imine (PEI). After 15 minutes of incubation with PEI, the fermentation broth was centrifuged at 9000 rcf for 15 minutes to recover the supernatant, which contained the collagen protein. The pellet containing the cells was discarded and the PEI-treated collagen containing supernatant was mixed with Sodium Bentonite (0.2% final w/v) (Wyopure®, Wyoming Bentonite) and centrifuged. The bentonite containing pellet was discarded and the supernatant was recovered.

The Bentonite treated supernatant was concentrated between 3-6 fold on a tangential flow filtration system (TFF) (EMD Millipore) using a 5 kDa cassette. The collagen was retained with almost no losses in the permeate stream. To remove salts, the retentate from the concentration step was diafiltered using the same TFF set-up. Final conductivity of the protein solution was <10 milliSiemens. The typical conductivity was between 400 microsiemens and 1.5 millisiemens. Highly concentrated collagen solutions had higher conductivities approaching 4 milliSiemens. A skilled artisan will understand that conductivities higher than 10 milliSiemens may be observed depending on the concentration of the collagen. Next, the desalted and concentrated protein was subjected to treatment with activated carbon using the W-L 9000 10×40 granulated resin (Carbon Activated Corporation). 5% w/v of the carbon resin was mixed with collagen containing protein feed and mixed at 45-50° C. with mild agitation. The carbon-treated slurry was filtered using a Buchner funnel lined with an Ertel Filter Press Pad M-953 (Ertel Alsop) in presence or absence of a filtration aid such as Diatomaceous Earth (Sigma Aldrich). Post-filtration, the collagen solution was filtered through a 0.2 micron filter followed by one to several hours of treatment with Sodium Bentonite (0.2% w/v final) (Wyopure®, Wyoming Bentonite) and centrifuged at 9000 rcf, 15-30 minutes to obtain a highly pure, clear and particulate free collagen solution. When removal of endotoxin proteins was desired, the protein was passed through a chromatographic filter like Sartobind-Q (Sartorius-Stedim) to specifically remove endotoxin proteins.

The purified collagen was analyzed on an SDS-PAGE gel and a thick and clear band was observed at 30 kilodaltons. The upshift in size is due to the structure of the collagen molecule and the high glycine/proline amino acid content. The purified collagen was also analyzed by mass spectrometry and it was confirmed that the 30 kilodalton protein was the truncated collagen.

The truncated collagens were further analyzed by HPLC using an Agilent 1100 series HPLC. The column was the 50 mm Agilent PLRP-S reverse phase column with an inner diameter of 4.6 mm, µM particle size and 1000 Angstrom pore size.

The sample was prepared by diluting 1:1 in a 0.04% sodium azide solution in HPLC-grade water. After dilution, the resulting mixture was filtered through a 0.45 um filter to remove any large particles that can clog the HPLC column. For analysis, the samples are diluted appropriately with a 20 mM ammonium acetate buffer in HPLC-grade water at a pH of about 4.5. After mixing the sample, it was transferred to a 300 µL microvial that was then placed in the autosampler. Using ChemStation, the software that operates the HPLC, the analysis parameters such as sample flowrate, column temperature, mobile phase flowrate, mobile phase composition, etc. can be altered. In one exemplary, but non-limiting analysis the parameters were: sample flow rate of 1 mL/min, column temperature of 80° C., column pressure of 60-70 bar, mobile phase composition of 97.9% water/1.9% acetonitrile with 0.2% trifluoroacetic acid; UV wavelength for analysis of 214.4 nm, injection volume of 10 µL, and sample run time of 10 minutes.

Under these conditions, the truncated jellyfish collation of SEQ ID NO: 91 has an elution time of about 5.4 minutes. ChemStation quantifies the peak area of the elution peak and calculates the protein concentration using a calibration curve that directly relates peak area to protein concentration. The calibration curve is generated using a known collagen solution that is serially diluted to contain collagen concentration ranges of 0.06 mg/mL to 1.00 mg/mL.

Truncated Collagen without His Tag-Linker-Thrombin Cleavage Site

A truncated jellyfish collagen without a His tag, linker, and thrombin cleavage site is disclosed below. The codon-optimized nucleotide sequence encoding this collagen is provided in SEQ ID NO: 11. The amino acid sequence is disclosed in SEQ ID NO: 12. The DsbA secretion tag is encoded by nucleotides 1-72 and encodes amino acids 1-24. The truncated collagen sequence is encoded by nucleotides 73-639 and encodes amino acids 25-213.

(SEQ ID NO: 11)
ATGAAAAAGATTTGGCTGGCGCTGGCTGGTTTAGTTTTAGCGTTTAGCGC

ATCGGCGGCGCAGTATGAAGATGGTCCGCAGGGTGTTGTTGGTGCAGATG

GTAAAGACGGTACCCCGGGTAATGCAGGTCAGAAAGGTCCGTCAGGTGAA

-continued

CCTGGCAGCCCTGGTAAAGCAGGTAGTGCCGGTGAGCAGGGTCCGCCGGG

CAAAGATGGTAGTAATGGTGAGCCGGGTAGCCCTGGCAAAGAAGGTGAAC

GTGGTCTGGCAGGACCGCCGGGTCCTGATGGTCGCCGCGGTGAAACGGGT

TCACCGGGTATTGCCGGTGCCCTGGGTAAACCAGGTCTGGAAGGTCCGAA

AGGTTATCCTGGTCTGCGCGGTCGTGATGGTACCAATGGCAAACGTGGCG

AACAGGGCGAAACCGGTCCAGATGGTGTTCGTGGTATTCCGGGTAACGAT

GGTCAGAGCGGTAAACCGGGCATTGATGGTATTGATGGCACCAATGGTCA

GCCTGGCGAAGCAGGTTATCAGGGTGGTCGCGGTACCCGTGGTCAGCTGG

GTGAAACAGGTGATGTTGGTCAGAATGGTGATCGCGGCGCACCGGGTCCG

GATGGTAGCAAAGGTAGCGCCGGTCGTCCGGGTTTACGTtaa (SEQ ID NO: 12)

MKKIWLALAGLVLAFSASAAQYEDGPQGVVGADGKDGTPGNAGQKGPSGE

PGSPGKAGSAGEQGPPGKDGSNGEPGSPGKEGERGLAGPPGPDGRRGETG

SPGIAGALGKPGLEGPKGYPGLRGRDGTNGKRGEQGETGPDGVRGIPGND

GQSGKPGIDGIDGTNGQPGEAGYQGGRGTRGQLGETGDVGQNGDRGAPGP

DGSKGSAGRPGLR

A polynucleotide encoding a truncated jellyfish collagen without a His tag, linker and thrombin cleavage site disclosed in SEQ ID NO: 90

(SEQ ID NO: 90)

GGTCCGCAGGGTGTTGTTGGTGCAGATGGTAAAGACGGTACCCCGGGTAA

TGCAGGTCAGAAAGGTCCGTCAGGTGAACCTGGCAGCCCTGGTAAAGCAG

GTAGTGCCGGTGAGCAGGGTCCGCCGGGCAAAGATGGTAGTAATGGTGAG

CCGGGTAGCCCTGGCAAAGAAGGTGAACGTGGTCTGGCAGGACCGCCGGG

TCCTGATGGTCGCCGCGGTGAAACGGGTTCACCGGGTATTGCCGGTGCCC

TGGGTAAACCAGGTCTGGAAGGTCCGAAAGGTTATCCTGGTCTGCGCGGT

CGTGATGGTACCAATGGCAAACGTGGCGAACAGGGCGAAACCGGTCCAGA

TGGTGTTCGTGGTATTCCGGGTAACGATGGTCAGAGCGGTAAACCGGGCA

TTGATGGTATTGATGGCACCAATGGTCAGCCTGGCGAAGCAGGTTATCAG

GGTGGTCGCGGTACCCGTGGTCAGCTGGGTGAAACAGGTGATGTTGGTCA

GAATGGTGATCGCGGCGCACCGGGTCCGGATGGTAGCAAAGGTAGCGCCG

GTCGTCCGGGTTTACGTtaa

A truncated jellyfish collagen without a His tag, linker and thrombin cleavage site disclosed in SEQ ID NO: 91

(SEQ ID NO: 91)

GPQGVVGADGKDGTPGNAGQKGPSGEPGSPGKAGSAGEQGPPGKDGSNGE

PGSPGKEGERGLAGPPGPDGRRGETGSPGIAGALGKPGLEGPKGYPGLRG

RDGTNGKRGEQGETGPDGVRGIPGNDGQSGKPGIDGIDGTNGQPGEAGYQ

GGRGTRGQLGETGDVGQNGDRGAPGPDGSKGSAGRPGLR

Truncated Collagen with GEK Repeats

A jellyfish collagen with GEK repeats is disclosed below. The codon-optimized nucleotide sequence encoding this collagen is provided in SEQ ID NO: 13. The amino acid sequence is disclosed in SEQ ID NO: 14. The DsbA secretion tag is encoded by nucleotides 1-72 and encodes amino acids 1-24. The GEK repeat is encoded by nucleotides 73-126 and encodes the GEK repeats of amino acids 25-42. The truncated collagen sequence is encoded by nucleotides 127-693 and encodes amino acids 43-231.

(SEQ ID NO: 13)

ATGAAAAAGATTTGGCTGGCGCTGGCTGGTTTAGTTTTAGCGTTTAGCGC

ATCGGCGGCGCAGTATGAAGATGGTGAAAAAGGTGAaAAGGGCGAGAAAG

GTGAGAAAGGCGAAAAGGGTGAAAAAGGTCCGCAGGGTGTTGTTGGTGCA

GATGGTAAAGACGGTACCCCGGGTAATGCAGGTCAGAAAGGTCCGTCAGG

TGAACCTGGCAGCCCTGGTAAAGCAGGTAGTGCCGGTGAGCAGGGTCCGC

CGGGCAAAGATGGTAGTAATGGTGAGCCGGGTAGCCCTGGCAAAGAAGGT

GAACGTGGTCTGGCAGGACCGCCGGGTCCTGATGGTCGCCGCGGTGAAAC

GGGTTCACCGGGTATTGCCGGTGCCCTGGGTAAACCAGGTCTGGAAGGTC

CGAAAGGTTATCCTGGTCTGCGCGGTCGTGATGGTACCAATGGCAAACGT

GGCGAACAGGGCGAAACCGGTCCAGATGGTGTTCGTGGTATTCCGGGTAA

CGATGGTCAGAGCGGTAAACCGGGCATTGATGGTATTGATGGCACCAATG

GTCAGCCTGGCGAAGCAGGTTATCAGGGTGGTCGCGGTACCCGTGGTCAG

CTGGGTGAAACAGGTGATGTTGGTCAGAATGGTGATCGCGGCGCACCGGG

TCCGGATGGTAGCAAAGGTAGCGCCGGTCGTCCGGGTTTACGTtaa (SEQ ID NO: 14)

MKKIWLALAGLVLAFSASAAQYEDGEKGEKGEKGEKGEKGEKGPQGVVGA

DGKDGTPGNAGQKGPSGEPGSPGKAGSAGEQGPPGKDGSNGEPGSPGKEG

ERGLAGPPGPDGRRGETGSPGIAGALGKPGLEGPKGYPGLRGRDGTNGKR

GEQGETGPDGVRGIPGNDGQSGKPGIDGIDGTNGQPGEAGYQGGRGTRGQ

LGETGDVGQNGDRGAPGPDGSKGSAGRPGLR

The polynucleotides of SEQ ID NO: 13 was codon optimized and synthesized by Gen9 DNA, now Ginkgo Bioworks internal synthesis. Overlaps between the pET28 vector and SEQ ID NO: 13 was designed to be between 30 and 40 bp long and added using PCR with the enzyme PrimeStar GXL polymerase (www.clontech.com/US/Products/PCR/GC_Rich/PrimeSTAR_GXL_DNA_Polymerase?sitex=10020:22372:US). The opened pET28a vector and insert DNA (SEQ ID NO: 13) was then assembled together into the final plasmid using SGI Gibson assembly (us.vwr.com/store/product/17613857/gibson-assembly-hifi-1-step-kit-synthetic-genomics-inc). Sequence of plasmid was then verified through Sanger sequencing through Eurofins Genomics (www.eurofinsgenomics.com).

The transformed cells were cultivated in minimal media and frozen in 1.5 aliquots with glycerol at a ratio of 50:50 of cells to glycerol. One vial of this frozen culture was revived in 50 ml of minimal media overnight at 37° C., 200 rpm. Cells were transferred into 300 ml of minimal media and grown for 6-9 hours to reach an OD600 of 5-10.

A bioreactor was prepared with 2.7 L of minimal media+glucose and 300 ml of OD600 of 5-10 culture was added to bring the starting volume to 3 L. Cells were grown at 28° C., pH7 with Dissolved Oxygen maintained at 20% saturation using a cascade containing agitation, air and oxygen. pH was controlled using 28% w/w Ammonium hydroxide solution. Fermentation was run in a fed-batch mode using a DO-stat based feeding algorithm once the initial bolus of 40 g/L was depleted around 13 hours. After 24-26 hours of initial growth, the OD600 reached above 100. At this point, 300 mL of 500 g/L sucrose was added and temperature was reduced to 25 C. High density culture was induced for protein production using 1 mM IPTG. Fermentation was continued for another 20-24 hours and cells were harvested using a bench top centrifuge at 9000 rcf, 15C for 60 minutes. Cell pellet recovered from centrifugation was resuspended in a buffer containing 0.5M NaCl and 0.1M KH2PO4 at pH8 in a weight by weight ratio of 2× buffer to 1× cells.

The harvested cells were disrupted in a homogenizer at 14,000 psi pressure in 2 passes. Resulting slurry contained the collagen protein along with other proteins.

The collagen was purified by acid treatment whole cells recovered from bioreactor after centrifugation and resuspension in a buffer as described above. The pH of either the homogenized slurry or the resuspended suspension was decreased to 3 using 6M Hydrochloric acid. Acidified cell slurry was incubated overnight at 4° C. with mixing, followed by centrifugation. Supernatant of the acidified slurry was tested on a polyacrylamide gel and found to contain collagen in relatively high abundance compared to starting pellet. The collagen slurry thus obtained was high in salts. To obtain volume and salt reduction, concentration and diafiltration steps were performed using an EMD Millipore Tangential Flow Filtration system with ultrafiltration cassettes of 0.1 $m^2$ each. Total area of filtration was 0.2 $m^2$ using 2 cassettes in parallel. A volume reduction of 5× and a salt reduction of 19× was achieved in the TFF stage. Final collagen slurry was run on an SDS-PAGE gel to confirm presence of the collagen. This slurry was dried using a multi-tray lyophilizer over 3 days to obtain a white, fluffy collagen powder.

The purified collagen was analyzed on an SDS-PAGE gel and was observed to run at an apparent molecular weight of 35 kilodaltons. The 35 kilodalton band does not correspond to the expected size of 22 kilodaltons. The upshift between the expected size and the apparent size is thought to be due to the GEK repeats interacting with the gel matrix. The 35 kDa band was confirmed by mass spectrometry to be the correct collagen with the GEK repeats.

Truncated Collagen with GDK Repeats

A jellyfish collagen with GDK repeats is disclosed below. The codon-optimized nucleotide sequence encoding this collagen is provided in SEQ ID NO: 15. The amino acid sequence is disclosed in SEQ ID NO: 16. The DsbA secretion tag is encoded by nucleotides 1-72 and encodes amino acids 1-24. The GDK repeat is encoded by nucleotides 73-126 and encodes the GDK repeats of amino acids 25-42. The truncated collagen sequence is encoded by nucleotides 127-693 and encodes amino acids 43-231.

(SEQ ID NO: 15)
ATGAAAAAGATTTGGCTGGCGCTGGCTGGTTTAGTTTTAGCGTTTAGC

GCATCGGCGGCGCAGTATGAAGATGGTGATAAAGGTGATAAGGGCGAC

AAAGGTGACAAAGGCGATAAGGGTGATAAAGGTCCGCAGGGTGTTGTT

GGTGCAGATGGTAAAGACGGTACCCCGGGTAATGCAGGTCAGAAAGGT

CCGTCAGGTGAACCTGGCAGCCCTGGTAAAGCAGGTAGTGCCGGTGAG

CAGGGTCCGCCGGGCAAAGATGGTAGTAATGGTGAGCCGGGTAGCCCT

GGCAAAGAAGGTGAACGTGGTCTGGCAGGACCGCCGGGTCCTGATGGT

CGCCGCGGTGAAACGGGTTCACCGGGTATTGCCGGTGCCCTGGGTAAA

-continued

CCAGGTCTGGAAGGTCCGAAAGGTTATCCTGGTCTGCGCGGTCGTGAT

GGTACCAATGGCAAACGTGGCGAACAGGGCGAAACCGGTCCAGATGGT

GTTCGTGGTATTCCGGGTAACGATGGTCAGAGCGGTAAACCGGGCATT

GATGGTATTGATGGCACCAATGGTCAGCCTGGCGAAGCAGGTTATCAG

GGTGGTCGCGGTACCCGTGGTCAGCTGGGTGAAACAGGTGATGTTGGT

CAGAATGGTGATCGCGGCGCACCGGGTCCGGATGGTAGCAAAGGTAGC

GCCGGTCGTCCGGGTTTACGTtaa (SEQ ID NO: 16)
MKKIWLALAGLVLAFSASAAQYEDGDKGDKGDKGDKGDKGDKGPQGVV

GADGKDGTPGNAGQKGPSGEPGSPGKAGSAGEQGPPGKDGSNGEPGSP

GKEGERGLAGPPGPDGRRGETGSPGIAGALGKPGLEGPKGYPGLRGRD

GTNGKRGEQGETGPDGVRGIPGNDGQSGKPGIDGIDGTNGQPGEAGYQ

GGRGTRGQLGETGDVGQNGDRGAPGPDGSKGSAGRPGLR

The polynucleotides of SEQ ID NO: 15 was codon optimized and synthesized by Gen9 DNA, now Ginkgo Bioworks internal synthesis. Overlaps between the pET28 vector and SEQ ID NO: 15 was designed to be between 30 and 40 bp long and added using PCR with the enzyme PrimeStar GXL polymerase (www.clontech.com/US/Products/PCR/GC_Rich/PrimeSTAR_GXL_DNA_Polymerase?sitex=10020:22372:US). The opened pET28a vector and insert DNA (SEQ ID NO: 15) was then assembled together into the final plasmid using SGI Gibson assembly (us.vwr.com/store/product/17613857/gibson-assembly-hifi-1-step-kit-synthetic-genomics-inc). Sequence of plasmid was then verified through sanger sequencing through Eurofins Genomics (www.eurofinsgenomics.com).

The transformed cells were cultivated in minimal media and frozen in 1.5 aliquots with glycerol at a ratio of 50:50 of cells to glycerol. One vial of this frozen culture was revived in 50 ml of minimal media overnight at 37° C., 200 rpm. Cells were transferred into 300 ml of minimal media and grown for 6-9 hours to reach an OD600 of 5-10.

A bioreactor was prepared with 2.7 L of minimal media+glucose and 300 ml of OD600 of 5-10 culture was added to bring the starting volume to 3 L. Cells were grown at 28° C., pH7 with Dissolved Oxygen maintained at 20% saturation using a cascade containing agitation, air and oxygen. pH was controlled using 28% w/w Ammonium hydroxide solution. Fermentation was run in a fed-batch mode using a DO-stat based feeding algorithm once the initial bolus of 40 g/L was depleted around 13 hours. After 24-26 hours of initial growth, the OD600 reached above 100. At this point, 300 mL of 500 g/L sucrose was added and temperature was reduced to 25 C. High density culture was induced for protein production using 1 mM IPTG. Fermentation was continued for another 20-24 hours and cells were harvested using a bench top centrifuge at 9000 rcf, 15C for 60 minutes. Cell pellet recovered from centrifugation was resuspended in a buffer containing 0.5M NaCl and 0.1M KH2PO4 at pH8 in a weight by weight ratio of 2× buffer to 1× cells.

The harvested cells were disrupted in a homogenizer at 14,000 psi pressure in 2 passes. Resulting slurry contained the collagen protein along with other proteins.

The collagen was purified by acid treatment of whole cells recovered from bioreactor after centrifugation and resuspension in a buffer as described above. The pH of either the homogenized slurry was decreased to 3 using 6M Hydrochloric acid. Acidified cell slurry was incubated overnight at 4° C. with mixing, followed by centrifugation. Supernatant of the acidified slurry was tested on a polyacrylamide gel and found to contain collagen in relatively high abundance compared to starting pellet. The collagen slurry thus obtained was high in salts. To obtain volume and salt reduction, concentration and diafiltration steps were performed using an EMD Millipore Tangential Flow Filtration system with ultrafiltration cassettes of 0.1 $m^2$ each. Total area of filtration was 0.2 $m^2$ using 2 cassettes in parallel. A volume reduction of 5× and a salt reduction of 19× was achieved in the TFF stage. Final collagen slurry was run on an SDS-PAGE gel to confirm presence of the collagen. This slurry was dried using a multi-tray lyophilizer over 3 days to obtain a white, fluffy collagen powder.

The purified collagen was analyzed on an SDS-PAGE gel and was observed to run at an apparent molecular weight of 35 kilodaltons. The 35 kilodalton band does not correspond to the expected size of 22 kilodaltons. The upshift between the expected size and the apparent size is thought to be due to the GDK repeats interacting with the gel matrix. The 35 kDa band was confirmed by mass spectrometry to be the correct collagen with the GDK repeats.

Truncated Collagen with DsbA Secretion Tag-His Tag-Linker-Thrombin Cleavage Site and GFP Beta-Lactamase Fusion (Version 1):

A jellyfish collagen with DsbA secretion tag-His tag-Linker-Thrombin cleavage site and GFP Beta-lactamase fusion is disclosed below. The codon-optimized nucleotide sequence encoding this collagen is provided in SEQ ID NO: 17. The amino acid sequence is disclosed in SEQ ID NO: 18. The DsbA secretion tag is encoded by nucleotides 1-72 and encodes amino acids 1-24. The His tag is encoded by nucleotides 73-99 and encodes a 9 histidine tag (SEQ ID NO: 129) of amino acids 25-33. The linker is encoded by nucleotides 100-111 and encodes amino acids 34-37. The thrombin cleavage side is encoded by nucleotides 112-135 and encodes amino acids 38-45. The green fluorescent protein (GFP) with linker is encoded by nucleotides 136-873 and encodes amino acids 46-291. The truncated collagen sequence is encoded by nucleotides 874-1440 and encodes amino acids 292-480. The Beta-lactamase with linker is encoded by nucleotides 1441-2232 and encodes amino acids 481-744. The Beta-lactamase was properly targeted to the periplasmic space even though the polypeptide did not have an independent secretion tag. The DsbA secretion tag directed the entire transcript (Truncated Collagen with DsbA secretion tag-His tag-Linker-Thrombin cleavage site and GFP Beta-lactamase fusion protein) to the periplasmic space and the Beta-lactamase functioned properly.

(SEQ ID NO: 17)

```
ATGAAAAAGATTTGGCTGGCGCTGGCTGGTTTAGTTTTAGCGTTTAGC
GCATCGGCGGCGCAGTATGAAGATCACCATCACCACCACCACCATCAC
CACTCTGGCTCGAGCCTGGTGCCGCGCGGCAGCCATATGTCTGGCTCG
AGCAGTAAAGGTGAAGAACTGTTCACCGGTGTTGTTCCGATCCTGGTT
GAACTGGATGGTGATGTTAACGGCCACAAATTCTCTGTTCGTGGTGAA
GGTGAAGGTGATGCAACCAACGGTAAACTGACCCTGAAATTCATCTGC
ACTACCGGTAAACTGCCGGTTCCATGGCCGACTCTGGTGACTACCCTG
ACCTATGGTGTTCAGTGTTTTTCTCGTTACCCGGATCACATGAAGCAG
```

-continued

```
CATGATTTCTTCAAATCTGCAATGCCGGAAGGTTATGTACAGGAGCGC
ACCATTTCTTTCAAAGACGATGGCACCTACAAAACCCGTGCAGAGGTT
AAATTTGAAGGTGATACTCTGGTGAACCGTATTGAACTGAAAGGCATT
GATTTCAAAGAGGACGGCAACATCCTGGGCCACAAACTGGAATATAAC
TTCAACTCCCATAACGTTTACATCACCGCAGACAAACAGAAGAACGGT
ATCAAAGCTAACTTCAAAATTCGCCATAACGTTGAAGACGGTAGCGTA
CAGCTGGCGGACCACTACCAGCAGAACACTCCGATCGGTGATGGTCCG
GTTCTGCTGCCGGATAACCACTACCTGTCCACCCAGTCTaaaCTGTCC
AAAGACCCGAACGAAAAGCGCGACCACATGGTGCTGCTGGAGTTCGTT
ACTGCAGCAGGTATCACGCACGGCATGGATGAACTCTACAAATCTGGC
GCGCCGGGCGGTCCGCAGGGTGTTGTTGGTGCAGATGGTAAAGACGGT
ACCCCGGGTAATGCAGGTCAGAAAGGTCCGTCAGGTGAACCTGGCAGC
CCTGGTAAAGCAGGTAGTGCCGGTGAGCAGGGTCCGCCGGGCAAAGAT
GGTAGTAATGGTGAGCCGGGTAGCCCTGGCAAAGAAGGTGAACGTGGT
CTGGCAGGACCGCCGGGTCCTGATGGTCGCCGCGGTGAAACGGGTTCA
CCGGGTATTGCCGGTGCCCTGGGTAAACCAGGTCTGGAAGGTCCGAAA
GGTTATCCTGGTCTGCGCGGTCGTGATGGTACCAATGGCAAACGTGGC
GAACAGGGCGAAACCGGTCCAGATGGTGTTCGTGGTATTCCGGGTAAC
GATGGTCAGAGCGGTAAACCGGGCATTGATGGTATTGATGGCACCAAT
GGTCAGCCTGGCGAAGCAGGTTATCAGGGTGGTCGCGGTACCCGTGGT
CAGCTGGGTGAAACAGGTGATGTTGGTCAGAATGGTGATCGCGGCGCA
CCGGGTCCGGATGGTAGCAAAGGTAGCGCCGGTCGTCCGGGTTTACGT
cacccagaaacgctggtgaaagtaaaagatgctgaagatcagttgggt
gcacgagtgggttacatcgaactggatctcaacagcggtaagatcctt
gagagttttcgccccgaagaacgttttccaatgatgagcacttttaaa
gttctgctatgtggcgcggtattatcccgtattgacgccgggcaagag
caactcggtcgccgcatacactattctcagaatgacttggttgagtac
tcaccagtcacagaaaagcatcttacggatggcatgacagtaagagaa
ttatgcagtgctgccataaccatgagtgataacactgcggccaactta
cttctgacaacgatcggaggaccgaaggagctaaccgcttttttgcac
aacatgggggatcatgtaactcgccttgatcgttgggaaccggagctg
aatgaagccataccaaacgacgagcgtgacaccacgatgcctgtagca
atggcaacaacgttgcgcaaactattaactggcgaactacttactcta
gcttcccggcaacaattaatagactggatggaggcggataaagttgca
ggaccacttctgcgctcggcccttccggctggctggtttattgctgat
aaatctggagccggtgagcgtgggtctcgcggtatcattgcagcactg
gggccagatggtaagccctcccgtatcgtagttatctacacgacgggg
agtcaggcaactatggatgaacgaaatagacagatcgctgagataggt
gcctcactgattaagcattggtaa
```

-continued (SEQ ID NO: 18)

MKKIWLALAGLVLAFSASAAQYEDHHHHHHHHHSGSSLVPRGSHMSGS

SSKGEELFTGVVPILVELDGDVNGHKFSVRGEGEGDATNGKLTLKFIC

TTGKLPVPWPTLVTTLTYGVQCFSRYPDHMKQHDFFKSAMPEGYVQER

TISFKDDGTYKTRAEVKFEGDTLVNRIELKGIDFKEDGNILGHKLEYN

FNSHNVYITADKQKNGIKANFKIRHNVEDGSVQLADHYQQNTPIGDGP

VLLPDNHYLSTQSKLSKDPNEKRDHMVLLEFVTAAGITHGMDELYKSG

APGGPQGVVGADGKDGTPGNAGQKGPSGEPGSPGKAGSAGEQGPPGKD

GSNGEPGSPGKEGERGLAGPPGPDGRRGETGSPGIAGALGKPGLEGPK

GYPGLRGRDGTNGKRGEQGETGPDGVRGIPGNDGQSGKPGIDGIDGTN

GQPGEAGYQGGRGTRGQLGETGDVGQNGDRGAPGPDGSKGSAGRPGLR

HPETLVKVKDAEDQLGARVGYIELDLNSGKILESFRPEERFPMMSTFK

VLLCGAVLSRIDAGQEQLGRRIHYSQNDLVEYSPVTEKHLTDGMTVRE

LCSAAITMSDNTAANLLLTTIGGPKELTAFLHNMGDHVTRLDRWEPEL

NEAIPNDERDTTMPVAMATTLRKLLTGELLTLASRQQLIDWMEADKVA

GPLLRSALPAGWFIADKSGAGERGSRGIIAALGPDGKPSRIVVIYTTG

SQATMDERNRQIAEIGASLIKHW

The polynucleotides of SEQ ID NO: 17 was constructed by assembling several DNA fragments. The collagen containing sequence was codon optimized and synthesized by Gen9 DNA, now Ginkgo Bioworks internal synthesis. The GFP was also synthesized by Gen9. The Beta-lactamase was cloned out of the plasmid pKD46 (cgsc2.biology.yale.edu/Strain.php?ID=68099) using PCR with the enzyme PrimeStar GXL polymerase (www.clontech.com/US/Products/PCR/GC_Rich/PrimeSTAR_GXL_DNA_Polymerase?sitex=10020:22372:US). Overlaps between the pET28 vector, GFP, Collagen, and Beta-lactamase was designed to be between 30 and 40 bp long and added using PCR with the enzyme PrimeStar GXL polymerase. The opened pET28a vector and inserts were then assembled together into the final plasmid using SGI Gibson assembly (us.vwr.com/store/product/17613857/gibson-assembly-hifi-1-step-kit-synthetic-genomics-inc). Sequence of plasmid was then verified through sanger sequencing through Eurofins Genomics (www.eurofinsgenomics.com).

The transformed cells were cultivated in minimal media and frozen in 1.5 aliquots with glycerol at a ratio of 50:50 of cells to glycerol. One vial of this frozen culture was revived in 50 ml of minimal media overnight at 37° C., 200 rpm. Cells were transferred into 300 ml of minimal media and grown for 6-9 hours to reach an OD600 of 5-10.

A bioreactor was prepared with 2.7 L of minimal media+glucose and 300 ml of OD600 of 5-10 culture was added to bring the starting volume to 3 L. Cells were grown at 28° C., pH7 with Dissolved Oxygen maintained at 20% saturation using a cascade containing agitation, air and oxygen. pH was controlled using 28% w/w Ammonium hydroxide solution. Fermentation was run in a fed-batch mode using a DO-stat based feeding algorithm once the initial bolus of 40 g/L was depleted around 13 hours. After 24-26 hours of initial growth, the OD600 reached above 100. At this point, 300 mL of 500 g/L sucrose was added and temperature was reduced to 25C. High density culture was induced for protein production using 1 mM IPTG. Fermentation was continued for another 20-24 hours and cells were harvested using a bench top centrifuge at 9000 rcf, 15C for 60 minutes. Cell pellet recovered from centrifugation was resuspended in a buffer containing 0.5M NaCl and 0.1M KH2PO4 at pH8 in a weight by weight ratio of 2× buffer to 1× cells.

The harvested cells were disrupted in a homogenizer at 14,000 psi pressure in 2 passes. Resulting slurry contained the collagen protein along with other proteins.

The collagen was purified by acid treatment of non-homogenized whole cells recovered from the bioreactor after centrifugation and resuspension in the buffer described above. The pH of the resuspended suspension—was decreased to 3 using 6M Hydrochloric acid. Acidified cell slurry was incubated overnight at 4° C. with mixing, followed by centrifugation. The pH was then raised to 9 using 10N NaOH and the supernatant of the slurry was tested on a polyacrylamide gel and found to contain collagen in relatively high abundance compared to starting pellet. The collagen slurry thus obtained was high in salts. To obtain volume and salt reduction, concentration and diafiltration steps were performed using an EMD Millipore Tangential Flow Filtration system with ultrafiltration cassettes of 0.1 m2 each. Total area of filtration was 0.2 m2 using 2 cassettes in parallel. A volume reduction of 5× and a salt reduction of 19× was achieved in the TFF stage. Final collagen slurry was run on an SDS-PAGE gel to confirm presence of the collagen. This slurry was dried using a multi-tray lyophilizer over 3 days to obtain a white, fluffy collagen powder.

The purified collagen-GFP-Beta-lactamase fusion protein was analyzed on an SDS-PAGE gel and was observed to run at an apparent molecular weight of 90 kilodaltons. The expected size of the fusion protein is 85 kd. The 90 kDa band was confirmed by mass spectrometry to be the correct collagen fusion protein.

Truncated Collagen with DsbA Secretion Tag-His Tag-Linker-Thrombin Cleavage Site and GFP Beta-Lactamase Fusion (Version 2):

A jellyfish collagen with DsbA secretion tag-His tag-Linker-Thrombin cleavage site and GFP Beta-lactamase fusion is disclosed below. The codon-optimized nucleotide sequence encoding this collagen is provided in SEQ ID NO: 19. The amino acid sequence is disclosed in SEQ ID NO: 20. The DsbA secretion tag is encoded by nucleotides 1-72 and encodes amino acids 1-24. The His tag is encoded by nucleotides 73-99 and encodes a 9 histidine tag (SEQ ID NO: 129) of amino acids 25-33. The linker is encoded by nucleotides 100-111 and encodes amino acids 34-37. The thrombin cleavage side is encoded by nucleotides 112-135 and encodes amino acids 38-45. The green fluorescent protein (GFP) with linker is encoded by nucleotides 136-873 and encodes amino acids 46-291 The truncated collagen sequence is encoded by nucleotides 874-1440 and encodes amino acids 292-480. The Beta-lactamase with linker is encoded by nucleotides 1441-2232 and encodes amino acids 481-744.

(SEQ ID NO: 19)

ATGAAAAAGATTTGGCTGGCGCTGGCTGGTTTAGTTTTAGCGTTTAGC

GCATCGGCGGCGCAGTATGAAGATCACCATCACCACCACCACCATCAC

CACTCTGGCTCGAGCCTGGTGCCGCGCGGCAGCCATATGTCTGGCTCG

AGCAGTAAAGGTGAAGAACTGTTCACCGGTGTTGTTCCGATCCTGGTT

GAACTGGATGGTGATGTTAACGGCCACAAATTCTCTGTTCGTGGTGAA

GGTGAAGGTGATGCAACCAACGGTAAACTGACCCTGAAATTCATCTGC

-continued

ACTACCGGTAAACTGCCGGTTCCATGGCCGACTCTGGTGACTACCCTG

ACCTATGGTGTTCAGTGTTTTTCTCGTTACCCGGATCACATGAAGCAG

CATGATTTCTTCAAATCTGCAATGCCGGAAGGTTATGTACAGGAGCGC

ACCATTTCTTTCAAAGACGATGGCACCTACAAAACCCGTGCAGAGGTT

AAATTTGAAGGTGATACTCTGGTGAACCGTATTGAACTGAAAGGCATT

GATTTCAAAGAGGACGGCAACATCCTGGGCCACAAACTGGAATATAAC

TTCAACTCCCATAACGTTTACATCACCGCAGACAAACAGAAGAACGGT

ATCAAAGCTAACTTCAAAATTCGCCATAACGTTGAAGACGGTAGCGTA

CAGCTGGCGGACCACTACCAGCAGAACACTCCGATCGGTGATGGTCCG

GTTCTGCTGCCGGATAACCACTACCTGTCCACCCAGTCTaaaCTGTCC

AAAGACCCGAACGAAAAGCGCGACCACATGGTGCTGCTGGAGTTCGTT

ACTGCAGCAGGTATCACGCACGGCATGGATGAACTCTACAAATCTGGC

GCGCCGGGCGGTCCGCAGGGTGTTGTTGGTGCAGATGGTAAAGACGGT

ACCCCGGGTAATGCAGGTCAGAAAGGTCCGTCAGGTGAACCTGGCAGC

CCTGGTAAAGCAGGTAGTGCCGGTGAGCAGGGTCCGCCGGGCAAAGAT

GGTAGTAATGGTGAGCCGGGTAGCCCTGGCAAAGAAGGTGAACGTGGT

CTGGCAGGACCGCCGGGTCCTGATGGTCGCCGCGGTGAAACGGGTTCA

CCGGGTATTGCCGGTGCCCTGGGTAAACCAGGTCTGGAAGGTCCGAAA

GGTTATCCTGGTCTGCGCGGTCGTGATGGTACCAATGGCAAACGTGGC

GAACAGGGCGAAACCGGTCCAGATGGTGTTCGTGGTATTCCGGGTAAC

GATGGTCAGAGCGGTAAACCGGGCATTGATGGTATTGATGGCACCAAT

GGTCAGCCTGGCGAAGCAGGTTATCAGGGTGGTCGCGGTACCCGTGGT

CAGCTGGGTGAAACAGGTGATGTTGGTCAGAATGGTGATCGCGGCGCA

CCGGGTCCGGATGGTAGCAAAGGTAGCGCCGGTCGTCCGGGTTTACGT cacccagaaacgctggtgaaagtaaaagatgctgaagatcagttgggt gcacgagtgggttacatcgaactggatctcaacagcggtaagatcctt gagagttttcgccccgaagaacgttttccaatgatgagcacttttaaa gttctgctatgtggcgcggtattatcccgtattgacgccgggcaagag caactcggtcgccgcatacactattctcagaatgacttggttgagtac tcaccagtcacagaaaagcatcttacggatggcatgacagtaagagaa ttatgcagtgctgccataaccatgagtgataacactgcggccaactta cttctgacaacgatcggaggaccgaaggagctaaccgcttttttgcac aacatgggggatcatgtaactcgccttgatcgttgggaaccggagctg aatgaagccataccaaacgacgagcgtgacaccacgatgcctgtagca atggcaacaacgttgcgcaaactattaactggcgaactacttactcta gcttcccggcaacaattaatagactggatggaggcggataaagttgca ggaccacttctgcgctcggcccttccggctggctggtttattgctgat aaatctggagccggtgagcgtgggtctcgcggtatcattgcagcactg gggccagatggtaagccctcccgtatcgtagttatctacacgacgggg agtcaggcaactatggatgaacgaaatagacagatcgctgagataggt -continued gcctcactgattaagcattggtaa (SEQ ID NO: 20)

MKKIWLALAGLVLAFSASAAQYEDHHHHHHHHHSGSSLVPRGSHMSGS

SSKGEELFTGVVPILVELDGDVNGHKFSVRGEGEGDATNGKLTLKFIC

TTGKLPVPWPTLVTTLTYGVQCFSRYPDHMKQHDFFKSAMPEGYVQER

TISFKDDGTYKTRAEVKFEGDTLVNRIELKGIDFKEDGNILGHKLEYN

FNSHNVYITADKQKNGIKANFKIRHNVEDGSVQLADHYQQNTPIGDGP

VLLPDNHYLSTQSKLSKDPNEKRDHMVLLEFVTAAGITHGMDELYKSG

APGGPQGVVGADGKDGTPGNAGQKGPSGEPGSPGKAGSAGEQGPPGKD

GSNGEPGSPGKEGERGLAGPPGPDGRRGETGSPGIAGALGKPGLEGPK

GYPGLRGRDGTNGKRGEQGETGPDGVRGIPGNDGQSGKPGIDGIDGTN

GQPGEAGYQGGRGTRGQLGETGDVGQNGDRGAPGPDGSKGSAGRPGLR

HPETLVKVKDAEDQLGARVGYIELDLNSGKILESFRPEERFPMMSTFK

VLLCGAVLSRIDAGQEQLGRRIHYSQNDLVEYSPVTEKHLTDGMTVRE

LCSAAITMSDNTAANLLLTTIGGPKELTAFLHNMGDHVTRLDRWEPEL

NEAIPNDERDTTMPVAMATTLRKLLTGELLTLASRQQLIDWMEADKVA

GPLLRSALPAGWFIADKSGAGERGSRGIIAALGPDGKPSRIVVIYTTG

SQATMDERNRQIAEIGASLIKHW

Example 4: Production of Full-Length Elastin

Full length human elastin were expressed as described below. The wild-type, full length amino acid sequence of human elastin is provided below.

(SEQ ID NO: 21)

MAGLTAAAPRPGVLLLLLSILHPSRPGGVPGAIPGGVPGGVFYPGAGL

GALGGGALGPGGKPLKPVPGGLAGAGLGAGLGAFPAVTFPGALVPGGV

ADAAAAYKAAKAGAGLGGVPGVGGLGVSAGAVVPQPGAGVKPGKVPGV

GLPGVYPGGVLPGARFPGVGVLPGVPTGAGVKPKAPGVGGAFAGIPGV

GPFGGPQPGVPLGYPIKAPKLPGGYGLPYTTGKLPYGYGPGGVAGAAG

KAGYPTGTGVGPQAAAAAAAKAAAKFGAGAAGVLPGVGGAGVPGVPGA

IPGIGGIAGVGTPAAAAAAAAAAKAAKYGAAAGLVPGGPGFGPGVVGV

PGAGVPGVGVPGAGIPVVPGAGIPGAAVPGVVSPEAAAKAAAKAAKYG

ARPGVGVGGIPTYGVGAGGFPGFGVGVGGIPGVAGVPGVGGVPGVGGV

PGVGISPEAQAAAAAKAAKYGAAGAGVLGGLVPGPQAAVPGVPGTGGV

PGVGTPAAAAAKAAAKAAQFGLVPGVGVAPGVGVAPGVGVAPGVGLAP

GVGVAPGVGVAPGVGVAPGIGPGGVAAAAKSAAKVAAKAQLRAAAGLG

AGIPGLGVGVGVPGLGVGAGVPGLGVGAGVPGFGAGADEGVRRSLSPE

LREGDPSSSQHLPSTPSSPRVPGALAAAKAAKYGAAVPGVLGGLGALG

GVGIPGGVVGAGPAAAAAAAKAAAKAAQFGLVGAAGLGGLGVGGLGVP

GVGGLGGIPPAAAAKAAKYGAAGLGGVLGGAGQFPLGGVAARPGFGLS

PIFPGGACLGKACGRKRK www.uniprot.org/uniprot/P15502

The non-codon optimized polynucleotide sequence encoding the full length elastin is disclosed below. In SEQ ID NO: 22, nucleotides 1-78 encode the DsbA secretion tag and nucleotides 79-2358 encode the full length human elastin.

(SEQ ID NO: 22)

ATGGCGGGTCTGACGGCGGCGGCCCCGCGGCCCGGAGTCCTCCTGCTC

CTGCTGTCCATCCTCCACCCCTCTCGGCCTGGAGGGGTCCCTGGGGCC

ATTCCTGGTGGAGTTCCTGGAGGAGTCTTTTATCCAGGGGCTGGTCTC

GGAGCCCTTGGAGGAGGAGCGCTGGGGCCTGGAGGCAAACCTCTTAAG

CCAGTTCCCGGAGGGCTTGCGGGTGCTGGCCTTGGGGCAGGGCTCGGC

GCCTTCCCCGCAGTTACCTTTCCGGGGGCTCTGGTGCCTGGTGGAGTG

GCTGACGCTGCTGCAGCCTATAAAGCTGCTAAGGCTGGCGCTGGGCTT

GGTGGTGTCCCAGGAGTTGGTGGCTTAGGAGTGTCTGCAGGTGCGGTG

GTTCCTCAGCCTGGAGCCGGAGTGAAGCCTGGGAAAGTGCCGGGTGTG

GGGCTGCCAGGTGTATACCCAGGTGGCGTGCTCCCAGGAGCTCGGTTC

CCCGGTGTGGGGGTGCTCCCTGGAGTTCCCACTGGAGCAGGAGTTAAG

CCCAAGGCTCCAGGTGTAGGTGGAGCTTTTGCTGGAATCCCAGGAGTT

GGACCCTTTGGGGGACCGCAACCTGGAGTCCCACTGGGGTATCCCATC

AAGGCCCCCAAGCTGCCTGGTGGCTATGGACTGCCCTACACCACAGGG

AAACTGCCCTATGGCTATGGGCCCGGAGGAGTGGCTGGTGCAGCGGGC

AAGGCTGGTTACCCAACAGGGACAGGGGTTGGCCCCCAGGCAGCAGCA

GCAGCGGCAGCTAAAGCAGCAGCAAAGTTCGGTGCTGGAGCAGCCGGA

GTCCTCCCTGGTGTTGGAGGGGCTGGTGTTCCTGGCGTGCCTGGGGCA

ATTCCTGGAATTGGAGGCATCGCAGGCGTTGGGACTCCAGCTGCAGCT

GCAGCTGCAGCAGCAGCCGCTAAGGCAGCCAAGTATGGAGCTGCTGCA

GGCTTAGTGCCTGGTGGGCCAGGCTTTGGCCCGGGAGTAGTTGGTGTC

CCAGGAGCTGGCGTTCCAGGTGTTGGTGTCCCAGGAGCTGGGATTCCA

GTTGTCCCAGGTGCTGGGATCCCAGGTGCTGCGGTTCCAGGGGTTGTG

TCACCAGAAGCAGCTGCTAAGGCAGCTGCAAAGGCAGCCAAATACGGG

GCCAGGCCCGGAGTCGGAGTTGGAGGCATTCCTACTTACGGGGTTGGA

GCTGGGGGCTTTCCCGGCTTTGGTGTCGGAGTCGGAGGTATCCCTGGA

GTCGCAGGTGTCCCTGGTGTCGGAGGTGTTCCCGGAGTCGGAGGTGTC

CCGGGAGTTGGCATTTCCCCCGAAGCTCAGGCAGCAGCTGCCGCCAAG

GCTGCCAAGTACGGTGCTGCAGGAGCAGGAGTGCTGGGTGGGCTAGTG

CCAGGTCCCCAGGCGGCAGTCCCAGGTGTGCCGGGCACGGGAGGAGTG

CCAGGAGTGGGGACCCCAGCAGCTGCAGCTGCTAAAGCAGCCGCCAAA

GCCGCCCAGTTTGGGTTAGTTCCTGGTGTCGGCGTGGCTCCTGGAGTT

GGCGTGGCTCCTGGTGTCGGTGTGGCTCCTGGAGTTGGCTTGGCTCCT

GGAGTTGGCGTGGCTCCTGGAGTTGGTGTGGCTCCTGGCGTTGGCGTG

GCTCCCGGCATTGGCCCTGGTGGAGTTGCAGCTGCAGCAAAATCCGCT

GCCAAGGTGGCTGCCAAAGCCCAGCTCCGAGCTGCAGCTGGGCTTGGT

GCTGGCATCCCTGGACTTGGAGTTGGTGTCGGCGTCCCTGGACTTGGA

-continued

GTTGGTGCTGGTGTTCCTGGACTTGGAGTTGGTGCTGGTGTTCCTGGC

TTCGGGGCAGGTGCAGATGAGGGAGTTAGGCGGAGCCTGTCCCCTGAG

CTCAGGGAAGGAGATCCCTCCTCCTCTCAGCACCTCCCCAGCACCCCC

TCATCACCCAGGGTACCTGGAGCCCTGGCTGCCGCTAAAGCAGCCAAA

TATGGAGCAGCAGTGCCTGGGGTCCTTGGAGGGCTCGGGGCTCTCGGT

GGAGTAGGCATCCCAGGCGGTGTGGTGGGAGCCGGACCCGCCGCCGCC

GCTGCCGCAGCCAAAGCTGCTGCCAAAGCCGCCCAGTTTGGCCTAGTG

GGAGCCGCTGGGCTCGGAGGACTCGGAGTCGGAGGGCTTGGAGTTCCA

GGTGTTGGGGGCCTTGGAGGTATACCTCCAGCTGCAGCCGCTAAAGCA

GCTAAATACGGTGCTGCTGGCCTTGGAGGTGTCCTAGGGGGTGCCGGG

CAGTTCCCACTTGGAGGAGTGGCAGCAAGACCTGGCTTCGGATTGTCT

CCCATTTTCCCAGGTGGGGCCTGCCTGGGGAAAGCTTGTGGCCGGAAG

AGAAAATGA

Codon Optimized Elastin with DsbA Secretion Tag-His Tag-Linker-Thrombin Cleavage Site The codon optimized polynucleotide sequence encoding the full length human elastin with DsbA secretion tag-His tag-Linker-Thrombin cleavage site is disclosed below. In SEQ ID NO: 23: nucleotides 1-72 encode the DsbA secretion tag encoding amino acids 1-24 of SEQ ID NO: 24; nucleotides 73-99 encode the 9 His tag (SEQ ID NO: 129) encoding amino acids 25-33 of SEQ ID NO: 24; nucleotides 100-111 encode the linker encoding amino acids 34-37 of SEQ ID NO: 24; nucleotides 112-135 encode the thrombin cleavage tag encoding amino acids 38-45 of SEQ ID NO: 24; nucleotides 136-2415 encode the amino acids 46-805 of the full length human elastin of SEQ ID NO: 24.

(SEQ ID NO: 23)

ATGAAAAAGATTTGGCTGGCGCTGGCTGGTTTAGTTTTAGCGTTTAGC

GCATCGGCGGCGCAGTATGAAGATCACCATCACCACCACCACCATCAC

CACTCTGGCTCGAGCCTGGTGCCGCGCGGCAGCCATATGGGTGGCGTA

CCAGGCGCAATTCCTGGGGGTGTCCCAGGCGGTGTTTTTTATCCGGGC

GCCGGTCTTGGCGCACTGGGTGGCGGTGCACTGGGCCCGGGCGGCAAA

CCGCTGAAACCGGTACCAGGTGGTTTAGCAGGCGCCGGCTTAGGCGCA

GGTCTGGGAGCATTTCCGGCAGTTACCTTTCCAGGGGCACTGGTTCCT

GGAGGTGTGGCCGATGCAGCCGCGGCATATAAAGCCGCTAAAGCCGGT

GCGGGTTTAGGAGGCGTCCCAGGTGTCGGTGGCCTGGGTGTTAGCGCC

GGTGCAGTTGTTCCGCAGCCGGGAGCAGGGGTTAAACCTGGTAAAGTG

CCGGGAGTAGGTCTGCCAGGCGTTTATCCTGGTGGTGTTTTGCCGGGT

GCCCGTTTTCCGGGCGTTGGTGTTCTTCCAGGCGTGCCGACCGGAGCC

GGTGTTAAACCGAAAGCCCCCGGTGTTGGAGGTGCATTTGCAGGCATC

CCGGGAGTTGGCCCGTTTGGTGGTCCGCAACCTGGGGTTCCGTTAGGT

TATCCGATTAAAGCACCGAAACTGCCCGGCGGTTATGGTCTGCCGTAC

ACAACCGGTAAACTGCCGTATGGTTATGGCCCGGGTGGAGTTGCGGGT

GCAGCAGGTAAAGCGGGTTATCCTACCGGAACCGGTGTAGGTCCGCAG

-continued

GCCGCTGCTGCCGCCGCCGCAAAAGCAGCGGCTAAATTTGGCGCCGGA

GCAGCGGGTGTTCTGCCTGGAGTTGGTGGTGCGGGCGTGCCAGGGGTA

CCTGGTGCAATTCCGGGTATTGGTGGTATTGCCGGTGTCGGCACCCCG

GCCGCGGCAGCTGCGGCAGCGGCGGCTGCCAAAGCTGCTAAATACGGT

GCCGCGGCGGGTCTGGTGCCAGGAGGTCCGGGTTTTGGTCCGGGAGTG

GTTGGCGTGCCTGGCGCAGGCGTTCCTGGTGTGGGCGTTCCAGGTGCA

GGGATTCCTGTTGTGCCTGGTGCCGGTATTCCCGGCGCGGCCGTTCCG

GGGGTGGTTAGCCCGGAAGCCGCAGCGAAGGCTGCGGCAAAGGCAGCA

AAGTATGGCGCACGCCCAGGAGTCGGCGTGGGTGGTATCCCGACCTAT

GGGGTGGGCGCAGGGGGTTTTCCTGGTTTCGGCGTAGGTGTAGGAGGT

ATACCGGGCGTGGCCGGTGTACCAGGGGTTGGTGGCGTCCCTGGTGTT

GGCGGTGTGCCAGGTGTTGGTATTTCACCGGAAGCACAGGCAGCAGCC

GCAGCTAAGGCAGCGAAATATGGTGCCGCCGGCGCAGGAGTTTTAGGT

GGGCTGGTTCCGGGCCCGCAGGCAGCTGTGCCGGGGGTTCCAGGCACC

GGTGGTGTCCCTGGAGTCGGTACGCCGGCTGCAGCGGCAGCCAAAGCG

GCTGCGAAAGCAGCACAGTTTGGCTTAGTACCGGGTGTGGGAGTTGCC

CCCGGCGTTGGCGTTGCTCCAGGGGTGGGTGTTGCTCCTGGCGTCGGT

CTGGCTCCTGGAGTGGGCGTAGCACCCGGTGTGGGGGTGGCCCCGGGT

GTTGGGGTTGCACCGGGTATCGGTCCGGGCGGTGTCGCAGCAGCAGCT

AAAAGCGCGGCGAAAGTTGCGGCCAAAGCCCAACTGCGCGCCGCCGCG

GGCCTCGGTGCAGGTATTCCGGGGCTGGGTGTCGGAGTTGGAGTCCCG

GGTTTGGGCGTGGGCGCGGGAGTTCCGGGACTGGGAGTGGGTGCCGGA

GTTCCTGGCTTTGGTGCAGGCGCAGATGAAGGTGTTCGTCGTAGCCTG

AGTCCGGAACTGCGTGAAGGTGATCCGAGTAGCAGCCAGCATCTGCCG

AGCACCCCGAGCAGCCCGCGTGTTCCGGGTGCATTAGCTGCAGCAAAA

GCCGCCAAGTATGGTGCAGCCGTGCCGGGCGTCTTAGGTGGTCTGGGC

GCCCTGGGTGGTGTAGGCATTCCGGGAGGTGTTGTGGGTGCAGGACCG

GCCGCCGCAGCTGCGGCCGCCAAAGCAGCTGCAAAAGCGGCCCAGTTT

GGTTTAGTGGGCGCCGCAGGTTTAGGCGGTTTAGGTGTGGGTGGACTG

GGTGTACCTGGCGTAGGCGGTCTGGGTGGAATTCCGCCCGCAGCGGCC

GCGAAAGCGGCAAAATATGGCGCGGCAGGCCTGGGCGGCGTGCTGGGT

GGGGCAGGTCAGTTTCCGCTGGGCGGGGTTGCCGCACGTCCGGGATTT

GGTCTGAGCCCGATTTTCCCTGGCGGCGCATGTCTGGGTAAAGCATGT

GGTCGTAAACGTAAAtaa (SEQ ID NO: 24)

MKKIWLALAGLVLAFSASAAQYEDHHHHHHHHHSGSSLVPRGSHMGGV

PGAIPGGVPGGVFYPGAGLGALGGGALGPGGKPLKPVPGGLAGAGLGA

GLGAFPAVTFPGALVPGGVADAAAAYKAAKAGAGLGGVPGVGGLGVSA

GAVVPQPGAGVKPGKVPGVGLPGVYPGGVLPGARFPGVGVLPGVPTGA

GVKPKAPGVGGAFAGIPGVGPFGGPQPGVPLGYPIKAPKLPGGYGLPY

TTGKLPYGYGPGGVAGAAGKAGYPTGTGVGPQAAAAAAAKAAAKFGAG

-continued

AAGVLPGVGGAGVPGVPGAIPGIGGIAGVGTPAAAAAAAAAKAAKYG

AAAGLVPGGPGFGPGVVGVPGAGVPGVGVPGAGIPVVPGAGIPGAAVP

GVVSPEAAAKAAAKAAKYGARPGVGVGGIPTYGVGAGGFPGFGVGVGG

IPGVAGVPGVGGVPGVGGVPGVGISPEAQAAAAAKAAKYGAAGAGVLG

GLVPGPQAAVPGVPGTGGVPGVGTPAAAAAKAAAKAAQFGLVPGVGVA

PGVGVAPGVGVAPGVGLAPGVGVAPGVGVAPGVGVAPGIGPGGVAAAA

KSAAKVAAKAQLRAAAGLGAGIPGLGVGVGVPGLGVGAGVPGLGVGAG

VPGFGAGADEGVRRSLSPELREGDPSSSQHLPSTPSSPRVPGALAAAK

AAKYGAAVPGVLGGLGALGGVGIPGGVVGAGPAAAAAAAKAAAKAAQF

GLVGAAGLGGLGVGGLGVPGVGGLGGIPPAAAAKAAKYGAAGLGGVLG

GAGQFPLGGVAARPGFGLSPIFPGGACLGKACGRKRK

The polynucleotide encoding the full length human elastin without the native sequence tag is disclosed in SEQ ID NO: 87.

(SEQ ID NO: 87)

GGTGGCGTACCAGGCGCAATTCCTGGGGGTGTCCCAGGCGGTGTTTTT

TATCCGGGCGCCGGTCTTGGCGCACTGGGTGGCGGTGCACTGGGCCCG

GGCGGCAAACCGCTGAAACCGGTACCAGGTGGTTTAGCAGGCGCCGGC

TTAGGCGCAGGTCTGGGAGCATTTCCGGCAGTTACCTTTCCAGGGGCA

CTGGTTCCTGGAGGTGTGGCCGATGCAGCCGCGGCATATAAAGCCGCT

AAAGCCGGTGCGGGTTTAGGAGGCGTCCCAGGTGTCGGTGGCCTGGGT

GTTAGCGCCGGTGCAGTTGTTCCGCAGCCGGGAGCAGGGGTTAAACCT

GGTAAAGTGCCGGGAGTAGGTCTGCCAGGCGTTTATCCTGGTGGTGTT

TTGCCGGGTGCCCGTTTTCCGGGCGTTGGTGTTCTTCCAGGCGTGCCG

ACCGGAGCCGGTGTTAAACCGAAAGCCCCCGGTGTTGGAGGTGCATTT

GCAGGCATCCCGGGAGTTGGCCCGTTTGGTGGTCCGCAACCTGGGGTT

CCGTTAGGTTATCCGATTAAAGCACCGAAACTGCCCGGCGGTTATGGT

CTGCCGTACACAACCGGTAAACTGCCGTATGGTTATGGCCCGGGTGGA

GTTGCGGGTGCAGCAGGTAAAGCGGGTTATCCTACCGGAACCGGTGTA

GGTCCGCAGGCCGCTGCTGCCGCCGCCGCAAAAGCAGCGGCTAAATTT

GGCGCCGGAGCAGCGGGTGTTCTGCCTGGAGTTGGTGGTGCGGGCGTG

CCAGGGGTACCTGGTGCAATTCCGGGTATTGGTGGTATTGCCGGTGTC

GGCACCCCGGCCGCGGCAGCTGCGGCAGCGGCGGCTGCCAAAGCTGCT

AAATACGGTGCCGCGGCGGGTCTGGTGCCAGGAGGTCCGGGTTTTGGT

CCGGGAGTGGTTGGCGTGCCTGGCGCAGGCGTTCCTGGTGTGGGCGTT

CCAGGTGCAGGGATTCCTGTTGTGCCTGGTGCCGGTATTCCCGGCGCG

GCCGTTCCGGGGGTGGTTAGCCCGGAAGCCGCAGCGAAGGCTGCGGCA

AAGGCAGCAAAGTATGGCGCACGCCCAGGAGTCGGCGTGGGTGGTATC

CCGACCTATGGGGTGGGCGCAGGGGGTTTTCCTGGTTTCGGCGTAGGT

GTAGGAGGTATACCGGGCGTGGCCGGTGTACCAGGGGTTGGTGGCGTC

CCTGGTGTTGGCGGTGTGCCAGGTGTTGGTATTTCACCGGAAGCACAG

-continued

GCAGCAGCCGCAGCTAAGGCAGCGAAATATGGTGCCGCCGGCGCAGGA

GTTTTAGGTGGGCTGGTTCCGGGCCCGCAGGCAGCTGTGCCGGGGGTT

CCAGGCACCGGTGGTGTCCCTGGAGTCGGTACGCCGGCTGCAGCGGCA

GCCAAAGCGGCTGCGAAAGCAGCACAGTTTGGCTTAGTACCGGGTGTG

GGAGTTGCCCCCGGCGTTGGCGTTGCTCCAGGGGTGGGTGTTGCTCCT

GGCGTCGGTCTGGCTCCTGGAGTGGGCGTAGCACCCGGTGTGGGGGTG

GCCCCGGGTGTTGGGGTTGCACCGGGTATCGGTCCGGGCGGTGTCGCA

GCAGCAGCTAAAAGCGCGGCGAAAGTTGCGGCCAAAGCCCAACTGCGC

GCCGCCGCGGGCCTCGGTGCAGGTATTCCGGGGCTGGGTGTCGGAGTT

GGAGTCCCGGGTTTGGGCGTGGGCGCGGGAGTTCCGGGACTGGGAGTG

GGTGCCGGAGTTCCTGGCTTTGGTGCAGGCGCAGATGAAGGTGTTCGT

CGTAGCCTGAGTCCGGAACTGCGTGAAGGTGATCCGAGTAGCAGCCAG

CATCTGCCGAGCACCCCGAGCAGCCCGCGTGTTCCGGGTGCATTAGCT

GCAGCAAAAGCCGCCAAGTATGGTGCAGCCGTGCCGGGCGTCTTAGGT

GGTCTGGGCGCCCTGGGTGGTGTAGGCATTCCGGGAGGTGTTGTGGGT

GCAGGACCGGCCGCCGCAGCTGCGGCCGCCAAAGCAGCTGCAAAAGCG

GCCCAGTTTGGTTTAGTGGGCGCCGCAGGTTTAGGCGGTTTAGGTGTG

GGTGGACTGGGTGTACCTGGCGTAGGCGGTCTGGGTGGAATTCCGCCC

GCAGCGGCCGCGAAAGCGGCAAAATATGGCGCGGCAGGCCTGGGCGGC

GTGCTGGGTGGGGCAGGTCAGTTTCCGCTGGGCGGGGTTGCCGCACGT

CCGGGATTTGGTCTGAGCCCGATTTTCCCTGGCGGCGCATGTCTGGGT

AAAGCATGTGGTCGTAAACGTAAAtaa

The full length human elastin sequence without the native sequence tag is disclosed in SEQ ID NO: 88.

(SEQ ID NO: 88)

GGVPGAIPGGVPGGVFYPGAGLGALGGGALGPGGKPLKPVPGGLAGAG

LGAGLGAFPAVTFPGALVPGGVADAAAAYKAAKAGAGLGGVPGVGGLG

VSAGAVVPQPGAGVKPGKVPGVGLPGVYPGGVLPGARFPGVGVLPGVP

TGAGVKPKAPGVGGAFAGIPGVGPFGGPQPGVPLGYPIKAPKLPGGYG

LPYTTGKLPYGYGPGGVAGAAGKAGYPTGTGVGPQAAAAAAAKAAAKF

GAGAAGVLPGVGGAGVPGVPGAIPGIGGIAGVGTPAAAAAAAAAAKAA

KYGAAAGLVPGGPGFGPGVVGVPGAGVPGVGVPGAGIPVVPGAGIPGA

AVPGVVSPEAAAKAAAKAAKYGARPGVGVGGIPTYGVGAGGFPGFGVG

VGGIPGVAGVPGVGGVPGVGGVPGVGISPEAQAAAAAKAAKYGAAGAG

VLGGLVPGPQAAVPGVPGTGGVPGVGTPAAAAAKAAAKAAQFGLVPGV

GVAPGVGVAPGVGVAPGVGLAPGVGVAPGVGVAPGVGVAPGIGPGGVA

AAAKSAAKVAAKAQLRAAAGLGAGIPGLGVGVGVPGLGVGAGVPGLGV

GAGVPGFGAGADEGVRRSLSPELREGDPSSSQHLPSTPSSPRVPGALA

-continued

AAKAAKYGAAVPGVLGGLGALGGVGIPGGVVGAGPAAAAAAAKAAAKA

AQFGLVGAAGLGGLGVGGLGVPGVGGLGGIPPAAAAKAAKYGAAGLGG

VLGGAGQFPLGGVAARPGFGLSPIFPGGACLGKACGRKRK

Codon Optimized Elastin with DsbA Secretion Tag

The codon optimized polynucleotide sequence encoding the full length human elastin with a DsbA secretion tag is disclosed in SEQ ID NO: 25. In SEQ ID NO: 25: nucleotides 1-72 encode the DsbA secretion tag encoding amino acids 1-24 of SEQ ID NO: 26; nucleotides 73-2355 encode the amino acids 25-785 of the full length human elastin of SEQ ID NO: 26.

(SEQ ID NO: 25)

ATGAAAAAGATTTGGCTGGCGCTGGCTGGTTTAGTTTTAGCGTTTAGC

GCATCGGCGGCGCAGTATGAAGATATGGGTGGCGTACCAGGCGCAATT

CCTGGGGGTGTCCCAGGCGGTGTTTTTATCCGGGCGCCGGTCTTGGC

GCACTGGGTGGCGGTGCACTGGGCCCGGGCGGCAAACCGCTGAAACCG

GTACCAGGTGGTTTAGCAGGCGCCGGCTTAGGCGCAGGTCTGGGAGCA

TTTCCGGCAGTTACCTTTCCAGGGGCACTGGTTCCTGGAGGTGTGGCC

GATGCAGCCGCGGCATATAAAGCCGCTAAAGCCGGTGCGGGTTTAGGA

GGCGTCCCAGGTGTCGGTGGCCTGGGTGTTAGCGCCGGTGCAGTTGTT

CCGCAGCCGGGAGCAGGGGTTAAACCTGGTAAAGTGCCGGGAGTAGGT

CTGCCAGGCGTTTATCCTGGTGGTGTTTTGCCGGGTGCCCGTTTTCCG

GGCGTTGGTGTTCTTCCAGGCGTGCCGACCGGAGCCGGTGTTAAACCG

AAAGCCCCCGGTGTTGGAGGTGCATTTGCAGGCATCCCGGGAGTTGGC

CCGTTTGGTGGTCCGCAACCTGGGGTTCCGTTAGGTTATCCGATTAAA

GCACCGAAACTGCCCGGCGGTTATGGTCTGCCGTACACAACCGGTAAA

CTGCCGTATGGTTATGGCCCGGGTGGAGTTGCGGGTGCAGCAGGTAAA

GCGGGTTATCCTACCGGAACCGGTGTAGGTCCGCAGGCCGCTGCTGCC

GCCGCCGCAAAAGCAGCGGCTAAATTTGGCGCCGGAGCAGCGGGTGTT

CTGCCTGGAGTTGGTGGTGCGGGCGTGCCAGGGGTACCTGGTGCAATT

CCGGGTATTGGTGGTATTGCCGGTGTCGGCACCCCGGCCGCGGCAGCT

GCGGCAGCGGCGGCTGCCAAAGCTGCTAAATACGGTGCCGCGGCGGGT

CTGGTGCCAGGAGGTCCGGGTTTTGGTCCGGGAGTGGTTGGCGTGCCT

GGCGCAGGCGTTCCTGGTGTGGGCGTTCCAGGTGCAGGGATTCCTGTT

GTGCCTGGTGCCGGTATTCCCGGCGCGGCCGTTCCGGGGGTGGTTAGC

CCGGAAGCCGCAGCGAAGGCTGCGGCAAAGGCAGCAAAGTATGGCGCA

CGCCCAGGAGTCGGCGTGGGTGGTATCCCGACCTATGGGGTGGGCGCA

GGGGGTTTTCCTGGTTTCGGCGTAGGTGTAGGAGGTATACCGGGCGTG

GCCGGTGTACCAGGGGTTGGTGGCGTCCCTGGTGTTGGCGGTGTGCCA

GGTGTTGGTATTTCACCGGAAGCACAGGCAGCAGCCGCAGCTAAGGCA

GCGAAATATGGTGCCGCCGGCGCAGGAGTTTTAGGTGGGCTGGTTCCG

GGCCCGCAGGCAGCTGTGCCGGGGGTTCCAGGCACCGGTGGTGTCCCT

GGAGTCGGTACGCCGGCTGCAGCGGCAGCCAAAGCGGCTGCGAAAGCA

-continued

GCACAGTTTGGCTTAGTACCGGGTGTGGGAGTTGCCCCCGGCGTTGGC

GTTGCTCCAGGGGTGGGTGTTGCTCCTGGCGTCGGTCTGGCTCCTGGA

GTGGGCGTAGCACCCGGTGTGGGGGTGGCCCCGGGTGTTGGGGTTGCA

CCGGGTATCGGTCCGGGCGGTGTCGCAGCAGCAGCTAAAAGCGCGGCG

AAAGTTGCGGCCAAAGCCCAACTGCGCGCCGCCGCGGGCCTCGGTGCA

GGTATTCCGGGGCTGGGTGTCGGAGTTGGAGTCCCGGGTTTGGGCGTG

GGCGCGGGAGTTCCGGGACTGGGAGTGGGTGCCGGAGTTCCTGGCTTT

GGTGCAGGCGCAGATGAAGGTGTTCGTCGTAGCCTGAGTCCGGAACTG

CGTGAAGGTGATCCGAGTAGCAGCCAGCATCTGCCGAGCACCCCGAGC

AGCCCGCGTGTTCCGGGTGCATTAGCTGCAGCAAAAGCCGCCAAGTAT

GGTGCAGCCGTGCCGGGCGTCTTAGGTGGTCTGGGCGCCCTGGGTGGT

GTAGGCATTCCGGGAGGTGTTGTGGGTGCAGGACCGGCCGCCGCAGCT

GCGGCCGCCAAAGCAGCTGCAAAAGCGGCCCAGTTTGGTTTAGTGGGC

GCCGCAGGTTTAGGCGGTTTAGGTGTGGGTGGACTGGGTGTACCTGGC

GTAGGCGGTCTGGGTGGAATTCCGCCCGCAGCGGCCGCGAAAGCGGCA

AAATATGGCGCGGCAGGCCTGGGCGGCGTGCTGGGTGGGGCAGGTCAG

TTTCCGCTGGGCGGGGTTGCCGCACGTCCGGGATTTGGTCTGAGCCCG

ATTTTCCCTGGCGGCGCATGTCTGGGTAAAGCATGTGGTCGTAAACGT

AAAtaa (SEQ ID NO: 26)

MKKIWLALAGLVLAFSASAAQYEDMGGVPGAIPGGVPGGVFYPGAGLG

ALGGGALGPGGKPLKPVPGGLAGAGLGAGLGAFPAVTFPGALVPGGVA

DAAAAYKAAKAGAGLGGVPGVGGLGVSAGAVVPQPGAGVKPGKVPGVG

LPGVYPGGVLPGARFPGVGVLPGVPTGAGVKPKAPGVGGAFAGIPGVG

PFGGPQPGVPLGYPIKAPKLPGGYGLPYTTGKLPYGYGPGGVAGAAGK

AGYPTGTGVGPQAAAAAAAKAAAKFGAGAAGVLPGVGGAGVPGVPGAI

PGIGGIAGVGTPAAAAAAAAAAKAAKYGAAAGLVPGGPGFGPGVVGVP

GAGVPGVGVPGAGIPVVPGAGIPGAAVPGVVSPEAAAKAAAKAAKYGA

RPGVGVGGIPTYGVGAGGFPGFGVGVGGIPGVAGVPGVGGVPGVGGVP

GVGISPEAQAAAAAKAAKYGAAGAGVLGGLVPGPQAAVPGVPGTGGVP

GVGTPAAAAAKAAAKAAQFGLVPGVGVAPGVGVAPGVGVAPGVGLAPG

VGVAPGVGVAPGVGVAPGIGPGGVAAAAKSAAKVAAKAQLRAAAGLGA

GIPGLGVGVGVPGLGVGAGVPGLGVGAGVPGFGAGADEGVRRSLSPEL

REGDPSSSQHLPSTPSSPRVPGALAAAKAAKYGAAVPGVLGGLGALGG

VGIPGGVVGAGPAAAAAAAKAAAKAAQFGLVGAAGLGGLGVGGLGVPG

VGGLGGIPPAAAAKAAKYGAAGLGGVLGGAGQFPLGGVAARPGFGLSP

IFPGGACLGKACGRKRK

The polynucleotides of SEQ ID NO: 22 was codon optimized and synthesized by Gen9 DNA, now Ginkgo Bioworks internal synthesis. Overlaps between the pET28 vector and SEQ ID NO: 22 was designed to be between 30 and 40 bp long and added using PCR with the enzyme PrimeStar GXL polymerase (www.clontech.com/US/Products/PCR/GC_Rich/PrimeSTAR_GXL_DNA_Polymerase?sitex=10020:22372:US). The opened pET28a vector and insert DNA (SEQ ID NO: 22) was then assembled together into the final plasmid using SGI Gibson assembly (us.vwr.com/store/product/17613857/gibson-assembly-hifi-1-step-kit-synthetic-genomics-inc). Sequence of plasmid was then verified through sanger sequencing through Eurofins Genomics (www.eurofinsgenomics.com).

The transformed cells were cultivated in minimal media and frozen in 1.5 aliquots with glycerol at a ratio of 50:50 of cells to glycerol. One vial of this frozen culture was revived in 50 ml of minimal media overnight at 37° C., 200 rpm. Cells were transferred into 300 ml of minimal media and grown for 6-9 hours to reach an OD600 of 5-10.

A bioreactor was prepared with 2.7 L of minimal media+glucose and 300 ml of OD600 of 5-10 culture was added to bring the starting volume to 3 L. Cells were grown at 28° C., pH7 with Dissolved Oxygen maintained at 20% saturation using a cascade containing agitation, air and oxygen. pH was controlled using 28% w/w Ammonium hydroxide solution. Fermentation was run in a fed-batch mode using a DO-stat based feeding algorithm once the initial bolus of 40 g/L was depleted around 13 hours. After 24-26 hours of initial growth, the OD600 reached above 100. At this point, 300 mL of 500 g/L sucrose was added and temperature was reduced to 25 C. High density culture was induced for protein production using 1 mM IPTG. Fermentation was continued for another 20-24 hours and cells were harvested using a bench top centrifuge at 9000 rcf, 15C for 60 minutes. Cell pellet recovered from centrifugation was resuspended in a buffer containing 0.5M NaCl and 0.1M KH2PO4 at pH8 in a weight by weight ratio of 2× buffer to 1× cells.

The fermentations were performed at various temperature ranging from 25° to 28° C. For some fermentations, the temperature of the fermentation was maintained at a constant temperature and immediately upon completion of fermentation (OD600 of 5-10) the elastin was purified. For other fermentations, the temperature of the fermentations is maintained for a desired period of time and when cell densities of OD600 of 5-10 are reached, the temperature is reduced to induce protein production. Typically, the temperature is reduced from 28° C. to 25° C. After the fermentation at 25° C. is continued for 40-60 hours, the elastin is isolated.

The harvested cells were disrupted in a homogenizer at 14,000 psi pressure in 2 passes. Resulting slurry contained the collagen protein along with other proteins.

The supernatant from the homogenized cells was analyzed on an SDS-PAGE gel and a clear band was observed at around 70 kilodaltons corresponding to the expected size of 68 kilodaltons. The purified elastin is analyzed by mass spectrometry.

Full Length Elastin with DsbA Secretion Tag-His Tag-Linker-Thrombin Cleavage Site and GFP Beta-Lactamase Fusion A human elastin with DsbA secretion tag-His tag-Linker-Thrombin cleavage site and GFP Beta-lactamase fusion is disclosed below. The codon-optimized nucleotide sequence encoding this elastin is provided in SEQ ID NO: 27. The amino acid sequence is disclosed in SEQ ID NO: 28. The DsbA secretion tag is encoded by nucleotides 1-72 and encodes amino acids 1-24. The His tag is encoded by nucleotides 73-99 and encodes a 9 histidine tag (SEQ ID NO: 129) of amino acids 25-33. The linker is encoded by nucleotides 100-111 and encodes amino acids 34-37. The thrombin cleavage side is encoded by nucleotides 112-135 and encodes amino acids 38-45. The green fluorescent protein (GFP) with linker is encoded by nucleotides 136-873 and encodes amino acids 46-291. The full-length elastin sequence is encoded by nucleotides 874-3153 and encodes amino acids 292-1051. The Beta-lactamase with linker is encoded by nucleotides 3154-3945 and encodes amino acids 1052-1315.

(SEQ ID NO: 27)

ATGAAAAAGATTTGGCTGGCGCTGGCTGGTTTAGTTTTAGCGTTTAGC

GCATCGGCGGCGCAGTATGAAGATCACCATCACCACCACCACCATCAC

CACTCTGGCTCGAGCCTGGTGCCGCGCGGCAGCCATATGTCTGGCTCG

AGCAGTAAAGGTGAAGAACTGTTCACCGGTGTTGTTCCGATCCTGGTT

GAACTGGATGGTGATGTTAACGGCCACAAATTCTCTGTTCGTGGTGAA

GGTGAAGGTGATGCAACCAACGGTAAACTGACCCTGAAATTCATCTGC

ACTACCGGTAAACTGCCGGTTCCATGGCCGACTCTGGTGACTACCCTG

ACCTATGGTGTTCAGTGTTTTTCTCGTTACCCGGATCACATGAAGCAG

CATGATTTCTTCAAATCTGCAATGCCGGAAGGTTATGTACAGGAGCGC

ACCATTTCTTTCAAAGACGATGGCACCTACAAAACCCGTGCAGAGGTT

AAATTTGAAGGTGATACTCTGGTGAACCGTATTGAACTGAAAGGCATT

GATTTCAAAGAGGACGGCAACATCCTGGGCCACAAACTGGAATATAAC

TTCAACTCCCATAACGTTTACATCACCGCAGACAAACAGAAGAACGGT

ATCAAAGCTAACTTCAAAATTCGCCATAACGTTGAAGACGGTAGCGTA

CAGCTGGCGGACCACTACCAGCAGAACACTCCGATCGGTGATGGTCCG

GTTCTGCTGCCGGATAACCACTACCTGTCCACCCAGTCTaaaCTGTCC

AAAGACCCGAACGAAAAGCGCGACCACATGGTGCTGCTGGAGTTCGTT

ACTGCAGCAGGTATCACGCACGGCATGGATGAACTCTACAAATCTGGC

GCGCCGGGCGGTGGCGTACCAGGCGCAATTCCTGGGGGTGTCCCAGGC

GGTGTTTTTTATCCGGGCGCCGGTCTTGGCGCACTGGGTGGCGGTGCA

CTGGGCCCGGGCGGCAAACCGCTGAAACCGGTACCAGGTGGTTTAGCA

GGCGCCGGCTTAGGCGCAGGTCTGGGAGCATTTCCGGCAGTTACCTTT

CCAGGGGCACTGGTTCCTGGAGGTGTGGCCGATGCAGCCGCGGCATAT

AAAGCCGCTAAAGCCGGTGCGGGTTTAGGAGGCGTCCCAGGTGTCGGT

GGCCTGGGTGTTAGCGCCGGTGCAGTTGTTCCGCAGCCGGGAGCAGGG

GTTAAACCTGGTAAAGTGCCGGGAGTAGGTCTGCCAGGCGTTTATCCT

GGTGGTGTTTTGCCGGGTGCCCGTTTTCCGGGCGTTGGTGTTCTTCCA

GGCGTGCCGACCGGAGCCGGTGTTAAACCGAAAGCCCCCGGTGTTGGA

GGTGCATTTGCAGGCATCCCGGGAGTTGGCCCGTTTGGTGGTCCGCAA

CCTGGGGTTCCGTTAGGTTATCCGATTAAAGCACCGAAACTGCCCGGC

GGTTATGGTCTGCCGTACACAACCGGTAAACTGCCGTATGGTTATGGC

CCGGGTGGAGTTGCGGGTGCAGCAGGTAAAGCGGGTTATCCTACCGGA

ACCGGTGTAGGTCCGCAGGCCGCTGCTGCCGCCGCCGCAAAAGCAGCG

GCTAAATTTGGCGCCGGAGCAGCGGGTGTTCTGCCTGGAGTTGGTGGT

GCGGGCGTGCCAGGGGTACCTGGTGCAATTCCGGGTATTGGTGGTATT

GCCGGTGTCGGCACCCCGGCCGCGGCAGCTGCGGCAGCGGCGGCTGCC

AAAGCTGCTAAATACGGTGCCGCGGCGGGTCTGGTGCCAGGAGGTCCG

-continued

GGTTTTGGTCCGGGAGTGGTTGGCGTGCCTGGCGCAGGCGTTCCTGGT

GTGGGCGTTCCAGGTGCAGGGATTCCTGTTGTGCCTGGTGCCGGTATT

CCCGGCGCGGCCGTTCCGGGGGTGGTTAGCCCGGAAGCCGCAGCGAAG

GCTGCGGCAAAGGCAGCAAAGTATGGCGCACGCCCAGGAGTCGGCGTG

GGTGGTATCCCGACCTATGGGGTGGGCGCAGGGGGTTTTCCTGGTTTC

GGCGTAGGTGTAGGAGGTATACCGGGCGTGGCCGGTGTACCAGGGGTT

GGTGGCGTCCCTGGTGTTGGCGGTGTGCCAGGTGTTGGTATTTCACCG

GAAGCACAGGCAGCAGCCGCAGCTAAGGCAGCGAAATATGGTGCCGCC

GGCGCAGGAGTTTTAGGTGGGCTGGTTCCGGGCCCGCAGGCAGCTGTG

CCGGGGGTTCCAGGCACCGGTGGTGTCCCTGGAGTCGGTACGCCGGCT

GCAGCGGCAGCCAAAGCGGCTGCGAAAGCAGCACAGTTTGGCTTAGTA

CCGGGTGTGGGAGTTGCCCCCGGCGTTGGCGTTGCTCCAGGGGTGGGT

GTTGCTCCTGGCGTCGGTCTGGCTCCTGGAGTGGGCGTAGCACCCGGT

GTGGGGGTGGCCCCGGGTGTTGGGGTTGCACCGGGTATCGGTCCGGGC

GGTGTCGCAGCAGCAGCTAAAAGCGCGGCGAAAGTTGCGGCCAAAGCC

CAACTGCGCGCCGCCGCGGGCCTCGGTGCAGGTATTCCGGGGCTGGGT

GTCGGAGTTGGAGTCCCGGGTTTGGGCGTGGGCGCGGGAGTTCCGGGA

CTGGGAGTGGGTGCCGGAGTTCCTGGCTTTGGTGCAGGCGCAGATGAA

GGTGTTCGTCGTAGCCTGAGTCCGGAACTGCGTGAAGGTGATCCGAGT

AGCAGCCAGCATCTGCCGAGCACCCCGAGCAGCCCGCGTGTTCCGGGT

GCATTAGCTGCAGCAAAAGCCGCCAAGTATGGTGCAGCCGTGCCGGGC

GTCTTAGGTGGTCTGGGCGCCCTGGGTGGTGTAGGCATTCCGGGAGGT

GTTGTGGGTGCAGGACCGGCCGCCGCAGCTGCGGCCGCCAAAGCAGCT

GCAAAAGCGGCCCAGTTTGGTTTAGTGGGCGCCGCAGGTTTAGGCGGT

TTAGGTGTGGGTGGACTGGGTGTACCTGGCGTAGGCGGTCTGGGTGGA

ATTCCGCCCGCAGCGGCCGCGAAAGCGGCAAAATATGGCGCGGCAGGC

CTGGGCGGCGTGCTGGGTGGGGCAGGTCAGTTTCCGCTGGGCGGGGTT

GCCGCACGTCCGGGATTTGGTCTGAGCCCGATTTTCCCTGGCGGCGCA

TGTCTGGGTAAAGCATGTGGTCGTAAACGTAAAcacccagaaacgctg gtgaaagtaaaagatgctgaagatcagttgggtgcacgagtgggttac atcgaactggatctcaacagcggtaagatccttgagagttttcgcccc gaagaacgttttccaatgatgagcacttttaaagttctgctatgtggc gcggtattatcccgtattgacgccgggcaagagcaactcggtcgccgc atacactattctcagaatgacttggttgagtactcaccagtcacagaa aagcatcttacggatggcatgacagtaagagaattatgcagtgctgcc ataaccatgagtgataacactgcggccaacttacttctgacaacgatc ggaggaccgaaggagctaaccgcttttttgcacaacatgggggatcat gtaactcgccttgatcgttgggaaccggagctgaatgaagccatacca aacgacgagcgtgacaccacgatgcctgtagcaatggcaacaacgttg cgcaaactattaactggcgaactacttactctagcttcccggcaacaa ttaatagactggatggaggcggataaagttgcaggaccacttctgcgc

```
tcggcccttccggctggctggtttattgctgataaatctggagccggt

gagcgtgggtctcgcggtatcattgcagcactggggccagatggtaag

ccctcccgtatcgtagttatctacacgacggggagtcaggcaactatg

gatgaacgaaatagacagatcgctgagataggtgcctcactgattaag

cattggtaa
```

(SEQ ID NO: 28)
```
MKKIWLALAGLVLAFSASAAQYEDHHHHHHHHHSGSSLVPRGSHMSGS
SSKGEELFTGVVPILVELDGDVNGHKFSVRGEGEGDATNGKLTLKFIC
TTGKLPVPWPTLVTTLTYGVQCFSRYPDHMKQHDFFKSAMPEGYVQER
TISFKDDGTYKTRAEVKFEGDTLVNRIELKGIDFKEDGNILGHKLEYN
FNSHNVYITADKQKNGIKANFKIRHNVEDGSVQLADHYQQNTPIGDGP
VLLPDNHYLSTQSKLSKDPNEKRDHMVLLEFVTAAGITHGMDELYKSG
APGGGVPGAIPGGVPGGVFYPGAGLGALGGGALGPGGKPLKPVPGGLA
GAGLGAGLGAFPAVTFPGALVPGGVADAAAAYKAAKAGAGLGGVPGVG
GLGVSAGAVVPQPGAGVKPGKVPGVGLPGVYPGGVLPGARFPGVGVLP
GVPTGAGVKPKAPGVGGAFAGIPGVGPFGGPQPGVPLGYPIKAPKLPG
GYGLPYTTGKLPYGYGPGGVAGAAGKAGYPTGTGVGPQAAAAAAAKAA
AKFGAGAAGVLPGVGGAGVPGVPGAIPGIGGIAGVGTPAAAAAAAAAA
KAAKYGAAAGLVPGGPGFGPGVVGVPGAGVPGVGVPGAGIPVVPGAGI
PGAAVPGVVSPEAAAKAAAKAAKYGARPGVGVGGIPTYGVGAGGFPGF
GVGVGGIPGVAGVPGVGGVPGVGGVPGVGISPEAQAAAAAKAAKYGAA
GAGVLGGLVPGPQAAVPGVPGTGGVPGVGTPAAAAAKAAAKAAQFGLV
PGVGVAPGVGVAPGVGVAPGVGLAPGVGVAPGVGVAPGVGVAPGIGPG
GVAAAAKSAAKVAAKAQLRAAAGLGAGIPGLGVGVGVPGLGVGAGVPG
LGVGAGVPGFGAGADEGVRRSLSPELREGDPSSSQHLPSTPSSPRVPG
ALAAAKAAKYGAAVPGVLGGLGALGGVGIPGGVVGAGPAAAAAAAKAA
AKAAQFGLVGAAGLGGLGVGGLGVPGVGGLGGIPPAAAAKAAKYGAAG
LGGVLGGAGQFPLGGVAARPGFGLSPIFPGGACLGKACGRKRKHPETL
VKVKDAEDQLGARVGYIELDLNSGKILESFRPEERFPMMSTFKVLLCG
AVLSRIDAGQEQLGRRIHYSQNDLVEYSPVTEKHLTDGMTVRELCSAA
ITMSDNTAANLLLTTIGGPKELTAFLHNMGDHVTRLDRWEPELNEAIP
NDERDTTMPVAMATTLRKLLTGELLTLASRQQLIDWMEADKVAGPLLR
SALPAGWFIADKSGAGERGSRGIIAALGPDGKPSRIVVIYTTGSQATM
DERNRQIAEIGASLIKHW
```

Example 5: Production of Truncated Elastin

Truncated human elastin is produced using the expression system as described in Example 4. The full length amino acid sequence lacking the native secretion tag is disclosed in SEQ ID NO: 29.

(SEQ ID NO: 29)
```
GGVPGAIPGGVPGGVFYPGAGLGALGGGALGPGGKPLKPVPGGLAGAG
LGAGLGAFPAVTFPGALVPGGVADAAAAYKAAKAGAGLGGVPGVGGLG
VSAGAVVPQPGAGVKPGKVPGVGLPGVYPGGVLPGARFPGVGVLPGVP
TGAGVKPKAPGVGGAFAGIPGVGPFGGPQPGVPLGYPIKAPKLPGGYG
LPYTTGKLPYGYGPGGVAGAAGKAGYPTGTGVGPQAAAAAAAKAAAKF
GAGAAGVLPGVGGAGVPGVPGAIPGIGGIAGVGTPAAAAAAAAAAKAA
KYGAAAGLVPGGPGFGPGVVGVPGAGVPGVGVPGAGIPVVPGAGIPGA
AVPGVVSPEAAAKAAAKAAKYGARPGVGVGGIPTYGVGAGGFPGFGVG
VGGIPGVAGVPGVGGVPGVGGVPGVGISPEAQAAAAAKAAKYGAAGAG
VLGGLVPGPQAAVPGVPGTGGVPGVGTPAAAAAKAAAKAAQFGLVPGV
GVAPGVGVAPGVGVAPGVGLAPGVGVAPGVGVAPGVGVAPGIGPGGVA
AAAKSAAKVAAKAQLRAAAGLGAGIPGLGVGVGVPGLGVGAGVPGLGV
GAGVPGFGAGADEGVRRSLSPELREGDPSSSQHLPSTPSSPRVPGALA
AAKAAKYGAAVPGVLGGLGALGGVGIPGGVVGAGPAAAAAAAKAAAKA
AQFGLVGAAGLGGLGVGGLGVPGVGGLGGIPPAAAAKAAKYGAAGLGG
VLGGAGQFPLGGVAARPGFGLSPIFPGGACLGKACGRKRK
```

The codon optimized polynucleotide sequence encoding the full length human elastin lacking the native secretion tag is disclosed in SEQ ID NO: 30.

(SEQ ID NO: 30)
```
GGTGGCGTACCAGGCGCAATTCCTGGGGGTGTCCCAGGCGGTGTTTTT
TATCCGGGCGCCGGTCTTGGCGCACTGGGTGGCGGTGCACTGGGCCCG
GGCGGCAAACCGCTGAAACCGGTACCAGGTGGTTTAGCAGGCGCCGGC
TTAGGCGCAGGTCTGGGAGCATTTCCGGCAGTTACCTTTCCAGGGGCA
CTGGTTCCTGGAGGTGTGGCCGATGCAGCCGCGGCATATAAAGCCGCT
AAAGCCGGTGCGGGTTTAGGAGGCGTCCCAGGTGTCGGTGGCCTGGGT
GTTAGCGCCGGTGCAGTTGTTCCGCAGCCGGGAGCAGGGGTTAAACCT
GGTAAAGTGCCGGGAGTAGGTCTGCCAGGCGTTTATCCTGGTGGTGTT
TTGCCGGGTGCCCGTTTTCCGGGCGTTGGTGTTCTTCCAGGCGTGCCG
ACCGGAGCCGGTGTTAAACCGAAAGCCCCCGGTGTTGGAGGTGCATTT
GCAGGCATCCCGGGAGTTGGCCCGTTTGGTGGTCCGCAACCTGGGGTT
CCGTTAGGTTATCCGATTAAAGCACCGAAACTGCCCGGCGGTTATGGT
CTGCCGTACACAACCGGTAAACTGCCGTATGGTTATGGCCCGGGTGGA
GTTGCGGGTGCAGCAGGTAAAGCGGGTTATCCTACCGGAACCGGTGTA
GGTCCGCAGGCCGCTGCTGCCGCCGCCGCAAAAGCAGCGGCTAAATTT
GGCGCCGGAGCAGCGGGTGTTCTGCCTGGAGTTGGTGGTGCGGGCGTG
CCAGGGGTACCTGGTGCAATTCCGGGTATTGGTGGTATTGCCGGTGTC
GGCACCCCGGCCGCGGCAGCTGCGGCAGCGGCGGCTGCCAAAGCTGCT
AAATACGGTGCCGCGGCGGGTCTGGTGCCAGGAGGTCCGGGTTTTGGT
CCGGGAGTGGTTGGCGTGCCTGGCGCAGGCGTTCCTGGTGTGGGCGTT
CCAGGTGCAGGGATTCCTGTTGTGCCTGGTGCCGGTATTCCCGGCGCG
```

-continued

GCCGTTCCGGGGGTGGTTAGCCCGGAAGCCGCAGCGAAGGCTGCGGCA

AAGGCAGCAAAGTATGGCGCACGCCCAGGAGTCGGCGTGGGTGGTATC

CCGACCTATGGGGTGGGCGCAGGGGGTTTTCCTGGTTTCGGCGTAGGT

GTAGGAGGTATACCGGGCGTGGCCGGTGTACCAGGGGTTGGTGGCGTC

CCTGGTGTTGGCGGTGTGCCAGGTGTTGGTATTTCACCGGAAGCACAG

GCAGCAGCCGCAGCTAAGGCAGCGAAATATGGTGCCGCCGGCGCAGGA

GTTTTAGGTGGGCTGGTTCCGGGCCCGCAGGCAGCTGTGCCGGGGGTT

CCAGGCACCGGTGGTGTCCCTGGAGTCGGTACGCCGGCTGCAGCGGCA

GCCAAAGCGGCTGCGAAAGCAGCACAGTTTGGCTTAGTACCGGGTGTG

GGAGTTGCCCCCGGCGTTGGCGTTGCTCCAGGGGTGGGTGTTGCTCCT

GGCGTCGGTCTGGCTCCTGGAGTGGGCGTAGCACCCGGTGTGGGGGTG

GCCCCGGGTGTTGGGGTTGCACCGGGTATCGGTCCGGGCGGTGTCGCA

GCAGCAGCTAAAAGCGCGGCGAAAGTTGCGGCCAAAGCCCAACTGCGC

GCCGCCGCGGGCCTCGGTGCAGGTATTCCGGGGCTGGGTGTCGGAGTT

GGAGTCCCGGGTTTGGGCGTGGGCGCGGGAGTTCCGGGACTGGGAGTG

GGTGCCGGAGTTCCTGGCTTTGGTGCAGGCGCAGATGAAGGTGTTCGT

CGTAGCCTGAGTCCGGAACTGCGTGAAGGTGATCCGAGTAGCAGCCAG

CATCTGCCGAGCACCCCGAGCAGCCCGCGTGTTCCGGGTGCATTAGCT

GCAGCAAAAGCCGCCAAGTATGGTGCAGCCGTGCCGGGCGTCTTAGGT

GGTCTGGGCGCCCTGGGTGGTGTAGGCATTCCGGGAGGTGTTGTGGGT

GCAGGACCGGCCGCCGCAGCTGCGGCCGCCAAAGCAGCTGCAAAAGCG

GCCCAGTTTGGTTTAGTGGGCGCCGCAGGTTTAGGCGGTTTAGGTGTG

GGTGGACTGGGTGTACCTGGCGTAGGCGGTCTGGGTGGAATTCCGCCC taa

The amino acid sequence of a 60.7 kDa human elastin truncated at the C-terminal is disclosed in SEQ ID NO: 31. The 60.7 kDa truncated elastin has amino acids 706-761 deleted from the full length elastin.

(SEQ ID NO: 31)

GGVPGAIPGGVPGGVFYPGAGLGALGGGALGPGGKPLKPVPGGLAGAG

LGAGLGAFPAVTFPGALVPGGVADAAAAYKAAKAGAGLGGVPGVGGLG

VSAGAVVPQPGAGVKPGKVPGVGLPGVYPGGVLPGARFPGVGVLPGVP

TGAGVKPKAPGVGGAFAGIPGVGPFGGPQPGVPLGYPIKAPKLPGGYG

LPYTTGKLPYGYGPGGVAGAAGKAGYPTGTGVGPQAAAAAAAKAAAKF

GAGAAGVLPGVGGAGVPGVPGAIPGIGGIAGVGTPAAAAAAAAAAKAA

KYGAAAGLVPGGPGFGPGVVGVPGAGVPGVGVPGAGIPVVPGAGIPGA

AVPGVVSPEAAAKAAAKAAKYGARPGVGVGGIPTYGVGAGGFPGFGVG

VGGIPGVAGVPGVGGVPGVGGVPGVGISPEAQAAAAAKAAKYGAAGAG

VLGGLVPGPQAAVPGVPGTGGVPGVGTPAAAAAKAAAKAAQFGLVPGV

GVAPGVGVAPGVGVAPGVGLAPGVGVAPGVGVAPGVGVAPGIGPGGVA

AAAKSAAKVAAKAQLRAAAGLGAGIPGLGVGVGVPGLGVGAGVPGLGV

-continued

GAGVPGFGAGADEGVRRSLSPELREGDPSSSQHLPSTPSSPRVPGALA

AAKAAKYGAAVPGVLGGLGALGGVGIPGGVVGAGPAAAAAAAKAAAKA

AQFGLVGAAGLGGLGVGGLGVPGVGGLGGIPP

The codon optimized polynucleotide sequence encoding the truncated 60.7 kDa human elastin is disclosed in SEQ ID NO: 32.

(SEQ ID NO: 32)

GGTGGCGTACCAGGCGCAATTCCTGGGGGTGTCCCAGGCGGTGTTTTT

TATCCGGGCGCCGGTCTTGGCGCACTGGGTGGCGGTGCACTGGGCCCG

GGCGGCAAACCGCTGAAACCGGTACCAGGTGGTTTAGCAGGCGCCGGC

TTAGGCGCAGGTCTGGGAGCATTTCCGGCAGTTACCTTTCCAGGGGCA

CTGGTTCCTGGAGGTGTGGCCGATGCAGCCGCGGCATATAAAGCCGCT

AAAGCCGGTGCGGGTTTAGGAGGCGTCCCAGGTGTCGGTGGCCTGGGT

GTTAGCGCCGGTGCAGTTGTTCCGCAGCCGGGAGCAGGGGTTAAACCT

GGTAAAGTGCCGGGAGTAGGTCTGCCAGGCGTTTATCCTGGTGGTGTT

TTGCCGGGTGCCCGTTTTCCGGGCGTTGGTGTTCTTCCAGGCGTGCCG

ACCGGAGCCGGTGTTAAACCGAAAGCCCCCGGTGTTGGAGGTGCATTT

GCAGGCATCCCGGGAGTTGGCCCGTTTGGTGGTCCGCAACCTGGGGTT

CCGTTAGGTTATCCGATTAAAGCACCGAAACTGCCCGGCGGTTATGGT

CTGCCGTACACAACCGGTAAACTGCCGTATGGTTATGGCCCGGGTGGA

GTTGCGGGTGCAGCAGGTAAAGCGGGTTATCCTACCGGAACCGGTGTA

GGTCCGCAGGCCGCTGCTGCCGCCGCCGCAAAAGCAGCGGCTAAATTT

GGCGCCGGAGCAGCGGGTGTTCTGCCTGGAGTTGGTGGTGCGGGCGTG

CCAGGGGTACCTGGTGCAATTCCGGGTATTGGTGGTATTGCCGGTGTC

GGCACCCCGGCCGCGGCAGCTGCGGCAGCGGCGGCTGCCAAAGCTGCT

AAATACGGTGCCGCGGCGGGTCTGGTGCCAGGAGGTCCGGGTTTTGGT

CCGGGAGTGGTTGGCGTGCCTGGCGCAGGCGTTCCTGGTGTGGGCGTT

CCAGGTGCAGGGATTCCTGTTGTGCCTGGTGCCGGTATTCCCGGCGCG

GCCGTTCCGGGGGTGGTTAGCCCGGAAGCCGCAGCGAAGGCTGCGGCA

AAGGCAGCAAAGTATGGCGCACGCCCAGGAGTCGGCGTGGGTGGTATC

CCGACCTATGGGGTGGGCGCAGGGGGTTTTCCTGGTTTCGGCGTAGGT

GTAGGAGGTATACCGGGCGTGGCCGGTGTACCAGGGGTTGGTGGCGTC

CCTGGTGTTGGCGGTGTGCCAGGTGTTGGTATTTCACCGGAAGCACAG

GCAGCAGCCGCAGCTAAGGCAGCGAAATATGGTGCCGCCGGCGCAGGA

GTTTTAGGTGGGCTGGTTCCGGGCCCGCAGGCAGCTGTGCCGGGGGTT

CCAGGCACCGGTGGTGTCCCTGGAGTCGGTACGCCGGCTGCAGCGGCA

GCCAAAGCGGCTGCGAAAGCAGCACAGTTTGGCTTAGTACCGGGTGTG

GGAGTTGCCCCCGGCGTTGGCGTTGCTCCAGGGGTGGGTGTTGCTCCT

GGCGTCGGTCTGGCTCCTGGAGTGGGCGTAGCACCCGGTGTGGGGGTG

GCCCCGGGTGTTGGGGTTGCACCGGGTATCGGTCCGGGCGGTGTCGCA

GCAGCAGCTAAAAGCGCGGCGAAAGTTGCGGCCAAAGCCCAACTGCGC

-continued

```
GCCGCCGCGGGCCTCGGTGCAGGTATTCCGGGGCTGGGTGTCGGAGTT
GGAGTCCCGGGTTTGGGCGTGGGCGCGGGAGTTCCGGGACTGGGAGTG
GGTGCCGGAGTTCCTGGCTTTGGTGCAGGCGCAGATGAAGGTGTTCGT
CGTAGCCTGAGTCCGGAACTGCGTGAAGGTGATCCGAGTAGCAGCCAG
CATCTGCCGAGCACCCCGAGCAGCCCGCGTGTTCCGGGTGCATTAGCT
GCAGCAAAAGCCGCCAAGTATGGTGCAGCCGTGCCGGGCGTCTTAGGT
GGTCTGGGCGCCCTGGGTGGTGTAGGCATTCCGGGAGGTGTTGTGGGT
GCAGGACCGGCCGCCGCAGCTGCGGCCGCCAAAGCAGCTGCAAAAGCG
GCCCAGTTTGGTTTAGTGGGCGCCGCAGGTTTAGGCGGTTTAGGTGTG
GGTGGACTGGGTGTACCTGGCGTAGGCGGTCTGGGTGGAATTCCGCCC
taa
```

The amino acid sequence of a 58.8 kDa human elastin truncated at the N-terminal is disclosed in SEQ ID NO: 33. The 58.8 kDa truncated elastin has amino acids 2-85 deleted from the full length elastin.

```
(SEQ ID NO: 33)
GLGGVPGVGGLGVSAGAVVPQPGAGVKPGKVPGVGLPGVYPGGVLPGA
RFPGVGVLPGVPTGAGVKPKAPGVGGAFAGIPGVGPFGGPQPGVPLGY
PIKAPKLPGGYGLPYTTGKLPYGYGPGGVAGAAGKAGYPTGTGVGPQA
AAAAAAKAAAKFGAGAAGVLPGVGGAGVPGVPGAIPGIGGIAGVGTPA
AAAAAAAAAKAAKYGAAAGLVPGGPGFGPGVVGVPGAGVPGVGVPGAG
IPVVPGAGIPGAAVPGVVSPEAAAKAAAKAAKYGARPGVGVGGIPTYG
VGAGGFPGFGVGVGGIPGVAGVPGVGGVPGVGGVPGVGISPEAQAAAA
AKAAKYGAAGAGVLGGLVPGPQAAVPGVPGTGGVPGVGTPAAAAAKAA
AKAAQFGLVPGVGVAPGVGVAPGVGVAPGVGLAPGVGVAPGVGVAPGV
GVAPGIGPGGVAAAAKSAAKVAAKAQLRAAAGLGAGIPGLGVGVGVPG
LGVGAGVPGLGVGAGVPGFGAGADEGVRRSLSPELREGDPSSSQHLPS
TPSSPRVPGALAAAKAAKYGAAVPGVLGGLGALGGVGIPGGVVGAGPA
AAAAAAKAAAKAAQFGLVGAAGLGGLGVGGLGVPGVGGLGGIPPAAAA
KAAKYGAAGLGGVLGGAGQFPLGGVAARPGFGLSPIFPGGACLGKACG
RKRK
```

The codon optimized polynucleotide sequence encoding the 58.8 kDa truncated human elastin is disclosed in SEQ ID NO: 34.

```
(SEQ ID NO: 34)
GGTTTAGGAGGCGTCCCAGGTGTCGGTGGCCTGGGTGTTAGCGCCGGTGC
AGTTGTTCCGCAGCCGGGAGCAGGGGTTAAACCTGGTAAAGTGCCGGGAG
TAGGTCTGCCAGGCGTTTATCCTGGTGGTGTTTTGCCGGGTGCCCGTTTT
CCGGGCGTTGGTGTTCTTCCAGGCGTGCCGACCGGAGCCGGTGTTAAACC
GAAAGCCCCCGGTGTTGGAGGTGCATTTGCAGGCATCCCGGGAGTTGGCC
CGTTTGGTGGTCCGCAACCTGGGGTTCCGTTAGGTTATCCGATTAAAGCA
CCGAAACTGCCCGGCGGTTATGGTCTGCCGTACACAACCGGTAAACTGCC
GTATGGTTATGGCCCGGGTGGAGTTGCGGGTGCAGCAGGTAAAGCGGGTT
ATCCTACCGGAACCGGTGTAGGTCCGCAGGCCGCTGCTGCCGCCGCCGCA
AAAGCAGCGGCTAAATTTGGCGCCGGAGCAGCGGGTGTTCTGCCTGGAGT
TGGTGGTGCGGGCGTGCCAGGGGTACCTGGTGCAATTCCGGGTATTGGTG
GTATTGCCGGTGTCGGCACCCCGGCCGCGGCAGCTGCGGCAGCGGCGGCT
GCCAAAGCTGCTAAATACGGTGCCGCGGCGGGTCTGGTGCCAGGAGGTCC
GGGTTTTGGTCCGGGAGTGGTTGGCGTGCCTGGCGCAGGCGTTCCTGGTG
TGGGCGTTCCAGGTGCAGGGATTCCTGTTGTGCCTGGTGCCGGTATTCCC
GGCGCGGCCGTTCCGGGGGTGGTTAGCCCGGAAGCCGCAGCGAAGGCTGC
GGCAAAGGCAGCAAAGTATGGCGCACGCCCAGGAGTCGGCGTGGGTGGTA
TCCCGACCTATGGGGTGGGCGCAGGGGGTTTTCCTGGTTTCGGCGTAGGT
GTAGGAGGTATACCGGGCGTGGCCGGTGTACCAGGGGTTGGTGGCGTCCC
TGGTGTTGGCGGTGTGCCAGGTGTTGGTATTTCACCGGAAGCACAGGCAG
CAGCCGCAGCTAAGGCAGCGAAATATGGTGCCGCCGGCGCAGGAGTTTTA
GGTGGGCTGGTTCCGGGCCCGCAGGCAGCTGTGCCGGGGGTTCCAGGCAC
CGGTGGTGTCCCTGGAGTCGGTACGCCGGCTGCAGCGGCAGCCAAAGCGG
CTGCGAAAGCAGCACAGTTTGGCTTAGTACCGGGTGTGGGAGTTGCCCCC
GGCGTTGGCGTTGCTCCAGGGGTGGGTGTTGCTCCTGGCGTCGGTCTGGC
TCCTGGAGTGGGCGTAGCACCCGGTGTGGGGGTGGCCCCGGGTGTTGGGG
TTGCACCGGGTATCGGTCCGGGCGGTGTCGCAGCAGCAGCTAAAAGCGCG
GCGAAAGTTGCGGCCAAAGCCCAACTGCGCGCCGCCGCGGGCCTCGGTGC
AGGTATTCCGGGGCTGGGTGTCGGAGTTGGAGTCCCGGGTTTGGGCGTGG
GCGCGGGAGTTCCGGGACTGGGAGTGGGTGCCGGAGTTCCTGGCTTTGGT
GCAGGCGCAGATGAAGGTGTTCGTCGTAGCCTGAGTCCGGAACTGCGTGA
AGGTGATCCGAGTAGCAGCCAGCATCTGCCGAGCACCCCGAGCAGCCCGC
GTGTTCCGGGTGCATTAGCTGCAGCAAAAGCCGCCAAGTATGGTGCAGCC
GTGCCGGGCGTCTTAGGTGGTCTGGGCGCCCTGGGTGGTGTAGGCATTCC
GGGAGGTGTTGTGGGTGCAGGACCGGCCGCCGCAGCTGCGGCCGCCAAAG
CAGCTGCAAAAGCGGCCCAGTTTGGTTTAGTGGGCGCCGCAGGTTTAGGC
GGTTTAGGTGTGGGTGGACTGGGTGTACCTGGCGTAGGCGGTCTGGGTGG
AATTCCGCCCGCAGCGGCCGCGAAAGCGGCAAAATATGGCGCGGCAGGCC
TGGGCGGCGTGCTGGGTGGGGCAGGTCAGTTTCCGCTGGGCGGGGTTGCC
GCACGTCCGGGATTTGGTCTGAGCCCGATTTTCCCTGGCGGCGCATGTCT
GGGTAAAGCATGTGGTCGTAAACGTAAAtaa
```

The amino acid sequence of a 57 kDa human elastin truncated at the C-terminal is disclosed in SEQ ID NO: 35. The 57 kDa truncated elastin has amino acids 661-761 deleted from the full length elastin.

```
(SEQ ID NO: 35)
GGVPGAIPGGVPGGVFYPGAGLGALGGGALGPGGKPLKPVPGGLAGAGLG
AGLGAFPAVTFPGALVPGGVADAAAAYKAAKAGAGLGGVPGVGGLGVSAG
AVVPQPGAGVKPGKVPGVGLPGVYPGGVLPGARFPGVGVLPGVPTGAGVK
```

PKAPGVGGAFAGIPGVGPFGGPQPGVPLGYPIKAPKLPGGYGLPYTTGKL

PYGYGPGGVAGAAGKAGYPTGTGVGPQAAAAAAAKAAAKFGAGAAGVLPG

VGGAGVPGVPGAIPGIGGIAGVGTPAAAAAAAAAAKAAKYGAAAGLVPGG

PGFGPGVVGVPGAGVPGVGVPGAGIPVVPGAGIPGAAVPGVVSPEAAAKA

AAKAAKYGARPGVGVGGIPTYGVGAGGFPGFGVGVGGIPGVAGVPGVGGV

PGVGGVPGVGISPEAQAAAAAKAAKYGAAGAGVLGGLVPGPQAAVPGVPG

TGGVPGVGTPAAAAAKAAAKAAQFGLVPGVGVAPGVGVAPGVGVAPGVGL

APGVGVAPGVGVAPGVGVAPGIGPGGVAAAAKSAAKVAAKAQLRAAAGLG

AGIPGLGVGVGVPGLGVGAGVPGLGVGAGVPGFGAGADEGVRRSLSPELR

EGDPSSSQHLPSTPSSPRVPGALAAAKAAKYGAAVPGVLGGLGALGGVGI

PGGVVGAGP

The codon optimized polynucleotide sequence encoding the 57 kDa truncated human elastin is disclosed in SEQ ID NO: 36

(SEQ ID NO: 36)
GGTGGCGTACCAGGCGCAATTCCTGGGGGTGTCCCAGGCGGTGTTTTTTA

TCCGGGCGCCGGTCTTGGCGCACTGGGTGGCGGTGCACTGGGCCCGGGCG

GCAAACCGCTGAAACCGGTACCAGGTGGTTTAGCAGGCGCCGGCTTAGGC

GCAGGTCTGGGAGCATTTCCGGCAGTTACCTTTCCAGGGGCACTGGTTCC

TGGAGGTGTGGCCGATGCAGCCGCGGCATATAAAGCCGCTAAAGCCGGTG

CGGGTTTAGGAGGCGTCCCAGGTGTCGGTGGCCTGGGTGTTAGCGCCGGT

GCAGTTGTTCCGCAGCCGGGAGCAGGGGTTAAACCTGGTAAAGTGCCGGG

AGTAGGTCTGCCAGGCGTTTATCCTGGTGGTGTTTTGCCGGGTGCCCGTT

TTCCGGGCGTTGGTGTTCTTCCAGGCGTGCCGACCGGAGCCGGTGTTAAA

CCGAAAGCCCCCGGTGTTGGAGGTGCATTTGCAGGCATCCCGGGAGTTGG

CCCGTTTGGTGGTCCGCAACCTGGGGTTCCGTTAGGTTATCCGATTAAAG

CACCGAAACTGCCCGGCGGTTATGGTCTGCCGTACACAACCGGTAAACTG

CCGTATGGTTATGGCCCGGGTGGAGTTGCGGGTGCAGCAGGTAAAGCGGG

TTATCCTACCGGAACCGGTGTAGGTCCGCAGGCCGCTGCTGCCGCCGCCG

CAAAAGCAGCGGCTAAATTTGGCGCCGGAGCAGCGGGTGTTCTGCCTGGA

GTTGGTGGTGCGGGCGTGCCAGGGGTACCTGGTGCAATTCCGGGTATTGG

TGGTATTGCCGGTGTCGGCACCCCGGCCGCGGCAGCTGCGGCAGCGGCGG

CTGCCAAAGCTGCTAAATACGGTGCCGCGGCGGGTCTGGTGCCAGGAGGT

CCGGGTTTTGGTCCGGGAGTGGTTGGCGTGCCTGGCGCAGGCGTTCCTGG

TGTGGGCGTTCCAGGTGCAGGGATTCCTGTTGTGCCTGGTGCCGGTATTC

CCGGCGCGGCCGTTCCGGGGGTGGTTAGCCCGGAAGCCGCAGCGAAGGCT

GCGGCAAAGGCAGCAAAGTATGGCGCACGCCCAGGAGTCGGCGTGGGTGG

TATCCCGACCTATGGGGTGGGCGCAGGGGGTTTTCCTGGTTTCGGCGTAG

GTGTAGGAGGTATACCGGGCGTGGCCGGTGTACCAGGGGTTGGTGGCGTC

CCTGGTGTTGGCGGTGTGCCAGGTGTTGGTATTTCACCGGAAGCACAGGC

AGCAGCCGCAGCTAAGGCAGCGAAATATGGTGCCGCCGGCGCAGGAGTTT

TAGGTGGGCTGGTTCCGGGCCCGCAGGCAGCTGTGCCGGGGGTTCCAGGC

ACCGGTGGTGTCCCTGGAGTCGGTACGCCGGCTGCAGCGGCAGCCAAAGC

GGCTGCGAAAGCAGCACAGTTTGGCTTAGTACCGGGTGTGGGAGTTGCCC

CCGGCGTTGGCGTTGCTCCAGGGGTGGGTGTTGCTCCTGGCGTCGGTCTG

GCTCCTGGAGTGGGCGTAGCACCCGGTGTGGGGGTGGCCCCGGGTGTTGG

GGTTGCACCGGGTATCGGTCCGGGCGGTGTCGCAGCAGCAGCTAAAAGCG

CGGCGAAAGTTGCGGCCAAAGCCCAACTGCGCGCCGCCGCGGGCCTCGGT

GCAGGTATTCCGGGGCTGGGTGTCGGAGTTGGAGTCCCGGGTTTGGGCGT

GGGCGCGGGAGTTCCGGGACTGGGAGTGGGTGCCGGAGTTCCTGGCTTTG

GTGCAGGCGCAGATGAAGGTGTTCGTCGTAGCCTGAGTCCGGAACTGCGT

GAAGGTGATCCGAGTAGCAGCCAGCATCTGCCGAGCACCCCGAGCAGCCC

GCGTGTTCCGGGTGCATTAGCTGCAGCAAAAGCCGCCAAGTATGGTGCAG

CCGTGCCGGGCGTCTTAGGTGGTCTGGGCGCCCTGGGTGGTGTAGGCATT

CCGGGAGGTGTTGTGGGTGCAGGACCGtaa

The amino acid sequence of a 53.9 kDa human elastin truncated at the C-terminal is disclosed in SEQ ID NO: 37. The 53.9 kDa truncated elastin has amino acids 624-761 deleted from the full length elastin.

(SEQ ID NO: 37)
GGVPGAIPGGVPGGVFYPGAGLGALGGGALGPGGKPLKPVPGGLAGAGLG

AGLGAFPAVTFPGALVPGGVADAAAAYKAAKAGAGLGGVPGVGGLGVSAG

AVVPQPGAGVKPGKVPGVGLPGVYPGGVLPGARFPGVGVLPGVPTGAGVK

PKAPGVGGAFAGIPGVGPFGGPQPGVPLGYPIKAPKLPGGYGLPYTTGKL

PYGYGPGGVAGAAGKAGYPTGTGVGPQAAAAAAAKAAAKFGAGAAGVLPG

VGGAGVPGVPGAIPGIGGIAGVGTPAAAAAAAAAAKAAKYGAAAGLVPGG

PGFGPGVVGVPGAGVPGVGVPGAGIPVVPGAGIPGAAVPGVVSPEAAAKA

AAKAAKYGARPGVGVGGIPTYGVGAGGFPGFGVGVGGIPGVAGVPGVGGV

PGVGGVPGVGISPEAQAAAAAKAAKYGAAGAGVLGGLVPGPQAAVPGVPG

TGGVPGVGTPAAAAAKAAAKAAQFGLVPGVGVAPGVGVAPGVGVAPGVGL

APGVGVAPGVGVAPGVGVAPGIGPGGVAAAAKSAAKVAAKAQLRAAAGLG

AGIPGLGVGVGVPGLGVGAGVPGLGVGAGVPGFGAGADEGVRRSLSPELR

EGDPSSSQHLPSTPSSPRVPGA

The codon optimized polynucleotide sequence encoding the 53.9 kDa truncated human elastin is disclosed in SEQ ID NO: 38

(SEQ ID NO: 38)
GGTGGCGTACCAGGCGCAATTCCTGGGGGTGTCCCAGGCGGTGTTTTTTA

TCCGGGCGCCGGTCTTGGCGCACTGGGTGGCGGTGCACTGGGCCCGGGCG

GCAAACCGCTGAAACCGGTACCAGGTGGTTTAGCAGGCGCCGGCTTAGGC

GCAGGTCTGGGAGCATTTCCGGCAGTTACCTTTCCAGGGGCACTGGTTCC

TGGAGGTGTGGCCGATGCAGCCGCGGCATATAAAGCCGCTAAAGCCGGTG

CGGGTTTAGGAGGCGTCCCAGGTGTCGGTGGCCTGGGTGTTAGCGCCGGT

-continued

GCAGTTGTTCCGCAGCCGGGAGCAGGGGTTAAACCTGGTAAAGTGCCGGG
AGTAGGTCTGCCAGGCGTTTATCCTGGTGGTGTTTTGCCGGGTGCCCGTT
TTCCGGGCGTTGGTGTTCTTCCAGGCGTGCCGACCGGAGCCGGTGTTAAA
CCGAAAGCCCCCGGTGTTGGAGGTGCATTTGCAGGCATCCCGGGAGTTGG
CCCGTTTGGTGGTCCGCAACCTGGGGTTCCGTTAGGTTATCCGATTAAAG
CACCGAAACTGCCCGGCGGTTATGGTCTGCCGTACACAACCGGTAAACTG
CCGTATGGTTATGGCCCGGGTGGAGTTGCGGGTGCAGCAGGTAAAGCGGG
TTATCCTACCGGAACCGGTGTAGGTCCGCAGGCCGCTGCTGCCGCCGCCG
CAAAAGCAGCGGCTAAATTTGGCGCCGGAGCAGCGGGTGTTCTGCCTGGA
GTTGGTGGTGCGGGCGTGCCAGGGGTACCTGGTGCAATTCCGGGTATTGG
TGGTATTGCCGGTGTCGGCACCCCGGCCGCGGCAGCTGCGGCAGCGGCGG
CTGCCAAAGCTGCTAAATACGGTGCCGCGGCGGGTCTGGTGCCAGGAGGT
CCGGGTTTTGGTCCGGGAGTGGTTGGCGTGCCTGGCGCAGGCGTTCCTGG
TGTGGGCGTTCCAGGTGCAGGGATTCCTGTTGTGCCTGGTGCCGGTATTC
CCGGCGCGGCCGTTCCGGGGGTGGTTAGCCCGGAAGCCGCAGCGAAGGCT
GCGGCAAAGGCAGCAAAGTATGGCGCACGCCCAGGAGTCGGCGTGGGTGG
TATCCCGACCTATGGGGTGGGCGCAGGGGGTTTTCCTGGTTTCGGCGTAG
GTGTAGGAGGTATACCGGGCGTGGCCGGTGTACCAGGGGTTGGTGGCGTC
CCTGGTGTTGGCGGTGTGCCAGGTGTTGGTATTTCACCGGAAGCACAGGC
AGCAGCCGCAGCTAAGGCAGCGAAATATGGTGCCGCCGGCGCAGGAGTTT
TAGGTGGGCTGGTTCCGGGCCCGCAGGCAGCTGTGCCGGGGGTTCCAGGC
ACCGGTGGTGTCCCTGGAGTCGGTACGCCGGCTGCAGCGGCAGCCAAAGC
GGCTGCGAAAGCAGCACAGTTTGGCTTAGTACCGGGTGTGGGAGTTGCCC
CCGGCGTTGGCGTTGCTCCAGGGGTGGGTGTTGCTCCTGGCGTCGGTCTG
GCTCCTGGAGTGGGCGTAGCACCCGGTGTGGGGGTGGCCCCGGGTGTTGG
GGTTGCACCGGGTATCGGTCCGGGCGGTGTCGCAGCAGCAGCTAAAAGCG
CGGCGAAAGTTGCGGCCAAAGCCCAACTGCGCGCCGCCGCGGGCCTCGGT
GCAGGTATTCCGGGGCTGGGTGTCGGAGTTGGAGTCCCGGGTTTGGGCGT
GGGCGCGGGAGTTCCGGGACTGGGAGTGGGTGCCGGAGTTCCTGGCTTTG
GTGCAGGCGCAGATGAAGGTGTTCGTCGTAGCCTGAGTCCGGAACTGCGT
GAAGGTGATCCGAGTAGCAGCCAGCATCTGCCGAGCACCCCGAGCAGCCC
GCGTGTTCCGGGTGCAtaa The amino acid sequence of a 45.3 kDa human elastin truncated at the C-terminal is disclosed in SEQ ID NO: 39. The 45.3 kDa truncated elastin has amino acids 529-761 deleted from the full length elastin.

(SEQ ID NO: 39)
GGVPGAIPGGVPGGVFYPGAGLGALGGGALGPGGKPLKPVPGGLAGAGLG
AGLGAFPAVTFPGALVPGGVADAAAAYKAAKAGAGLGGVPGVGGLGVSAG
AVVPQPGAGVKPGKVPGVGLPGVYPGGVLPGARFPGVGVLPGVPTGAGVK
PKAPGVGGAFAGIPGVGPFGGPQPGVPLGYPIKAPKLPGGYGLPYTTGKL
PYGYGPGGVAGAAGKAGYPTGTGVGPQAAAAAAAKAAAKFGAGAAGVLPG
VGGAGVPGVPGAIPGIGGIAGVGTPAAAAAAAAAKAAKYGAAAGLVPGG
PGFGPGVVGVPGAGVPGVGVPGAGIPVVPGAGIPGAAVPGVVSPEAAAKA
AAKAAKYGARPGVGVGGIPTYGVGAGGFPGFGVGVGGIPGVAGVPGVGGV
PGVGGVPGVGISPEAQAAAAAKAAKYGAAGAGVLGGLVPGPQAAVPGVPG
TGGVPGVGTPAAAAAKAAAKAAQFGLVPGVGVAPGVGVAPGVGVAPGVGL
APGVGVAPGVGVAPGVGVAPGIGPGGV

The codon optimized polynucleotide sequence encoding the 45.3 kDa truncated human elastin is disclosed in SEQ ID NO: 40

(SEQ ID NO: 40)
GGTGGCGTACCAGGCGCAATTCCTGGGGGTGTCCCAGGCGGTGTTTTTA
TCCGGGCGCCGGTCTTGGCGCACTGGGTGGCGGTGCACTGGGCCCGGGCG
GCAAACCGCTGAAACCGGTACCAGGTGGTTTAGCAGGCGCCGGCTTAGGC
GCAGGTCTGGGAGCATTTCCGGCAGTTACCTTTCCAGGGGCACTGGTTCC
TGGAGGTGTGGCCGATGCAGCCGCGGCATATAAAGCCGCTAAAGCCGGTG
CGGGTTTAGGAGGCGTCCCAGGTGTCGGTGGCCTGGGTGTTAGCGCCGGT
GCAGTTGTTCCGCAGCCGGGAGCAGGGGTTAAACCTGGTAAAGTGCCGGG
AGTAGGTCTGCCAGGCGTTTATCCTGGTGGTGTTTTGCCGGGTGCCCGTT
TTCCGGGCGTTGGTGTTCTTCCAGGCGTGCCGACCGGAGCCGGTGTTAAA
CCGAAAGCCCCCGGTGTTGGAGGTGCATTTGCAGGCATCCCGGGAGTTGG
CCCGTTTGGTGGTCCGCAACCTGGGGTTCCGTTAGGTTATCCGATTAAAG
CACCGAAACTGCCCGGCGGTTATGGTCTGCCGTACACAACCGGTAAACTG
CCGTATGGTTATGGCCCGGGTGGAGTTGCGGGTGCAGCAGGTAAAGCGGG
TTATCCTACCGGAACCGGTGTAGGTCCGCAGGCCGCTGCTGCCGCCGCCG
CAAAAGCAGCGGCTAAATTTGGCGCCGGAGCAGCGGGTGTTCTGCCTGGA
GTTGGTGGTGCGGGCGTGCCAGGGGTACCTGGTGCAATTCCGGGTATTGG
TGGTATTGCCGGTGTCGGCACCCCGGCCGCGGCAGCTGCGGCAGCGGCGG
CTGCCAAAGCTGCTAAATACGGTGCCGCGGCGGGTCTGGTGCCAGGAGGT
CCGGGTTTTGGTCCGGGAGTGGTTGGCGTGCCTGGCGCAGGCGTTCCTGG
TGTGGGCGTTCCAGGTGCAGGGATTCCTGTTGTGCCTGGTGCCGGTATTC
CCGGCGCGGCCGTTCCGGGGGTGGTTAGCCCGGAAGCCGCAGCGAAGGCT
GCGGCAAAGGCAGCAAAGTATGGCGCACGCCCAGGAGTCGGCGTGGGTGG
TATCCCGACCTATGGGGTGGGCGCAGGGGGTTTTCCTGGTTTCGGCGTAG
GTGTAGGAGGTATACCGGGCGTGGCCGGTGTACCAGGGGTTGGTGGCGTC
CCTGGTGTTGGCGGTGTGCCAGGTGTTGGTATTTCACCGGAAGCACAGGC
AGCAGCCGCAGCTAAGGCAGCGAAATATGGTGCCGCCGGCGCAGGAGTTT
TAGGTGGGCTGGTTCCGGGCCCGCAGGCAGCTGTGCCGGGGGTTCCAGGC
ACCGGTGGTGTCCCTGGAGTCGGTACGCCGGCTGCAGCGGCAGCCAAAGC
GGCTGCGAAAGCAGCACAGTTTGGCTTAGTACCGGGTGTGGGAGTTGCCC
CCGGCGTTGGCGTTGCTCCAGGGGTGGGTGTTGCTCCTGGCGTCGGTCTG

-continued

GCTCCTGGAGTGGGCGTAGCACCCGGTGTGGGGGTGGCCCCGGGTGTTGG

GGTTGCACCGGGTATCGGTCCGGGCGGTGTCtaa

The amino acid sequence of a 44.4 kDa human elastin truncated at the N-terminal is disclosed in SEQ ID NO: 41. The 44.4 kDa truncated elastin has amino acids 2-246 deleted from the full length elastin.

(SEQ ID NO: 41)

GVLPGVGGAGVPGVPGAIPGIGGIAGVGTPAAAAAAAAAAKAAKYGAAAG

LVPGGPGFGPGVVGVPGAGVPGVGVPGAGIPVVPGAGIPGAAVPGVVSPE

AAAKAAAKAAKYGARPGVGVGGIPTYGVGAGGFPGFGVGVGGIPGVAGVP

GVGGVPGVGGVPGVGISPEAQAAAAAKAAKYGAAGAGVLGGLVPGPQAAV

PGVPGTGGVPGVGTPAAAAAKAAAKAAQFGLVPGVGVAPGVGVAPGVGVA

PGVGLAPGVGVAPGVGVAPGVGVAPGIGPGGVAAAAKSAAKVAAKAQLRA

AAGLGAGIPGLGVGVGVPGLGVGAGVPGLGVGAGVPGFGAGADEGVRRSL

SPELREGDPSSSQHLPSTPSSPRVPGALAAAKAAKYGAAVPGVLGGLGAL

GGVGIPGGVVGAGPAAAAAAAKAAAKAAQFGLVGAAGLGGLGVGGLGVPG

VGGLGGIPPAAAAKAAKYGAAGLGGVLGGAGQFPLGGVAARPGFGLSPIF

PGGACLGKACGRKRK

The codon optimized polynucleotide sequence encoding the 44.4 kDa truncated human elastin is disclosed in SEQ ID NO: 42

(SEQ ID NO: 42)

GGTGTTCTGCCTGGAGTTGGTGGTGCGGGCGTGCCAGGGGTACCTGGTGC

AATTCCGGGTATTGGTGGTATTGCCGGTGTCGGCACCCCGGCCGCGGCAG

CTGCGGCAGCGGCGGCTGCCAAAGCTGCTAAATACGGTGCCGCGGCGGGT

CTGGTGCCAGGAGGTCCGGGTTTTGGTCCGGGAGTGGTTGGCGTGCCTGG

CGCAGGCGTTCCTGGTGTGGGCGTTCCAGGTGCAGGGATTCCTGTTGTGC

CTGGTGCCGGTATTCCCGGCGCGGCCGTTCCGGGGGTGGTTAGCCCGGAA

GCCGCAGCGAAGGCTGCGGCAAAGGCAGCAAAGTATGGCGCACGCCCAGG

AGTCGGCGTGGGTGGTATCCCGACCTATGGGGTGGGCGCAGGGGGTTTTC

CTGGTTTCGGCGTAGGTGTAGGAGGTATACCGGGCGTGGCCGGTGTACCA

GGGGTTGGTGGCGTCCCTGGTGTTGGCGGTGTGCCAGGTGTTGGTATTTC

ACCGGAAGCACAGGCAGCAGCCGCAGCTAAGGCAGCGAAATATGGTGCCG

CCGGCGCAGGAGTTTTAGGTGGGCTGGTTCCGGGCCCGCAGGCAGCTGTG

CCGGGGGTTCCAGGCACCGGTGGTGTCCCTGGAGTCGGTACGCCGGCTGC

AGCGGCAGCCAAAGCGGCTGCGAAAGCAGCACAGTTTGGCTTAGTACCGG

GTGTGGGAGTTGCCCCCGGCGTTGGCGTTGCTCCAGGGGTGGGTGTTGCT

CCTGGCGTCGGTCTGGCTCCTGGAGTGGGCGTAGCACCCGGTGTGGGGGT

GGCCCCGGGTGTTGGGGTTGCACCGGGTATCGGTCCGGGCGGTGTCGCAG

CAGCAGCTAAAAGCGCGGCGAAAGTTGCGGCCAAAGCCCAACTGCGCGCC

GCCGCGGGCCTCGGTGCAGGTATTCCGGGGCTGGGTGTCGGAGTTGGAGT

CCCGGGTTTGGGCGTGGGCGCGGGAGTTCCGGGACTGGGAGTGGGTGCCG

-continued

GAGTTCCTGGCTTTGGTGCAGGCGCAGATGAAGGTGTTCGTCGTAGCCTG

AGTCCGGAACTGCGTGAAGGTGATCCGAGTAGCAGCCAGCATCTGCCGAG

CACCCCGAGCAGCCCGCGTGTTCCGGGTGCATTAGCTGCAGCAAAAGCCG

CCAAGTATGGTGCAGCCGTGCCGGGCGTCTTAGGTGGTCTGGGCGCCCTG

GGTGGTGTAGGCATTCCGGGAGGTGTTGTGGGTGCAGGACCGGCCGCCGC

AGCTGCGGCCGCCAAAGCAGCTGCAAAAGCGGCCCAGTTTGGTTTAGTGG

GCGCCGCAGGTTTAGGCGGTTTAGGTGTGGGTGGACTGGGTGTACCTGGC

GTAGGCGGTCTGGGTGGAATTCCGCCCGCAGCGGCCGCGAAAGCGGCAAA

ATATGGCGCGGCAGGCCTGGGCGGCGTGCTGGGTGGGGCAGGTCAGTTTC

CGCTGGGCGGGGTTGCCGCACGTCCGGGATTTGGTCTGAGCCCGATTTTC

CCTGGCGGCGCATGTCTGGGTAAAGCATGTGGTCGTAAACGTAAAtaa

The amino acid sequence of a 40.4 kDa human elastin truncated at the N-terminal is disclosed in SEQ ID NO: 43. The 40.4 kDa truncated elastin has amino acids 2-295 deleted from the full length elastin.

(SEQ ID NO: 43)

GLVPGGPGFGPGVVGVPGAGVPGVGVPGAGIPVVPGAGIPGAAVPGVVSP

EAAAKAAAKAAKYGARPGVGVGGIPTYGVGAGGFPGFGVGVGGIPGVAGV

PGVGGVPGVGGVPGVGISPEAQAAAAAKAAKYGAAGAGVLGGLVPGPQAA

VPGVPGTGGVPGVGTPAAAAAKAAAKAAQFGLVPGVGVAPGVGVAPGVGV

APGVGLAPGVGVAPGVGVAPGVGVAPGIGPGGVAAAAKSAAKVAAKAQLR

AAAGLGAGIPGLGVGVGVPGLGVGAGVPGLGVGAGVPGFGAGADEGVRRS

LSPELREGDPSSSQHLPSTPSSPRVPGALAAAKAAKYGAAVPGVLGGLGA

LGGVGIPGGVVGAGPAAAAAAAKAAAKAAQFGLVGAAGLGGLGVGGLGVP

GVGGLGGIPPAAAAKAAKYGAAGLGGVLGGAGQFPLGGVAARPGFGLSPI

FPGGACLGKACGRKRK

The codon optimized polynucleotide sequence encoding the 40.4 kDa truncated human elastin is disclosed in SEQ ID NO: 44

(SEQ ID NO: 44)

GGTCTGGTGCCAGGAGGTCCGGGTTTTGGTCCGGGAGTGGTTGGCGTGCC

TGGCGCAGGCGTTCCTGGTGTGGGCGTTCCAGGTGCAGGGATTCCTGTTG

TGCCTGGTGCCGGTATTCCCGGCGCGGCCGTTCCGGGGGTGGTTAGCCCG

GAAGCCGCAGCGAAGGCTGCGGCAAAGGCAGCAAAGTATGGCGCACGCCC

AGGAGTCGGCGTGGGTGGTATCCCGACCTATGGGGTGGGCGCAGGGGGTT

TTCCTGGTTTCGGCGTAGGTGTAGGAGGTATACCGGGCGTGGCCGGTGTA

CCAGGGGTTGGTGGCGTCCCTGGTGTTGGCGGTGTGCCAGGTGTTGGTAT

TTCACCGGAAGCACAGGCAGCAGCCGCAGCTAAGGCAGCGAAATATGGTG

CCGCCGGCGCAGGAGTTTTAGGTGGGCTGGTTCCGGGCCCGCAGGCAGCT

GTGCCGGGGGTTCCAGGCACCGGTGGTGTCCCTGGAGTCGGTACGCCGGC

TGCAGCGGCAGCCAAAGCGGCTGCGAAAGCAGCACAGTTTGGCTTAGTAC

CGGGTGTGGGAGTTGCCCCCGGCGTTGGCGTTGCTCCAGGGGTGGGTGTT

```
GCTCCTGGCGTCGGTCTGGCTCCTGGAGTGGGCGTAGCACCCGGTGTGGG
GGTGGCCCCGGGTGTTGGGGTTGCACCGGGTATCGGTCCGGGCGGTGTCG
CAGCAGCAGCTAAAAGCGCGGCGAAAGTTGCGGCCAAAGCCCAACTGCGC
GCCGCCGCGGGCCTCGGTGCAGGTATTCCGGGGCTGGGTGTCGGAGTTGG
AGTCCCGGGTTTGGGCGTGGGCGCGGGAGTTCCGGGACTGGGAGTGGGTG
CCGGAGTTCCTGGCTTTGGTGCAGGCGCAGATGAAGGTGTTCGTCGTAGC
CTGAGTCCGGAACTGCGTGAAGGTGATCCGAGTAGCAGCCAGCATCTGCC
GAGCACCCCGAGCAGCCCGCGTGTTCCGGGTGCATTAGCTGCAGCAAAAG
CCGCCAAGTATGGTGCAGCCGTGCCGGGCGTCTTAGGTGGTCTGGGCGCC
CTGGGTGGTGTAGGCATTCCGGGAGGTGTTGTGGGTGCAGGACCGGCCGC
CGCAGCTGCGGCCGCCAAAGCAGCTGCAAAAGCGGCCCAGTTTGGTTTAG
TGGGCGCCGCAGGTTTAGGCGGTTTAGGTGTGGGTGGACTGGGTGTACCT
GGCGTAGGCGGTCTGGGTGGAATTCCGCCCGCAGCGGCCGCGAAAGCGGC
AAAATATGGCGCGGCAGGCCTGGGCGGCGTGCTGGGTGGGGCAGGTCAGT
TTCCGCTGGGCGGGGTTGCCGCACGTCCGGGATTTGGTCTGAGCCCGATT
TTCCCTGGCGGCGCATGTCTGGGTAAAGCATGTGGTCGTAAACGTAAAta
a
```

The amino acid sequence of a 39.8 kDa human elastin truncated at the C-terminal is disclosed in SEQ ID NO: 45. The 39.8 kDa truncated elastin has amino acids 462-761 deleted from the full length elastin.

```
                                          (SEQ ID NO: 45)
GGVPGAIPGGVPGGVFYPGAGLGALGGGALGPGGKPLKPVPGGLAGAGLG
AGLGAFPAVTFPGALVPGGVADAAAAYKAAKAGAGLGGVPGVGGLGVSAG
AVVPQPGAGVKPGKVPGVGLPGVYPGGVLPGARFPGVGVLPGVPTGAGVK
PKAPGVGGAFAGIPGVGPFGGPQPGVPLGYPIKAPKLPGGYGLPYTTGKL
PYGYGPGGVAGAAGKAGYPTGTGVGPQAAAAAAAKAAAKFGAGAAGVLPG
VGGAGVPGVPGAIPGIGGIAGVGTPAAAAAAAAAAKAAKYGAAAGLVPGG
PGFGPGVVGVPGAGVPGVGVPGAGIPVVPGAGIPGAAVPGVVSPEAAAKA
AAKAAKYGARPGVGVGGIPTYGVGAGGFPGFGVGVGGIPGVAGVPGVGGV
PGVGGVPGVGISPEAQAAAAAAKAAKYGAAGAGVLGGLVPGPQAAVPGVPG
TGGVPGVGTP
```

The codon optimized polynucleotide sequence encoding the 39.8 kDa truncated human elastin is disclosed in SEQ ID NO: 46

```
                                          (SEQ ID NO: 46)
GGTGGCGTACCAGGCGCAATTCCTGGGGGTGTCCCAGGCGGTGTTTTTTA
TCCGGGCGCCGGTCTTGGCGCACTGGGTGGCGGTGCACTGGGCCCGGGCG
GCAAACCGCTGAAACCGGTACCAGGTGGTTTAGCAGGCGCCGGCTTAGGC
GCAGGTCTGGGAGCATTTCCGGCAGTTACCTTTCCAGGGGCACTGGTTCC
TGGAGGTGTGGCCGATGCAGCCGCGGCATATAAAGCCGCTAAAGCCGGTG
CGGGTTTAGGAGGCGTCCCAGGTGTCGGTGGCCTGGGTGTTAGCGCCGGT
GCAGTTGTTCCGCAGCCGGGAGCAGGGGTTAAACCTGGTAAAGTGCCGGG
AGTAGGTCTGCCAGGCGTTTATCCTGGTGGTGTTTTGCCGGGTGCCCGTT
TTCCGGGCGTTGGTGTTCTTCCAGGCGTGCCGACCGGAGCCGGTGTTAAA
CCGAAAGCCCCCGGTGTTGGAGGTGCATTTGCAGGCATCCCGGGAGTTGG
CCCGTTTGGTGGTCCGCAACCTGGGGTTCCGTTAGGTTATCCGATTAAAG
CACCGAAACTGCCCGGCGGTTATGGTCTGCCGTACACAACCGGTAAACTG
CCGTATGGTTATGGCCCGGGTGGAGTTGCGGGTGCAGCAGGTAAAGCGGG
TTATCCTACCGGAACCGGTGTAGGTCCGCAGGCCGCTGCTGCCGCCGCCG
CAAAAGCAGCGGCTAAATTTGGCGCCGGAGCAGCGGGTGTTCTGCCTGGA
GTTGGTGGTGCGGGCGTGCCAGGGGTACCTGGTGCAATTCCGGGTATTGG
TGGTATTGCCGGTGTCGGCACCCCGGCCGCGGCAGCTGCGGCAGCGGCGG
CTGCCAAAGCTGCTAAATACGGTGCCGCGGCGGGTCTGGTGCCAGGAGGT
CCGGGTTTTGGTCCGGGAGTGGTTGGCGTGCCTGGCGCAGGCGTTCCTGG
TGTGGGCGTTCCAGGTGCAGGGATTCCTGTTGTGCCTGGTGCCGGTATTC
CCGGCGCGGCCGTTCCGGGGGTGGTTAGCCCGGAAGCCGCAGCGAAGGCT
GCGGCAAAGGCAGCAAAGTATGGCGCACGCCCAGGAGTCGGCGTGGGTGG
TATCCCGACCTATGGGGTGGGCGCAGGGGGTTTTCCTGGTTTCGGCGTAG
GTGTAGGAGGTATACCGGGCGTGGCCGGTGTACCAGGGGTTGGTGGCGTC
CCTGGTGTTGGCGGTGTGCCAGGTGTTGGTATTTCACCGGAAGCACAGGC
AGCAGCCGCAGCTAAGGCAGCGAAATATGGTGCCGCCGGCGCAGGAGTTT
TAGGTGGGCTGGTTCCGGGCCCGCAGGCAGCTGTGCCGGGGGTTCCAGGC
ACCGGTGGTGTCCCTGGAGTCGGTACGCCGtaa
```

The amino acid sequence of a 36.1 kDa human elastin truncated at the C-terminal is disclosed in SEQ ID NO: 47. The 36.1 kDa truncated elastin has amino acids 418-761 deleted from the full length elastin.

```
                                          (SEQ ID NO: 47)
GGVPGAIPGGVPGGVFYPGAGLGALGGGALGPGGKPLKPVPGGLAGAGLG
AGLGAFPAVTFPGALVPGGVADAAAAYKAAKAGAGLGGVPGVGGLGVSAG
AVVPQPGAGVKPGKVPGVGLPGVYPGGVLPGARFPGVGVLPGVPTGAGVK
PKAPGVGGAFAGIPGVGPFGGPQPGVPLGYPIKAPKLPGGYGLPYTTGKL
PYGYGPGGVAGAAGKAGYPTGTGVGPQAAAAAAAKAAAKFGAGAAGVLPG
VGGAGVPGVPGAIPGIGGIAGVGTPAAAAAAAAAAKAAKYGAAAGLVPGG
PGFGPGVVGVPGAGVPGVGVPGAGIPVVPGAGIPGAAVPGVVSPEAAAKA
AAKAAKYGARPGVGVGGIPTYGVGAGGFPGFGVGVGGIPGVAGVPGVGGV
PGVGGVPGVGISPEAQ
```

The codon optimized polynucleotide sequence encoding the 36.1 kDa truncated human elastin is disclosed in SEQ ID NO: 48

```
                                          (SEQ ID NO: 48)
GGTGGCGTACCAGGCGCAATTCCTGGGGGTGTCCCAGGCGGTGTTTTTTA
TCCGGGCGCCGGTCTTGGCGCACTGGGTGGCGGTGCACTGGGCCCGGGCG
```

-continued

GCAAACCGCTGAAACCGGTACCAGGTGGTTTAGCAGGCGCCGGCTTAGGC

GCAGGTCTGGGAGCATTTCCGGCAGTTACCTTTCCAGGGGCACTGGTTCC

TGGAGGTGTGGCCGATGCAGCCGCGGCATATAAAGCCGCTAAAGCCGGTG

CGGGTTTAGGAGGCGTCCCAGGTGTCGGTGGCCTGGGTGTTAGCGCCGGT

GCAGTTGTTCCGCAGCCGGGAGCAGGGGTTAAACCTGGTAAAGTGCCGGG

AGTAGGTCTGCCAGGCGTTTATCCTGGTGGTGTTTTGCCGGGTGCCCGTT

TTCCGGGCGTTGGTGTTCTTCCAGGCGTGCCGACCGGAGCCGGTGTTAAA

CCGAAAGCCCCCGGTGTTGGAGGTGCATTTGCAGGCATCCCGGGAGTTGG

CCCGTTTGGTGGTCCGCAACCTGGGGTTCCGTTAGGTTATCCGATTAAAG

CACCGAAACTGCCCGGCGGTTATGGTCTGCCGTACACAACCGGTAAACTG

CCGTATGGTTATGGCCCGGGTGGAGTTGCGGGTGCAGCAGGTAAAGCGGG

TTATCCTACCGGAACCGGTGTAGGTCCGCAGGCCGCTGCTGCCGCCGCCG

CAAAAGCAGCGGCTAAATTTGGCGCCGGAGCAGCGGGTGTTCTGCCTGGA

GTTGGTGGTGCGGGCGTGCCAGGGGTACCTGGTGCAATTCCGGGTATTGG

TGGTATTGCCGGTGTCGGCACCCCGGCCGCGGCAGCTGCGGCAGCGGCGG

CTGCCAAAGCTGCTAAATACGGTGCCGCGGCGGGTCTGGTGCCAGGAGGT

CCGGGTTTTGGTCCGGGAGTGGTTGGCGTGCCTGGCGCAGGCGTTCCTGG

TGTGGGCGTTCCAGGTGCAGGGATTCCTGTTGTGCCTGGTGCCGGTATTC

CCGGCGCGGCCGTTCCGGGGGTGGTTAGCCCGGAAGCCGCAGCGAAGGCT

GCGGCAAAGGCAGCAAAGTATGGCGCACGCCCAGGAGTCGGCGTGGGTGG

TATCCCGACCTATGGGGTGGGCGCAGGGGGTTTTCCTGGTTTCGGCGTAG

GTGTAGGAGGTATACCGGGCGTGGCCGGTGTACCAGGGGTTGGTGGCGTC

CCTGGTGTTGGCGGTGTGCCAGGTGTTGGTATTTCACCGGAAGCACAGta a

The amino acid sequence of a 34.9 kDa human elastin truncated at the N-terminal is disclosed in SEQ ID NO: 49. The 34.9 kDa truncated elastin has amino acids 2-360 deleted from the full length elastin.

(SEQ ID NO: 49)

RPGVGVGGIPTYGVGAGGFPGFGVGVGGIPGVAGVPGVGGVPGVGGVP

GVGISPEAQAAAAKAAKYGAAGAGVLGGLVPGPQAAVPGVPGTGGVP

GVGTPAAAAAKAAAKAAQFGLVPGVGVAPGVGVAPGVGVAPGVGLAPG

VGVAPGVGVAPGVGVAPGIGPGGVAAAAKSAAKVAAKAQLRAAAGLGA

GIPGLGVGVGVPGLGVGAGVPGLGVGAGVPGFGAGADEGVRRSLSPEL

REGDPSSSQHLPSTPSSPRVPGALAAAKAAKYGAAVPGVLGGLGALGG

VGIPGGVVGAGPAAAAAAAKAAAKAAQFGLVGAAGLGGLGVGGLGVPG

VGGLGGIPPAAAAKAAKYGAAGLGGVLGGAGQFPLGGVAARPGFGLSP

IFPGGACLGKACGRKRK

The codon optimized polynucleotide sequence encoding the 34.9 kDa truncated human elastin is disclosed in SEQ ID NO: 50

(SEQ ID NO: 50)

CGCCCAGGAGTCGGCGTGGGTGGTATCCCGACCTATGGGGTGGGCGCA

GGGGGTTTTCCTGGTTTCGGCGTAGGTGTAGGAGGTATACCGGGCGTG

GCCGGTGTACCAGGGGTTGGTGGCGTCCCTGGTGTTGGCGGTGTGCCA

GGTGTTGGTATTTCACCGGAAGCACAGGCAGCAGCCGCAGCTAAGGCA

GCGAAATATGGTGCCGCCGGCGCAGGAGTTTTAGGTGGGCTGGTTCCG

GGCCCGCAGGCAGCTGTGCCGGGGGTTCCAGGCACCGGTGGTGTCCCT

GGAGTCGGTACGCCGGCTGCAGCGGCAGCCAAAGCGGCTGCGAAAGCA

GCACAGTTTGGCTTAGTACCGGGTGTGGGAGTTGCCCCCGGCGTTGGC

GTTGCTCCAGGGGTGGGTGTTGCTCCTGGCGTCGGTCTGGCTCCTGGA

GTGGGCGTAGCACCCGGTGTGGGGGTGGCCCCGGGTGTTGGGGTTGCA

CCGGGTATCGGTCCGGGCGGTGTCGCAGCAGCAGCTAAAAGCGCGGCG

AAAGTTGCGGCCAAAGCCCAACTGCGCGCCGCCGCGGGCCTCGGTGCA

GGTATTCCGGGGCTGGGTGTCGGAGTTGGAGTCCCGGGTTTGGGCGTG

GGCGCGGGAGTTCCGGGACTGGGAGTGGGTGCCGGAGTTCCTGGCTTT

GGTGCAGGCGCAGATGAAGGTGTTCGTCGTAGCCTGAGTCCGGAACTG

CGTGAAGGTGATCCGAGTAGCAGCCAGCATCTGCCGAGCACCCCGAGC

AGCCCGCGTGTTCCGGGTGCATTAGCTGCAGCAAAAGCCGCCAAGTAT

GGTGCAGCCGTGCCGGGCGTCTTAGGTGGTCTGGGCGCCCTGGGTGGT

GTAGGCATTCCGGGAGGTGTTGTGGGTGCAGGACCGGCCGCCGCAGCT

GCGGCCGCCAAAGCAGCTGCAAAAGCGGCCCAGTTTGGTTTAGTGGGC

GCCGCAGGTTTAGGCGGTTTAGGTGTGGGTGGACTGGGTGTACCTGGC

GTAGGCGGTCTGGGTGGAATTCCGCCCGCAGCGGCCGCGAAAGCGGCA

AAATATGGCGCGGCAGGCCTGGGCGGCGTGCTGGGTGGGGCAGGTCAG

TTTCCGCTGGGCGGGGTTGCCGCACGTCCGGGATTTGGTCTGAGCCCG

ATTTTCCCTGGCGGCGCATGTCTGGGTAAAGCATGTGGTCGTAAACGT

AAAtaa

The amino acid sequence of a 32 kDa human elastin truncated at the C-terminal is disclosed in SEQ ID NO: 51. The 32 kDa truncated elastin has amino acids 373-761 deleted from the full length elastin.

(SEQ ID NO: 51)

GGVPGAIPGGVPGGVFYPGAGLGALGGGALGPGGKPLKPVPGGLAGAG

LGAGLGAFPAVTFPGALVPGGVADAAAAYKAAKAGAGLGGVPGVGGLG

VSAGAVVPQPGAGVKPGKVPGVGLPGVYPGGVLPGARFPGVGVLPGVP

TGAGVKPKAPGVGGAFAGIPGVGPFGGPQPGVPLGYPIKAPKLPGGYG

LPYTTGKLPYGYGPGGVAGAAGKAGYPTGTGVGPQAAAAAAAKAAAKF

GAGAAGVLPGVGGAGVPGVPGAIPGIGGIAGVGTPAAAAAAAAAAKAA

KYGAAAGLVPGGPGFGPGVVGVPGAGVPGVGVPGAGIPVVPGAGIPGA

AVPGVVSPEAAAKAAAKAAKYGARPGVGVGGIPTY

The codon optimized polynucleotide sequence encoding the 32 kDa truncated human elastin is disclosed in SEQ ID NO: 52

(SEQ ID NO: 52)
GGTGGCGTACCAGGCGCAATTCCTGGGGGTGTCCCAGGCGGTGTTTTT
TATCCGGGCGCCGGTCTTGGCGCACTGGGTGGCGGTGCACTGGGCCCG
GGCGGCAAACCGCTGAAACCGGTACCAGGTGGTTTAGCAGGCGCCGGC
TTAGGCGCAGGTCTGGGAGCATTTCCGGCAGTTACCTTTCCAGGGGCA
CTGGTTCCTGGAGGTGTGGCCGATGCAGCCGCGGCATATAAAGCCGCT
AAAGCCGGTGCGGGTTTAGGAGGCGTCCCAGGTGTCGGTGGCCTGGGT
GTTAGCGCCGGTGCAGTTGTTCCGCAGCCGGGAGCAGGGGTTAAACCT
GGTAAAGTGCCGGGAGTAGGTCTGCCAGGCGTTTATCCTGGTGGTGTT
TTGCCGGGTGCCCGTTTTCCGGGCGTTGGTGTTCTTCCAGGCGTGCCG
ACCGGAGCCGGTGTTAAACCGAAAGCCCCCGGTGTTGGAGGTGCATTT
GCAGGCATCCCGGGAGTTGGCCCGTTTGGTGGTCCGCAACCTGGGGTT
CCGTTAGGTTATCCGATTAAAGCACCGAAACTGCCCGGCGGTTATGGT
CTGCCGTACACAACCGGTAAACTGCCGTATGGTTATGGCCCGGGTGGA
GTTGCGGGTGCAGCAGGTAAAGCGGGTTATCCTACCGGAACCGGTGTA
GGTCCGCAGGCCGCTGCTGCCGCCGCCGCAAAAGCAGCGGCTAAATTT
GGCGCCGGAGCAGCGGGTGTTCTGCCTGGAGTTGGTGGTGCGGGCGTG
CCAGGGGTACCTGGTGCAATTCCGGGTATTGGTGGTATTGCCGGTGTC
GGCACCCCGGCCGCGGCAGCTGCGGCAGCGGCGGCTGCCAAAGCTGCT
AAATACGGTGCCGCGGCGGGTCTGGTGCCAGGAGGTCCGGGTTTTGGT
CCGGGAGTGGTTGGCGTGCCTGGCGCAGGCGTTCCTGGTGTGGGCGTT
CCAGGTGCAGGGATTCCTGTTGTGCCTGGTGCCGGTATTCCCGGCGCG
GCCGTTCCGGGGGTGGTTAGCCCGGAAGCCGCAGCGAAGGCTGCGGCA
AAGGCAGCAAAGTATGGCGCACGCCCAGGAGTCGGCGTGGGTGGTATC
CCGACCTATtaa The amino acid sequence of a 29.9 kDa human elastin truncated at the C-terminal is disclosed in SEQ ID NO: 53. The 60.7 kDa truncated elastin has amino acids 347-761 deleted from the full length elastin.

(SEQ ID NO: 53)
GGVPGAIPGGVPGGVFYPGAGLGALGGGALGPGGKPLKPVPGGLAGAG
LGAGLGAFPAVTFPGALVPGGVADAAAAYKAAKAGAGLGGVPGVGGLG
VSAGAVVPQPGAGVKPGKVPGVGLPGVYPGGVLPGARFPGVGVLPGVP
TGAGVKPKAPGVGGAFAGIPGVGPFGGPQPGVPLGYPIKAPKLPGGYG
LPYTTGKLPYGYGPGGVAGAAGKAGYPTGTGVGPQAAAAAAAKAAAKF
GAGAAGVLPGVGGAGVPGVPGAIPGIGGIAGVGTPAAAAAAAAAAKAA
KYGAAAGLVPGGPGFGPGVVGVPGAGVPGVGVPGAGIPVVPGAGIPGA
AVPGVVSPE

The codon optimized polynucleotide sequence encoding the 29.9 kDa truncated human elastin is disclosed in SEQ ID NO: 54

(SEQ ID NO: 54)
GGTGGCGTACCAGGCGCAATTCCTGGGGGTGTCCCAGGCGGTGTTTTT
TATCCGGGCGCCGGTCTTGGCGCACTGGGTGGCGGTGCACTGGGCCCG
GGCGGCAAACCGCTGAAACCGGTACCAGGTGGTTTAGCAGGCGCCGGC
TTAGGCGCAGGTCTGGGAGCATTTCCGGCAGTTACCTTTCCAGGGGCA
CTGGTTCCTGGAGGTGTGGCCGATGCAGCCGCGGCATATAAAGCCGCT
AAAGCCGGTGCGGGTTTAGGAGGCGTCCCAGGTGTCGGTGGCCTGGGT
GTTAGCGCCGGTGCAGTTGTTCCGCAGCCGGGAGCAGGGGTTAAACCT
GGTAAAGTGCCGGGAGTAGGTCTGCCAGGCGTTTATCCTGGTGGTGTT
TTGCCGGGTGCCCGTTTTCCGGGCGTTGGTGTTCTTCCAGGCGTGCCG
ACCGGAGCCGGTGTTAAACCGAAAGCCCCCGGTGTTGGAGGTGCATTT
GCAGGCATCCCGGGAGTTGGCCCGTTTGGTGGTCCGCAACCTGGGGTT
CCGTTAGGTTATCCGATTAAAGCACCGAAACTGCCCGGCGGTTATGGT
CTGCCGTACACAACCGGTAAACTGCCGTATGGTTATGGCCCGGGTGGA
GTTGCGGGTGCAGCAGGTAAAGCGGGTTATCCTACCGGAACCGGTGTA
GGTCCGCAGGCCGCTGCTGCCGCCGCCGCAAAAGCAGCGGCTAAATTT
GGCGCCGGAGCAGCGGGTGTTCTGCCTGGAGTTGGTGGTGCGGGCGTG
CCAGGGGTACCTGGTGCAATTCCGGGTATTGGTGGTATTGCCGGTGTC
GGCACCCCGGCCGCGGCAGCTGCGGCAGCGGCGGCTGCCAAAGCTGCT
AAATACGGTGCCGCGGCGGGTCTGGTGCCAGGAGGTCCGGGTTTTGGT
CCGGGAGTGGTTGGCGTGCCTGGCGCAGGCGTTCCTGGTGTGGGCGTT
CCAGGTGCAGGGATTCCTGTTGTGCCTGGTGCCGGTATTCCCGGCGCG
GCCGTTCCGGGGGTGGTTAGCCCGGAAtaa The amino acid sequence of a 29.4 kDa human elastin truncated at the N-terminal is disclosed in SEQ ID NO: 55. The 29.4 kDa truncated elastin has amino acids 2-425 deleted from the full length elastin.

(SEQ ID NO: 55)
KYGAAGAGVLGGLVPGPQAAVPGVPGTGGVPGVGTPAAAAAKAAAKAA
QFGLVPGVGVAPGVGVAPGVGVAPGVGLAPGVGVAPGVGVAPGVGVAP
GIGPGGVAAAAKSAAKVAAKAQLRAAAGLGAGIPGLGVGVGVPGLGVG
AGVPGLGVGAGVPGFGAGADEGVRRSLSPELREGDPSSSQHLPSTPSS
PRVPGALAAAKAAKYGAAVPGVLGGLGALGGVGIPGGVVGAGPAAAAA
AAKAAAKAAQFGLVGAAGLGGLGVGGLGVPGVGGLGGIPPAAAAKAAK
YGAAGLGGVLGGAGQFPLGGVAARPGFGLSPIFPGGACLGKACGRKRK

The codon optimized polynucleotide sequence encoding the 29.4 kDa truncated human elastin is disclosed in SEQ ID NO: 56

(SEQ ID NO: 56)
AAATATGGTGCCGCCGGCGCAGGAGTTTTAGGTGGGCTGGTTCCGGGC
CCGCAGGCAGCTGTGCCGGGGGTTCCAGGCACCGGTGGTGTCCCTGGA
GTCGGTACGCCGGCTGCAGCGGCAGCCAAAGCGGCTGCGAAAGCAGCA
CAGTTTGGCTTAGTACCGGGTGTGGGAGTTGCCCCCGGCGTTGGCGTT

-continued

GCTCCAGGGGTGGGTGTTGCTCCTGGCGTCGGTCTGGCTCCTGGAGTG

GGCGTAGCACCCGGTGTGGGGGTGGCCCCGGGTGTTGGGGTTGCACCG

GGTATCGGTCCGGGCGGTGTCGCAGCAGCAGCTAAAAGCGCGGCGAAA

GTTGCGGCCAAAGCCCAACTGCGCGCCGCCGCGGGCCTCGGTGCAGGT

ATTCCGGGGCTGGGTGTCGGAGTTGGAGTCCCGGGTTTGGGCGTGGGC

GCGGGAGTTCCGGGACTGGGAGTGGGTGCCGGAGTTCCTGGCTTTGGT

GCAGGCGCAGATGAAGGTGTTCGTCGTAGCCTGAGTCCGGAACTGCGT

GAAGGTGATCCGAGTAGCAGCCAGCATCTGCCGAGCACCCCGAGCAGC

CCGCGTGTTCCGGGTGCATTAGCTGCAGCAAAAGCCGCCAAGTATGGT

GCAGCCGTGCCGGGCGTCTTAGGTGGTCTGGGCGCCCTGGGTGGTGTA

GGCATTCCGGGAGGTGTTGTGGGTGCAGGACCGGCCGCCGCAGCTGCG

GCCGCCAAAGCAGCTGCAAAAGCGGCCCAGTTTGGTTTAGTGGGCGCC

GCAGGTTTAGGCGGTTTAGGTGTGGGTGGACTGGGTGTACCTGGCGTA

GGCGGTCTGGGTGGAATTCCGCCCGCAGCGGCCGCGAAAGCGGCAAAA

TATGGCGCGGCAGGCCTGGGCGGCGTGCTGGGTGGGGCAGGTCAGTTT

CCGCTGGGCGGGGTTGCCGCACGTCCGGGATTTGGTCTGAGCCCGATT

TTCCCTGGCGGCGCATGTCTGGGTAAAGCATGTGGTCGTAAACGTAAA taa

The amino acid sequence of a 25.3 kDa human elastin truncated at the N-terminal is disclosed in SEQ ID NO: 57. The 25.3 kDa truncated elastin has amino acids 2-473 deleted from the full length elastin.

(SEQ ID NO: 57)

QFGLVPGVGVAPGVGVAPGVGVAPGVGLAPGVGVAPGVGVAPGVGVAP

GIGPGGVAAAAKSAAKVAAKAQLRAAAGLGAGIPGLGVGVGVPGLGVG

AGVPGLGVGAGVPGFGAGADEGVRRSLSPELREGDPSSSQHLPSTPSS

PRVPGALAAAKAAKYGAAVPGVLGGLGALGGVGIPGGVVGAGPAAAAA

AAKAAAKAAQFGLVGAAGLGGLGVGGLGVPGVGGLGGIPPAAAAKAAK

YGAAGLGGVLGGAGQFPLGGVAARPGFGLSPIFPGGACLGKACGRKRK

The codon optimized polynucleotide sequence encoding the 25.3 kDa truncated human elastin is disclosed in SEQ ID NO: 58

(SEQ ID NO: 58)

CAGTTTGGCTTAGTACCGGGTGTGGGAGTTGCCCCCGGCGTTGGCGTT

GCTCCAGGGGTGGGTGTTGCTCCTGGCGTCGGTCTGGCTCCTGGAGTG

GGCGTAGCACCCGGTGTGGGGGTGGCCCCGGGTGTTGGGGTTGCACCG

GGTATCGGTCCGGGCGGTGTCGCAGCAGCAGCTAAAAGCGCGGCGAAA

GTTGCGGCCAAAGCCCAACTGCGCGCCGCCGCGGGCCTCGGTGCAGGT

ATTCCGGGGCTGGGTGTCGGAGTTGGAGTCCCGGGTTTGGGCGTGGGC

GCGGGAGTTCCGGGACTGGGAGTGGGTGCCGGAGTTCCTGGCTTTGGT

GCAGGCGCAGATGAAGGTGTTCGTCGTAGCCTGAGTCCGGAACTGCGT

GAAGGTGATCCGAGTAGCAGCCAGCATCTGCCGAGCACCCCGAGCAGC

-continued

CCGCGTGTTCCGGGTGCATTAGCTGCAGCAAAAGCCGCCAAGTATGGT

GCAGCCGTGCCGGGCGTCTTAGGTGGTCTGGGCGCCCTGGGTGGTGTA

GGCATTCCGGGAGGTGTTGTGGGTGCAGGACCGGCCGCCGCAGCTGCG

GCCGCCAAAGCAGCTGCAAAAGCGGCCCAGTTTGGTTTAGTGGGCGCC

GCAGGTTTAGGCGGTTTAGGTGTGGGTGGACTGGGTGTACCTGGCGTA

GGCGGTCTGGGTGGAATTCCGCCCGCAGCGGCCGCGAAAGCGGCAAAA

TATGGCGCGGCAGGCCTGGGCGGCGTGCTGGGTGGGGCAGGTCAGTTT

CCGCTGGGCGGGGTTGCCGCACGTCCGGGATTTGGTCTGAGCCCGATT

TTCCCTGGCGGCGCATGTCTGGGTAAAGCATGTGGTCGTAAACGTAAA taa

The amino acid sequence of a 24.1 kDa human elastin truncated at the C-terminal is disclosed in SEQ ID NO: 59. The 24.1 kDa truncated elastin has amino acids 277-761 deleted from the full length elastin.

(SEQ ID NO: 59)

GGVPGAIPGGVPGGVFYPGAGLGALGGGALGPGGKPLKPVPGGLAGAG

LGAGLGAFPAVTFPGALVPGGVADAAAAYKAAKAGAGLGGVPGVGGLG

VSAGAVVPQPGAGVKPGKVPGVGLPGVYPGGVLPGARFPGVGVLPGVP

TGAGVKPKAPGVGGAFAGIPGVGPFGGPQPGVPLGYPIKAPKLPGGYG

LPYTTGKLPYGYGPGGVAGAAGKAGYPTGTGVGPQAAAAAAAKAAAKF

GAGAAGVLPGVGGAGVPGVPGAIPGIGGIAGVGTP

The codon optimized polynucleotide sequence encoding the 24.1 kDa truncated human elastin is disclosed in SEQ ID NO: 60

(SEQ ID NO: 60)

GGTGGCGTACCAGGCGCAATTCCTGGGGGTGTCCCAGGCGGTGTTTTT

TATCCGGGCGCCGGTCTTGGCGCACTGGGTGGCGGTGCACTGGGCCCG

GGCGGCAAACCGCTGAAACCGGTACCAGGTGGTTTAGCAGGCGCCGGC

TTAGGCGCAGGTCTGGGAGCATTTCCGGCAGTTACCTTTCCAGGGGCA

CTGGTTCCTGGAGGTGTGGCCGATGCAGCCGCGGCATATAAAGCCGCT

AAAGCCGGTGCGGGTTTAGGAGGCGTCCCAGGTGTCGGTGGCCTGGGT

GTTAGCGCCGGTGCAGTTGTTCCGCAGCCGGGAGCAGGGGTTAAACCT

GGTAAAGTGCCGGGAGTAGGTCTGCCAGGCGTTTATCCTGGTGGTGTT

TTGCCGGGTGCCCGTTTTCCGGGCGTTGGTGTTCTTCCAGGCGTGCCG

ACCGGAGCCGGTGTTAAACCGAAAGCCCCCGGTGTTGGAGGTGCATTT

GCAGGCATCCCGGGAGTTGGCCCGTTTGGTGGTCCGCAACCTGGGGTT

CCGTTAGGTTATCCGATTAAAGCACCGAAACTGCCCGGCGGTTATGGT

CTGCCGTACACAACCGGTAAACTGCCGTATGGTTATGGCCCGGGTGGA

GTTGCGGGTGCAGCAGGTAAAGCGGGTTATCCTACCGGAACCGGTGTA

GGTCCGCAGGCCGCTGCTGCCGCCGCCGCAAAAGCAGCGGCTAAATTT

-continued

GGCGCCGGAGCAGCGGGTGTTCTGCCTGGAGTTGGTGGTGCGGGCGTG

CCAGGGGTACCTGGTGCAATTCCGGGTATTGGTGGTATTGCCGGTGTC

GGCACCCCGtaa

The amino acid sequence of a 20.3 kDa human elastin truncated at the C-terminal is disclosed in SEQ ID NO: 61. The 20.3 kDa truncated elastin has amino acids 229-761 deleted from the full length elastin.

(SEQ ID NO: 61)

GGVPGAIPGGVPGGVFYPGAGLGALGGGALGPGGKPLKPVPGGLAGAG

LGAGLGAFPAVTFPGALVPGGVADAAAAYKAAKAGAGLGGVPGVGGLG

VSAGAVVPQPGAGVKPGKVPGVGLPGVYPGGVLPGARFPGVGVLPGVP

TGAGVKPKAPGVGGAFAGIPGVGPFGGPQPGVPLGYPIKAPKLPGGYG

LPYTTGKLPYGYGPGGVAGAAGKAGYPTGTGVGPQ

The codon optimized polynucleotide sequence encoding the 20.3 kDa truncated human elastin is disclosed in SEQ ID NO: 62

(SEQ ID NO: 62)

GGTGGCGTACCAGGCGCAATTCCTGGGGGTGTCCCAGGCGGTGTTTTT

TATCCGGGCGCCGGTCTTGGCGCACTGGGTGGCGGTGCACTGGGCCCG

GGCGGCAAACCGCTGAAACCGGTACCAGGTGGTTTAGCAGGCGCCGGC

TTAGGCGCAGGTCTGGGAGCATTTCCGGCAGTTACCTTTCCAGGGGCA

CTGGTTCCTGGAGGTGTGGCCGATGCAGCCGCGGCATATAAAGCCGCT

AAAGCCGGTGCGGGTTTAGGAGGCGTCCCAGGTGTCGGTGGCCTGGGT

GTTAGCGCCGGTGCAGTTGTTCCGCAGCCGGGAGCAGGGGTTAAACCT

GGTAAAGTGCCGGGAGTAGGTCTGCCAGGCGTTTATCCTGGTGGTGTT

TTGCCGGGTGCCCGTTTTCCGGGCGTTGGTGTTCTTCCAGGCGTGCCG

ACCGGAGCCGGTGTTAAACCGAAAGCCCCCGGTGTTGGAGGTGCATTT

GCAGGCATCCCGGGAGTTGGCCCGTTTGGTGGTCCGCAACCTGGGGTT

CCGTTAGGTTATCCGATTAAAGCACCGAAACTGCCCGGCGGTTATGGT

CTGCCGTACACAACCGGTAAACTGCCGTATGGTTATGGCCCGGGTGGA

GTTGCGGGTGCAGCAGGTAAAGCGGGTTATCCTACCGGAACCGGTGTA

GGTCCGCAGtaa

The amino acid sequence of a 19.6 kDa human elastin truncated at the N-terminal is disclosed in SEQ ID NO: 63. The 19.6 kDa truncated elastin has amino acids 2-542 deleted from the full length elastin.

(SEQ ID NO: 63)

QLRAAAGLGAGIPGLGVGVGVPGLGVGAGVPGLGVGAGVPGFGAGADE

GVRRSLSPELREGDPSSSQHLPSTPSSPRVPGALAAAKAAKYGAAVPG

VLGGLGALGGVGIPGGVVGAGPAAAAAAAKAAAKAAQFGLVGAAGLGG

LGVGGLGVPGVGGLGGIPPAAAAKAAKYGAAGLGGVLGGAGQFPLGGV

AARPGFGLSPIFPGGACLGKACGRKRK

The codon optimized polynucleotide sequence encoding the 19.6 kDa truncated human elastin is disclosed in SEQ ID NO: 64

(SEQ ID NO: 64)

CAACTGCGCGCCGCCGCGGGCCTCGGTGCAGGTATTCCGGGGCTGGGTGT

CGGAGTTGGAGTCCCGGGTTTGGGCGTGGGCGCGGGAGTTCCGGGACTGG

GAGTGGGTGCCGGAGTTCCTGGCTTTGGTGCAGGCGCAGATGAAGGTGTT

CGTCGTAGCCTGAGTCCGGAACTGCGTGAAGGTGATCCGAGTAGCAGCCA

GCATCTGCCGAGCACCCCGAGCAGCCCGCGTGTTCCGGGTGCATTAGCTG

CAGCAAAAGCCGCCAAGTATGGTGCAGCCGTGCCGGGCGTCTTAGGTGGT

CTGGGCGCCCTGGGTGGTGTAGGCATTCCGGGAGGTGTTGTGGGTGCAGG

ACCGGCCGCCGCAGCTGCGGCCGCCAAAGCAGCTGCAAAAGCGGCCCAGT

TTGGTTTAGTGGGCGCCGCAGGTTTAGGCGGTTTAGGTGTGGGTGGACTG

GGTGTACCTGGCGTAGGCGGTCTGGGTGGAATTCCGCCCGCAGCGGCCGC

GAAAGCGGCAAAATATGGCGCGGCAGGCCTGGGCGGCGTGCTGGGTGGGG

CAGGTCAGTTTCCGCTGGGCGGGGTTGCCGCACGTCCGGGATTTGGTCTG

AGCCCGATTTTCCCTGGCGGCGCATGTCTGGGTAAAGCATGTGGTCGTAA

ACGTAAAtaa

The amino acid sequence of a 11 kDa human elastin truncated at the N-terminal is disclosed in SEQ ID NO: 65. The 11 kDa truncated elastin has amino acids 2-635 deleted from the full length elastin.

(SEQ ID NO: 65)

VPGVLGGLGALGGVGIPGGVVGAGPAAAAAAAKAAAKAAQFGLVGAAGLG

GLGVGGLGVPGVGGLGGIPPAAAAKAAKYGAAGLGGVLGGAGQFPLGGVA

ARPGFGLSPIFPGGACLGKACGRKRK

The codon optimized polynucleotide sequence encoding the 11 kDa truncated human elastin is disclosed in SEQ ID NO: 66

(SEQ ID NO: 66)

GTGCCGGGCGTCTTAGGTGGTCTGGGCGCCCTGGGTGGTGTAGGCATTCC

GGGAGGTGTTGTGGGTGCAGGACCGGCCGCCGCAGCTGCGGCCGCCAAAG

CAGCTGCAAAAGCGGCCCAGTTTGGTTTAGTGGGCGCCGCAGGTTTAGGC

GGTTTAGGTGTGGGTGGACTGGGTGTACCTGGCGTAGGCGGTCTGGGTGG

AATTCCGCCCGCAGCGGCCGCGAAAGCGGCAAAATATGGCGCGGCAGGCC

TGGGCGGCGTGCTGGGTGGGGCAGGTCAGTTTCCGCTGGGCGGGGTTGCC

GCACGTCCGGGATTTGGTCTGAGCCCGATTTTCCCTGGCGGCGCATGTCT

GGGTAAAGCATGTGGTCGTAAACGTAAAtaa

The amino acid sequence of a 7.9 kDa human elastin truncated at the N-terminal is disclosed in SEQ ID NO: 67. The 7.9 kDa truncated elastin has amino acids 2-674 deleted from the full length elastin.

(SEQ ID NO: 67)

QFGLVGAAGLGGLGVGGLGVPGVGGLGGIPPAAAAKAAKYGAAGLGGVLG

GAGQFPLGGVAARPGFGLSPIFPGGACLGKACGRKRK

The codon optimized polynucleotide sequence encoding the 7.9 kDa truncated human elastin is disclosed in SEQ ID NO: 68

(SEQ ID NO: 68)
CAGTTTGGTTTAGTGGGCGCCGCAGGTTTAGGCGGTTTAGGTGTGGGTGG

ACTGGGTGTACCTGGCGTAGGCGGTCTGGGTGGAATTCCGCCCGCAGCGG

CCGCGAAAGCGGCAAAATATGGCGCGGCAGGCCTGGGCGGCGTGCTGGGT

GGGGCAGGTCAGTTTCCGCTGGGCGGGGTTGCCGCACGTCCGGGATTTGG

TCTGAGCCCGATTTTCCCTGGCGGCGCATGTCTGGGTAAAGCATGTGGTC

GTAAACGTAAAtaa

The amino acid sequence of a 6.3 kDa human elastin truncated at the C-terminal is disclosed in SEQ ID NO: 69. The 6.3 kDa truncated elastin has amino acids 74-761 deleted from the full length elastin.

(SEQ ID NO: 69)
GGVPGAIPGGVPGGVFYPGAGLGALGGGALGPGGKPLKPVPGGLAGAGLG

AGLGAFPAVTFPGALVPGGVAD

The codon optimized polynucleotide sequence encoding the 6.3 kDa truncated human elastin is disclosed in SEQ ID NO: 70:

(SEQ ID NO: 70)
GGTGGCGTACCAGGCGCAATTCCTGGGGGTGTCCCAGGCGGTGTTTTTTA

TCCGGGCGCCGGTCTTGGCGCACTGGGTGGCGGTGCACTGGGCCCGGGCG

GCAAACCGCTGAAACCGGTACCAGGTGGTTTAGCAGGCGCCGGCTTAGGC

GCAGGTCTGGGAGCATTTCCGGCAGTTACCTTTCCAGGGGCACTGGTTCC

TGGAGGTGTGGCCGATtaa

The amino acid sequence of a 4.3 kDa human elastin truncated at the N-terminal is disclosed in SEQ ID NO: 71. The 4.3 kDa truncated elastin has amino acids 2-717 deleted from the full length elastin.

(SEQ ID NO: 71)
GLGGVLGGAGQFPLGGVAARPGFGLSPIFPGGACLGKACGRKRK

The codon optimized polynucleotide sequence encoding the 4.3 kDa truncated human elastin is disclosed in SEQ ID NO: 72

(SEQ ID NO: 72)
GGCCTGGGCGGCGTGCTGGGTGGGGCAGGTCAGTTTCCGCTGGGCGGGGT

TGCCGCACGTCCGGGATTTGGTCTGAGCCCGATTTTCCCTGGCGGCGCAT

GTCTGGGTAAAGCATGTGGTCGTAAACGTAAAtaa

Truncated Human Elastin 1 with DsbA Secretion and FLAG Tag

The amino acid sequence of truncated human elastin 1 with DsbA secretion and FLAG tag is disclosed in SEQ ID NO: 98. The DsbA secretion tag is encoded by nucleotides 1-57 of SEQ ID NO: 99 and the amino acid sequences are amino acids 1-19 of SEQ ID NO: 98. The elastin nucleotide sequences are nucleotides 58-657 of SEQ ID NO: 99 and the amino acid sequences are amino acids 20-219 of SEQ ID NO: 98. The FLAG nucleotide sequences are nucleotides 658-684 of SEQ ID NO: 99 and the amino acid sequences are amino acids 220-228 of SEQ ID NO: 98.

(SEQ ID NO: 98)
MKKIWLALAGLVLAFSASAGGVPGAIPGGVPGGVFYPGAGLGALGGGALG

PGGKPLKPVPGGLAGAGLGAGLGAFPAVTFPGALVPGGVADAAAAYKAAK

AGAGLGGVPGVGGLGVSAGAVVPQPGAGVKPGKVPGVGLPGVYPGGVLPG

ARFPGVGVLPGVPTGAGVKPKAPGVGGAFAGIPGVGPFGGPQPGVPLGYP

IKAPKLPGGYGLPYTTGKLGDYKDDDDK

The nucleic acid sequence of truncated human elastin 1 with DsbA secretion and FLAG tag is disclosed in SEQ ID NO: 99.

(SEQ ID NO: 99)
ATGAAAAAGATTTGGCTGGCGCTGGCTGGTTTAGTTTTAGCGTTTAGCGC

ATCGGCGGGTGGCGTACCAGGCGCAATTCCTGGGGGTGTCCCAGGCGGTG

TTTTTTATCCGGGCGCCGGTCTTGGCGCACTGGGTGGCGGTGCACTGGGC

CCGGGCGGCAAACCGCTGAAACCGGTACCAGGTGGTTTAGCAGGCGCCGG

CTTAGGCGCAGGTCTGGGAGCATTTCCGGCAGTTACCTTTCCAGGGGCAC

TGGTTCCTGGAGGTGTGGCCGATGCAGCCGCGGCATATAAAGCCGCTAAA

GCCGGTGCGGGTTTAGGAGGCGTCCCAGGTGTCGGTGGCCTGGGTGTTAG

CGCCGGTGCAGTTGTTCCGCAGCCGGGAGCAGGGGTTAAACCTGGTAAAG

TGCCGGGAGTAGGTCTGCCAGGCGTTTATCCTGGTGGTGTTTTGCCGGGT

GCCCGTTTTCCGGGCGTTGGTGTTCTTCCAGGCGTGCCGACCGGAGCCGG

TGTTAAACCGAAAGCCCCCGGTGTTGGAGGTGCATTTGCAGGCATCCCGG

GAGTTGGCCCGTTTGGTGGTCCGCAACCTGGGGTTCCGTTAGGTTATCCG

ATTAAAGCACCGAAACTGCCCGGCGGTTATGGTCTGCCGTACACAACCGG

TAAACTGGGTGACTACAAAGACGACGACGACAAAtaa

The polynucleotide of SEQ ID NO: 99 was subcloned into vector pET28a, expressed host *E. coli* cells and the truncated elastin was purified as described herein.

The purified elastin produced a clear band on SDS-PAGE and an anti-FLAG western was observed at around 25 kilodaltons. There were no existing bands that appear at that location on the gel in the absence of expression of this protein.

Truncated Human Elastin 2 with DsbA Secretion and FLAG Tag

The amino acid sequence of truncated human elastin type 2 with DsbA secretion and FLAG tag is disclosed in SEQ ID NO: 100. The DsbA secretion tag is encoded by nucleotides 1-57 of SEQ ID NO: 101 and the amino acid sequences are amino acids 1-19 of SEQ ID NO: 100. The elastin nucleotide sequences are nucleotides 58-657 of SEQ ID NO: 101 and the amino acid sequences are amino acids 20-219 of SEQ ID NO: 100. The FLAG nucleotide sequences are nucleotides 658-684 of SEQ ID NO: 101 and the amino acid sequences are amino acids 220-228 of SEQ ID NO: 100.

(SEQ ID NO: 100)
MKKIWLALAGLVLAFSASAPYGYGPGGVAGAAGKAGYPTGTGVGPQAAAA

AAAKAAAKFGAGAAGVLPGVGGAGVPGVPGAIPGIGGIAGVGTPAAAAAA

AAAAKAAKYGAAAGLVPGGPGFGPGVVGVPGAGVPGVGVPGAGIPVVPGA

-continued

GIPGAAVPGVVSPEAAAKAAAKAAKYGARPGVGVGGIPTYGVGAGGFPGF

GVGVGGIPGVAGVPGVGGVGDYKDDDDK

The nucleic acid sequence of truncated human elastin 2 with DsbA secretion and FLAG tag is disclosed in SEQ ID NO: 101.

(SEQ ID NO: 101)

ATGAAAAAGATTTGGCTGGCGCTGGCTGGTTTAGTTTTAGCGTTTAGCGC

ATCGGCGCCGTATGGTTATGGCCCGGGTGGAGTTGCGGGTGCAGCAGGTA

AAGCGGGTTATCCTACCGGAACCGGTGTAGGTCCGCAGGCCGCTGCTGCC

GCCGCCGCAAAAGCAGCGGCTAAATTTGGCGCCGGAGCAGCGGGTGTTCT

GCCTGGAGTTGGTGGTGCGGGCGTGCCAGGGGTACCTGGTGCAATTCCGG

GTATTGGTGGTATTGCCGGTGTCGGCACCCCGGCCGCGGCAGCTGCGGCA

GCGGCGGCTGCCAAAGCTGCTAAATACGGTGCCGCGGCGGGTCTGGTGCC

AGGAGGTCCGGGTTTTGGTCCGGGAGTGGTTGGCGTGCCTGGCGCAGGCG

TTCCTGGTGTGGGCGTTCCAGGTGCAGGGATTCCTGTTGTGCCTGGTGCC

GGTATTCCCGGCGCGGCCGTTCCGGGGGTGGTTAGCCCGGAAGCCGCAGC

GAAGGCTGCGGCAAAGGCAGCAAAGTATGGCGCACGCCCAGGAGTCGGCG

TGGGTGGTATCCCGACCTATGGGGTGGGCGCAGGGGGTTTTCCTGGTTTC

GGCGTAGGTGTAGGAGGTATACCGGGCGTGGCCGGTGTACCAGGGGTTGG

TGGCGTCGGTGACTACAAAGACGACGACGACAAAtaa

The polynucleotide of SEQ ID NO: 101 was subcloned into vector pET28a, expressed host *E. coli* cells and the truncated elastin was purified as described herein. The purified elastin produced a clear band on SDS-PAGE and an anti-FLAG western was observed at around 25 kilodaltons. There were no existing bands that appear at that location on the gel in the absence of expression of this protein.

Example 6: Effect of Truncated Collagen on Fibroblast Cell Viability, Procollagen Synthesis, and Elastin Synthesis A human fibroblast cell culture was used to assess the ability of the truncated jellyfish collagen molecule of Example 2 to determine its effect on procollagen, and elastin synthesis. The human fibroblast cell culture was also used to determine the increased viability of the human fibroblast cells after exposure to the truncated jellyfish collagen.

A stock solution of 2% w/w truncated collagen was prepared from the histidine tagged truncated collagen of example 3. Aliquots from the 2% stock truncated collagen solution were then used in the experiments described below.

Preparation of Fibroblasts

Fibroblasts were seeded into the individual wells of a 24-well plate in 0.5 ml of Fibroblast Growth Media (FGM) and incubated overnight at 37±2° C. and 5±1% $CO_2$. On the following day the media was removed via aspiration to eliminate any non-adherent cells and replaced with 0.5 ml of fresh FGM. The cells were grown until confluent, with a media change every 48 to 72 hours. Upon reaching confluency the cells were treated for 24 hours with DMEM supplemented with 1.5% FBS to wash out any effects from the growth factors included in the normal culture media. After the 24-hour wash out period the cells were treated with the truncated jellyfish collagen at specified concentrations dissolved in FGM with 1.5% FBS. Transforming Growth Factor Beta (TGF-β) (20 ng/ml) was used as a positive control for collagen and elastin synthesis. Untreated cells (negative controls) just received DMEM with 1.5% FBS. The cells were incubated for 48 hours and at the end of the incubation period cell culture medium was collected and either stored frozen (−75° C.) or assayed immediately. Materials were tested in triplicate.

MTT Assay

The MTT (3-(4,5-Dimethylthiazol-2-yl)-2,5-diphenyltetrazolium bromide, a tetrazole) assay is a colorimetric assay used to determine the metabolic activity of cells. Changes in cell number were assessed via an MTT assay. When cells are exposed to MTT, reduction of MTT by mitochondria in viable cells results in the formation of insoluble purple formazin crystals that are extracted from the cells with isopropanol and quantified spectrophotometrically. Non-living cells cannot reduce MTT and therefore cannot produce the purple formazin crystals. The intensity of the purple color is directly proportional to the number of living cells (metabolically active cells). The intensity of the purple color is directly proportional to the metabolic activity of the cells and is inversely proportional to the toxicity of the test material.

After the 2-day incubation discussed above, the cell culture medium was removed (see above) and the fibroblasts were washed twice with PBS to remove any remaining jellyfish glycogen molecules. After the final wash, 500 μl of DMEM supplemented with 0.5 mg/ml MTT was added to each well and the cells were incubated for 1 hour at 37±2° C. and 5±1% $CO_2$. After the incubation, the DMEM/MTT solution was removed and the cells were washed again once with PBS and then 0.5 ml of isopropyl alcohol was added to the well to extract the purple formazin crystals. Two hundred microliters of the isopropyl extracts was transferred to a 96-well plate and the plate was read at 540 nm using isopropyl alcohol as a blank.

The mean MTT absorbance value for the negative control cells was calculated and used to represent 100% cell viability. The individual MTT absorbance values from the cells undergoing the various treatments were then divided by the mean value for the negative control cells and expressed as a percent to determine the change in cell viability caused by each treatment.

In Tables 1, 2 and 3 of this example, the experiments were performed by using the designated aliquots of the 2% stock truncated collagen solution in the assays. For example, in the samples that tested the "10% Collagen Solution," an aliquot of the 2% truncated collagens in an amount sufficient to provide 10% of the assay volume was used. For a total assay volume of 1.0 ml, 100 μl of the 2% stock truncated collagen solution was used. In Tables 1, 2 and 3, "10% Collagen Solution" is 0.2% collagen, "5% Collagen Solution" is 0.1% collagen, "1% Collagen Solution" is 0.02% collagen, "0.5% Collagen Solution" is 0.01% collagen, "0.1% Collagen Solution" is 0.002% collagen, "0.05% Collagen Solution" is 0.001% collagen, "0.01% Collagen Solution" is 0.0002% collagen, "0.005% Collagen Solution" is 0.0001% collagen, f The results for the MTT assay are presented in Table 3. The values are presented as the mean percent viability±the deviation from the mean.

TABLE 3

| MTT Assay | |
|---|---|
| Untreated | 100 ± 6.1 |
| 20 ng/ml TGF-B | 110 ± 2.9 |
| 10% Collagen Solution | 131 ± 7.8* |
| 5% Collagen Solution | 140 ± 8.3* |
| 1% Collagen Solution | 116 ± 0.9 |
| 0.5% Collagen Solution | 105 ± 4.8 |
| 0.1% Collagen Solution | 102 ± 1.1 |
| 0.05% Collagen Solution | 106 ± 3.4 |
| 0.01% Collagen Solution | 112 ± 1.9 |
| 0.005% Collagen Solution | 103 ± 3.9 |

*Denotes values that are significantly different from the Untreated group ($p < 0.05$).

The histidine tagged truncated jellyfish collagen showed protective effect by increasing the cell viability of human fibroblast cells. As can be seen in Table 3, the highest value in the MTT assay was observed when the fibroblast cells were exposed to 0.02% to 0.2% truncated jellyfish collagen.

Procollagen Synthesis

Fibroblasts are the main source of the extracellular matrix peptides, including the structural proteins collagen and elastin. Procollagen is a large peptide synthesized by fibroblasts in the dermal layer of the skin and is the precursor for collagen. As the peptide is processed to form a mature collagen protein, the propeptide portion is cleaved off (type I C-peptide). Both the mature collagen protein and the type I C-peptide fragment are then released into the extracellular environment. As collagen is synthesized the type I C-peptide fragment accumulates into the tissue culture medium. Since there is a 1:1 stoichiometric ratio between the two parts of the procollagen peptide, assaying for type I C-peptide will reflect the amount of collagen synthesized. Type 1 C-peptide can be assayed via an ELISA based method.

A series of type I C-peptide standards was prepared ranging from 0 ng/ml to 640 ng/ml. Next, an ELISA microplate was prepared by removing any unneeded strips from the plate frame followed by the addition of 100 μl of peroxidase-labeled anti procollagen type I-C peptide antibody to each well used in the assay. Twenty (20) μl of either sample (collected tissue culture media) or standard was then added to appropriate wells and the microplate was covered and allowed to incubate for 3±0.25 hours at 37° C. After the incubation the wells were aspirated and washed three times with 400 μl of wash buffer. After the last wash was removed 100 μl of peroxidase substrate solution (hydrogen peroxide+tetramethylbenzidine as a chromagen) was added to each well and the plate was incubated for 15±5 minutes at room temperature. After the incubation 100 μl of stop solution (1 N sulfuric acid) was added to each well and the plate was read using a microplate reader at 450 nm.

To quantify the amount of each substance present, a standard curve was generated using known concentrations of each substance. A regression analysis was performed to establish the line that best fits these data points. Absorbance values for the test materials and untreated samples were used to estimate the amount of each substance present in each sample.

The results for the ELISA assays are presented in Table 4.

TABLE 4

Type I Collagen Assay.
The values presented are mean concentration (ng/ml) ± the deviation from the mean.

| Treatment | Type I C-Peptide (ng/ml) |
|---|---|
| Untreated | 1718 ± 94 |
| 20 ng/ml TGF-B | 3028 ± 332* |
| 10% Collagen Solution | 1940 ± 100 |
| 5% Collagen Solution | 2394 ± 125* |
| 1% Collagen Solution | 1773 ± 183 |
| 0.5% Collagen Solution | 1127 ± 19* |
| 0.1% Collagen Solution | 1158 ± 10* |
| 0.05% Collagen Solution | 1416 ± 64 |
| 0.01% Collagen Solution | 1835 ± 404 |
| 0.005% Collagen Solution | 1551 ± 149 |

*Denotes values that are significantly different from the Untreated group ($p < 0.05$).

The truncated histidine tagged jellyfish collagen was observed to have a biphasic effect on collagen synthesis. At the 1%, 5% and the 10% levels, collagen synthesis increased. At the 5% concentration truncated jellyfish collagen significantly increased collagen synthesis with a p-value of less than 0.05.

Elastin Synthesis

Elastin is the main component of a network of elastic fibers that give tissues their ability to recoil after a transient stretch. This protein is released by fibroblasts (soluble elastin) into the extracellular space where it is then cross-linked to other elastin proteins to form an extensive network of fibers and sheets (insoluble elastin). Soluble elastin can be readily measured from cell culture medium via an ELISA based method.

Soluble α-elastin was dissolved in 0.1 M sodium carbonate (pH 9.0) at a concentration of 1.25 μg/ml. 150 μl of this solution was then applied to the wells of a 96-well maxisorp Nunc plate and the plate was incubated overnight at 4° C. On the following day the wells were saturated with PBS containing 0.25% BSA and 0.05% Tween 20. The plate was then incubated with this blocking solution for 1 hour at 37° C. and then washed two times with PBS containing 0.05% Tween 20.

A set of α-elastin standards was generated ranging from 0 to 100 ng/ml. 180 μl of either standard or truncated jellyfish collagen was then transferred to a 650 μl microcentrifuge tube. An anti-elastin antibody solution was prepared (the antibody was diluted 1:100 in PBS containing 0.25% BSA and 0.05% Tween 20) and 20 μl of the solution was added to the tube. The tubes were then incubated overnight at 4±2° C. On the following day, 150 μl was transferred from each tube to the 96-well elastin ELISA plate, and the plate was incubated for 1 hour at room temperature. The plate was then washed 3 times with PBS containing 0.05% Tween 20. After washing, 200 μl of a solution containing a peroxidase linked secondary antibody diluted in PBS containing 0.25% BSA and 0.05% Tween 20 was added, and the plate was incubated for 1 hour at room temperature. After washing the plate three times, 200 μl of a substrate solution was added and the plate was incubated for 10 to 30 minutes in the dark at room temperature. After this final incubation the plate was read at 460 nm using a plate reader.

TABLE 5

| The values are also presented as mean concentration (ng/ml) ± deviation from the mean. | |
|---|---|
| Treatment | Elastin (ng/ml) |
| Untreated | 79 ± 19 |
| 20 ng/ml TGFB1 | 243 ± 35* |
| 10% Collagen Solution | 68 ± 18 |
| 5% Collagen Solution | 99 ± 13 |
| 1% Collagen Solution | 126 ± 21 |
| 0.5% Collagen Solution | 145 ± 21* |
| 0.1% Collagen Solution | 76 ± 14 |
| 0.05% Collagen Solution | 58 ± 6 |
| 0.01% Collagen Solution | 53 ± 5 |
| 0.005% Collagen Solution | 56 ± 24 |

*Denotes values that are significantly different from the Untreated group ($p < 0.05$).

Truncated his-tagged jellyfish collagen significantly increased elastin production when it was used at the 0.5% concentration as shown in Table 5.

Example 7: Effect of Truncated Collagen on Keratinocyte Proliferation and UVB Protection A human keratinocyte cell culture model was used to assess the ability of the test materials to exert an effect on cell proliferation. In addition, the impact of the test materials on the cell viability after an exposure to UVB was also assessed.

A stock solution of 2% w/w truncated collagen was prepared from the truncated collagen of example 1. Aliquots from the 2% stock truncated collagen solution was then used in the experiments described below.

This study was conducted in two parts. In the first part cultured keratinocytes were incubated with the test materials for 48 hours, after which changes in the number of viable cells were assessed using an MTT assay. In the second part of the study cultured keratinocytes were irradiated with UVB and then treated with the test materials for 48 hours. At the end of the 48 hour period the number of viable cells was again assessed via an MTT assay.

Changes in cell number of viable cells can be determined using an MTT (3-(4,5-Dimethylthiazol-2-yl)-2,5-diphenyltetrazolium bromide, a tetrazole) assay. The MTT assay is a colorimetric analysis of the metabolic activity of the cell, which is a reflection of the number of viable cells. Reduction of MTT by mitochondria in viable cells results in the formation of insoluble purple formazin crystals that are extracted from the cells with isopropanol and quantified spectrophotometrically. The intensity of the purple color is directly proportional to the number of metabolically active cells.

Proliferation Assay

For the proliferation assay the keratinocytes were seeded into 96-well plates using without growth factors and incubated for 24 hours at 37±2° C. and 5±1% CO2. After this initial incubation the media was replaced with media supplemented with the test materials. Normal media (with growth factors) was used as a positive control. After the addition of the test materials the cells were cultured for 48 hours as described above. At the end of the incubation period changes in the number of viable cells was determined using an MTT assay.

UVB Protection Assay

For the UVB protection assay the keratinocytes were seeded into 96-well plates using normal media and incubated for 24 hours at 37±2° C. and 5±1% CO2. After this initial incubation the media was replaced with 100 μl of phosphate buffered saline (PBS) and the cells were exposed to UVB (40 mJ/cm2). After the UVB exposure, the PBS was replaced with fresh media supplemented with the test materials (ascorbic acid at 100 μg/ml served as the positive control) and the cells were cultured for 48 hours at 37±2° C. and 5±1% CO2. At the end of the 48 hour incubation cell viability was determined using an MTT assay.

MTT Assay

After the 48-hour incubation the cell culture medium was removed and replaced with 200 μl of culture media supplemented with 0.5 mg/ml MTT. The well plates were incubated for 1 hour at 37±2° C. and 5±1% CO2. After the incubation, the MTT solution was removed and the cells were washed once with phosphate buffered saline and then 200 μl of isopropyl alcohol was added to the well to extract the purple formazin crystals. The 96-well plate was read at 540 nm using isopropyl alcohol as a blank.

The mean absorbance value for the cells not treated with test materials (proliferation assay: Untreated Group) or not exposed to UVB (UVB protection assay: Non-UVB Exposed Group) was calculated and used to represent 100% cell viability. The individual absorbance values from the cells undergoing the various treatments were then divided by the mean absorbance value representing 100% cell viability and expressed as a percent to determine the change in cell viability caused by each treatment.

The results for the Proliferation assay using the his-tagged truncated jellyfish collagen are presented in Table 6. The results for the UVB Protection assay using the his-tagged truncated jellyfish collagen are presented in Table 7. The values for both assays are presented as mean viability±standard deviation.

TABLE 6

| Proliferation Assay | |
|---|---|
| Untreated | 100 ± 3.4 |
| Positive Control (Growth Factors) | 139 ± 3.8* |
| 10% Collagen Solution | 103 ± 9.4 |
| 5% Collagen Solution | 97 ± 7.3 |
| 1% Collagen Solution | 94 ± 5.0 |
| 0.5% Collagen Solution | 93 ± 7.0 |
| 0.1% Collagen Solution | 95 ± 2.5 |
| 0.05% Collagen Solution | 99 ± 6.0 |
| 0.01% Collagen Solution | 96 ± 6.4 |
| 0.005% Collagen Solution | 96 ± 2.8 |

*Denotes values which are significantly different from the Untreated Group ($p < 0.05$)

TABLE7

| UVB Protection Assay | |
|---|---|
| Non-UVB Exposed | 100 ± 1.7* |
| Untreated | 77 ± 1.8 |
| 100 ug/ml Trolox | 92 ± 2.0* |
| 10% Collagen Solution | 76 ± 8.6 |
| 5% Collagen Solution | 92 ± 3.9* |
| 1% Collagen Solution | 91 ± 2.9* |
| 0.5% Collagen Solution | 100 ± 4.5* |
| 0.1% Collagen Solution | 86 ± 4.8 |
| 0.05% Collagen Solution | 91 ± 1.6* |
| 0.01% Collagen Solution | 83 ± 7.5 |
| 0.005% Collagen Solution | 82 ± 4.7 |

*Denotes values which are significantly different from the Untreated Group ($p < 0.05$)

For the proliferation assay the Untreated group was used to represent 100% cell viability. Values above 100% reflect an increase in the number of viable cells and hence are indicative of cell proliferation. In this study, the test material was not observed to promote cell proliferation.

In addition, the keratinocyte proliferation assay was performed using the truncated collagen of SEQ ID NO: 91. A 1% and 0.5% collagen solution of a 5% stock solution was prepared according to Example 8 and tested. The truncated collagen of SEQ ID NO: 91 had keratinocyte cell viability assay values of 102±2.9 and 102±2.0, respectively. The observed values were statistically significant ($p<0.05$).

In addition to its effects on cell proliferation, the test material was also screened to determine if it had an impact on cell recovery after UVB exposure. In this study, exposure to UVB was observed to result in a significant reduction in the number of viable cells 48 hours post exposure. However, treatment with the test material prevented this decrease in cell viability. The effect was evident within a concentration range between 0.05% and 5% of the test material, with an optimal effect at a concentration of 0.05%. Within this range of concentrations cell viability was significantly greater than the untreated group (with the lone exception of the 0.01% concentration), demonstrating that the material has UVB protective effect. Since this material was added after the UVB exposure it could be acting to reduce the damaging effects of the UVB irradiation, or it could be helping the damaged cells to recover at a faster rate. With respect to the latter, then truncated collagen is beneficial when applied topically to the skin and has a regenerative effect on skin cells damaged by UVB.

In addition, the UVB protection assay was performed using the truncated collagen of SEQ ID NO: 91. A 1% and 0.5% collagen solution of SEQ ID NO: 91 had keratinocyte cell viability assay values of 80±4.6 and 78±2.5, respectively.

The observed values were statistically significant ($p<0.05$).

Example 8: Effect of Truncated Collagen on Thymine Dimer Formation

Upon exposure to ultraviolet radiation the thymine dimer (TT dimer) content in DNA present in cells increases. Increases in TT dimer formation are correlated with skin damage and certain types of cell proliferative diseases including skin cancer.

The polynucleotide of SEQ ID NO: 11 was expressed in the expression system of Example 1 and purified as described in this example. The encoded polypeptide includes the DsbA secretion tag. As the polypeptide is processed through the secretion pathway, the DsbA tag, amino acids 1-24 of SEQ ID NO: 12 is cleaved by the host cell. The truncated collagen without the DsbA secretion tag is provided in SEQ ID NO: 91.

The truncated collagen of SEQ ID NO: 91 was tested to determine if it could reduce TT dimer formation is human epidermal keratinocytes. For this study, the cells were exposed to UVB (25 mJ/cm2). Following the exposures cells were treated with the test materials or Trolox (100 ug/ml) and incubated overnight. On the following day cellular DNA was extracted and assayed for thymine dimer content using an ELISA based method.

Human keratinocytes were seeded into 12-well plates using normal media and incubated for 24 hours at 37±2° C. and 5±1% CO2. After this initial incubation the media was replaced with 100 μl of phosphate buffered saline (PBS) and the cells were exposed to UVB (25 mJ/cm2). After the UVB exposure, the PBS was replaced with fresh media supplemented with the test materials or Trolox (100 μg/ml, this served as the positive control) and the cells were cultured overnight at 37±2° C. and 5±1% CO2. At the end of the incubation cellular DNA was extracted.

After the overnight incubation the cell culture media was removed from the wells and replaced with 200 μl of PBS and 20 μl of Proteinase K. After swirling the plate to mix the PBS and Proteinase K, 200 μl of buffer AL was added to each well. After again swirling the plate to mix the reagents, the plates were incubated for 10 minutes at 55±2° C. After cooling the plate to room temperature, the DNA was precipitated by the addition of 200 μl of 100% ethanol. The precipitated DNA mixtures were then transferred to DNEasy Spin Columns in 2 ml collection tubes and centrifuged at 8,000 RPM for 1 minute. The flow through and collection tubes were discarded, and 500 μl of Wash Buffer One was added to the spin column and the column was placed into a new collection tube and centrifuged at 8,000 RPM for 1 minute. The flow through and collection tube were again discarded, and 500 μl of Wash Buffer Two was added to the spin column and the column was placed into a new collection tube and centrifuged at 14,000 RPM for 3 minutes. The spin column was then placed into a new 1.5 ml centrifuge tube and 110 μl of ultrapure water was added to the column. The column was incubated for 1 minute at room temperature and then centrifuged at 8,000 RPM for 1 minute.

Extracted DNA was quantified via a fluorometric assay. A 2 μl aliquot of the DNA sample was mixed with 100 μl TE buffer in a 96-well plate. A series of DNA standards was also transferred to wells in a 96-well plate (in duplicate). Finally, 100 μl of dilute Cyquant Green dye was added to each well and the fluorescence intensity of each well was determined using an excitation wavelength of 480 nm and an emission wavelength of 520 nm.

Thymine Dimer Detection was determined using an OxiSelect™ UV-Induced DNA Damage ELISA Kit)

Aliquots of genomic DNA samples or standards were converted to single stranded DNA by incubating the samples at 95° C. for 10 minutes and then chilled on ice. 100 μl or each sample or standard was transferred to a DNA binding ELISA plate and incubated overnight at 4° C. On the following day the wells were rinsed once with 100 μl of PBS and then blocked with 150 μl of Assay Diluent for one hour at room temperature. After removing the Assay Diluent, 100 μl of anti-CPD antibody was added to each well and the plate was incubated for one hour at room temperature. After this incubation, the plate was washed three times with 250 μl of wash buffer per well, and then 150 μl of Blocking Reagent was added to the plate. The plate will be blocked again for one hour at room temperature, and then washed three times as described before. 100 μl of Secondary Antibody was then added to each well and the plate was incubated for 1 hour at room temperature. After washing the plate again, 100 μl of substrate was added to each well and the plate was incubated for 5-20 minutes to allow for color generation in the plate. The color generation reaction was stopped by the addition of 100 μl of stop solution and the plate was read at 460 nm using a plate reader.

To quantify the amount of DNA present, a standard curve was generated using known concentrations of DNA and their respective fluorescence intensity (measured in RFUs or relative fluorescence units). A regression analysis was performed to establish the line that best fits these data points. The Relative Fluorescence Units (RFU) for each unknown sample was then used to estimate the amount of DNA.

Figure 5:
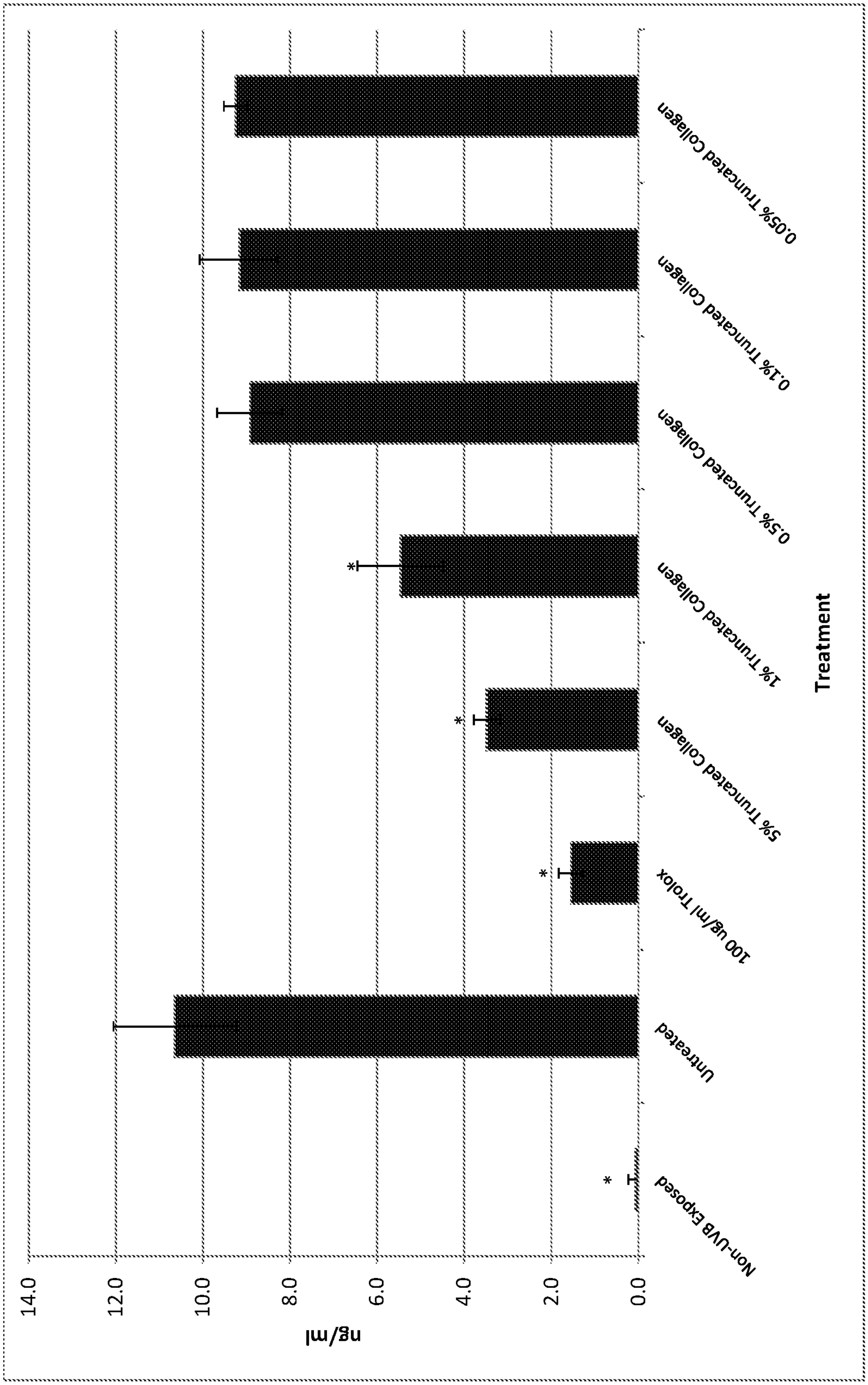
FIG. 5 illustrates the reduction in TT dimer formation by treatment of human keratinocytes with truncated collagen.

A series of DNA standards with known amounts of thymine dimer content were used to generate a standard curve. This standard curve was used to determine the amount of DNA damage in the sample DNA. Means for each treatment group were calculated and compared using an ANOVA. In table 8 and FIG. 5, a standard 5% collagen solution (5 g truncated collagen in 95 ml deionized water was further diluted with phosphate buffered saline (PBS) to the indicated percent solution.

TABLE 8

Thymine Dimer Assay

| Treatment | Thymine Dimer, ng/ml |
|---|---|
| Non-UVB Exposed | 0.1 ± 0.2* |
| Untreated | 10.7 ± 1.4* |
| 100 μg/ml Trolox | 1.6 ± 0.3* |
| 5% Truncated Collagen | 3.5 ± 0.3* |
| 1% Truncated Collagen | 5.5 ± 1.0* |
| 0.5% Truncated Collagen | 8.9 ± 0.8 |
| 0.1% Truncated Collagen | 9.2 ± 0.9 |
| 0.05% Truncated Collagen | 9.2 ± 0.3 |

*Denotes values which are statistically significantly different from untreated with P < 0.05

Table 8 shows that the 5% and the 1% truncated collagen solution reduced TT dimer formation with statistical significance ($p<0.05$). The data is presented graphically in FIG. 5.

The experiment was repeated with a different lot of truncated collagen (SEQ ID NO: 91). The amount of TT dimer in ng/ml in non-UVB exposed cells was 1.3±1.2, untreated cells was 18.1±0.4, 100 μg/ml Trolox treated cells was 7.9±0.3, 5% collagen was 13.1±0.2, and 1% collagen was 17.4±0.7. The reduction in TT dimer formation for non-UVB exposed cells, Trolox treated cells, 5% collagen treated cells and 1% collagen treated cells was statistically significant compared to untreated cells ($p<0.05$).

Example 9: Human Collagens

Truncated Human Collagen Type 21 Alpha 1

A truncated human collagen type 21 alpha 1 without a His tag, linker, and thrombin cleavage site is disclosed below. The codon-optimized nucleotide sequence encoding this collagen and the amino acid sequence are disclosed below. In SEQ ID NOs: 73 and 74, the DsbA secretion tag is encoded by nucleotides 1-72 and encodes amino acids 1-24. In SEQ ID NOs: 73 and 74, the truncated collagen sequence is encoded by nucleotides 73-633 and encodes amino acids 25-211.

The codon-optimized nucleotide sequence encoding this collagen is provided in SEQ ID NO: 73.

```
                                          (SEQ ID NO: 73)
ATGAAAAAGATTTGGCTGGCGCTGGCTGGTTTAGTTTTAGCGTTTAGCGC

ATCGGCGGCGCAGTATGAAGATGCAGGTTTTCCGGGTCTGCCTGGTCCGG

CAGGCGAACCGGGTCGTCATGGTAAAGATGGTCTGATGGGTAGTCCGGGT

TTTAAAGGTGAAGCAGGTTCACCGGGTGCACCTGGTCAGGATGGCACCCG

TGGTGAACCGGGTATTCCGGGATTTCCGGGTAATCGTGGCCTGATGGGTC

AGAAAGGTGAAATTGGTCCGCCTGGTCAGCAGGGTAAAAAAGGCGCACCG

GGTATGCCAGGACTGATGGGTTCAAATGGCAGTCCGGGTCAGCCAGGCAC

ACCGGGTTCAAAAGGTAGCAAAGGCGAACCTGGTATTCAGGGTATGCCTG

GTGCAAGCGGTCTGAAAGGCGAGCCAGGTGCCACCGGTTCTCCGGGTGAA

CCAGGTTATATGGGTCTGCCAGGTATCCAAGGCAAAAAAGGTGATAAAGG
```

-continued

```
TAATCAGGGCGAAAAAGGCATTCAGGGCCAGAAAGGCGAAAATGGCCGT

CAGGGTATTCCAGGCCAGCAGGGCATCCAGGGTCATCATGGTGCAAAAGG

TGAACGTGGTGAAAAGGGCGAACCAGGTGTTCGTtaa
```

The amino acid sequence is disclosed in SEQ ID NO: 74.

```
                                          (SEQ ID NO: 74)
MKKIWLALAGLVLAFSASAAQYEDAGFPGLPGPAGEPGRHGKDGLMGSPG

FKGEAGSPGAPGQDGTRGEPGIPGFPGNRGLMGQKGEIGPPGQQGKKGAP

GMPGLMGSNGSPGQPGTPGSKGSKGEPGIQGMPGASGLKGEPGATGSPGE

PGYMGLPGIQGKKGDKGNQGEKGIQGQKGENGRQGIPGQQGIQGHHGAKG

ERGEKGEPGVR
```

The codon-optimized nucleotide sequence encoding the truncated human collagen type 21 alpha 1 without the DsbA secretion tag collagen is provided in SEQ ID NO: 75.

```
                                          (SEQ ID NO: 75)
TGCAGGTTTTCCGGGTCTGCCTGGTCCGGCAGGCGAACCGGGTCGTCATG

GTAAAGATGGTCTGATGGGTAGTCCGGGTTTTAAAGGTGAAGCAGGTTCA

CCGGGTGCACCTGGTCAGGATGGCACCCGTGGTGAACCGGGTATTCCGGG

ATTTCCGGGTAATCGTGGCCTGATGGGTCAGAAAGGTGAAATTGGTCCGC

CTGGTCAGCAGGGTAAAAAAGGCGCACCGGGTATGCCAGGACTGATGGGT

TCAAATGGCAGTCCGGGTCAGCCAGGCACACCGGGTTCAAAAGGTAGCAA

AGGCGAACCTGGTATTCAGGGTATGCCTGGTGCAAGCGGTCTGAAAGGCG

AGCCAGGTGCCACCGGTTCTCCGGGTGAACCAGGTTATATGGGTCTGCCA

GGTATCCAAGGCAAAAAAGGTGATAAAGGTAATCAGGGCGAAAAAGGCAT

TCAGGGCCAGAAAGGCGAAAATGGCCGTCAGGGTATTCCAGGCCAGCAGG

GCATCCAGGGTCATCATGGTGCAAAAGGTGAACGTGGTGAAAAGGGCGAA

CCAGGTGTTCGTtaa
```

The amino acid sequence of truncated human collagen type 21 alpha 1 without the DsbA secretion tag is disclosed in SEQ ID NO: 76.

```
                                          (SEQ ID NO: 76)
AGFPGLPGPAGEPGRHGKDGLMGSPGFKGEAGSPGAPGQDGTRGEPGIPG

FPGNRGLMGQKGEIGPPGQQGKKGAPGMPGLMGSNGSPGQPGTPGSKGSK

GEPGIQGMPGASGLKGEPGATGSPGEPGYMGLPGIQGKKGDKGNQGEKGI

QGQKGENGRQGIPGQQGIQGHHGAKGERGEKGEPGVR
```

Truncated Human Collagen Type 1 Alpha 2 (1)

A truncated human collagen type 1 alpha 2 without a His tag, linker, and thrombin cleavage site is disclosed below. The codon-optimized nucleotide sequence and the amino acid sequences are disclosed below. In SEQ ID NOs: 78 and 79, The DsbA secretion tag is encoded by nucleotides 1-72 and encodes amino acids 1-24. The truncated collagen sequence is encoded by nucleotides 73-636 and encodes amino acids 25-212.

The codon-optimized nucleotide sequence encoding this collagen is provided in SEQ ID NO: 77.

(SEQ ID NO: 77)
ATGAAAAAGATTTGGCTGGCGCTGGCTGGTTTAGTTTTAGCGTTTAGCGC

ATCGGCGGCGCAGTATGAAGATATGGGTCCGCCTGGTAGCCGTGGTGCAA

GTGGTCCGGCAGGCGTTCGTGGTCCGAATGGTGATGCAGGTCGTCCGGGT

GAACCGGGTCTGATGGGTCCTCGTGGTCTGCCTGGTTCACCGGGTAATAT

TGGTCCTGCAGGTAAAGAAGGTCCGGTTGGTCTGCCAGGTATTGATGGCC

GTCCGGGTCCGATTGGTCCAGCCGGTGCACGTGGTGAACCTGGCAATATT

GGTTTTCCGGGTCCTAAAGGTCCGACCGGTGATCCGGGTAAAAATGGTGA

TAAAGGTCATGCAGGTCTGGCAGGCGCACGCGGTGCACCTGGTCCGGATG

GTAATAATGGTGCACAGGGTCCACCGGGTCCGCAGGGTGTTCAAGGTGGT

AAAGGCGAACAGGGTCCTGCCGGTCCTCCGGGTTTTCAGGGACTGCCTGG

TCCGAGCGGTCCTGCGGGTGAAGTTGGTAAACCTGGTGAACGCGGTCTGC

ATGGTGAATTTGGCCTGCCTGGGCCTGCAGGTCCGCGTGGCGAACGTGGT

CCGCCAGGTGAAAGCGGTGCAGCAGGTCCGACAGGTtaa

The amino acid sequence is disclosed in SEQ ID NO: 78.

(SEQ ID NO: 78)
MKKIWLALAGLVLAFSASAAQYEDMGPPGSRGASGPAGVRGPNGDAGRPG

EPGLMGPRGLPGSPGNIGPAGKEGPVGLPGIDGRPGPIGPAGARGEPGNI

GFPGPKGPTGDPGKNGDKGHAGLAGARGAPGPDGNNGAQGPPGPQGVQGG

KGEQGPAGPPGFQGLPGPSGPAGEVGKPGERGLHGEFGLPGPAGPRGERG

PPGESGAAGPTG

The nucleic acid sequence of truncated human collagen type 1 alpha 2(1) without the DsbA secretion tag is disclosed in SEQ ID NO: 79.

(SEQ ID NO: 79)
ATGGGTCCGCCTGGTAGCCGTGGTGCAAGTGGTCCGGCAGGCGTTCGTGG

TCCGAATGGTGATGCAGGTCGTCCGGGTGAACCGGGTCTGATGGGTCCTC

GTGGTCTGCCTGGTTCACCGGGTAATATTGGTCCTGCAGGTAAAGAAGGT

CCGGTTGGTCTGCCAGGTATTGATGGCCGTCCGGGTCCGATTGGTCCAGC

CGGTGCACGTGGTGAACCTGGCAATATTGGTTTTCCGGGTCCTAAAGGTC

CGACCGGTGATCCGGGTAAAAATGGTGATAAAGGTCATGCAGGTCTGGCA

GGCGCACGCGGTGCACCTGGTCCGGATGGTAATAATGGTGCACAGGGTCC

ACCGGGTCCGCAGGGTGTTCAAGGTGGTAAAGGCGAACAGGGTCCTGCCG

GTCCTCCGGGTTTTCAGGGACTGCCTGGTCCGAGCGGTCCTGCGGGTGAA

GTTGGTAAACCTGGTGAACGCGGTCTGCATGGTGAATTTGGCCTGCCTGG

GCCTGCAGGTCCGCGTGGCGAACGTGGTCCGCCAGGTGAAAGCGGTGCAG

CAGGTCCGACAGGTtaa

The amino acid sequence of truncated human collagen type 1 alpha 2(1) without the DsbA secretion tag is disclosed in SEQ ID NO: 80.

(SEQ ID NO: 80)
MGPPGSRGASGPAGVRGPNGDAGRPGEPGLMGPRGLPGSPGNIGPAGKEG

PVGLPGIDGRPGPIGPAGARGEPGNIGFPGPKGPTGDPGKNGDKGHAGLA

GARGAPGPDGNNGAQGPPGPQGVQGGKGEQGPAGPPGFQGLPGPSGPAGE

VGKPGERGLHGEFGLPGPAGPRGERGPPGESGAAGPTG

Truncated Human Collagen Type 1 Alpha 2 (2)

A truncated human collagen type 1 alpha 2 without a His tag, linker, and thrombin cleavage site is disclosed below. The codon-optimized nucleotide sequence and the amino acid sequences are disclosed below. In SEQ ID NO: 82 and 83, the DsbA secretion tag is encoded by nucleotides 1-72 and encodes amino acids 1-24. The truncated collagen sequence is encoded by nucleotides 73-609 and encodes amino acids 25-203.

The codon-optimized nucleotide sequence encoding this collagen is provided in SEQ ID NO: 81.

(SEQ ID NO: 81)
ATGAAAAAGATTTGGCTGGCGCTGGCTGGTTTAGTTTTAGCGTTTAGCGC

ATCGGCGGCGCAGTATGAAGATGGTTTTCAGGGTCCTGCCGGTGAACCGG

GTGAACCTGGTCAGACAGGTCCGGCAGGCGCACGTGGTCCTGCAGGTCCT

CCTGGTAAAGCCGGTGAAGATGGTCATCCGGGTAAACCGGGTCGTCCTGG

TGAACGTGGTGTTGTTGGTCCGCAGGGTGCCCGTGGTTTTCCGGGTACTC

CGGGTCTGCCAGGTTTTAAAGGTATTCGTGGTCATAATGGTCTGGATGGT

CTGAAAGGTCAGCCTGGTGCACCGGGTGTTAAAGGTGAACCAGGTGCTCC

GGGTGAAAATGGCACACCGGGTCAGACCGGTGCGCGTGGTCTGCCTGGCG

AACGCGGTCGTGTTGGTGCACCTGGTCCAGCCGGTGCACGCGGTAGTGAT

GGTAGCGTTGGTCCGGTTGGTCCAGCGGGTCCGATTGGTAGCGCAGGTCC

ACCGGGTTTTCCAGGCGCACCGGGTCCGAAAGGTGAAATTGGTGCAGTTG

GTAATGCAGGCCCTGCCGGTCCAGCAGGACCGCGTGGTGAAGTTGGCCTG

CCTGGTCTGtaa

The amino acid sequence is disclosed in SEQ ID NO: 82.

(SEQ ID NO: 82)
MKKIWLALAGLVLAFSASAAQYEDGFQGPAGEPGEPGQTGPAGARGPAGP

PGKAGEDGHPGKPGRPGERGVVGPQGARGFPGTPGLPGFKGIRGHNGLDG

LKGQPGAPGVKGEPGAPGENGTPGQTGARGLPGERGRVGAPGPAGARGSD

GSVGPVGPAGPIGSAGPPGFPGAPGPKGEIGAVGNAGPAGPAGPRGEVGL

PGL

The nucleic acid sequence of truncated human collagen type 1 alpha 2(2) without the DsbA secretion tag is disclosed in SEQ ID NO: 83.

(SEQ ID NO: 83)
GGTTTTCAGGGTCCTGCCGGTGAACCGGGTGAACCTGGTCAGACAGGTCC

GGCAGGCGCACGTGGTCCTGCAGGTCCTCCTGGTAAAGCCGGTGAAGATG

GTCATCCGGGTAAACCGGGTCGTCCTGGTGAACGTGGTGTTGTTGGTCCG

CAGGGTGCCCGTGGTTTTCCGGGTACTCCGGGTCTGCCAGGTTTTAAAGG

-continued

TATTCGTGGTCATAATGGTCTGGATGGTCTGAAAGGTCAGCCTGGTGCAC

CGGGTGTTAAAGGTGAACCAGGTGCTCCGGGTGAAAATGGCACACCGGGT

CAGACCGGTGCGCGTGGTCTGCCTGGCGAACGCGGTCGTGTTGGTGCACC

TGGTCCAGCCGGTGCACGCGGTAGTGATGGTAGCGTTGGTCCGGTTGGTC

CAGCGGGTCCGATTGGTAGCGCAGGTCCACCGGGTTTTCCAGGCGCACCG

GGTCCGAAAGGTGAAATTGGTGCAGTTGGTAATGCAGGCCCTGCCGGTCC

AGCAGGACCGCGTGGTGAAGTTGGCCTGCCTGGTCTGtaa

The amino acid sequence of truncated human collagen type 1 alpha 2(2) without the DsbA secretion tag is disclosed in SEQ ID NO: 84.

(SEQ ID NO: 84)

GFQGPAGEPGEPGQTGPAGARGPAGPPGKAGEDGHPGKPGRPGERGVVGP

QGARGFPGTPGLPGFKGIRGHNGLDGLKGQPGAPGVKGEPGAPGENGTPG

QTGARGLPGERGRVGAPGPAGARGSDGSVGPVGPAGPIGSAGPPGFPGAP

GPKGEIGAVGNAGPAGPAGPRGEVGLPGL

The polynucleotides of SEQ ID NO: 73, 77 or 81 were subcloned in vector pET28a as described herein to prepare a transformation vector. Host cells were transformed with the vector the polynucleotides were expressed as described in Example 2.

After the fermentation was completed, the truncated human collagen was purified from the fermentation broth using the procedures disclosed in Example 3.

The purified truncated human collagens were analyzed using SDS-PAGE and HPLC as disclosed in Example 3.

All three truncated human collagens ran at the expected molecular weights in the SDS-PAGE analysis. In analyzing the truncated human collagens using HPLC, a standard curve using the jellyfish collagen of Example 3 was utilized. The retention times of the human collagens were slightly different than the jellyfish collagen. The retention time of SEQ ID NO: 76 was 5.645 minutes, the retention time of SEQ ID NO: 80 was 5.631 minutes, and SEQ ID NO: 84 ran at two peaks and the retention times were 5.531 and 5.7 minutes.

Truncated Human Collagen Type 1 Alpha 2 Truncation 5 with DsbA Secretion and FLAG Tag The amino acid sequence of truncated human collagen type 1 alpha 2 truncation 5 with DsbA secretion and FLAG tag is disclosed in SEQ ID NO: 92. The DsbA secretion tag is encoded by nucleotides 1-57 of SEQ ID NO: 93 and the amino acid sequences are amino acids 1-19 of SEQ ID NO: 92. The collagen nucleotide sequences are nucleotides 58-657 of SEQ ID NO: 93 and the amino acid sequences are amino acids 20-219 of SEQ ID NO: 92. The FLAG nucleotide sequences are nucleotides 658-684 of SEQ ID NO: 93 and the amino acid sequences are amino acids 220-228.

(SEQ ID NO: 92)

MKKIWLALAGLVLAFSASAGDQGPVGRTGEVGAVGPPGFAGEKGPSGEAG

TAGPPGTPGPQGLLGAPGILGLPGSRGERGLPGVAGAVGEPGPLGIAGPP

GARGPPGAVGSPGVNGAPGEAGRDGNPGNDGPPGRDGQPGHKGERGYPGN

-continued

IGPVGAAGAPGPHGPVGPAGKHGNRGETGPSGPVGPAGAVGPRGPSGPQG

IRGDKGEPGEKGPRGLPGLGDYKDDDDK

The nucleic acid sequence of truncated human collagen type 1 alpha 2 truncation 5 with DsbA secretion and FLAG tag is disclosed in SEQ ID NO: 93.

(SEQ ID NO: 93)

ATGAAAAAGATTTGGCTGGCGCTGGCTGGTTTAGTTTTAGCGTTTAGCGC

ATCGGCGGGTGATCAGGGTCCGGTTGGTCGTACCGGTGAAGTTGGTGCAG

TCGGGCCGCCGGGTTTTGCGGGTGAAAAAGGCCCGTCAGGTGAAGCAGGC

ACCGCTGGCCCTCCTGGCACGCCTGGCCCACAGGGTTTACTGGGCGCACC

TGGAATTCTGGGACTGCCGGGCAGCCGTGGAGAACGCGGTTTACCAGGTG

TTGCCGGTGCCGTTGGTGAACCTGGTCCACTGGGCATTGCAGGGCCGCCT

GGCGCACGGGGACCGCCTGGTGCTGTTGGTAGTCCGGGTGTGAATGGTGC

TCCGGGTGAAGCCGGTCGTGACGGTAATCCGGGAAATGACGGCCCGCCAG

GCCGCGATGGTCAGCCGGGTCATAAAGGTGAGCGTGGTTACCCAGGTAAT

ATTGGTCCAGTCGGTGCCGCCGGTGCGCCGGGTCCTCATGGCCCTGTCGG

TCCAGCCGGTAAACATGGTAATCGCGGTGAGACAGGTCCGTCAGGACCAG

TGGGCCCTGCTGGCGCAGTCGGTCCGCGCGGGCCGAGTGGCCCTCAGGGT

ATTCGTGGCGATAAAGGGGAACCGGGCGAAAAAGGGCCGCGGGGTCTGCC

AGGCCTGGGTGACTACAAAGACGACGACGACAAAtaa

The polynucleotide of SEQ ID NO: 93 was subcloned into vector pET28a, expressed host *E. coli* cells and the truncated collagen was purified as described herein. The purified collagen produced a clear band on SDS-PAGE and an anti-FLAG western was observed at around 100 kilodaltons. There were no existing bands that appear at that location on the gel in the absence of expression of this protein.

Truncated Human Collagen Type 1 Alpha 2 Truncation 6 with DsbA Secretion and FLAG Tag The amino acid sequence of truncated human collagen type 1 alpha 2 truncation 6 with DsbA secretion and FLAG tag is disclosed in SEQ ID NO: 94. The DsbA secretion tag is encoded by nucleotides 1-57 of SEQ ID NO: 95 and the amino acid sequences are amino acids 1-19 of SEQ ID NO: 94. The collagen nucleotide sequences are nucleotides 58-657 of SEQ ID NO: 95 and the amino acid sequences are amino acids 20-219 of SEQ ID NO: 94. The FLAG nucleotide sequences are nucleotides 658-684 of SEQ ID NO: 95 and the amino acid sequences are amino acids 220-228 of SEQ ID NO: 94.

(SEQ ID NO: 94)

MKKIWLALAGLVLAFSASAKGHNGLQGLPGIAGHHGDQGAPGSVGPAGPR

GPAGPSGPAGKDGRTGHPGTVGPAGIRGPQGHQGPAGPPGPPGPPGPPGV

SGGGYDFGYDGDFYRADQPRSAPSLRPKDYEVDATLKSLNNQIETLLTPE

GSRKNPARTCRDLRLSHPEWSSGYYWIDPNQGCTMDAIKVYCDFSTGETC

IRAQPENIPAKNWYRSSKDGDYKDDDDK

The nucleic acid sequence of truncated human collagen type 1 alpha 2 truncation 6 with DsbA secretion and FLAG tag is disclosed in SEQ ID NO: 95.

(SEQ ID NO: 95)
ATGAAAAAGATTTGGCTGGCGCTGGCTGGTTTAGTTTTAGCGTTTAGCGC
ATCGGCGAAAGGTCACAATGGACTGCAAGGCCTGCCAGGTATTGCAGGTC
ATCATGGTGATCAAGGTGCCCCGGGAAGCGTTGGTCCGGCGGGGCCGAGA
GGCCCTGCGGGACCTTCAGGTCCGGCAGGCAAAGATGGTCGGACAGGCCA
TCCGGGCACCGTTGGCCCTGCAGGAATTCGTGGACCGCAGGGTCATCAGG
GACCTGCTGGTCCGCCAGGTCCCCCGGGCCCTCCGGGACCACCGGGTGTT
AGTGGTGGTGGTTATGATTTTGGCTATGATGGTGATTTTTATCGTGCAGA
TCAGCCGCGTAGCGCACCGAGCCTGCGTCCTAAAGATTATGAAGTTGATG
CAACCCTGAAAAGCCTGAATAATCAGATTGAAACACTGCTGACACCGGAA
GGTAGCCGTAAAAATCCGGCCCGTACCTGTCGTGATCTGCGTCTGAGCCA
CCCGGAATGGAGCAGCGGTTATTATTGGATTGATCCGAATCAAGGTTGTA
CCATGGATGCAATTAAAGTTTATTGTGATTTTAGCACAGGTGAAACATGT
ATCCGTGCACAGCCGGAAAATATTCCGGCCAAAAATTGGTATCGTAGTAG
CAAAGATGGTGACTACAAAGACGACGACGACAAAtaa The polynucleotide of SEQ ID NO: 94 was subcloned into vector pET28a, expressed host *E. coli* cells and the truncated collagen was purified as described herein. The purified collagen produced a clear band on SDS-PAGE and an anti-FLAG western was observed at around 25 kilodaltons. There were no existing bands that appear at that location on the gel in the absence of expression of this protein.

Truncated Human Collagen Type 1 Alpha 2 Truncation 7 with DsbA Secretion and FLAG Tag The amino acid sequence of truncated human collagen type 1 alpha 2 truncation 7 with DsbA secretion and FLAG tag is disclosed in SEQ ID NO: 96. The DsbA secretion tag is encoded by nucleotides 1-57 of SEQ ID NO: 97 and the amino acid sequences are amino acids 1-19 of SEQ ID NO: 96. The collagen nucleotide sequences are nucleotides 58-759 of SEQ ID NO: 96 and the amino acid sequences are amino acids 20-253 of SEQ ID NO: 96. The FLAG nucleotide sequences are nucleotides 760-786 of SEQ ID NO: 97 and the amino acid sequences are amino acids 254-262 of SEQ ID NO: 96.

(SEQ ID NO: 96)
MKKIWLALAGLVLAFSASAYEVDATLKSLNNQIETLLTPEGSRKNPARTC
RDLRLSHPEWSSGYYWIDPNQGCTMDAIKVYCDFSTGETCIRAQPENIPA
KNWYRSSKDKKHVWLGETINAGSQFEYNVEGVTSKEMATQLAFMRLLANY
ASQNITYHCKNSIAYMDEETGNLKKAVILQGSNDVELVAEGNSRFTYTVL
VDGCSKKTNEWGKTIIEYKTNKPSRLPFLDIAPLDIGGADQEFFVDIGPV
CFKGDYKDDDDK

The nucleic acid sequence of truncated human collagen type 1 alpha 2 truncation 7 with DsbA secretion and FLAG tag is disclosed in SEQ ID NO: 97.

(SEQ ID NO: 97)
TGAAAAAGATTTGGCTGGCGCTGGCTGGTTTAGTTTTAGCGTTTAGCGCA
TCGGCGTATGAAGTTGATGCAACCCTGAAAAGCCTGAATAATCAGATTGA

-continued
AACACTGCTGACACCGGAAGGTAGCCGTAAAAATCCGGCCCGTACCTGTC
GTGATCTGCGTCTGAGCCACCCGGAATGGAGCAGCGGTTATTATTGGATT
GATCCGAATCAAGGTTGTACCATGGATGCAATTAAAGTTTATTGTGATTT
TAGCACAGGTGAAACATGTATCCGTGCACAGCCGGAAAATATTCCGGCCA
AAAATTGGTATCGTAGTAGCAAAGATAAAAAACATGTGTGGCTGGGTGAA
ACCATTAATGCAGGTAGCCAGTTTGAATACAATGTTGAAGGTGTTACCAG
CAAAGAAATGGCAACACAGCTGGCATTTATGCGTCTGCTGGCAAATTATG
CAAGCCAGAATATTACATATCATTGTAAAAATAGCATTGCATATATGGAT
GAAGAAACCGGTAATCTGAAAAAAGCAGTTATTCTGCAGGGTAGCAATGA
TGTTGAACTGGTTGCCGAAGGTAATAGCCGTTTTACATATACCGTTCTGG
TTGATGGTTGTAGCAAAAAAACCAATGAATGGGGTAAAACCATCATTGAA
TATAAAACCAACAAACCGAGCCGTCTGCCGTTTCTGGATATCGCTCCGCT
GGATATTGGTGGTGCCGATCAGGAATTTTTTGTCGATATCGGTCCTGTGT
GTTTTAAAGGTGACTACAAAGACGACGACGACAAAtaa The polynucleotide of SEQ ID NO: 97 was subcloned into vector pET28a, expressed host *E. coli* cells and the truncated collagen was purified as described herein. The purified collagen produced a clear band on SDS-PAGE and an anti-FLAG western was observed at around 30 kilodaltons. There were no existing bands that appear at that location on the gel in the absence of expression of this protein.

Example 10: Protective Effect of Truncated Human Collagen on Fibroblasts

The effect of truncated human collagen on fibroblast cell viability, procollagen synthesis, and elastin Synthesis is determined according to the methods of Example 6.

The effect of truncated human collagen on Keratinocyte proliferation and UVB protection is determined according to the methods of Example 7.

The effect of truncated collagen on thymine dimer formation after exposure to UV radiation is determined according to the methods of Example 8.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Example 11: Effect of Truncated Collagen on Inflammatory Cytokines

Keratinocytes and dermal fibroblasts play an important role in the immune response of the skin. In response to irritating chemicals or UV radiation (pro-inflammatory/pro-irriation stimuli), keratinocytes can release a vast array of cytokines. These cytokines are thought to help engage immune cells to the site of inflammation. Cytokines released by the keratinocytes include TNFα, IL-1α, IL-1β, IL-3, IL-6, IL-7, IL-8, IL-10, IL-18, and IL-1RA.

The testing model used for this study was the MatTek EpiDerm. This skin model consists of normal human-derived epidermal keratinocytes that have been cultured to form a multilayered, highly differentiated model of the human epidermis. Ultrastructural analysis has revealed the presence of keratohyalin granules, tonofilament bundles, desmosomes, and a multi-layered stratum corneum containing intercellular lamellar lipid layers arranged in patterns characteristic of in vivo epidermis. Markers of mature epidermis specific differentiation such as pro-filaggrin, the K1/K10 cytokeratin pair, involucrin, and type I epidermal transglutaminase have been localized in this model. The MatTek EpiDerm is also mitotically and metabolically active.

The MatTek EpiDerm tissues were used to assess the ability of various test materials to inhibit the release the inflammatory mediator IL-1α. Test materials were compared to an over the counter topical hydrocortisone preparation (positive control) as well as to untreated tissues (negative control 1) and untreated, non-inflamed tissues (negative control 2). This test was also used to assess the viability of the tissues after exposure to the test materials.

IL-1α, IL-6 and IL-8 are synthesized and stored in keratinocytes and have been identified as a mediators of skin irritation and inflammation. Release of these cytokines can be directly measured in tissue culture media via a colorimetric based enzyme linked immunosorbent assay (ELISA). Briefly, antibodies covalently linked to a solid support will bind IL-1α, IL-6 or IL-8 present in spent culture media samples. A second antibody that is covalently attached to an acetylcholinesterase enzyme will in turn detect the specific bound cytokines. Upon addition of an appropriate color substrate the acetylcholinesterase enzyme will generate a colored end product that can be measured spectrophotometrically.

MatTek EpiDerm Tissues were purchased from MatTek corporation and were stored at 4° C. until used. Prior to use, the tissues to be used were removed from the agarose-shipping tray and placed into a 6-well plate containing 0.9 ml of hydrocortisone free assay medium (37±2° C.). The tissues were allowed to incubate overnight at 37±2° C. and 5±1% CO2. After this initial incubation, the assay medium was replaced with 0.9 ml of fresh hydrocortisone free medium (37±2° C.). Three tissues were prepared for each test material.

An inflammatory response in the tissues was initiated via UV irradiation (UVB). A UV lamp was used to give a 300 $mJ/cm^2$ dose of UVB radiation to the tissues. Immediately after the application of the inflammatory stimuli 50 μl or mg of test material was applied directly onto the surface of the tissue. An over the counter hydrocortisone cream was used as a positive control. For a negative control tissues were exposed to the inflammatory stimuli but were not treated with any type of anti-inflammatory material. One additional set of tissues was left without exposure to the inflammatory stimuli to provide a baseline measurement for the cytokines. The tissues were incubated at 37±2° C. and 5±1% $CO_2$ for 24 hours after exposure to the inflammatory stimuli. After the 24-hour incubation the cell culture medium was collect and stored at −75° C. until analyzed for cytokines.

The ELISA plates were prepared by diluting the appropriate capture antibody in PBS. Next, 100 μl of the diluted capture antibody was added to the wells of a 96-well ELISA plate and the plate was incubated overnight at room temperature. On the following day the plate was washed three times with 300 μl wash buffer (0.05% Tween 20 in PBS) and then blocked by adding 300 μl of blocking buffer (1% BSA in PBS) to each well. The plate was incubated with the blocking buffer for at least one hour. After the incubation the blocking buffer was removed and the plate was washed three times as described above.

A series of standards was prepared and 100 μl of each of these standards was dispensed into two wells (duplicates) in the appropriate 96-well plate. Subsequently, 100 μl of each sample was added to additional wells and the plate was incubated for two hours at room temperature. After the incubation the plate was washed three times as described above. Once the last wash was removed, 100 μl of a biotin conjugated detection antibody was added. After incubating the plate for two hours at room temperature the plate was washed again as described above. 100 μl of HRP-streptavidin was then added to each well and the plate was incubated for 20 minutes at room temperature. Once the last wash was removed, 100 μl of substrate solution (hydrogen peroxide+tetramethylbenzidine as a chromagen) was added to each well. Once a sufficient level of color development had occurred, 50 μl of stop solution (2N sulfuric acid) was added to each well and the plate was read at 460 nm.

After the 24 hour incubation, the tissues were rinsed twice with at least 100 μl of phosphate buffered saline to remove the test material and then transferred to a 6-well plate containing 1.0 ml of assay medium supplemented with MTT (1 mg/ml) and allowed to incubate for 3±0.25 hours at 37±2° C. and 5±1% CO2. After the incubation, the tissues were rinsed at least twice with 100 μl of phosphate buffered saline, blotted dry, and then placed into a 24-well plate containing 2 ml of isopropanol per well. The 24-well plate was covered and allowed to incubate at room temperature for at least 2 hours on a rocking platform to extract the reduced MTT from the tissues. After the extraction, a 200 μl sample of the isopropanol/MTT mixture was transferred to a 96-well plate and the absorbance of the sample was read at 540 nm with a plate reader using 200 μl of isopropanol as the blank. The MTT assay is described in Example 6 herein. The cell viability results of the MTT assay were similar to the results obtained in Example 6

The results of the IL-1a assay are shown in Table 9 below. A 2% stock solution of the jellyfish collagen of SEQ ID NO: 91 is Sample 4 and Sample 3 is a 2% stock solution of the truncated jellyfish collagen of SEQ ID NO: 10. In Table 9 below, the indicated percentage is the percent dilution of the stock solution used for the test. For example, the 1% Sample 4 treatment is a 1% solution of the 2% stock truncated collagen solution. The untreated cells produced 18.2 pg/ml of Il-1a. Upon treatment with truncated collagen, all samples showed decreases in Il-1a production. The 1% Sample 4 treatment reduced IL-1A production to 13.4 pg/ml, which is significant with a p value of less than 0.05. The decrease in IL-1a production indicates that the truncated collagen has anti-inflammatory effects.

TABLE 9

| IL-1a Assay | |
|---|---|
| Treatment | Il-1a pg/ml |
| Non-UVB Exposed | 4.9 ± 2.1 |
| Untreated | 18.2 ± 1.4 |
| 1% Hydrocortisone | 6.7 ± 0.6 |
| 5% Sample 4 | 18.1 ± 1.1 |
| 1% Sample 4 | 13.4 ± 0.9* |
| 0.5% Sample 4 | 15.7 ± 0.7 |
| 0.1% Sample 4 | 13.9 ± 1.7* |
| 5% Sample 3 | 15.8 ± 2.0 |

Denotes values that are significantly different from Untreated ($p < 0.05$)

Example 11: Urban Dust Protection by Truncated Collagen

A keratinocyte cell culture model was used to assess the ability of truncated collagens to exert a protective effect by promoting cell survival after exposure to urban dust.

Human epidermal keratinocytes were pretreated with the test materials and then exposed to urban dust. At the end of the treatment period changes in cell viability were then determined via an MTT assay.

Keratinocytes were seeded into the individual wells of a 96 well plate in 100 μl of medium and incubated overnight at 37±2° C. and 5±1% $CO_2$. On the following day the media was removed via aspiration to eliminate any non-adherent cells and replaced with 100 μl of fresh medium. The cells were grown until confluent, with a media change every 48 to 72 hours.

Pretreatment with Test Material Followed by Urban Dust Treatment

Test materials were prepared at 2× their final desired concentrations in cell culture media. Urban dust (NIST 1649B from Sigma Chemicals) was also prepared at 2× solutions. For the pretreatment, 50 μl of 2× test material was combined with 50 μl of culture media and the cells were incubated for 24 hours. At the end of the pretreatment period the test material containing culture media was removed and replaced with 50 μl of 2× urban dust and 50 μl of media. Another set of cells was treated with media alone (non-dust exposed) and used as a reference control to represent 100% cell viability. The cells were then incubated for 24 hours and then subjected to an MTT assay to determine changes in cell viability.

At the end of the treatment period, the cell culture medium was removed and the cells were washed with PBS. After the wash, 100 μl of cell culture media supplemented with 0.5 mg/ml MTT was added to each well and the cells were incubated for 30 minutes at 37+2° C. and 5+1% CO2. After the incubation, the media/MTT solution was removed and the cells were washed again once with PBS and then 100 μl of isopropyl alcohol was added to the wells to extract the purple formazin crystals. The 96-well plate was then read at 540 nm using isopropyl alcohol as a blank.

The mean MTT absorbance value for the non-dust exposed cells was calculated and used to represent 100% value for cell number. The individual MTT values from the cells undergoing the various treatments was then divided by the mean value for the non-dust exposed cells and expressed as a percent to determine the change in cell number caused by each treatment.

The MTT results for the pretreatment with the test material then dust treatments are presented in Table 10. Table 10 shows that as the cells were treated with increasing amounts of collagen, cell viability increased upon pretreatment with truncated collagen and subsequent exposure to urban dust. These results show that truncated collagen protects against the decline in cell viability associated with urban dust exposure.

TABLE 10

MTT Assay, Truncated Collagen Pretreatment

| Treatment | Viability (% Non-Dust Exposed) 4 mg/ml Urban Dust | Viability (% Non-Dust Exposed) 2 mg/ml Urban Dust |
|---|---|---|
| Non-Dust Exposed | 100 ± 4.4* | 100 ± 1.8 |
| Untreated | 59 ± 3.8 | 70 ± 0.9 |
| 0.1% Collagen | 61 ± 4.7 | 72 ± 3.5 |
| 0.5% Collagen | 59 ± 2.2 | 73 ± 2.2 |
| 1% Collagen | 58 ± 0.5 | 74 ± 2.6 |
| 5% Collagen | 66 ± 1.0 | 83 ± 6.5* |

*Denotes values that are significantly different from untreated group ($p < 0.05$)

Example 12: Truncated *Chondrosia reniformis* (Kidney Sponge) Collagen

Truncated *Chondrosia reniformis* (Kidney Sponge) Fibrillar Collagen 1 with DsbA Secretion and FLAG Tag The amino acid sequence of truncated *Chondrosia reniformis* fibrillar collagen 1 with DsbA secretion and FLAG tag is disclosed in SEQ ID NO: 102. The DsbA secretion tag is encoded by nucleotides 1-57 of SEQ ID NO: 103 and the amino acid sequences are amino acids 1-19 of SEQ ID NO: 102. The fibrillary collagen nucleotide sequences are nucleotides 58-792 of SEQ ID NO: 103 and the amino acid sequences are amino acids 20-264 of SEQ ID NO: 102. The FLAG nucleotide sequences are nucleotides 793-819 of SEQ ID NO: 103 and the amino acid sequences are amino acids 265-273 of SEQ ID NO: 102.

```
                                           (SEQ ID NO: 102)
MKKIWLALAGLVLAFSASAPVGRRGPKGSRGDPGDGGAAGPKGPEGVDGL

IGEPGQPGPIGAEGSSGLEGFLGDKGSKGARGGPGNRGRPGQDGVPGQDG

RAGEKGEGGETGDRGQQGLRGKVGDPGLVGDLGAQGPQGSQGLVGPPGIP

GEPGSGGEPGDQGPRGPEGPQGSPGVRGGRGERGTPGAVGPKGPPGKNGA

DGPRGLPGASGPPGSPGNQGPEGSRGADGNNGFPGDDGENGLVGIPGEPG

PKGARGTRGELGKTGDYKDDDDK
```

The nucleic acid sequence of truncated *Chondrosia reniformis* fibrillar collagen 1 with DsbA secretion and FLAG tag is disclosed in SEQ ID NO: 103.

```
                                           (SEQ ID NO: 103)
ATGAAAAAGATTTGGCTGGCGCTGGCTGGTTTAGTTTTAGCGTTTAGCGC

ATCGGCGCCGGTTGGTCGTCGTGGTCCGAAAGGTAGCCGTGGTGATCCTG

GTGATGGTGGTGCAGCAGGTCCTAAAGGTCCGGAAGGTGTTGATGGTCTG

ATTGGTGAACCGGGTCAGCCTGGTCCGATTGGCGCAGAAGGTAGCAGCGG

TCTGGAAGGTTTTCTGGGTGATAAAGGTAGCAAAGGTGCACGTGGTGGTC

CGGGTAATCGCGGTCGTCCTGGTCAGGATGGTGTTCCGGGTCAAGATGGT

CGTGCCGGTGAAAAAGGTGAAGGTGGTGAAACCGGTGATCGCGGTCAGCA

GGGTCTGCGTGGTAAAGTTGGTGATCCAGGTCTGGTGGGTGATCTGGGTG

CACAGGGTCCGCAGGGTAGCCAAGGTCTGGTTGGTCCGCCTGGTATTCCG

GGTGAACCTGGTAGCGGTGGCGAACCGGGTGATCAGGGTCCTCGCGGTCC

AGAAGGTCCTCAGGGTTCACCGGGTGTTCGCGGTGGTCGTGGTGAACGTG
```

-continued

```
GTACACCGGGTGCAGTTGGACCGAAAGGTCCGCCAGGTAAAAATGGTGCA

GATGGTCCGCGTGGTCTGCCTGGTGCAAGCGGTCCTCCGGGTAGTCCTGG

TAACCAGGGTCCTGAAGGTTCTCGTGGTGCCGATGGTAATAATGGTTTTC

CAGGTGATGATGGTGAAAATGGCCTGGTTGGTATCCCTGGCGAACCAGGT

CCAAAAGGCGCACGCGGTACACGCGGTGAACTGGGTAAAACCGGTGACTA

CAAAGACGACGACGACAAAtaa
```

The polynucleotide of SEQ ID NO: 103 was subcloned into vector pET28a, expressed host *E. coli* cells and the truncated *Chondrosia reniformis* fibrillar collagen 1 was purified as described herein. The purified fibrillary collagen produced a clear band on SDS-PAGE and an anti-FLAG western was observed at around 40 kilodaltons. There were no existing bands that appear at that location on the gel in the absence of expression of this protein.

Truncated *Chondrosia reniformis* (Kidney Sponge) Fibrillar Collagen 2 with DsbA Secretion and FLAG Tag The amino acid sequence of truncated *Chondrosia reniformis* fibrillar collagen 2 with DsbA secretion and FLAG tag is disclosed in SEQ ID NO: 104. The DsbA secretion tag is encoded by nucleotides 1-57 of SEQ ID NO: 105 and the amino acid sequences are amino acids 1-19 of SEQ ID NO: 104. The fibrillary collagen nucleotide sequences are nucleotides 58-1323 of SEQ ID NO: 105 and the amino acid sequences are amino acids 20-441 of SEQ ID NO: 104. The FLAG nucleotide sequences are nucleotides 1324-1350 of SEQ ID NO: 105 and the amino acid sequences are amino acids 442-450 of SEQ ID NO: 105.

```
                                                  (SEQ ID NO: 104)
MKKIWLALAGLVLAFSASAGRGGPAGLQGAAGNPGDPGDRGQAGEIGLPG

TEGQRGQGGSRGDDGIGGQSGTDGDPGNDGVAGIRGARGEPGATGPEGAA

GQKGDRGRFGEQGRPGNDGPPGRRGRVGNLGETGAEGDEGTRGYTGDRGP

EGAIGISGVTGNPGPQGIKGPPGDTGHPGRQGPSGPQGPPGIPGTDGLTI

HNLIKPPSQFFDATSSSDPLTDAVVESILKSFQYAELEIDLTKKPDGTMK

YPAISCDDLHKDYPQLPSGNYTLDPNGGCKNDAFETYCEFNNSVKMCLTP

KIPTLLPMGTYKYYVNSEGYYSPNDFGLNLRFFEYYGSVTQLKFLQTKAT

RVTQTIRVLCKNYDPLHKQPVFIGMNDETVMDEPRMEENQCQYFNGLSAH

VELELSSNDPSYLPIYEMRLYLGRKTNEELGIELGDLCFEYGDYKDDDDK
```

The nucleic acid sequence of truncated *Chondrosia reniformis* fibrillar collagen 2 with DsbA secretion and FLAG tag is disclosed in SEQ ID NO: 105.

```
                                                  (SEQ ID NO: 105)
ATGAAAAAGATTTGGCTGGCGCTGGCTGGTTTAGTTTTAGCGTTTAGCGC

ATCGGCGGGTCGTGGCGGTCCGGCAGGTCTGCAGGGTGCTGCAGGTAATC

CTGGCGACCCTGGCGATCGTGGTCAGGCAGGCGAAATTGGTCTGCCAGGC

ACCGAAGGTCAGCGTGGTCAAGGTGGTTCACGTGGTGATGACGGTATTGG

TGGTCAGAGCGGCACCGATGGCGATCCGGGTAACGATGGTGTTGCAGGTA

TTCGTGGTGCACGCGGAGAACCTGGTGCCACCGGACCTGAAGGTGCAGCC

GGTCAGAAAGGTGATCGTGGCCGTTTTGGCGAACAGGGTCGTCCGGGAAA
```

-continued

```
TGATGGTCCACCGGGTCGCCGTGGCCGTGTGGGCAATCTGGGTGAAACAG

GTGCCGAAGGTGATGAAGGCACCCGTGGTTATACAGGTGACCGTGGACCG

GAAGGCGCAATTGGTATTAGCGGTGTGACCGGTAATCCGGGTCCACAGGG

CATTAAAGGCCCTCCGGGTGATACGGGTCATCCGGGTCGTCAGGGACCGA

GCGGTCCGCAAGGACCACCGGGTATTCCAGGTACAGATGGCCTGACCATT

CATAATCTGATTAAACCGCCTAGCCAGTTTTTTGATGCAACCAGCAGCAG

CGATCCGCTGACCGATGCAGTTGTTGAAAGCATTCTGAAATCTTTTCAGT

ATGCCGAGCTGGAAATTGACCTGACCAAAAAACCGGATGGCACCATGAAA

TATCCGGCAATTAGCTGTGATGATCTGCACAAAGATTATCCGCAGCTGCC

GAGCGGTAATTATACCCTGGATCCGAATGGTGGTTGTAAAAATGATGCCT

TTGAAACCTATTGCGAGTTCAACAATAGCGTGAAAATGTGTCTGACCCCG

AAAATTCCGACACTGCTGCCGATGGGCACCTATAAATACTATGTTAATAG

CGAGGGTTACTACAGCCCGAATGATTTTGGTCTGAATCTGCGCTTTTTTG

AGTATTATGGTAGCGTTACCCAGCTGAAATTTCTGCAGACCAAAGCAACC

CGTGTTACCCAGACCATTCGTGTTCTGTGTAAAAACTATGATCCGCTGCA

TAAACAGCCGGTTTTTATTGGTATGAATGACGAAACCGTTATGGATGAAC

CGCGTATGGAAGAAAATCAGTGCCAGTATTTTAACGGTCTGAGCGCACAT

GTTGAACTGGAACTGAGCAGCAATGATCCGAGCTATCTGCCGATTTATGA

AATGCGTCTGTATCTGGGTCGTAAAACCAATGAAGAACTGGGCATTGAAC

TGGGCGATCTGTGTTTTGAATATGGTGACTACAAAGACGACGACGACAAA

taa
```

The polynucleotide of SEQ ID NO: 105 was subcloned into vector pET28a, expressed host *E. coli* cells and the truncated *Chondrosia reniformis* fibrillar collagen 2 was purified as described herein. The purified fibrillary collagen produced a clear band on SDS-PAGE and an anti-FLAG western was observed at around 55 kilodaltons. There were no existing bands that appear at that location on the gel in the absence of expression of this protein.

Truncated *Chondrosia reniformis* (Kidney Sponge) Non-Fibrillar Collagen 1 with DsbA Secretion and FLAG Tag The amino acid sequence of truncated *Chondrosia reniformis* non-fibrillar collagen 1 with DsbA secretion and FLAG tag is disclosed in SEQ ID NO: 106. The DsbA secretion tag is encoded by nucleotides 1-57 of SEQ ID NO: 107 and the amino acid sequences are amino acids 1-19 of SEQ ID NO: 106. The non-fibrillar collagen nucleotide sequences are nucleotides 58-831 of SEQ ID NO: 107 and the amino acid sequences are amino acids 20-277 of SEQ ID NO: 106. The FLAG nucleotide sequences are nucleotides 832-858 of SEQ ID NO: 107 and the amino acid sequences are amino acids 278-286 of SEQ ID NO: 106.

```
                                                  (SEQ ID NO: 106)
MKKIWLALAGLVLAFSASAEKTSSKVALMTVLVVITGALIIEGTSITRGS

THVNRGLRKRQTSEDNCEAVKVGLPGRDGREGPPGPPGPAGRDGRDAVCS

NQTTGLGAKGDRGPPGTPGFPGEVGRPGPPGADGIPGPQGERGAVGPGGK

PGPRGEVGTPGADGADGATGATGVQGPDGAKGEKGASGTAGLKGEKGDTC
```

-continued

IPDSNSTLGMPGTPGAGGSKGQKGESGIVGPKGERGEIGTPGHPGFRGAD

GEPGHKGVPGRAGAQGDRGDPGDDGLTGDYKDDDDK

The nucleic acid sequence of truncated *Chondrosia reniformis* non-fibrillar collagen 1 with DsbA secretion and FLAG tag is disclosed in SEQ ID NO: 107.

(SEQ ID NO: 107)

ATGAAAAAGATTTGGCTGGCGCTGGCTGGTTTAGTTTTAGCGTTTAGCGC

ATCGGCGGAAAAAACCAGCAGCAAAGTTGCACTGATGACCGTTCTGGTTG

TTATTACCGGTGCACTGATTATTGAAGGCACCAGCATTACCCGTGGTAGC

ACCCATGTTAATCGTGGTCTGCGTAAACGTCAGACCAGCGAAGATAATTG

TGAAGCAGTTAAAGTTGGTCTGCCAGGTCGTGATGGTCGTGAAGGTCCTC

CGGGTCCGCCTGGTCCGGCTGGCAGAGATGGCCGTGATGCAGTTTGTAGC

AATCAGACCACCGGTCTGGGTGCAAAAGGTGATCGTGGTCCGCCAGGTAC

ACCGGGTTTTCCGGGTGAAGTTGGCCGTCCGGGTCCACCGGGTGCAGATG

GTATTCCGGGTCCTCAGGGTGAACGTGGTGCAGTTGGTCCTGGTGGTAAA

CCTGGTCCGCGTGGTGAAGTGGGCACCCCTGGTGCCGATGGCGCAGATGG

TGCAACCGGTGCGACCGGTGTTCAGGGTCCTGATGGTGCCAAAGGCGAAA

AAGGTGCAAGCGGCACCGCAGGTCTGAAAGGTGAGAAAGGCGATACCTGT

ATTCCGGATAGCAATAGCACCCTGGGTATGCCTGGTACACCAGGTGCCGG

TGGTAGCAAAGGCCAGAAAGGTGAAAGTGGTATTGTTGGTCCGAAAGGCG

AACGCGGTGAAATTGGCACACCGGGTCATCCTGGTTTTCGTGGTGCGGAT

GGTGAACCAGGTCATAAAGGTGTTCCGGGTCGTGCCGGTGCGCAGGGTGA

TCGCGGTGATCCGGGTGATGATGGTCTGACCGGTGACTACAAAGACGACG

ACGACAAAtaa

The polynucleotide of SEQ ID NO: 107 was subcloned into vector pET28a, expressed host *E. coli* cells and the truncated *Chondrosia reniformis* non-fibrillar collagen 1 was purified as described herein. The purified non-fibrillar collagen produced a clear band on SDS-PAGE and an anti-FLAG western was observed at around 30 kilodaltons. There were no existing bands that appear at that location on the gel in the absence of expression of this protein.

Truncated *Chondrosia reniformis* (Kidney Sponge) Non Fibrillar Collagen 2 with DsbA Secretion and FLAG Tag The amino acid sequence of truncated *Chondrosia reniformis* non-fibrillar collagen 2 with DsbA secretion and FLAG tag is disclosed in SEQ ID NO: 108. The DsbA secretion tag is encoded by nucleotides 1-57 of SEQ ID NO: 109 and the amino acid sequences are amino acids 1-19 of SEQ ID NO: 108. The non-fibrillar collagen nucleotide sequences are nucleotides 58-1509 of SEQ ID NO: 109 and the amino acid sequences are amino acids 20-503 of SEQ ID NO: 108. The FLAG nucleotide sequences are nucleotides 1510-1536 of SEQ ID NO: 109 and the amino acid sequences are amino acids 504-512 of SEQ ID NO: 108.

(SEQ ID NO: 108)

MKKIWLALAGLVLAFSASAGFPGAPGADGAPGQKGELGAVGPQGTPGLSG

PSGPTGPPGPKGVRGAPGSSGAKGDAGNPGDDGPVGPQGVPGVDGSPGQK

-continued

GETGRVGPRGHDGINGTPGEDGATGFPGPDGAKGEKGTSGTAGLKGEKGD

TCIPDSNSTLGMPGTPGAGWSKGQKGESGIVGPKGEKGEIGTPGPPGFRG

ADGEPGQRGEPGRAGAQGERGAPGNNGRDGFPGDPGADGAPGQKGELGAI

GHPGFSGPSGPSGPTGPPGPKGVRGAQGRPGDRGSPGDVGPIGAPGPPGA

DGVPGLTGVQGRDGPKGESASSGAVYVRWGRTTCPSGADVVYSGRAAGAK

YDHSGGTSDHHCLPNNPQYLSEDDTNALGAQLYGVEYEIRDRSSPYNSLD

QSDMPCVVCNANGRSQLLMVPARYTCPTGWSREYYGYMMSEGKAKNREGR

KTTICMDFSAEAVPGSGANTNPSPGIMMRANCNGLACPPYQSNTPLTCAV

CTKGDYKDDDDK

The nucleic acid sequence of truncated *Chondrosia reniformis* non-fibrillar collagen 2 with DsbA secretion and FLAG tag is disclosed in SEQ ID NO: 109.

(SEQ ID NO: 109)

ATGAAAAAGATTTGGCTGGCGCTGGCTGGTTTAGTTTTAGCGTTTAGCGC

ATCGGCGGGTTTTCCTGGCGCTCCGGGTGCCGACGGTGCTCCGGGTCAAA

AAGGTGAACTGGGTGCCGTGGGTCCGCAGGGCACTCCGGGTCTGAGTGGT

CCTAGTGGTCCGACCGGTCCACCAGGTCCAAAAGGCGTGCGTGGTGCACC

GGGTAGCAGCGGAGCCAAAGGTGATGCAGGTAACCCTGGTGATGACGGTC

CGGTTGGTCCACAGGGCGTTCCAGGTGTTGATGGTAGCCCTGGCCAAAAG

GGTGAAACCGGTCGTGTGGGTCCTCGTGGTCATGATGGTATTAATGGCAC

CCCAGGTGAAGATGGTGCGACAGGCTTTCCAGGTCCGGATGGCGCAAAGG

GTGAGAAGGGCACCAGCGGTACAGCTGGCCTGAAGGGCGAAAAGGGCGAT

ACATGCATCCCGGATTCAAATTCAACACTGGGCATGCCAGGTACGCCTGG

CGCAGGTTGGAGTAAAGGACAAAAAGGCGAATCAGGCATTGTGGGACCTA

AAGGCGAGAAGGGTGAGATTGGTACTCCGGGACCGCCAGGCTTTCGCGGT

GCAGACGGCGAACCGGGTCAGCGTGGCGAACCTGGTCGTGCAGGCGCACA

AGGTGAACGCGGAGCCCCTGGTAATAATGGACGTGATGGCTTTCCTGGTG

ATCCAGGTGCAGATGGCGCACCTGGCCAGAAAGGCGAACTGGGAGCAATT

GGTCATCCGGGATTTAGCGGTCCGTCAGGTCCGAGCGGACCGACAGGTCC

TCCTGGACCGAAAGGTGTACGTGGCGCACAGGGTCGTCCTGGCGATCGTG

GCAGTCCAGGTGATGTGGGTCCGATTGGTGCACCTGGTCCTCCAGGTGCG

GACGGCGTGCCTGGTTTAACAGGTGTGCAGGGTCGCGACGGTCCTAAAGG

TGAATCAGCAAGCAGCGGTGCAGTTTATGTTCGTTGGGGTCGTACCACCT

GTCCTAGCGGAGCAGATGTTGTTTATAGCGGTCGCGCAGCCGGTGCAAAA

TATGATCATTCAGGTGGCACCTCAGATCATCATTGTCTGCCGAATAATCC

GCAGTATCTGAGCGAAGATGATACCAATGCACTGGGTGCACAGCTGTATG

GTGTGGAATATGAAATTCGTGATCGTAGCAGCCCGTATAATAGCCTGGAT

CAGAGCGATATGCCGTGTGTTGTTTGTAATGCAAATGGTCGTAGCCAGCT

GCTGATGGTTCCGGCACGTTATACATGCCCGACCGGTTGGAGCCGTGAAT

ATTATGGTTATATGATGAGCGAAGGCAAAGCCAAAAATCGCGAAGGTCGT

AAAACCACCATTTGTATGGATTTTAGCGCAGAAGCAGTTCCTGGTAGCGG

-continued

TGCAAATACCAATCCGAGTCCGGGTATTATGATGCGTGCAAATTGTAATG

GTCTGGCATGTCCGCCTTATCAGAGCAATACACCGCTGACCTGTGCCGTT

TGTACCAAAGGTGACTACAAAGACGACGACGACAAAtaa

The polynucleotide of SEQ ID NO: 109 was subcloned into vector pET28a, expressed host *E. coli* cells and the truncated *Chondrosia reniformis* non-fibrillar collagen 2 was purified as described herein. The purified fibrillary collagen produced a clear band on SDS-PAGE and an anti-FLAG western was observed at around 60 kilodaltons. There were no existing bands that appear at that location on the gel in the absence of expression of this protein.

Example 13: Truncated *Rhincodon typus* (Whale Shark) Collagen

Truncated *Rhincodon typus* (Whale Shark) Collagen Type 1 Alpha 1 Truncation 1 with DsbA Secretion and FLAG Tag The amino acid sequence of truncated *Rhincodon typus* collagen type 1 truncation 1 with DsbA secretion and FLAG tag is disclosed in SEQ ID NO: 110. The DsbA secretion tag is encoded by nucleotides 1-57 of SEQ ID NO: 111 and the amino acid sequences are amino acids 1-19 of SEQ ID NO: 110. The collagen nucleotide sequences are nucleotides 58-630 of SEQ ID NO: 111 and the amino acid sequences are amino acids 20-210 of SEQ ID NO: 110. The FLAG nucleotide sequences are nucleotides 631-657 of SEQ ID NO: 111 and the amino acid sequences are amino acids 211-219 of SEQ ID NO: 110.

(SEQ ID NO: 110)

MKKIWLALAGLVLAFSASAGPAGAKGPSGDIGRPGESGSPGARGHSGQPG

RTGIAGNQGLPGTAGEEGRTGPPGPAGLRGQAGMMGFPGPKGAAGLPGKP

GDRGNVGLAGPRGAPGKDGEVGAQGPPGVAGPTGPRGETGLAGSVGFQGM

PGPSGAAGEPGKPGNQGLRGDAGSPGMIGPRGERGLPGERGASGAQGLLG

PRGTSGAPGLGDYKDDDDK

The nucleic acid sequence of truncated *Rhincodon typus* collagen type 1 truncation 1 with DsbA secretion and FLAG tag is disclosed in SEQ ID NO: 111.

(SEQ ID NO: 111)

ATGAAAAAGATTTGGCTGGCGCTGGCTGGTTTAGTTTTAGCGTTTAGCGC

ATCGGCGGGTCCGGCAGGCGCAAAAGGTCCGAGCGGTGATATTGGTCGTC

CGGGTGAAAGCGGTAGTCCGGGTGCACGTGGTCATAGCGGTCAGCCTGGT

CGTACCGGTATTGCAGGTAATCAGGGTCTGCCTGGTACAGCCGGTGAAGA

AGGTCGCACCGGTCCGCCAGGTCCTGCAGGTCTGCGTGGTCAGGCAGGTA

TGATGGGTTTTCCGGGTCCGAAAGGTGCAGCGGGTCTGCCAGGCAAACCG

GGTGATCGTGGTAATGTTGGTCTGGCTGGTCCGCGTGGTGCACCGGGTAA

AGATGGTGAAGTTGGTGCACAGGGTCCTCCGGGTGTTGCAGGTCCGACCG

GTCCTCGTGGTGAAACCGGTCTGGCAGGTAGCGTTGGTTTTCAGGGTATG

CCAGGTCCGTCAGGTGCAGCAGGCGAACCTGGTAAACCGGGTAACCAGGG

CCTGCGTGGTGATGCCGGTTCACCGGGTATGATTGGTCCACGCGGTGAAC

GTGGCCTGCCTGGCGAACGTGGTGCAAGCGGTGCACAAGGTCTGCTGGGT

-continued

CCACGTGGCACCTCAGGCGCACCAGGTCTGGGTGACTACAAAGACGACGA

CGACAAAtaa

The polynucleotide of SEQ ID NO: 111 was subcloned into vector pET28a, expressed host *E. coli* cells and the truncated *Rhincodon typus* collagen type 1 truncation 1 was purified as described herein. The purified collagen produced a clear band on SDS-PAGE and an anti-FLAG western was observed at around 25 kilodaltons. There were no existing bands that appear at that location on the gel in the absence of expression of this protein.

Truncated *Rhincodon typus* (Whale Shark) Collagen Type 6 Alpha 1 Truncation 2 with DsbA Secretion and FLAG Tag The amino acid sequence of truncated *Rhincodon typus* collagen type 6 truncation 2 with DsbA secretion and FLAG tag is disclosed in SEQ ID NO: 112. The DsbA secretion tag is encoded by nucleotides 1-57 of SEQ ID NO: 113 and the amino acid sequences are amino acids 1-19 of SEQ ID NO: 112. The collagen nucleotide sequences are nucleotides 58-684 of SEQ ID NO: 113 and the amino acid sequences are amino acids 20-228 of SEQ ID NO: 112. The FLAG nucleotide sequences are nucleotides 685-711 of SEQ ID NO: 113 and the amino acid sequences are amino acids 229-237 of SEQ ID NO: 112.

(SEQ ID NO: 112)

MKKIWLALAGLVLAFSASAQGIPGSAGKEGGKGDPGPLGSPGKPGPDGLR

GFAGARGLPGAAGPPGLKGAEGPMGAPGLTGSTGERGPNGPAGAIGLPGR

PGGPGPPGPVGEKGDPGDKGLPGPAGDDGVQGAMGLPGPIGSQGPPGDYG

DKGELGKPGQKGSKGDKGESGPPGPIGIQGPIGHPGPIGSDGSPGLRGYL

GMRGQKGDDGIRGLPGSAGPVGLQGLPGGDYKDDDDK

The nucleic acid sequence of truncated *Rhincodon typus* collagen type 6 truncation 2 with DsbA secretion and FLAG tag is disclosed in SEQ ID NO: 113.

(SEQ ID NO: 113)

ATGAAAAAGATTTGGCTGGCGCTGGCTGGTTTAGTTTTAGCGTTTAGCGC

ATCGGCGCAGGGTATTCCGGGTAGCGCAGGTAAAGAAGGTGGTAAAGGCG

ATCCGGGTCCGCTGGGTTCACCGGGTAAACCGGGTCCTGATGGTCTGCGT

GGTTTTGCCGGTGCACGTGGTCTGCCTGGTGCAGCAGGTCCGCCTGGTCT

GAAAGGTGCCGAAGGTCCGATGGGTGCTCCGGGTCTGACCGGTAGCACCG

GTGAACGCGGTCCGAATGGTCCGGCAGGCGCAATTGGTCTGCCAGGTCGT

CCTGGTGGTCCGGGTCCTCCTGGTCCGGTTGGTGAAAAAGGTGATCCTGG

TGATAAAGGCCTGCCTGGTCCTGCCGGTGATGATGGTGTTCAGGGTGCCA

TGGGCTTACCGGGTCCGATTGGTAGCCAGGGTCCTCCGGGTGATTATGGC

GATAAAGGTGAACTGGGTAAACCTGGCCAGAAAGGTAGCAAAGGTGACAA

AGGCGAAAGCGGTCCGCCAGGTCCGATCGGCATTCAGGGTCCTATTGGTC

ATCCAGGTCCAATTGGTTCAGATGGCTCACCGGGACTGCGTGGCTATCTG

GGTATGCGTGGACAGAAAGGTGATGACGGTATTCGTGGCCTGCCAGGTAG

TGCAGGTCCGGTGGGTCTGCAGGGACTGCCTGGTGGTGACTACAAAGACG

ACGACGACAAAtaa

The polynucleotide of SEQ ID NO: 113 was subcloned into vector pET28a, expressed host *E. coli* cells and the truncated *Rhincodon typus* collagen type 6 truncation 2 was purified as described herein. The purified collagen produced a clear band on SDS-PAGE and an anti-FLAG western was observed at around 35 kilodaltons. There were no existing bands that appear at that location on the gel in the absence of expression of this protein.

Truncated *Rhincodon typus* (Whale Shark) Collagen Type 6 Alpha 1 Truncation 3 with DsbA Secretion and FLAG Tag The amino acid sequence of truncated *Rhincodon typus* collagen type 6 alpha 1 truncation 3 with DsbA secretion and FLAG tag is disclosed in SEQ ID NO: 114. The DsbA secretion tag is encoded by nucleotides 1-57 of SEQ ID NO: 115 and the amino acid sequences are amino acids 1-19 of SEQ ID NO: 114. The collagen nucleotide sequences are nucleotides 58-735 of SEQ ID NO: 115 and the amino acid sequences are amino acids 20-245 of SEQ ID NO: 114. The FLAG nucleotide sequences are nucleotides 736-762 of SEQ ID NO: 115 and the amino acid sequences are amino acids 246-254 of SEQ ID NO: 114.

(SEQ ID NO: 114)

MKKIWLALAGLVLAFSASAKGETGEAGDPGTPGEPGIAGPKGDVGDKGDA

GPPGAAGPAGVKGPPGEDGAKGDVGPAGFPGDPGPTGEPGVPGMDGGVGE

KGSLGDPGLTGPRGASGEPGPPGSPGKRGPPGPAGPEGREGLKGSKGSPG

QEGPVGRTGPIGPQGSPGNVGPKGLRGIPGPTGEQGLLGPPGQAGPPGPM

GPPGMPGLRGAQGLKGDKGHVGLIGLIGPPGEMGEKGDQGLPGIQGDYKD

DDDK

The nucleic acid sequence of truncated *Rhincodon typus* collagen type 6 alpha 1 truncation 3 with DsbA secretion and FLAG tag is disclosed in SEQ ID NO: 115.

(SEQ ID NO: 115)

ATGAAAAAGATTTGGCTGGCGCTGGCTGGTTTAGTTTTAGCGTTTAGCGC

ATCGGCGAAAGGTGAAACCGGTGAAGCGGGTGATCCGGGTACACCGGGTG

AACCTGGTATTGCAGGTCCGAAAGGTGATGTTGGTGATAAAGGTGACGCA

GGTCCGCCTGGTGCAGCAGGTCCGGCAGGCGTTAAAGGTCCTCCGGGTGA

AGATGGTGCAAAAGGCGACGTTGGTCCTGCAGGTTTTCCTGGCGATCCGG

GTCCGACTGGTGAACCGGGTGTGCCAGGTATGGATGGTGGTGTGGGTGAA

AAAGGTAGCCTGGGTGATCCTGGTCTGACCGGTCCGCGTGGCGCAAGTGG

TGAACCAGGTCCACCGGGTAGTCCGGGTAAACGTGGTCCTCCTGGACCGG

CTGGTCCGGAAGGTCGTGAAGGTCTGAAAGGTAGCAAAGGTTCACCGGGT

CAAGAAGGTCCGGTTGGTCGTACCGGTCCGATTGGTCCGCAGGGCTCACC

GGGTAATGTTGGTCCTAAAGGTCTGCGTGGTATTCCGGGTCCTACAGGCG

AACAGGGTCTGCTGGGTCCGCCAGGCCAAGCAGGTCCTCCAGGTCCTATG

GGTCCACCTGGTATGCCTGGCCTGCGTGGTGCCCAGGGCCTGAAAGGCGA

TAAAGGCCATGTTGGTCTGATTGGCCTGATTGGTCCACCAGGTGAAATGG

GAGAAAAAGGCGATCAGGGCCTGCCTGGTATTCAGGGTGACTACAAAGA

CGACGACGACAAAtaa

The polynucleotide of SEQ ID NO: 115 was subcloned into vector pET28a, expressed host *E. coli* cells and the truncated *Rhincodon typus* collagen type 1 truncation 1 was purified as described herein. The purified collagen produced a clear band on SDS-PAGE and an anti-FLAG western was observed at around 25 kilodaltons. There were no existing bands that appear at that location on the gel in the absence of expression of this protein.

What is claimed is:

1. A recombinant cell comprising at least one copy of a heterologous nucleic acid sequence encoding a recombinant polypeptide comprising the amino acid sequence of SEQ ID NO: 1 with an internal truncation of from 50 amino acids to 250 amino acids.

2. The recombinant cell of claim 1, wherein the recombinant cell is a microbial cell.

3. The recombinant cell of claim 2, wherein the microbial cell is a bacterial cell.

4. The recombinant cell of claim 3, wherein the bacterial cell is of the species *Escherichia coli.*

5. The recombinant cell of claim 1, wherein the heterologous nucleic acid sequence comprises SEQ ID NO: 90.

6. The recombinant cell of claim 1, wherein the heterologous nucleic acid sequence is codon-optimized for expression in a cell.

7. The recombinant cell of claim 1, wherein the recombinant polypeptide is non-naturally occurring.

8. The recombinant cell of claim 1, wherein the recombinant polypeptide further comprises a truncation at the N-terminal end relative to SEQ ID NO: 1, a truncation at the C-terminal end relative to SEQ ID NO: 1, or both.

9. The recombinant cell of claim 1, wherein the recombinant polypeptide comprises an amino acid sequence according to SEQ ID NO: 91.

10. The recombinant cell of claim 1, wherein the recombinant polypeptide consists of an amino acid sequence according to SEQ ID NO: 91.

11. The recombinant cell of claim 1, wherein the recombinant polypeptide further comprises a secretion tag.

12. The recombinant cell of claim 11, wherein the secretion tag is a DsbA secretion tag.

13. The recombinant cell of claim 12, wherein the recombinant cell is capable of secreting the recombinant polypeptide extracellularly.

14. A composition comprising a recombinant cell of claim 1, and a culture media comprising a recombinant polypeptide comprising the amino acid sequence of SEQ ID NO: 1 with an internal truncation of from 50 amino acids to 250 amino acids.

15. The composition of claim 14, wherein the recombinant cell is a bacterial cell of the species *Escherichia coli.*

16. The composition of claim 15, wherein the heterologous nucleic acid sequence is a nucleic acid sequence according to SEQ ID NO: 90, and the recombinant polypeptide has an amino acid sequence according to SEQ ID NO: 91.

17. A method for producing a recombinant polypeptide, the method comprising:

a. incubating a recombinant cell of claim 1 in a culture media wherein the recombinant cell secretes the recombinant polypeptide into the culture media;

b. collecting the culture media comprising the recombinant polypeptide secreted thereto; and c. purifying the recombinant polypeptide from the culture media.

18. The method of claim 17, wherein the recombinant cell is a bacterial cell of the species *Escherichia coli.*

19. The method of claim 18, wherein the heterologous nucleic acid sequence is a nucleic acid sequence according to SEQ ID NO: 90, and the recombinant polypeptide has an amino acid sequence according to SEQ ID NO: 91.

* * * * *

SEQUENCE LISTING

```
<160> NUMBER OF SEQ ID NOS: 153

<210> SEQ ID NO 1
<211> LENGTH: 429
<212> TYPE: PRT
<213> ORGANISM: Podocoryna carnea

<400> SEQUENCE: 1

Gly Pro Gln Gly Val Val Gly Ala Asp Gly Lys Asp Gly Thr Pro Gly
1               5                   10                  15

Glu Lys Gly Glu Gln Gly Arg Thr Gly Ala Ala Gly Lys Gln Gly Ser
            20                  25                  30

Pro Gly Ala Asp Gly Ala Arg Gly Pro Leu Gly Ser Ile Gly Gln Gln
        35                  40                  45

Gly Ala Arg Gly Glu Pro Gly Asp Pro Gly Ser Pro Gly Leu Arg Gly
    50                  55                  60

Asp Thr Gly Leu Ala Gly Val Lys Gly Val Ala Gly Pro Ser Gly Arg
65                  70                  75                  80

Pro Gly Gln Pro Gly Ala Asn Gly Leu Pro Gly Val Asn Gly Arg Gly
                85                  90                  95

Gly Leu Arg Gly Lys Pro Gly Ala Lys Gly Ile Ala Gly Ser Asp Gly
            100                 105                 110

Glu Ala Gly Glu Ser Gly Ala Pro Gly Gln Ser Gly Pro Thr Gly Pro
        115                 120                 125
```

```
Arg Gly Gln Arg Gly Pro Ser Gly Glu Asp Gly Asn Pro Gly Leu Gln
    130                 135                 140

Gly Leu Pro Gly Ser Asp Gly Glu Pro Gly Glu Glu Gly Gln Pro Gly
145                 150                 155                 160

Arg Ser Gly Gln Pro Gly Gln Gln Gly Pro Arg Gly Ser Pro Gly Glu
                165                 170                 175

Val Gly Pro Arg Gly Ser Lys Gly Pro Ser Gly Asp Arg Gly Asp Arg
            180                 185                 190

Gly Glu Arg Gly Val Pro Gly Gln Thr Gly Ser Ala Gly Asn Val Gly
        195                 200                 205

Glu Asp Gly Glu Gln Gly Gly Lys Gly Val Asp Gly Ala Ser Gly Pro
    210                 215                 220

Ser Gly Ala Leu Gly Ala Arg Gly Pro Pro Gly Ser Arg Gly Asp Thr
225                 230                 235                 240

Gly Ala Val Gly Pro Pro Gly Pro Thr Gly Arg Ser Gly Leu Pro Gly
                245                 250                 255

Asn Ala Gly Gln Lys Gly Pro Ser Gly Glu Pro Gly Ser Pro Gly Lys
            260                 265                 270

Ala Gly Ser Ala Gly Glu Gln Gly Pro Pro Gly Lys Asp Gly Ser Asn
        275                 280                 285

Gly Glu Pro Gly Ser Pro Gly Lys Glu Gly Glu Arg Gly Leu Ala Gly
    290                 295                 300

Pro Pro Gly Pro Asp Gly Arg Arg Gly Glu Thr Gly Ser Pro Gly Ile
305                 310                 315                 320

Ala Gly Ala Leu Gly Lys Pro Gly Leu Glu Gly Pro Lys Gly Tyr Pro
                325                 330                 335

Gly Leu Arg Gly Arg Asp Gly Thr Asn Gly Lys Arg Gly Glu Gln Gly
            340                 345                 350

Glu Thr Gly Pro Asp Gly Val Arg Gly Ile Pro Gly Asn Asp Gly Gln
        355                 360                 365

Ser Gly Lys Pro Gly Ile Asp Gly Ile Asp Gly Thr Asn Gly Gln Pro
    370                 375                 380

Gly Glu Ala Gly Tyr Gln Gly Gly Arg Gly Thr Arg Gly Gln Leu Gly
385                 390                 395                 400

Glu Thr Gly Asp Val Gly Gln Asn Gly Asp Arg Gly Ala Pro Gly Pro
                405                 410                 415

Asp Gly Ser Lys Gly Ser Ala Gly Arg Pro Gly Leu Arg
            420                 425
```

<210> SEQ ID NO 2
<211> LENGTH: 1289
<212> TYPE: DNA
<213> ORGANISM: Podocoryna carnea

<400> SEQUENCE: 2

```
ggaccacaag gtgttgtagg agctgatggc aaagatggaa caccgggaga gaaaggtgag      60

caaggacgaa ccggagctgc aggaaaacag ggaagccctg gagcagatgg agcaagaggc     120

cctcttggat caattggaca acaaggtgct cgtggagaac ctggtgatcc aggatctccc     180

ggcttaagag gagatactgg attggctgga gtcaaaggag tagcaggacc atctggtcga     240

cctggacaac ccggtgcaaa tggattacct ggtgtgaatg gcagaggcgg tttgagaggc     300

aaacctggtg ctaaaggaat tgctggcagt gatggagaag cgggagaatc tggcgcacct     360

ggacagtccg gacctaccgg tccacgtggt caacgaggac caagtggtga ggatggtaat     420
```

```
cctggattac agggattgcc tggttctgat ggagagcccg gagaggaagg acaacctgga    480

agatctggtc aaccaggaca gcaaggacca cgtggttccc ctggagaggt aggaccaaga    540

ggatctaaag gtccatcagg agatcgtggt gacaggggag agagaggtgt tcctggacaa    600

acaggttcgg ctggaaatgt aggagaagat ggagagcaag gaggcaaagg tgtcgatgga    660

gcgagtggac caagtggagc tcttggtgct cgtggtcccc caggaagtag aggtgacacc    720

ggggcagtgg gacctcccgg acctactggg cgatctggtt tacctggaaa cgcaggacaa    780

aagggaccaa gtggtgaacc aggtagtcca ggaaaagcag gatcagctgg tgaacagggt    840

cctcctggta aagacggatc aaatggtgaa cctggatctc ctggcaaaga gggtgaacgt    900

ggtcttgctg gtccaccagg tccagatggc agacgtggtg aaacgggatc tccaggtatc    960

gctggtgctc ttggtaaacc aggtttggaa ggacctaaag gttatccagg attaagagga   1020

agagatggaa ccaatggcaa acgaggagaa caaggagaaa ctggtcctga tggagtcaga   1080

ggtattcctg gaaatgatgg acaatctggc aaaccaggta ttgatggtat tgacggaaca   1140

aatggtcaac caggtgaggc tggataccaa ggtggtagag gtacacgtgg tcagttaggt   1200

gaaactggtg atgtcggaca gaatggagat cgaggagctc ctggtcctga tggatctaaa   1260

ggttctgctg gtagaccagg acttcgtgg                                    1289
```

<210> SEQ ID NO 3
<211> LENGTH: 1425
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
atgaaaaaga tttggctggc gctggctggt ttagttttag cgtttagcgc atcggcggcg     60

cagtatgaag atcaccatca ccaccaccac catcaccact ctggctcgag cctggtgccg    120

cgcggcagcc atatgggtcc gcagggtgtt gttggtgcag atggtaaaga cggtaccccg    180

ggtgaaaaag gagaacaggg acgtacaggt gcagcaggta aacagggcag cccgggtgcc    240

gatggtgccc gtggcccgct gggtagcatt ggtcagcagg gtgcaagagg cgaaccgggc    300

gatccgggta gtccgggcct gcgtggtgat acgggtctgg ccggtgttaa aggcgttgca    360

ggtccttcag gtcgtccagg tcaaccgggt gcaaatggtc tgccgggtgt taatggtcgt    420

ggcggtctgc gtggcaaacc gggagcaaaa ggtattgcag gtagcgatgg agaagccggt    480

gaaagcggtg ccccgggtca gagtggtccg accggtccgc gcggtcagcg tggtccgtct    540

ggtgaagatg gcaatccggg tctgcagggt ctgcctggta gtgatggcga accaggtgaa    600

gaaggtcagc cgggtcgttc aggccagccg ggccagcagg gcccgcgtgg tagcccgggc    660

gaagttggcc cgcggggtag taaaggtcct agtggcgatc gcggtgatcg tggtgaacgc    720

ggtgttcctg gtcagaccgg tagcgcaggt aatgttggcg aagatggtga acagggtggc    780

aaaggtgttg atggtgcaag cggtccgagc ggtgcactgg gtgcacgtgg tcctccgggc    840

agccgtggtg acaccggtgc agttggtccg cctggcccga ccggccgtag tggcttaccg    900

ggtaatgcag gtcagaaagg tccgtcaggt gaacctggca gccctggtaa agcaggtagt    960

gccggtgagc agggtccgcc gggcaaagat ggtagtaatg gtgagccggg tagccctggc   1020

aaagaaggtg aacgtggtct ggcaggaccg ccgggtcctg atggtcgccg cggtgaaacg   1080

ggttcaccgg gtattgccgg tgccctgggt aaaccaggtc tggaaggtcc gaaaggttat   1140
```

```
cctggtctgc gcggtcgtga tggtaccaat ggcaaacgtg gcgaacaggg cgaaaccggt   1200

ccagatggtg ttcgtggtat tccgggtaac gatggtcaga gcggtaaacc gggcattgat   1260

ggtattgatg gcaccaatgg tcagcctggc gaagcaggtt atcagggtgg tcgcggtacc   1320

cgtggtcagc tgggtgaaac aggtgatgtt ggtcagaatg gtgatcgcgg cgcaccgggt   1380

ccggatggta gcaaaggtag cgccggtcgt ccgggtttac gttaa                   1425
```

```
<210> SEQ ID NO 4
<211> LENGTH: 1425
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

atgaaaaaga tttggctggc gctggctggt ttagttttag cgtttagcgc atcggcggcg     60

cagtatgaag atcaccatca ccaccaccac catcaccact ctggctcgag cctggtgccg    120

cgcggcagcc atatgggtcc gcagggtgtt gttggtgcag atggtaaaga cggtaccccg    180

ggtgaaaaag gtgaacaggg tcgtaccggt gcagcaggta aacagggcag cccgggtgcc    240

gatggtgccc gtggcccgct gggtagcatt ggtcagcagg gtgcacgtgg cgaaccgggc    300

gatccgggta gcccgggcct gcgtggtgat acgggtctgg ccggtgttaa aggcgttgca    360

ggtccttctg gtcgtccagg tcaaccgggt gcaaatggtc tgccgggtgt taatggtcgt    420

ggcggtctgc gtggcaaacc gggtgcaaaa ggtattgcag gtagcgatgg cgaagccggt    480

gaaagcggtg ccccgggtca gagcggtccg accggtccgc gcggtcagcg tggtccgtct    540

ggtgaagatg gcaatccggg tctgcagggt ctgcctggta gcgatggcga accaggtgaa    600

gaaggtcagc cgggtcgttc tggccagccg ggccagcagg gcccgcgtgg tagcccgggc    660

gaagttggcc cgcgcggttc taaaggtcct agcggcgatc gcggtgatcg tggtgaacgc    720

ggtgttcctg gtcagaccgg tagcgcaggt aatgttggcg aagatggtga acagggtggc    780

aaaggtgttg atggtgcaag cggtccgagc ggtgcactgg gtgcacgtgg tcctccgggc    840

agccgtggtg acaccggtgc agttggtccg cctggcccga ccggccgtag cggcctgccg    900

ggtaatgcag gtcagaaagg tccgtctggt gaacctggca gccctggtaa agcaggtagc    960

gccggtgagc agggtccgcc gggcaaagat ggtagcaatg gtgagccggg tagccctggc   1020

aaagaaggtg aacgtggtct ggcaggtccg ccgggtcctg atggtcgccg cggtgaaacg   1080

ggttctccgg gtattgccgg tgccctgggt aaaccaggtc tggaaggtcc gaaaggttat   1140

cctggtctgc gcggtcgtga tggtaccaat ggcaaacgtg gcgaacaggg cgaaaccggt   1200

ccagatggtg ttcgtggtat tccgggtaac gatggtcaga gcggtaaacc gggcattgat   1260

ggtattgatg gcaccaatgg tcagcctggc gaagcaggtt atcagggtgg tcgcggtacc   1320

cgtggtcagc tgggtgaaac cggtgatgtt ggtcagaatg gtgatcgcgg cgcaccgggt   1380

ccggatggta gcaaaggtag cgccggtcgt ccgggtctgc gttaa                   1425
```

```
<210> SEQ ID NO 5
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 5

```
Met Lys Lys Ile Trp Leu Ala Leu Ala Gly Leu Val Leu Ala Phe Ser
1               5                   10                  15

Ala Ser Ala Ala Gln Tyr Glu Asp His His His His His His His His
            20                  25                  30

His Ser Gly Ser Ser Leu Val Pro Arg Gly Ser His Met Gly Pro Gln
        35                  40                  45

Gly Val Val Gly Ala Asp Gly Lys Asp Gly Thr Pro Gly Glu Lys Gly
    50                  55                  60

Glu Gln Gly Arg Thr Gly Ala Ala Gly Lys Gln Gly Ser Pro Gly Ala
65                  70                  75                  80

Asp Gly Ala Arg Gly Pro Leu Gly Ser Ile Gly Gln Gln Gly Ala Arg
                85                  90                  95

Gly Glu Pro Gly Asp Pro Gly Ser Pro Gly Leu Arg Gly Asp Thr Gly
            100                 105                 110

Leu Ala Gly Val Lys Gly Val Ala Gly Pro Ser Gly Arg Pro Gly Gln
        115                 120                 125

Pro Gly Ala Asn Gly Leu Pro Gly Val Asn Gly Arg Gly Gly Leu Arg
    130                 135                 140

Gly Lys Pro Gly Ala Lys Gly Ile Ala Gly Ser Asp Gly Glu Ala Gly
145                 150                 155                 160

Glu Ser Gly Ala Pro Gly Gln Ser Gly Pro Thr Gly Pro Arg Gly Gln
                165                 170                 175

Arg Gly Pro Ser Gly Glu Asp Gly Asn Pro Gly Leu Gln Gly Leu Pro
            180                 185                 190

Gly Ser Asp Gly Glu Pro Gly Glu Glu Gly Gln Pro Gly Arg Ser Gly
        195                 200                 205

Gln Pro Gly Gln Gln Gly Pro Arg Gly Ser Pro Gly Glu Val Gly Pro
    210                 215                 220

Arg Gly Ser Lys Gly Pro Ser Gly Asp Arg Gly Asp Arg Gly Glu Arg
225                 230                 235                 240

Gly Val Pro Gly Gln Thr Gly Ser Ala Gly Asn Val Gly Glu Asp Gly
                245                 250                 255

Glu Gln Gly Gly Lys Gly Val Asp Gly Ala Ser Gly Pro Ser Gly Ala
            260                 265                 270

Leu Gly Ala Arg Gly Pro Pro Gly Ser Arg Gly Asp Thr Gly Ala Val
        275                 280                 285

Gly Pro Pro Gly Pro Thr Gly Arg Ser Gly Leu Pro Gly Asn Ala Gly
    290                 295                 300

Gln Lys Gly Pro Ser Gly Glu Pro Gly Ser Pro Gly Lys Ala Gly Ser
305                 310                 315                 320

Ala Gly Glu Gln Gly Pro Pro Gly Lys Asp Gly Ser Asn Gly Glu Pro
                325                 330                 335

Gly Ser Pro Gly Lys Glu Gly Glu Arg Gly Leu Ala Gly Pro Pro Gly
            340                 345                 350

Pro Asp Gly Arg Arg Gly Glu Thr Gly Ser Pro Gly Ile Ala Gly Ala
        355                 360                 365

Leu Gly Lys Pro Gly Leu Glu Gly Pro Lys Gly Tyr Pro Gly Leu Arg
    370                 375                 380

Gly Arg Asp Gly Thr Asn Gly Lys Arg Gly Glu Gln Gly Glu Thr Gly
385                 390                 395                 400

Pro Asp Gly Val Arg Gly Ile Pro Gly Asn Asp Gly Gln Ser Gly Lys
                405                 410                 415
```

-continued

```
Pro Gly Ile Asp Gly Ile Asp Gly Thr Asn Gly Gln Pro Gly Glu Ala
            420                 425                 430

Gly Tyr Gln Gly Gly Arg Gly Thr Arg Gly Gln Leu Gly Glu Thr Gly
        435                 440                 445

Asp Val Gly Gln Asn Gly Asp Arg Gly Ala Pro Gly Pro Asp Gly Ser
    450                 455                 460

Lys Gly Ser Ala Gly Arg Pro Gly Leu Arg
465                 470
```

<210> SEQ ID NO 6
<211> LENGTH: 1362
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
atgaaaaaga tttggctggc gctggctggt ttagttttag cgtttagcgc atcggcggcg     60

cagtatgaag atggtccgca gggtgttgtt ggtgcagatg gtaaagacgg taccccgggt    120

gaaaaaggag aacagggacg tacaggtgca gcaggtaaac agggcagccc gggtgccgat    180

ggtgcccgtg gcccgctggg tagcattggt cagcagggtg caagaggcga accgggcgat    240

ccgggtagtc cgggcctgcg tggtgatacg ggtctggccg gtgttaaagg cgttgcaggt    300

ccttcaggtc gtccaggtca accgggtgca aatggtctgc cgggtgttaa tggtcgtggc    360

ggtctgcgtg gcaaaccggg agcaaaaggt attgcaggta gcgatggaga agccggtgaa    420

agcggtgccc cgggtcagag tggtccgacc ggtccgcgcg gtcagcgtgg tccgtctggt    480

gaagatggca atccgggtct gcagggtctg cctggtagtg atggcgaacc aggtgaagaa    540

ggtcagccgg gtcgttcagg ccagccgggc cagcagggcc cgcgtggtag cccgggcgaa    600

gttggcccgc ggggtagtaa aggtcctagt ggcgatcgcg gtgatcgtgg tgaacgcggt    660

gttcctggtc agaccggtag cgcaggtaat gttggcgaag atggtgaaca gggtggcaaa    720

ggtgttgatg gtgcaagcgg tccgagcggt gcactgggtg cacgtggtcc tccgggcagc    780

cgtggtgaca ccggtgcagt tggtccgcct ggcccgaccg gccgtagtgg cttaccgggt    840

aatgcaggtc agaaaggtcc gtcaggtgaa cctggcagcc ctggtaaagc aggtagtgcc    900

ggtgagcagg gtccgccggg caaagatggt agtaatggtg agccgggtag ccctggcaaa    960

gaaggtgaac gtggtctggc aggaccgccg ggtcctgatg gtcgccgcgg tgaaacgggt   1020

tcaccgggta ttgccggtgc cctgggtaaa ccaggtctgg aaggtccgaa aggttatcct   1080

ggtctgcgcg gtcgtgatgg taccaatggc aaacgtggcg aacagggcga aaccggtcca   1140

gatggtgttc gtggtattcc gggtaacgat ggtcagagcg gtaaaccggg cattgatggt   1200

attgatggca ccaatggtca gcctggcgaa gcaggttatc agggtggtcg cggtacccgt   1260

ggtcagctgg gtgaaacagg tgatgttggt cagaatggtg atcgcggcgc accgggtccg   1320

gatggtagca aaggtagcgc cggtcgtccg ggtttacgtt aa                      1362
```

<210> SEQ ID NO 7
<211> LENGTH: 1362
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7
atgaaaaaga tttggctggc gctggctggt ttagttttag cgtttagcgc atcggcggcg 60
cagtatgaag atggtccgca gggtgttgtt ggtgcagatg gtaaagacgg taccccgggt 120
gaaaaaggtg aacagggtcg taccggtgca gcaggtaaac agggcagccc gggtgccgat 180
ggtgcccgtg gcccgctggg tagcattggt cagcagggtg cacgtggcga accgggcgat 240
ccgggtagcc cgggcctgcg tggtgatacg ggtctggccg gtgttaaagg cgttgcaggt 300
ccttctggtc gtccaggtca accgggtgca aatggtctgc cgggtgttaa tggtcgtggc 360
ggtctgcgtg gcaaaccggg tgcaaaaggt attgcaggta gcgatggcga agccggtgaa 420
agcggtgccc cgggtcagag cggtccgacc ggtccgcgcg gtcagcgtgg tccgtctggt 480
gaagatggca atccgggtct gcagggtctg cctggtagcg atggcgaacc aggtgaagaa 540
ggtcagccgg gtcgttctgg ccagccgggc cagcagggcc cgcgtggtag cccgggcgaa 600
gttggcccgc gcggttctaa aggtcctagc ggcgatcgcg gtgatcgtgg tgaacgcggt 660
gttcctggtc agaccggtag cgcaggtaat gttggcgaag atggtgaaca gggtggcaaa 720
ggtgttgatg gtgcaagcgg tccgagcggt gcactgggtg cacgtggtcc tccgggcagc 780
cgtggtgaca ccggtgcagt tggtccgcct ggcccgaccg gccgtagcgg cctgccgggt 840
aatgcaggtc agaaaggtcc gtctggtgaa cctggcagcc ctggtaaagc aggtagcgcc 900
ggtgagcagg gtccgccggg caaagatggt agcaatggtg agccgggtag ccctggcaaa 960
gaaggtgaac gtggtctggc aggtccgccg ggtcctgatg gtcgccgcgg tgaaacgggt 1020
tctccgggta ttgccggtgc cctgggtaaa ccaggtctgg aaggtccgaa aggttatcct 1080
ggtctgcgcg gtcgtgatgg taccaatggc aaacgtggcg aacagggcga aaccggtcca 1140
gatggtgttc gtggtattcc gggtaacgat ggtcagagcg gtaaaccggg cattgatggt 1200
attgatggca ccaatggtca gcctggcgaa gcaggttatc agggtggtcg cggtacccgt 1260
ggtcagctgg gtgaaaccgg tgatgttggt cagaatggtg atcgcggcgc accgggtccg 1320
gatggtagca aaggtagcgc cggtcgtccg ggtctgcgtt aa 1362

<210> SEQ ID NO 8
<211> LENGTH: 453
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

Met Lys Lys Ile Trp Leu Ala Leu Ala Gly Leu Val Leu Ala Phe Ser
1 5 10 15

Ala Ser Ala Ala Gln Tyr Glu Asp Gly Pro Gln Gly Val Val Gly Ala
20 25 30

Asp Gly Lys Asp Gly Thr Pro Gly Glu Lys Gly Glu Gln Gly Arg Thr
35 40 45

Gly Ala Ala Gly Lys Gln Gly Ser Pro Gly Ala Asp Gly Ala Arg Gly
50 55 60

Pro Leu Gly Ser Ile Gly Gln Gln Gly Ala Arg Gly Glu Pro Gly Asp
65 70 75 80

Pro Gly Ser Pro Gly Leu Arg Gly Asp Thr Gly Leu Ala Gly Val Lys
85 90 95

Gly Val Ala Gly Pro Ser Gly Arg Pro Gly Gln Pro Gly Ala Asn Gly
100 105 110

```
Leu Pro Gly Val Asn Gly Arg Gly Gly Leu Arg Gly Lys Pro Gly Ala
        115                 120                 125

Lys Gly Ile Ala Gly Ser Asp Gly Glu Ala Gly Glu Ser Gly Ala Pro
    130                 135                 140

Gly Gln Ser Gly Pro Thr Gly Pro Arg Gly Gln Arg Gly Pro Ser Gly
145                 150                 155                 160

Glu Asp Gly Asn Pro Gly Leu Gln Gly Leu Pro Gly Ser Asp Gly Glu
                165                 170                 175

Pro Gly Glu Glu Gly Gln Pro Gly Arg Ser Gly Gln Pro Gly Gln Gln
            180                 185                 190

Gly Pro Arg Gly Ser Pro Gly Glu Val Gly Pro Arg Gly Ser Lys Gly
        195                 200                 205

Pro Ser Gly Asp Arg Gly Asp Arg Gly Glu Arg Gly Val Pro Gly Gln
    210                 215                 220

Thr Gly Ser Ala Gly Asn Val Gly Glu Asp Gly Glu Gln Gly Gly Lys
225                 230                 235                 240

Gly Val Asp Gly Ala Ser Gly Pro Ser Gly Ala Leu Gly Ala Arg Gly
                245                 250                 255

Pro Pro Gly Ser Arg Gly Asp Thr Gly Ala Val Gly Pro Pro Gly Pro
            260                 265                 270

Thr Gly Arg Ser Gly Leu Pro Gly Asn Ala Gly Gln Lys Gly Pro Ser
        275                 280                 285

Gly Glu Pro Gly Ser Pro Gly Lys Ala Gly Ser Ala Gly Glu Gln Gly
    290                 295                 300

Pro Pro Gly Lys Asp Gly Ser Asn Gly Glu Pro Gly Ser Pro Gly Lys
305                 310                 315                 320

Glu Gly Glu Arg Gly Leu Ala Gly Pro Pro Gly Pro Asp Gly Arg Arg
                325                 330                 335

Gly Glu Thr Gly Ser Pro Gly Ile Ala Gly Ala Leu Gly Lys Pro Gly
            340                 345                 350

Leu Glu Gly Pro Lys Gly Tyr Pro Gly Leu Arg Gly Arg Asp Gly Thr
        355                 360                 365

Asn Gly Lys Arg Gly Glu Gln Gly Glu Thr Gly Pro Asp Gly Val Arg
    370                 375                 380

Gly Ile Pro Gly Asn Asp Gly Gln Ser Gly Lys Pro Gly Ile Asp Gly
385                 390                 395                 400

Ile Asp Gly Thr Asn Gly Gln Pro Gly Glu Ala Gly Tyr Gln Gly Gly
                405                 410                 415

Arg Gly Thr Arg Gly Gln Leu Gly Glu Thr Gly Asp Val Gly Gln Asn
            420                 425                 430

Gly Asp Arg Gly Ala Pro Gly Pro Asp Gly Ser Lys Gly Ser Ala Gly
        435                 440                 445

Arg Pro Gly Leu Arg
    450
```

<210> SEQ ID NO 9
<211> LENGTH: 825
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 9

```
atgaaaaaga tttggctggc gctggctggt ttagttttag cgtttagcgc atcggcggcg      60
```

```
cagtatgaag atcaccatca ccaccaccac catcaccact ctggctcgag cctggtgccg    120

cgcggcagcc atatgggtcc gcagggtgtt gttggtgcag atggtaaaga cggtaccccg    180

ggtgaaaaag gagaacaggg acgtacaggt gcagcaggta aacagggcag cccgggtgcc    240

gatggtgccc gtggcccgct gggtagcatt ggtcagcagg gtgcaagagg cgaaccgggc    300

gatccgggta gtccgggcct gcgtggtgat acgggtctgg ccggtgttaa aggcgttgca    360

ggtccttcag gtcgtccagg tcaaccgggt gcaaatggtc tgccgggtgt taatggtcgt    420

ggcggtctgg aacgtggtct ggcaggaccg ccgggtcctg atggtcgccg cggtgaaacg    480

ggttcaccgg gtattgccgg tgccctgggt aaaccaggtc tggaaggtcc gaaaggttat    540

cctggtctgc gcggtcgtga tggtaccaat ggcaaacgtg gcgaacaggg cgaaaccggt    600

ccagatggtg ttcgtggtat tccgggtaac gatggtcaga gcggtaaacc gggcattgat    660

ggtattgatg gcaccaatgg tcagcctggc gaagcaggtt atcagggtgg tcgcggtacc    720

cgtggtcagc tgggtgaaac aggtgatgtt ggtcagaatg gtgatcgcgg cgcaccgggt    780

ccggatggta gcaaaggtag cgccggtcgt ccgggtttac gttaa                    825
```

```
<210> SEQ ID NO 10
<211> LENGTH: 274
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Lys Lys Ile Trp Leu Ala Leu Ala Gly Leu Val Leu Ala Phe Ser
1               5                   10                  15

Ala Ser Ala Ala Gln Tyr Glu Asp His His His His His His His His
            20                  25                  30

His Ser Gly Ser Ser Leu Val Pro Arg Gly Ser His Met Gly Pro Gln
        35                  40                  45

Gly Val Val Gly Ala Asp Gly Lys Asp Gly Thr Pro Gly Glu Lys Gly
    50                  55                  60

Glu Gln Gly Arg Thr Gly Ala Ala Gly Lys Gln Gly Ser Pro Gly Ala
65                  70                  75                  80

Asp Gly Ala Arg Gly Pro Leu Gly Ser Ile Gly Gln Gln Gly Ala Arg
                85                  90                  95

Gly Glu Pro Gly Asp Pro Gly Ser Pro Gly Leu Arg Gly Asp Thr Gly
            100                 105                 110

Leu Ala Gly Val Lys Gly Val Ala Gly Pro Ser Gly Arg Pro Gly Gln
        115                 120                 125

Pro Gly Ala Asn Gly Leu Pro Gly Val Asn Gly Arg Gly Gly Leu Glu
    130                 135                 140

Arg Gly Leu Ala Gly Pro Pro Gly Pro Asp Gly Arg Arg Gly Glu Thr
145                 150                 155                 160

Gly Ser Pro Gly Ile Ala Gly Ala Leu Gly Lys Pro Gly Leu Glu Gly
                165                 170                 175

Pro Lys Gly Tyr Pro Gly Leu Arg Gly Arg Asp Gly Thr Asn Gly Lys
            180                 185                 190

Arg Gly Glu Gln Gly Glu Thr Gly Pro Asp Gly Val Arg Gly Ile Pro
        195                 200                 205

Gly Asn Asp Gly Gln Ser Gly Lys Pro Gly Ile Asp Gly Ile Asp Gly
    210                 215                 220
```

```
Thr Asn Gly Gln Pro Gly Glu Ala Gly Tyr Gln Gly Gly Arg Gly Thr
225                 230                 235                 240

Arg Gly Gln Leu Gly Glu Thr Gly Asp Val Gly Gln Asn Gly Asp Arg
                245                 250                 255

Gly Ala Pro Gly Pro Asp Gly Ser Lys Gly Ser Ala Gly Arg Pro Gly
            260                 265                 270

Leu Arg


<210> SEQ ID NO 11
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

atgaaaaaga tttggctggc gctggctggt ttagttttag cgtttagcgc atcggcggcg      60

cagtatgaag atggtccgca gggtgttgtt ggtgcagatg gtaaagacgg taccccgggt     120

aatgcaggtc agaaaggtcc gtcaggtgaa cctggcagcc ctggtaaagc aggtagtgcc     180

ggtgagcagg gtccgccggg caaagatggt agtaatggtg agccgggtag ccctggcaaa     240

gaaggtgaac gtggtctggc aggaccgccg ggtcctgatg gtcgccgcgg tgaaacgggt     300

tcaccgggta ttgccggtgc cctgggtaaa ccaggtctgg aaggtccgaa aggttatcct     360

ggtctgcgcg gtcgtgatgg taccaatggc aaacgtggcg aacagggcga aaccggtcca     420

gatggtgttc gtggtattcc gggtaacgat ggtcagagcg gtaaaccggg cattgatggt     480

attgatggca ccaatggtca gcctggcgaa gcaggttatc agggtggtcg cggtacccgt     540

ggtcagctgg gtgaaacagg tgatgttggt cagaatggtg atcgcggcgc accgggtccg     600

gatggtagca aaggtagcgc cggtcgtccg ggtttacgtt aa                        642


<210> SEQ ID NO 12
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Lys Lys Ile Trp Leu Ala Leu Ala Gly Leu Val Leu Ala Phe Ser
1               5                   10                  15

Ala Ser Ala Ala Gln Tyr Glu Asp Gly Pro Gln Gly Val Val Gly Ala
            20                  25                  30

Asp Gly Lys Asp Gly Thr Pro Gly Asn Ala Gly Gln Lys Gly Pro Ser
        35                  40                  45

Gly Glu Pro Gly Ser Pro Gly Lys Ala Gly Ser Ala Gly Glu Gln Gly
    50                  55                  60

Pro Pro Gly Lys Asp Gly Ser Asn Gly Glu Pro Gly Ser Pro Gly Lys
65                  70                  75                  80

Glu Gly Glu Arg Gly Leu Ala Gly Pro Pro Gly Pro Asp Gly Arg Arg
                85                  90                  95

Gly Glu Thr Gly Ser Pro Gly Ile Ala Gly Ala Leu Gly Lys Pro Gly
            100                 105                 110

Leu Glu Gly Pro Lys Gly Tyr Pro Gly Leu Arg Gly Arg Asp Gly Thr
        115                 120                 125
```

```
Asn Gly Lys Arg Gly Glu Gln Gly Glu Thr Gly Pro Asp Gly Val Arg
    130                 135                 140

Gly Ile Pro Gly Asn Asp Gly Gln Ser Gly Lys Pro Gly Ile Asp Gly
145                 150                 155                 160

Ile Asp Gly Thr Asn Gly Gln Pro Gly Glu Ala Gly Tyr Gln Gly Gly
                165                 170                 175

Arg Gly Thr Arg Gly Gln Leu Gly Glu Thr Gly Asp Val Gly Gln Asn
            180                 185                 190

Gly Asp Arg Gly Ala Pro Gly Pro Asp Gly Ser Lys Gly Ser Ala Gly
        195                 200                 205

Arg Pro Gly Leu Arg
    210


<210> SEQ ID NO 13
<211> LENGTH: 696
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

atgaaaaaga tttggctggc gctggctggt ttagttttag cgtttagcgc atcggcggcg      60

cagtatgaag atggtgaaaa aggtgaaaag ggcgagaaag gtgagaaagg cgaaaagggt     120

gaaaaaggtc cgcagggtgt tgttggtgca gatggtaaag acggtacccc gggtaatgca     180

ggtcagaaag gtccgtcagg tgaacctggc agccctggta aagcaggtag tgccggtgag     240

cagggtccgc cgggcaaaga tggtagtaat ggtgagccgg gtagccctgg caaagaaggt     300

gaacgtggtc tggcaggacc gccgggtcct gatggtcgcc gcggtgaaac gggttcaccg     360

ggtattgccg gtgccctggg taaaccaggt ctggaaggtc cgaaaggtta tcctggtctg     420

cgcggtcgtg atggtaccaa tggcaaacgt ggcgaacagg gcgaaaccgg tccagatggt     480

gttcgtggta ttccgggtaa cgatggtcag agcggtaaac cgggcattga tggtattgat     540

ggcaccaatg gtcagcctgg cgaagcaggt tatcagggtg gtcgcggtac ccgtggtcag     600

ctgggtgaaa caggtgatgt tggtcagaat ggtgatcgcg gcgcaccggg tccggatggt     660

agcaaaggta gcgccggtcg tccgggttta cgttaa                               696


<210> SEQ ID NO 14
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Lys Lys Ile Trp Leu Ala Leu Ala Gly Leu Val Leu Ala Phe Ser
1               5                   10                  15

Ala Ser Ala Ala Gln Tyr Glu Asp Gly Glu Lys Gly Glu Lys Gly Glu
            20                  25                  30

Lys Gly Glu Lys Gly Glu Lys Gly Glu Lys Gly Pro Gln Gly Val Val
        35                  40                  45

Gly Ala Asp Gly Lys Asp Gly Thr Pro Gly Asn Ala Gly Gln Lys Gly
    50                  55                  60

Pro Ser Gly Glu Pro Gly Ser Pro Gly Lys Ala Gly Ser Ala Gly Glu
65                  70                  75                  80
```

```
Gln Gly Pro Pro Gly Lys Asp Gly Ser Asn Gly Glu Pro Gly Ser Pro
                85                  90                  95

Gly Lys Glu Gly Glu Arg Gly Leu Ala Gly Pro Pro Gly Pro Asp Gly
            100                 105                 110

Arg Arg Gly Glu Thr Gly Ser Pro Gly Ile Ala Gly Ala Leu Gly Lys
        115                 120                 125

Pro Gly Leu Glu Gly Pro Lys Gly Tyr Pro Gly Leu Arg Gly Arg Asp
    130                 135                 140

Gly Thr Asn Gly Lys Arg Gly Glu Gln Gly Glu Thr Gly Pro Asp Gly
145                 150                 155                 160

Val Arg Gly Ile Pro Gly Asn Asp Gly Gln Ser Gly Lys Pro Gly Ile
                165                 170                 175

Asp Gly Ile Asp Gly Thr Asn Gly Gln Pro Gly Glu Ala Gly Tyr Gln
            180                 185                 190

Gly Gly Arg Gly Thr Arg Gly Gln Leu Gly Glu Thr Gly Asp Val Gly
        195                 200                 205

Gln Asn Gly Asp Arg Gly Ala Pro Gly Pro Asp Gly Ser Lys Gly Ser
    210                 215                 220

Ala Gly Arg Pro Gly Leu Arg
225                 230
```

<210> SEQ ID NO 15
<211> LENGTH: 696
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

```
atgaaaaaga tttggctggc gctggctggt ttagttttag cgtttagcgc atcggcggcg     60

cagtatgaag atggtgataa aggtgataag ggcgacaaag gtgacaaagg cgataagggt    120

gataaaggtc cgcagggtgt tgttggtgca gatggtaaag acggtacccc gggtaatgca    180

ggtcagaaag gtccgtcagg tgaacctggc agccctggta aagcaggtag tgccggtgag    240

cagggtccgc cgggcaaaga tggtagtaat ggtgagccgg gtagccctgg caaagaaggt    300

gaacgtggtc tggcaggacc gccgggtcct gatggtcgcc gcggtgaaac gggttcaccg    360

ggtattgccg gtgccctggg taaaccaggt ctggaaggtc cgaaaggtta tcctggtctg    420

cgcggtcgtg atggtaccaa tggcaaacgt ggcgaacagg gcgaaaccgg tccagatggt    480

gttcgtggta ttccgggtaa cgatggtcag agcggtaaac cgggcattga tggtattgat    540

ggcaccaatg gtcagcctgg cgaagcaggt tatcagggtg gtcgcggtac ccgtggtcag    600

ctgggtgaaa caggtgatgt tggtcagaat ggtgatcgcg gcgcaccggg tccggatggt    660

agcaaaggta gcgccggtcg tccgggttta cgttaa                              696
```

<210> SEQ ID NO 16
<211> LENGTH: 231
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Met Lys Lys Ile Trp Leu Ala Leu Ala Gly Leu Val Leu Ala Phe Ser
1               5                   10                  15
```

-continued

Ala Ser Ala Ala Gln Tyr Glu Asp Gly Asp Lys Gly Asp Lys Gly Asp
20 25 30

Lys Gly Asp Lys Gly Asp Lys Gly Asp Lys Gly Pro Gln Gly Val Val
35 40 45

Gly Ala Asp Gly Lys Asp Gly Thr Pro Gly Asn Ala Gly Gln Lys Gly
50 55 60

Pro Ser Gly Glu Pro Gly Ser Pro Gly Lys Ala Gly Ser Ala Gly Glu
65 70 75 80

Gln Gly Pro Pro Gly Lys Asp Gly Ser Asn Gly Glu Pro Gly Ser Pro
85 90 95

Gly Lys Glu Gly Glu Arg Gly Leu Ala Gly Pro Pro Gly Pro Asp Gly
100 105 110

Arg Arg Gly Glu Thr Gly Ser Pro Gly Ile Ala Gly Ala Leu Gly Lys
115 120 125

Pro Gly Leu Glu Gly Pro Lys Gly Tyr Pro Gly Leu Arg Gly Arg Asp
130 135 140

Gly Thr Asn Gly Lys Arg Gly Glu Gln Gly Glu Thr Gly Pro Asp Gly
145 150 155 160

Val Arg Gly Ile Pro Gly Asn Asp Gly Gln Ser Gly Lys Pro Gly Ile
165 170 175

Asp Gly Ile Asp Gly Thr Asn Gly Gln Pro Gly Glu Ala Gly Tyr Gln
180 185 190

Gly Gly Arg Gly Thr Arg Gly Gln Leu Gly Glu Thr Gly Asp Val Gly
195 200 205

Gln Asn Gly Asp Arg Gly Ala Pro Gly Pro Asp Gly Ser Lys Gly Ser
210 215 220

Ala Gly Arg Pro Gly Leu Arg
225 230

<210> SEQ ID NO 17
<211> LENGTH: 2232
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17
atgaaaaaga tttggctggc gctggctggt ttagttttag cgtttagcgc atcggcggcg 60
cagtatgaag atcaccatca ccaccaccac catcaccact ctggctcgag cctggtgccg 120
cgcggcagcc atatgtctgg ctcgagcagt aaaggtgaag aactgttcac cggtgttgtt 180
ccgatcctgg ttgaactgga tggtgatgtt aacggccaca aattctctgt tcgtggtgaa 240
ggtgaaggtg atgcaaccaa cggtaaactg accctgaaat tcatctgcac taccggtaaa 300
ctgccggttc catggccgac tctggtgact accctgacct atggtgttca gtgtttttct 360
cgttacccgg atcacatgaa gcagcatgat ttcttcaaat ctgcaatgcc ggaaggttat 420
gtacaggagc gcaccatttc tttcaaagac gatggcacct acaaaacccg tgcagaggtt 480
aaatttgaag gtgatactct ggtgaaccgt attgaactga aaggcattga tttcaaagag 540
gacggcaaca tcctgggcca caaactggaa tataacttca actcccataa cgtttacatc 600
accgcagaca aacagaagaa cggtatcaaa gctaacttca aaattcgcca taacgttgaa 660
gacggtagcg tacagctggc ggaccactac cagcagaaca ctccgatcgg tgatggtccg 720
gttctgctgc cggataacca ctacctgtcc acccagtcta aactgtccaa agacccgaac 780
gaaaagcgcg accacatggt gctgctggag ttcgttactg cagcaggtat cacgcacggc 840
atggatgaac tctacaaatc tggcgcgccg ggcggtccgc agggtgttgt tggtgcagat 900
ggtaaagacg gtaccccggg taatgcaggt cagaaaggtc cgtcaggtga acctggcagc 960
cctggtaaag caggtagtgc cggtgagcag ggtccgccgg gcaaagatgg tagtaatggt 1020
gagccgggta gccctggcaa agaaggtgaa cgtggtctgg caggaccgcc gggtcctgat 1080
ggtcgccgcg gtgaaacggg ttcaccgggt attgccggtg ccctgggtaa accaggtctg 1140
gaaggtccga aaggttatcc tggtctgcgc ggtcgtgatg gtaccaatgg caaacgtggc 1200
gaacagggcg aaaccggtcc agatggtgtt cgtggtattc cgggtaacga tggtcagagc 1260
ggtaaaccgg gcattgatgg tattgatggc accaatggtc agcctggcga agcaggttat 1320
cagggtggtc gcggtacccg tggtcagctg ggtgaaacag gtgatgttgg tcagaatggt 1380
gatcgcggcg caccgggtcc ggatggtagc aaaggtagcg ccggtcgtcc gggtttacgt 1440
cacccagaaa cgctggtgaa agtaaaagat gctgaagatc agttgggtgc acgagtgggt 1500
tacatcgaac tggatctcaa cagcggtaag atccttgaga gttttcgccc cgaagaacgt 1560
tttccaatga tgagcacttt taaagttctg ctatgtggcg cggtattatc ccgtattgac 1620
gccgggcaag agcaactcgg tcgccgcata cactattctc agaatgactt ggttgagtac 1680
tcaccagtca cagaaaagca tcttacggat ggcatgacag taagagaatt atgcagtgct 1740
gccataacca tgagtgataa cactgcggcc aacttacttc tgacaacgat cggaggaccg 1800
aaggagctaa ccgctttttt gcacaacatg ggggatcatg taactcgcct tgatcgttgg 1860
gaaccggagc tgaatgaagc cataccaaac gacgagcgtg acaccacgat gcctgtagca 1920
atggcaacaa cgttgcgcaa actattaact ggcgaactac ttactctagc ttcccggcaa 1980
caattaatag actggatgga ggcggataaa gttgcaggac cacttctgcg ctcggccctt 2040
ccggctggct ggtttattgc tgataaatct ggagccggtg agcgtgggtc tcgcggtatc 2100
attgcagcac tggggccaga tggtaagccc tcccgtatcg tagttatcta cacgacgggg 2160
agtcaggcaa ctatggatga acgaaataga cagatcgctg agataggtgc ctcactgatt 2220
aagcattggt aa 2232

<210> SEQ ID NO 18
<211> LENGTH: 743
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 18

Met Lys Lys Ile Trp Leu Ala Leu Ala Gly Leu Val Leu Ala Phe Ser
1 5 10 15

Ala Ser Ala Ala Gln Tyr Glu Asp His His His His His His His His
20 25 30

His Ser Gly Ser Ser Leu Val Pro Arg Gly Ser His Met Ser Gly Ser
35 40 45

Ser Ser Lys Gly Glu Glu Leu Phe Thr Gly Val Val Pro Ile Leu Val
50 55 60

Glu Leu Asp Gly Asp Val Asn Gly His Lys Phe Ser Val Arg Gly Glu
65 70 75 80

Gly Glu Gly Asp Ala Thr Asn Gly Lys Leu Thr Leu Lys Phe Ile Cys
85 90 95

-continued

```
Thr Thr Gly Lys Leu Pro Val Pro Trp Pro Thr Leu Val Thr Thr Leu
            100                 105                 110

Thr Tyr Gly Val Gln Cys Phe Ser Arg Tyr Pro Asp His Met Lys Gln
        115                 120                 125

His Asp Phe Phe Lys Ser Ala Met Pro Glu Gly Tyr Val Gln Glu Arg
    130                 135                 140

Thr Ile Ser Phe Lys Asp Asp Gly Thr Tyr Lys Thr Arg Ala Glu Val
145                 150                 155                 160

Lys Phe Glu Gly Asp Thr Leu Val Asn Arg Ile Glu Leu Lys Gly Ile
                165                 170                 175

Asp Phe Lys Glu Asp Gly Asn Ile Leu Gly His Lys Leu Glu Tyr Asn
            180                 185                 190

Phe Asn Ser His Asn Val Tyr Ile Thr Ala Asp Lys Gln Lys Asn Gly
        195                 200                 205

Ile Lys Ala Asn Phe Lys Ile Arg His Asn Val Glu Asp Gly Ser Val
    210                 215                 220

Gln Leu Ala Asp His Tyr Gln Gln Asn Thr Pro Ile Gly Asp Gly Pro
225                 230                 235                 240

Val Leu Leu Pro Asp Asn His Tyr Leu Ser Thr Gln Ser Lys Leu Ser
                245                 250                 255

Lys Asp Pro Asn Glu Lys Arg Asp His Met Val Leu Leu Glu Phe Val
            260                 265                 270

Thr Ala Ala Gly Ile Thr His Gly Met Asp Glu Leu Tyr Lys Ser Gly
        275                 280                 285

Ala Pro Gly Gly Pro Gln Gly Val Val Gly Ala Asp Gly Lys Asp Gly
    290                 295                 300

Thr Pro Gly Asn Ala Gly Gln Lys Gly Pro Ser Gly Glu Pro Gly Ser
305                 310                 315                 320

Pro Gly Lys Ala Gly Ser Ala Gly Glu Gln Gly Pro Pro Gly Lys Asp
                325                 330                 335

Gly Ser Asn Gly Glu Pro Gly Ser Pro Gly Lys Glu Gly Glu Arg Gly
            340                 345                 350

Leu Ala Gly Pro Pro Gly Pro Asp Gly Arg Arg Gly Glu Thr Gly Ser
        355                 360                 365

Pro Gly Ile Ala Gly Ala Leu Gly Lys Pro Gly Leu Glu Gly Pro Lys
    370                 375                 380

Gly Tyr Pro Gly Leu Arg Gly Arg Asp Gly Thr Asn Gly Lys Arg Gly
385                 390                 395                 400

Glu Gln Gly Glu Thr Gly Pro Asp Gly Val Arg Gly Ile Pro Gly Asn
                405                 410                 415

Asp Gly Gln Ser Gly Lys Pro Gly Ile Asp Gly Ile Asp Gly Thr Asn
            420                 425                 430

Gly Gln Pro Gly Glu Ala Gly Tyr Gln Gly Gly Arg Gly Thr Arg Gly
        435                 440                 445

Gln Leu Gly Glu Thr Gly Asp Val Gly Gln Asn Gly Asp Arg Gly Ala
    450                 455                 460

Pro Gly Pro Asp Gly Ser Lys Gly Ser Ala Gly Arg Pro Gly Leu Arg
465                 470                 475                 480

His Pro Glu Thr Leu Val Lys Val Lys Asp Ala Glu Asp Gln Leu Gly
                485                 490                 495

Ala Arg Val Gly Tyr Ile Glu Leu Asp Leu Asn Ser Gly Lys Ile Leu
            500                 505                 510
```

```
Glu Ser Phe Arg Pro Glu Glu Arg Phe Pro Met Met Ser Thr Phe Lys
        515                 520                 525

Val Leu Leu Cys Gly Ala Val Leu Ser Arg Ile Asp Ala Gly Gln Glu
    530                 535                 540

Gln Leu Gly Arg Arg Ile His Tyr Ser Gln Asn Asp Leu Val Glu Tyr
545                 550                 555                 560

Ser Pro Val Thr Glu Lys His Leu Thr Asp Gly Met Thr Val Arg Glu
                565                 570                 575

Leu Cys Ser Ala Ala Ile Thr Met Ser Asp Asn Thr Ala Ala Asn Leu
            580                 585                 590

Leu Leu Thr Thr Ile Gly Gly Pro Lys Glu Leu Thr Ala Phe Leu His
        595                 600                 605

Asn Met Gly Asp His Val Thr Arg Leu Asp Arg Trp Glu Pro Glu Leu
    610                 615                 620

Asn Glu Ala Ile Pro Asn Asp Glu Arg Asp Thr Thr Met Pro Val Ala
625                 630                 635                 640

Met Ala Thr Thr Leu Arg Lys Leu Leu Thr Gly Glu Leu Leu Thr Leu
                645                 650                 655

Ala Ser Arg Gln Gln Leu Ile Asp Trp Met Glu Ala Asp Lys Val Ala
            660                 665                 670

Gly Pro Leu Leu Arg Ser Ala Leu Pro Ala Gly Trp Phe Ile Ala Asp
        675                 680                 685

Lys Ser Gly Ala Gly Glu Arg Gly Ser Arg Gly Ile Ile Ala Ala Leu
    690                 695                 700

Gly Pro Asp Gly Lys Pro Ser Arg Ile Val Val Ile Tyr Thr Thr Gly
705                 710                 715                 720

Ser Gln Ala Thr Met Asp Glu Arg Asn Arg Gln Ile Ala Glu Ile Gly
                725                 730                 735

Ala Ser Leu Ile Lys His Trp
            740
```

<210> SEQ ID NO 19
<211> LENGTH: 2232
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19

```
atgaaaaaga tttggctggc gctggctggt ttagttttag cgtttagcgc atcggcggcg     60

cagtatgaag atcaccatca ccaccaccac catcaccact ctggctcgag cctggtgccg    120

cgcggcagcc atatgtctgg ctcgagcagt aaaggtgaag aactgttcac cggtgttgtt    180

ccgatcctgg ttgaactgga tggtgatgtt aacggccaca aattctctgt tcgtggtgaa    240

ggtgaaggtg atgcaaccaa cggtaaactg accctgaaat tcatctgcac taccggtaaa    300

ctgccggttc catggccgac tctggtgact accctgacct atggtgttca gtgtttttct    360

cgttacccgg atcacatgaa gcagcatgat ttcttcaaat ctgcaatgcc ggaaggttat    420

gtacaggagc gcaccatttc tttcaaagac gatggcacct acaaaacccg tgcagaggtt    480

aaatttgaag gtgatactct ggtgaaccgt attgaactga aaggcattga tttcaaagag    540

gacggcaaca tcctgggcca caaactggaa tataacttca actcccataa cgtttacatc    600

accgcagaca aacagaagaa cggtatcaaa gctaacttca aaattcgcca taacgttgaa    660

gacggtagcg tacagctggc ggaccactac cagcagaaca ctccgatcgg tgatggtccg    720
```

-continued

```
gttctgctgc cggataacca ctacctgtcc acccagtcta aactgtccaa agacccgaac    780

gaaaagcgcg accacatggt gctgctggag ttcgttactg cagcaggtat cacgcacggc    840

atggatgaac tctacaaatc tggcgcgccg ggcggtccgc agggtgttgt tggtgcagat    900

ggtaaagacg gtaccccggg taatgcaggt cagaaaggtc cgtcaggtga acctggcagc    960

cctggtaaag caggtagtgc cggtgagcag ggtccgccgg gcaaagatgg tagtaatggt   1020

gagccgggta gccctggcaa agaaggtgaa cgtggtctgg caggaccgcc gggtcctgat   1080

ggtcgccgcg gtgaaacggg ttcaccgggt attgccggtg ccctgggtaa accaggtctg   1140

gaaggtccga aaggttatcc tggtctgcgc ggtcgtgatg gtaccaatgg caaacgtggc   1200

gaacagggcg aaaccggtcc agatggtgtt cgtggtattc cgggtaacga tggtcagagc   1260

ggtaaaccgg gcattgatgg tattgatggc accaatggtc agcctggcga agcaggttat   1320

cagggtggtc gcggtacccg tggtcagctg ggtgaaacag gtgatgttgg tcagaatggt   1380

gatcgcggcg caccgggtcc ggatggtagc aaaggtagcg ccggtcgtcc gggtttacgt   1440

cacccagaaa cgctggtgaa agtaaaagat gctgaagatc agttgggtgc acgagtgggt   1500

tacatcgaac tggatctcaa cagcggtaag atccttgaga gttttcgccc cgaagaacgt   1560

tttccaatga tgagcacttt taaagttctg ctatgtggcg cggtattatc ccgtattgac   1620

gccgggcaag agcaactcgg tcgccgcata cactattctc agaatgactt ggttgagtac   1680

tcaccagtca cagaaaagca tcttacggat ggcatgacag taagagaatt atgcagtgct   1740

gccataacca tgagtgataa cactgcggcc aacttacttc tgacaacgat cggaggaccg   1800

aaggagctaa ccgctttttt gcacaacatg ggggatcatg taactcgcct tgatcgttgg   1860

gaaccggagc tgaatgaagc cataccaaac gacgagcgtg acaccacgat gcctgtagca   1920

atggcaacaa cgttgcgcaa actattaact ggcgaactac ttactctagc ttcccggcaa   1980

caattaatag actggatgga ggcggataaa gttgcaggac cacttctgcg ctcggccctt   2040

ccggctggct ggtttattgc tgataaatct ggagccggtg agcgtgggtc tcgcggtatc   2100

attgcagcac tggggccaga tggtaagccc tcccgtatcg tagttatcta cacgacgggg   2160

agtcaggcaa ctatggatga acgaaataga cagatcgctg agataggtgc ctcactgatt   2220

aagcattggt aa                                                       2232
```

```
<210> SEQ ID NO 20
<211> LENGTH: 743
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Lys Lys Ile Trp Leu Ala Leu Ala Gly Leu Val Leu Ala Phe Ser
1               5                   10                  15

Ala Ser Ala Ala Gln Tyr Glu Asp His His His His His His His His
            20                  25                  30

His Ser Gly Ser Ser Leu Val Pro Arg Gly Ser His Met Ser Gly Ser
        35                  40                  45

Ser Ser Lys Gly Glu Glu Leu Phe Thr Gly Val Val Pro Ile Leu Val
    50                  55                  60

Glu Leu Asp Gly Asp Val Asn Gly His Lys Phe Ser Val Arg Gly Glu
65                  70                  75                  80
```

```
Gly Glu Gly Asp Ala Thr Asn Gly Lys Leu Thr Leu Lys Phe Ile Cys
                85                  90                  95

Thr Thr Gly Lys Leu Pro Val Pro Trp Pro Thr Leu Val Thr Thr Leu
            100                 105                 110

Thr Tyr Gly Val Gln Cys Phe Ser Arg Tyr Pro Asp His Met Lys Gln
        115                 120                 125

His Asp Phe Phe Lys Ser Ala Met Pro Glu Gly Tyr Val Gln Glu Arg
    130                 135                 140

Thr Ile Ser Phe Lys Asp Asp Gly Thr Tyr Lys Thr Arg Ala Glu Val
145                 150                 155                 160

Lys Phe Glu Gly Asp Thr Leu Val Asn Arg Ile Glu Leu Lys Gly Ile
                165                 170                 175

Asp Phe Lys Glu Asp Gly Asn Ile Leu Gly His Lys Leu Glu Tyr Asn
            180                 185                 190

Phe Asn Ser His Asn Val Tyr Ile Thr Ala Asp Lys Gln Lys Asn Gly
        195                 200                 205

Ile Lys Ala Asn Phe Lys Ile Arg His Asn Val Glu Asp Gly Ser Val
    210                 215                 220

Gln Leu Ala Asp His Tyr Gln Gln Asn Thr Pro Ile Gly Asp Gly Pro
225                 230                 235                 240

Val Leu Leu Pro Asp Asn His Tyr Leu Ser Thr Gln Ser Lys Leu Ser
                245                 250                 255

Lys Asp Pro Asn Glu Lys Arg Asp His Met Val Leu Leu Glu Phe Val
            260                 265                 270

Thr Ala Ala Gly Ile Thr His Gly Met Asp Glu Leu Tyr Lys Ser Gly
        275                 280                 285

Ala Pro Gly Gly Pro Gln Gly Val Val Gly Ala Asp Gly Lys Asp Gly
    290                 295                 300

Thr Pro Gly Asn Ala Gly Gln Lys Gly Pro Ser Gly Glu Pro Gly Ser
305                 310                 315                 320

Pro Gly Lys Ala Gly Ser Ala Gly Glu Gln Gly Pro Pro Gly Lys Asp
                325                 330                 335

Gly Ser Asn Gly Glu Pro Gly Ser Pro Gly Lys Glu Gly Glu Arg Gly
            340                 345                 350

Leu Ala Gly Pro Pro Gly Pro Asp Gly Arg Arg Gly Glu Thr Gly Ser
        355                 360                 365

Pro Gly Ile Ala Gly Ala Leu Gly Lys Pro Gly Leu Glu Gly Pro Lys
    370                 375                 380

Gly Tyr Pro Gly Leu Arg Gly Arg Asp Gly Thr Asn Gly Lys Arg Gly
385                 390                 395                 400

Glu Gln Gly Glu Thr Gly Pro Asp Gly Val Arg Gly Ile Pro Gly Asn
                405                 410                 415

Asp Gly Gln Ser Gly Lys Pro Gly Ile Asp Gly Ile Asp Gly Thr Asn
            420                 425                 430

Gly Gln Pro Gly Glu Ala Gly Tyr Gln Gly Gly Arg Gly Thr Arg Gly
        435                 440                 445

Gln Leu Gly Glu Thr Gly Asp Val Gly Gln Asn Gly Asp Arg Gly Ala
    450                 455                 460

Pro Gly Pro Asp Gly Ser Lys Gly Ser Ala Gly Arg Pro Gly Leu Arg
465                 470                 475                 480

His Pro Glu Thr Leu Val Lys Val Lys Asp Ala Glu Asp Gln Leu Gly
                485                 490                 495

Ala Arg Val Gly Tyr Ile Glu Leu Asp Leu Asn Ser Gly Lys Ile Leu
```

```
            500                 505                 510

Glu Ser Phe Arg Pro Glu Glu Arg Phe Pro Met Met Ser Thr Phe Lys
        515                 520                 525

Val Leu Leu Cys Gly Ala Val Leu Ser Arg Ile Asp Ala Gly Gln Glu
    530                 535                 540

Gln Leu Gly Arg Arg Ile His Tyr Ser Gln Asn Asp Leu Val Glu Tyr
545                 550                 555                 560

Ser Pro Val Thr Glu Lys His Leu Thr Asp Gly Met Thr Val Arg Glu
                565                 570                 575

Leu Cys Ser Ala Ala Ile Thr Met Ser Asp Asn Thr Ala Ala Asn Leu
            580                 585                 590

Leu Leu Thr Thr Ile Gly Gly Pro Lys Glu Leu Thr Ala Phe Leu His
        595                 600                 605

Asn Met Gly Asp His Val Thr Arg Leu Asp Arg Trp Glu Pro Glu Leu
    610                 615                 620

Asn Glu Ala Ile Pro Asn Asp Glu Arg Asp Thr Thr Met Pro Val Ala
625                 630                 635                 640

Met Ala Thr Thr Leu Arg Lys Leu Leu Thr Gly Glu Leu Leu Thr Leu
                645                 650                 655

Ala Ser Arg Gln Gln Leu Ile Asp Trp Met Glu Ala Asp Lys Val Ala
            660                 665                 670

Gly Pro Leu Leu Arg Ser Ala Leu Pro Ala Gly Trp Phe Ile Ala Asp
        675                 680                 685

Lys Ser Gly Ala Gly Glu Arg Gly Ser Arg Gly Ile Ile Ala Ala Leu
    690                 695                 700

Gly Pro Asp Gly Lys Pro Ser Arg Ile Val Val Ile Tyr Thr Thr Gly
705                 710                 715                 720

Ser Gln Ala Thr Met Asp Glu Arg Asn Arg Gln Ile Ala Glu Ile Gly
                725                 730                 735

Ala Ser Leu Ile Lys His Trp
            740


<210> SEQ ID NO 21
<211> LENGTH: 786
<212> TYPE: PRT
<213> ORGANISM: Homo sapiens

<400> SEQUENCE: 21

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Gly Val Pro Gly Ala
            20                  25                  30

Ile Pro Gly Gly Val Pro Gly Gly Val Phe Tyr Pro Gly Ala Gly Leu
        35                  40                  45

Gly Ala Leu Gly Gly Gly Ala Leu Gly Pro Gly Gly Lys Pro Leu Lys
    50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
                85                  90                  95

Ala Asp Ala Ala Ala Ala Tyr Lys Ala Ala Lys Ala Gly Ala Gly Leu
            100                 105                 110

Gly Gly Val Pro Gly Val Gly Gly Leu Gly Val Ser Ala Gly Ala Val
        115                 120                 125
```

-continued

```
Val Pro Gln Pro Gly Ala Gly Val Lys Pro Gly Lys Val Pro Gly Val
    130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
            180                 185                 190

Gly Pro Phe Gly Gly Pro Gln Pro Gly Val Pro Leu Gly Tyr Pro Ile
        195                 200                 205

Lys Ala Pro Lys Leu Pro Gly Gly Tyr Gly Leu Pro Tyr Thr Thr Gly
    210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Ala Lys Phe Gly Ala Gly Ala Ala Gly
            260                 265                 270

Val Leu Pro Gly Val Gly Gly Ala Gly Val Pro Gly Val Pro Gly Ala
        275                 280                 285

Ile Pro Gly Ile Gly Gly Ile Ala Gly Val Gly Thr Pro Ala Ala Ala
    290                 295                 300

Ala Ala Ala Ala Ala Ala Ala Lys Ala Ala Lys Tyr Gly Ala Ala Ala
305                 310                 315                 320

Gly Leu Val Pro Gly Gly Pro Gly Phe Gly Pro Gly Val Val Gly Val
                325                 330                 335

Pro Gly Ala Gly Val Pro Gly Val Gly Val Pro Gly Ala Gly Ile Pro
            340                 345                 350

Val Val Pro Gly Ala Gly Ile Pro Gly Ala Ala Val Pro Gly Val Val
        355                 360                 365

Ser Pro Glu Ala Ala Ala Lys Ala Ala Ala Lys Ala Ala Lys Tyr Gly
    370                 375                 380

Ala Arg Pro Gly Val Gly Val Gly Gly Ile Pro Thr Tyr Gly Val Gly
385                 390                 395                 400

Ala Gly Gly Phe Pro Gly Phe Gly Val Gly Val Gly Gly Ile Pro Gly
                405                 410                 415

Val Ala Gly Val Pro Gly Val Gly Gly Val Pro Gly Val Gly Gly Val
            420                 425                 430

Pro Gly Val Gly Ile Ser Pro Glu Ala Gln Ala Ala Ala Ala Ala Lys
        435                 440                 445

Ala Ala Lys Tyr Gly Ala Ala Gly Ala Gly Val Leu Gly Gly Leu Val
    450                 455                 460

Pro Gly Pro Gln Ala Ala Val Pro Gly Val Pro Gly Thr Gly Gly Val
465                 470                 475                 480

Pro Gly Val Gly Thr Pro Ala Ala Ala Ala Ala Lys Ala Ala Ala Lys
                485                 490                 495

Ala Ala Gln Phe Gly Leu Val Pro Gly Val Gly Val Ala Pro Gly Val
            500                 505                 510

Gly Val Ala Pro Gly Val Gly Val Ala Pro Gly Val Gly Leu Ala Pro
        515                 520                 525

Gly Val Gly Val Ala Pro Gly Val Gly Val Ala Pro Gly Val Gly Val
    530                 535                 540

Ala Pro Gly Ile Gly Pro Gly Gly Val Ala Ala Ala Ala Lys Ser Ala
```

```
545                 550                 555                 560

Ala Lys Val Ala Ala Lys Ala Gln Leu Arg Ala Ala Ala Gly Leu Gly
                565                 570                 575

Ala Gly Ile Pro Gly Leu Gly Val Gly Val Gly Val Pro Gly Leu Gly
            580                 585                 590

Val Gly Ala Gly Val Pro Gly Leu Gly Val Gly Ala Gly Val Pro Gly
        595                 600                 605

Phe Gly Ala Gly Ala Asp Glu Gly Val Arg Arg Ser Leu Ser Pro Glu
    610                 615                 620

Leu Arg Glu Gly Asp Pro Ser Ser Ser Gln His Leu Pro Ser Thr Pro
625                 630                 635                 640

Ser Ser Pro Arg Val Pro Gly Ala Leu Ala Ala Ala Lys Ala Ala Lys
                645                 650                 655

Tyr Gly Ala Ala Val Pro Gly Val Leu Gly Gly Leu Gly Ala Leu Gly
            660                 665                 670

Gly Val Gly Ile Pro Gly Gly Val Val Gly Ala Gly Pro Ala Ala Ala
        675                 680                 685

Ala Ala Ala Ala Lys Ala Ala Ala Lys Ala Ala Gln Phe Gly Leu Val
    690                 695                 700

Gly Ala Ala Gly Leu Gly Gly Leu Gly Val Gly Gly Leu Gly Val Pro
705                 710                 715                 720

Gly Val Gly Gly Leu Gly Gly Ile Pro Pro Ala Ala Ala Ala Lys Ala
                725                 730                 735

Ala Lys Tyr Gly Ala Ala Gly Leu Gly Gly Val Leu Gly Gly Ala Gly
            740                 745                 750

Gln Phe Pro Leu Gly Gly Val Ala Ala Arg Pro Gly Phe Gly Leu Ser
        755                 760                 765

Pro Ile Phe Pro Gly Gly Ala Cys Leu Gly Lys Ala Cys Gly Arg Lys
    770                 775                 780

Arg Lys
785


<210> SEQ ID NO 22
<211> LENGTH: 2361
<212> TYPE: DNA
<213> ORGANISM: Homo sapiens

<400> SEQUENCE: 22

atggcgggtc tgacggcggc ggccccgcgg cccggagtcc tcctgctcct gctgtccatc      60

ctccacccct ctcggcctgg aggggtccct ggggccattc ctggtggagt tcctggagga     120

gtcttttatc caggggctgg tctcggagcc cttggaggag gagcgctggg gcctggaggc     180

aaacctctta agccagttcc cggagggctt gcgggtgctg gccttggggc agggctcggc     240

gccttccccg cagttacctt tccgggggct ctggtgcctg gtggagtggc tgacgctgct     300

gcagcctata aagctgctaa ggctggcgct gggcttggtg gtgtcccagg agttggtggc     360

ttaggagtgt ctgcaggtgc ggtggttcct cagcctggag ccggagtgaa gcctgggaaa     420

gtgccgggtg tggggctgcc aggtgtatac ccaggtggcg tgctcccagg agctcggttc     480

cccggtgtgg gggtgctccc tggagttccc actggagcag gagttaagcc caaggctcca     540

ggtgtaggtg gagcttttgc tggaatccca ggagttggac cctttggggg accgcaacct     600

ggagtcccac tggggtatcc catcaaggcc cccaagctgc ctggtggcta tggactgccc     660

tacaccacag ggaaactgcc ctatggctat gggcccggag gagtggctgg tgcagcgggc     720
```

aaggctggtt acccaacagg gacaggggtt ggcccccagg cagcagcagc agcggcagct 780
aaagcagcag caaagttcgg tgctggagca gccggagtcc tccctggtgt tggaggggct 840
ggtgttcctg gcgtgcctgg ggcaattcct ggaattggag gcatcgcagg cgttgggact 900
ccagctgcag ctgcagctgc agcagcagcc gctaaggcag ccaagtatgg agctgctgca 960
ggcttagtgc ctggtgggcc aggctttggc ccgggagtag ttggtgtccc aggagctggc 1020
gttccaggtg ttggtgtccc aggagctggg attccagttg tcccaggtgc tgggatccca 1080
ggtgctgcgg ttccaggggt tgtgtcacca gaagcagctg ctaaggcagc tgcaaaggca 1140
gccaaatacg gggccaggcc cggagtcgga gttggaggca ttcctactta cggggttgga 1200
gctgggggct ttcccggctt tggtgtcgga gtcggaggta tccctggagt cgcaggtgtc 1260
cctggtgtcg gaggtgttcc cggagtcgga ggtgtcccgg gagttggcat ttcccccgaa 1320
gctcaggcag cagctgccgc caaggctgcc aagtacggtg ctgcaggagc aggagtgctg 1380
ggtgggctag tgccaggtcc ccaggcggca gtcccaggtg tgccgggcac gggaggagtg 1440
ccaggagtgg ggaccccagc agctgcagct gctaaagcag ccgccaaagc cgcccagttt 1500
gggttagttc ctggtgtcgg cgtggctcct ggagttggcg tggctcctgg tgtcggtgtg 1560
gctcctggag ttggcttggc tcctggagtt ggcgtggctc ctggagttgg tgtggctcct 1620
ggcgttggcg tggctcccgg cattggccct ggtggagttg cagctgcagc aaaatccgct 1680
gccaaggtgg ctgccaaagc ccagctccga gctgcagctg ggcttggtgc tggcatccct 1740
ggacttggag ttggtgtcgg cgtccctgga cttggagttg gtgctggtgt tcctggactt 1800
ggagttggtg ctggtgttcc tggcttcggg gcaggtgcag atgagggagt taggcggagc 1860
ctgtcccctg agctcaggga aggagatccc tcctcctctc agcacctccc cagcaccccc 1920
tcatcaccca gggtacctgg agccctggct gccgctaaag cagccaaata tggagcagca 1980
gtgcctgggg tccttggagg gctcggggct ctcggtggag taggcatccc aggcggtgtg 2040
gtgggagccg gacccgccgc cgccgctgcc gcagccaaag ctgctgccaa agccgcccag 2100
tttggcctag tgggagccgc tgggctcgga ggactcggag tcggagggct tggagttcca 2160
ggtgttgggg gccttggagg tatacctcca gctgcagccg ctaaagcagc taaatacggt 2220
gctgctggcc ttggaggtgt cctagggggt gccgggcagt tcccacttgg aggagtggca 2280
gcaagacctg gcttcggatt gtctcccatt ttcccaggtg ggcctgcct ggggaaagct 2340 tgtggccgga agagaaaatg a 2361

<210> SEQ ID NO 23
<211> LENGTH: 2418
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 23
atgaaaaaga tttggctggc gctggctggt ttagttttag cgtttagcgc atcggcggcg 60
cagtatgaag atcaccatca ccaccaccac catcaccact ctggctcgag cctggtgccg 120
cgcggcagcc atatgggtgg cgtaccaggc gcaattcctg gggggtgtccc aggcggtgtt 180 ttttatccgg gcgccggtct tggcgcactg ggtggcggtg cactgggccc gggcggcaaa 240
ccgctgaaac cggtaccagg tggtttagca ggcgccggct taggcgcagg tctgggagca 300
tttccggcag ttacctttcc aggggcactg gttcctggag gtgtggccga tgcagccgcg 360

```
gcatataaag ccgctaaagc cggtgcgggt ttaggaggcg tcccaggtgt cggtggcctg    420

ggtgttagcg ccggtgcagt tgttccgcag ccgggagcag gggttaaacc tggtaaagtg    480

ccgggagtag gtctgccagg cgtttatcct ggtggtgttt tgccgggtgc ccgttttccg    540

ggcgttggtg ttcttccagg cgtgccgacc ggagccggtg ttaaaccgaa agcccccggt    600

gttggaggtg catttgcagg catcccggga gttggcccgt ttggtggtcc gcaacctggg    660

gttccgttag gttatccgat taaagcaccg aaactgcccg gcggttatgg tctgccgtac    720

acaaccggta aactgccgta tggttatggc ccgggtggag ttgcgggtgc agcaggtaaa    780

gcgggttatc ctaccggaac cggtgtaggt ccgcaggccg ctgctgccgc cgccgcaaaa    840

gcagcggcta aatttggcgc cggagcagcg ggtgttctgc ctggagttgg tggtgcgggc    900

gtgccagggg tacctggtgc aattccgggt attggtggta ttgccggtgt cggcaccccg    960

gccgcggcag ctgcggcagc ggcggctgcc aaagctgcta aatacggtgc cgcggcgggt   1020

ctggtgccag gaggtccggg ttttggtccg ggagtggttg gcgtgcctgg cgcaggcgtt   1080

cctggtgtgg gcgttccagg tgcagggatt cctgttgtgc ctggtgccgg tattcccggc   1140

gcggccgttc cgggggtggt tagcccggaa gccgcagcga aggctgcggc aaaggcagca   1200

aagtatggcg cacgcccagg agtcggcgtg ggtggtatcc cgacctatgg ggtgggcgca   1260

gggggttttc ctggtttcgg cgtaggtgta ggaggtatac cgggcgtggc cggtgtacca   1320

ggggttggtg gcgtccctgg tgttggcggt gtgccaggtg ttggtatttc accggaagca   1380

caggcagcag ccgcagctaa ggcagcgaaa tatggtgccg ccggcgcagg agttttaggt   1440

gggctggttc cgggcccgca ggcagctgtg ccgggggttc caggcaccgg tggtgtccct   1500

ggagtcggta cgccggctgc agcggcagcc aaagcggctg cgaaagcagc acagtttggc   1560

ttagtaccgg gtgtgggagt tgcccccggc gttggcgttg ctccaggggt gggtgttgct   1620

cctggcgtcg gtctggctcc tggagtgggc gtagcacccg gtgtgggggt ggccccgggt   1680

gttggggttg caccgggtat cggtccgggc ggtgtcgcag cagcagctaa aagcgcggcg   1740

aaagttgcgg ccaaagccca actgcgcgcc gccgcgggcc tcggtgcagg tattccgggg   1800

ctgggtgtcg gagttggagt cccgggtttg ggcgtgggcg cgggagttcc gggactggga   1860

gtgggtgccg gagttcctgg ctttggtgca ggcgcagatg aaggtgttcg tcgtagcctg   1920

agtccggaac tgcgtgaagg tgatccgagt agcagccagc atctgccgag caccccgagc   1980

agcccgcgtg ttccgggtgc attagctgca gcaaaagccg ccaagtatgg tgcagccgtg   2040

ccgggcgtct taggtggtct gggcgccctg ggtggtgtag gcattccggg aggtgttgtg   2100

ggtgcaggac cggccgccgc agctgcggcc gccaaagcag ctgcaaaagc ggcccagttt   2160

ggtttagtgg gcgccgcagg tttaggcggt ttaggtgtgg gtggactggg tgtacctggc   2220

gtaggcggtc tgggtggaat tccgcccgca gcggccgcga aagcggcaaa atatggcgcg   2280

gcaggcctgg gcggcgtgct gggtggggca ggtcagtttc cgctgggcgg ggttgccgca   2340

cgtccgggat ttggtctgag cccgattttc cctggcggcg catgtctggg taaagcatgt   2400

ggtcgtaaac gtaaataa                                                 2418
```

```
<210> SEQ ID NO 24
<211> LENGTH: 805
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 24

```
Met Lys Lys Ile Trp Leu Ala Leu Ala Gly Leu Val Leu Ala Phe Ser
1               5                   10                  15

Ala Ser Ala Ala Gln Tyr Glu Asp His His His His His His His His
            20                  25                  30

His Ser Gly Ser Ser Leu Val Pro Arg Gly Ser His Met Gly Gly Val
        35                  40                  45

Pro Gly Ala Ile Pro Gly Gly Val Pro Gly Gly Val Phe Tyr Pro Gly
    50                  55                  60

Ala Gly Leu Gly Ala Leu Gly Gly Gly Ala Leu Gly Pro Gly Gly Lys
65                  70                  75                  80

Pro Leu Lys Pro Val Pro Gly Gly Leu Ala Gly Ala Gly Leu Gly Ala
                85                  90                  95

Gly Leu Gly Ala Phe Pro Ala Val Thr Phe Pro Gly Ala Leu Val Pro
            100                 105                 110

Gly Gly Val Ala Asp Ala Ala Ala Ala Tyr Lys Ala Ala Lys Ala Gly
        115                 120                 125

Ala Gly Leu Gly Gly Val Pro Gly Val Gly Gly Leu Gly Val Ser Ala
    130                 135                 140

Gly Ala Val Val Pro Gln Pro Gly Ala Gly Val Lys Pro Gly Lys Val
145                 150                 155                 160

Pro Gly Val Gly Leu Pro Gly Val Tyr Pro Gly Gly Val Leu Pro Gly
                165                 170                 175

Ala Arg Phe Pro Gly Val Gly Val Leu Pro Gly Val Pro Thr Gly Ala
            180                 185                 190

Gly Val Lys Pro Lys Ala Pro Gly Val Gly Gly Ala Phe Ala Gly Ile
        195                 200                 205

Pro Gly Val Gly Pro Phe Gly Gly Pro Gln Pro Gly Val Pro Leu Gly
    210                 215                 220

Tyr Pro Ile Lys Ala Pro Lys Leu Pro Gly Gly Tyr Gly Leu Pro Tyr
225                 230                 235                 240

Thr Thr Gly Lys Leu Pro Tyr Gly Tyr Gly Pro Gly Gly Val Ala Gly
                245                 250                 255

Ala Ala Gly Lys Ala Gly Tyr Pro Thr Gly Thr Gly Val Gly Pro Gln
            260                 265                 270

Ala Ala Ala Ala Ala Ala Ala Lys Ala Ala Ala Lys Phe Gly Ala Gly
        275                 280                 285

Ala Ala Gly Val Leu Pro Gly Val Gly Gly Ala Gly Val Pro Gly Val
    290                 295                 300

Pro Gly Ala Ile Pro Gly Ile Gly Gly Ile Ala Gly Val Gly Thr Pro
305                 310                 315                 320

Ala Ala Ala Ala Ala Ala Ala Ala Ala Ala Lys Ala Ala Lys Tyr Gly
                325                 330                 335

Ala Ala Ala Gly Leu Val Pro Gly Gly Pro Gly Phe Gly Pro Gly Val
            340                 345                 350

Val Gly Val Pro Gly Ala Gly Val Pro Gly Val Gly Val Pro Gly Ala
        355                 360                 365

Gly Ile Pro Val Val Pro Gly Ala Gly Ile Pro Gly Ala Ala Val Pro
    370                 375                 380

Gly Val Val Ser Pro Glu Ala Ala Ala Lys Ala Ala Ala Lys Ala Ala
385                 390                 395                 400

Lys Tyr Gly Ala Arg Pro Gly Val Gly Val Gly Gly Ile Pro Thr Tyr
                405                 410                 415
```

-continued

```
Gly Val Gly Ala Gly Gly Phe Pro Gly Phe Gly Val Gly Val Gly Gly
            420                 425                 430

Ile Pro Gly Val Ala Gly Val Pro Gly Val Gly Gly Val Pro Gly Val
        435                 440                 445

Gly Gly Val Pro Gly Val Gly Ile Ser Pro Glu Ala Gln Ala Ala Ala
    450                 455                 460

Ala Ala Lys Ala Ala Lys Tyr Gly Ala Ala Gly Ala Gly Val Leu Gly
465                 470                 475                 480

Gly Leu Val Pro Gly Pro Gln Ala Ala Val Pro Gly Val Pro Gly Thr
                485                 490                 495

Gly Gly Val Pro Gly Val Gly Thr Pro Ala Ala Ala Ala Ala Lys Ala
            500                 505                 510

Ala Ala Lys Ala Ala Gln Phe Gly Leu Val Pro Gly Val Gly Val Ala
        515                 520                 525

Pro Gly Val Gly Val Ala Pro Gly Val Gly Val Ala Pro Gly Val Gly
    530                 535                 540

Leu Ala Pro Gly Val Gly Val Ala Pro Gly Val Gly Val Ala Pro Gly
545                 550                 555                 560

Val Gly Val Ala Pro Gly Ile Gly Pro Gly Gly Val Ala Ala Ala Ala
                565                 570                 575

Lys Ser Ala Ala Lys Val Ala Ala Lys Ala Gln Leu Arg Ala Ala Ala
            580                 585                 590

Gly Leu Gly Ala Gly Ile Pro Gly Leu Gly Val Gly Val Gly Val Pro
        595                 600                 605

Gly Leu Gly Val Gly Ala Gly Val Pro Gly Leu Gly Val Gly Ala Gly
    610                 615                 620

Val Pro Gly Phe Gly Ala Gly Ala Asp Glu Gly Val Arg Arg Ser Leu
625                 630                 635                 640

Ser Pro Glu Leu Arg Glu Gly Asp Pro Ser Ser Ser Gln His Leu Pro
                645                 650                 655

Ser Thr Pro Ser Ser Pro Arg Val Pro Gly Ala Leu Ala Ala Ala Lys
            660                 665                 670

Ala Ala Lys Tyr Gly Ala Ala Val Pro Gly Val Leu Gly Gly Leu Gly
        675                 680                 685

Ala Leu Gly Gly Val Gly Ile Pro Gly Gly Val Val Gly Ala Gly Pro
    690                 695                 700

Ala Ala Ala Ala Ala Ala Ala Lys Ala Ala Ala Lys Ala Ala Gln Phe
705                 710                 715                 720

Gly Leu Val Gly Ala Ala Gly Leu Gly Gly Leu Gly Val Gly Gly Leu
                725                 730                 735

Gly Val Pro Gly Val Gly Gly Leu Gly Gly Ile Pro Pro Ala Ala Ala
            740                 745                 750

Ala Lys Ala Ala Lys Tyr Gly Ala Ala Gly Leu Gly Gly Val Leu Gly
        755                 760                 765

Gly Ala Gly Gln Phe Pro Leu Gly Gly Val Ala Ala Arg Pro Gly Phe
    770                 775                 780

Gly Leu Ser Pro Ile Phe Pro Gly Gly Ala Cys Leu Gly Lys Ala Cys
785                 790                 795                 800

Gly Arg Lys Arg Lys
                805
```

<210> SEQ ID NO 25
<211> LENGTH: 2358

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
atgaaaaaga tttggctggc gctggctggt ttagttttag cgtttagcgc atcggcggcg     60

cagtatgaag atatgggtgg cgtaccaggc gcaattcctg ggggtgtccc aggcggtgtt    120

ttttatccgg gcgccggtct tggcgcactg ggtggcggtg cactgggccc gggcggcaaa    180

ccgctgaaac cggtaccagg tggtttagca ggcgccggct taggcgcagg tctgggagca    240

tttccggcag ttacctttcc aggggcactg gttcctggag gtgtggccga tgcagccgcg    300

gcatataaag ccgctaaagc cggtgcgggt ttaggaggcg tcccaggtgt cggtggcctg    360

ggtgttagcg ccggtgcagt tgttccgcag ccgggagcag gggttaaacc tggtaaagtg    420

ccgggagtag gtctgccagg cgtttatcct ggtggtgttt tgccgggtgc ccgttttccg    480

ggcgttggtg ttcttccagg cgtgccgacc ggagccggtg ttaaaccgaa agcccccggt    540

gttggaggtg catttgcagg catcccggga gttggcccgt ttggtggtcc gcaacctggg    600

gttccgttag gttatccgat taaagcaccg aaactgcccg gcggttatgg tctgccgtac    660

acaaccggta aactgccgta tggttatggc ccgggtggag ttgcgggtgc agcaggtaaa    720

gcgggttatc ctaccggaac cggtgtaggt ccgcaggccg ctgctgccgc cgccgcaaaa    780

gcagcggcta aatttggcgc cggagcagcg ggtgttctgc ctggagttgg tggtgcgggc    840

gtgccagggg tacctggtgc aattccgggt attggtggta ttgccggtgt cggcaccccg    900

gccgcggcag ctgcggcagc ggcggctgcc aaagctgcta aatacggtgc cgcggcgggt    960

ctggtgccag gaggtccggg ttttggtccg ggagtggttg gcgtgcctgg cgcaggcgtt   1020

cctggtgtgg gcgttccagg tgcagggatt cctgttgtgc ctggtgccgg tattcccggc   1080

gcggccgttc cgggggtggt tagcccggaa gccgcagcga aggctgcggc aaaggcagca   1140

aagtatggcg cacgcccagg agtcggcgtg ggtggtatcc cgacctatgg ggtgggcgca   1200

gggggttttc ctggtttcgg cgtaggtgta ggaggtatac cgggcgtggc cggtgtacca   1260

ggggttggtg gcgtccctgg tgttggcggt gtgccaggtg ttggtatttc accggaagca   1320

caggcagcag ccgcagctaa ggcagcgaaa tatggtgccg ccggcgcagg agttttaggt   1380

gggctggttc cgggcccgca ggcagctgtg ccgggggttc caggcaccgg tggtgtccct   1440

ggagtcggta cgccggctgc agcggcagcc aaagcggctg cgaaagcagc acagtttggc   1500

ttagtaccgg gtgtgggagt tgccccccggc gttggcgttg ctccaggggt gggtgttgct   1560

cctggcgtcg gtctggctcc tggagtgggc gtagcacccg gtgtgggggt ggccccgggt   1620

gttggggttg caccgggtat cggtccgggc ggtgtcgcag cagcagctaa aagcgcggcg   1680

aaagttgcgg ccaaagccca actgcgcgcc gccgcgggcc tcggtgcagg tattccgggg   1740

ctgggtgtcg gagttggagt cccgggtttg ggcgtgggcg cgggagttcc gggactggga   1800

gtgggtgccg gagttcctgg ctttggtgca ggcgcagatg aaggtgttcg tcgtagcctg   1860

agtccggaac tgcgtgaagg tgatccgagt agcagccagc atctgccgag caccccgagc   1920

agcccgcgtg ttccgggtgc attagctgca gcaaaagccg ccaagtatgg tgcagccgtg   1980

ccgggcgtct taggtggtct gggcgccctg ggtggtgtag gcattccggg aggtgttgtg   2040

ggtgcaggac cggccgccgc agctgcggcc gccaaagcag ctgcaaaagc ggcccagttt   2100

ggtttagtgg gcgccgcagg tttaggcggt ttaggtgtgg gtggactggg tgtacctggc   2160
```

gtaggcggtc tgggtggaat tccgcccgca gcggccgcga aagcggcaaa atatggcgcg 2220
gcaggcctgg gcggcgtgct gggtggggca ggtcagtttc cgctgggcgg ggttgccgca 2280
cgtccgggat ttggtctgag cccgattttc cctggcggcg catgtctggg taaagcatgt 2340
ggtcgtaaac gtaaataa 2358

<210> SEQ ID NO 26
<211> LENGTH: 785
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

Met Lys Lys Ile Trp Leu Ala Leu Ala Gly Leu Val Leu Ala Phe Ser
1 5 10 15

Ala Ser Ala Ala Gln Tyr Glu Asp Met Gly Gly Val Pro Gly Ala Ile
20 25 30

Pro Gly Gly Val Pro Gly Gly Val Phe Tyr Pro Gly Ala Gly Leu Gly
35 40 45

Ala Leu Gly Gly Gly Ala Leu Gly Pro Gly Gly Lys Pro Leu Lys Pro
50 55 60

Val Pro Gly Gly Leu Ala Gly Ala Gly Leu Gly Ala Gly Leu Gly Ala
65 70 75 80

Phe Pro Ala Val Thr Phe Pro Gly Ala Leu Val Pro Gly Gly Val Ala
85 90 95

Asp Ala Ala Ala Ala Tyr Lys Ala Ala Lys Ala Gly Ala Gly Leu Gly
100 105 110

Gly Val Pro Gly Val Gly Gly Leu Gly Val Ser Ala Gly Ala Val Val
115 120 125

Pro Gln Pro Gly Ala Gly Val Lys Pro Gly Lys Val Pro Gly Val Gly
130 135 140

Leu Pro Gly Val Tyr Pro Gly Gly Val Leu Pro Gly Ala Arg Phe Pro
145 150 155 160

Gly Val Gly Val Leu Pro Gly Val Pro Thr Gly Ala Gly Val Lys Pro
165 170 175

Lys Ala Pro Gly Val Gly Gly Ala Phe Ala Gly Ile Pro Gly Val Gly
180 185 190

Pro Phe Gly Gly Pro Gln Pro Gly Val Pro Leu Gly Tyr Pro Ile Lys
195 200 205

Ala Pro Lys Leu Pro Gly Gly Tyr Gly Leu Pro Tyr Thr Thr Gly Lys
210 215 220

Leu Pro Tyr Gly Tyr Gly Pro Gly Gly Val Ala Gly Ala Ala Gly Lys
225 230 235 240

Ala Gly Tyr Pro Thr Gly Thr Gly Val Gly Pro Gln Ala Ala Ala Ala
245 250 255

Ala Ala Ala Lys Ala Ala Ala Lys Phe Gly Ala Gly Ala Ala Gly Val
260 265 270

Leu Pro Gly Val Gly Gly Ala Gly Val Pro Gly Val Pro Gly Ala Ile
275 280 285

Pro Gly Ile Gly Gly Ile Ala Gly Val Gly Thr Pro Ala Ala Ala Ala
290 295 300

Ala Ala Ala Ala Ala Ala Lys Ala Ala Lys Tyr Gly Ala Ala Ala Gly
305 310 315 320

```
Leu Val Pro Gly Gly Pro Gly Phe Gly Pro Gly Val Val Gly Val Pro
                325                 330                 335

Gly Ala Gly Val Pro Gly Val Gly Val Pro Gly Ala Gly Ile Pro Val
            340                 345                 350

Val Pro Gly Ala Gly Ile Pro Gly Ala Ala Val Pro Gly Val Val Ser
        355                 360                 365

Pro Glu Ala Ala Ala Lys Ala Ala Ala Lys Ala Ala Lys Tyr Gly Ala
    370                 375                 380

Arg Pro Gly Val Gly Val Gly Gly Ile Pro Thr Tyr Gly Val Gly Ala
385                 390                 395                 400

Gly Gly Phe Pro Gly Phe Gly Val Gly Val Gly Gly Ile Pro Gly Val
                405                 410                 415

Ala Gly Val Pro Gly Val Gly Gly Val Pro Gly Val Gly Gly Val Pro
            420                 425                 430

Gly Val Gly Ile Ser Pro Glu Ala Gln Ala Ala Ala Ala Ala Lys Ala
        435                 440                 445

Ala Lys Tyr Gly Ala Ala Gly Ala Gly Val Leu Gly Gly Leu Val Pro
    450                 455                 460

Gly Pro Gln Ala Ala Val Pro Gly Val Pro Gly Thr Gly Gly Val Pro
465                 470                 475                 480

Gly Val Gly Thr Pro Ala Ala Ala Ala Ala Lys Ala Ala Ala Lys Ala
                485                 490                 495

Ala Gln Phe Gly Leu Val Pro Gly Val Gly Val Ala Pro Gly Val Gly
            500                 505                 510

Val Ala Pro Gly Val Gly Val Ala Pro Gly Val Gly Leu Ala Pro Gly
        515                 520                 525

Val Gly Val Ala Pro Gly Val Gly Val Ala Pro Gly Val Gly Val Ala
    530                 535                 540

Pro Gly Ile Gly Pro Gly Gly Val Ala Ala Ala Ala Lys Ser Ala Ala
545                 550                 555                 560

Lys Val Ala Ala Lys Ala Gln Leu Arg Ala Ala Ala Gly Leu Gly Ala
                565                 570                 575

Gly Ile Pro Gly Leu Gly Val Gly Val Gly Val Pro Gly Leu Gly Val
            580                 585                 590

Gly Ala Gly Val Pro Gly Leu Gly Val Gly Ala Gly Val Pro Gly Phe
        595                 600                 605

Gly Ala Gly Ala Asp Glu Gly Val Arg Arg Ser Leu Ser Pro Glu Leu
    610                 615                 620

Arg Glu Gly Asp Pro Ser Ser Ser Gln His Leu Pro Ser Thr Pro Ser
625                 630                 635                 640

Ser Pro Arg Val Pro Gly Ala Leu Ala Ala Ala Lys Ala Ala Lys Tyr
                645                 650                 655

Gly Ala Ala Val Pro Gly Val Leu Gly Gly Leu Gly Ala Leu Gly Gly
            660                 665                 670

Val Gly Ile Pro Gly Gly Val Val Gly Ala Gly Pro Ala Ala Ala Ala
        675                 680                 685

Ala Ala Ala Lys Ala Ala Ala Lys Ala Ala Gln Phe Gly Leu Val Gly
    690                 695                 700

Ala Ala Gly Leu Gly Gly Leu Gly Val Gly Gly Leu Gly Val Pro Gly
705                 710                 715                 720

Val Gly Gly Leu Gly Gly Ile Pro Pro Ala Ala Ala Ala Lys Ala Ala
                725                 730                 735
```

```
Lys Tyr Gly Ala Ala Gly Leu Gly Gly Val Leu Gly Gly Ala Gly Gln
            740                 745                 750

Phe Pro Leu Gly Gly Val Ala Ala Arg Pro Gly Phe Gly Leu Ser Pro
        755                 760                 765

Ile Phe Pro Gly Gly Ala Cys Leu Gly Lys Ala Cys Gly Arg Lys Arg
    770                 775                 780

Lys
785


<210> SEQ ID NO 27
<211> LENGTH: 3945
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

atgaaaaaga tttggctggc gctggctggt ttagttttag cgtttagcgc atcggcggcg     60

cagtatgaag atcaccatca ccaccaccac catcaccact ctggctcgag cctggtgccg    120

cgcggcagcc atatgtctgg ctcgagcagt aaaggtgaag aactgttcac cggtgttgtt    180

ccgatcctgg ttgaactgga tggtgatgtt aacggccaca aattctctgt tcgtggtgaa    240

ggtgaaggtg atgcaaccaa cggtaaactg accctgaaat tcatctgcac taccggtaaa    300

ctgccggttc catggccgac tctggtgact accctgacct atggtgttca gtgtttttct    360

cgttacccgg atcacatgaa gcagcatgat ttcttcaaat ctgcaatgcc ggaaggttat    420

gtacaggagc gcaccatttc tttcaaagac gatggcacct acaaaacccg tgcagaggtt    480

aaatttgaag gtgatactct ggtgaaccgt attgaactga aaggcattga tttcaaagag    540

gacggcaaca tcctgggcca caaactggaa tataacttca actcccataa cgtttacatc    600

accgcagaca aacagaagaa cggtatcaaa gctaacttca aaattcgcca taacgttgaa    660

gacggtagcg tacagctggc ggaccactac cagcagaaca ctccgatcgg tgatggtccg    720

gttctgctgc cggataacca ctacctgtcc acccagtcta aactgtccaa agacccgaac    780

gaaaagcgcg accacatggt gctgctggag ttcgttactg cagcaggtat cacgcacggc    840

atggatgaac tctacaaatc tggcgcgccg ggcggtggcg taccaggcgc aattcctggg    900

ggtgtcccag gcggtgtttt ttatccgggc gccggtcttg gcgcactggg tggcggtgca    960

ctgggcccgg gcggcaaacc gctgaaaccg gtaccaggtg gtttagcagg cgccggctta   1020

ggcgcaggtc tgggagcatt tccggcagtt acctttccag ggcactggt tcctggaggt   1080

gtggccgatg cagccgcggc atataaagcc gctaaagccg gtgcgggttt aggaggcgtc   1140

ccaggtgtcg gtggcctggg tgttagcgcc ggtgcagttg ttccgcagcc gggagcaggg   1200

gttaaacctg gtaaagtgcc gggagtaggt ctgccaggcg tttatcctgg tggtgttttg   1260

ccgggtgccc gttttccggg cgttggtgtt cttccaggcg tgccgaccgg agccggtgtt   1320

aaaccgaaag cccccggtgt tggaggtgca tttgcaggca tcccgggagt tggcccgttt   1380

ggtggtccgc aacctggggt tccgttaggt tatccgatta aagcaccgaa actgcccggc   1440

ggttatggtc tgccgtacac aaccggtaaa ctgccgtatg gttatggccc gggtggagtt   1500

gcgggtgcag caggtaaagc gggttatcct accggaaccg gtgtaggtcc gcaggccgct   1560

gctgccgccg ccgcaaaagc agcggctaaa tttggcgccg gagcagcggg tgttctgcct   1620

ggagttggtg gtgcgggcgt gccaggggta cctggtgcaa ttccgggtat tggtggtatt   1680
```

-continued

```
gccggtgtcg gcaccccggc cgcggcagct gcggcagcgg cggctgccaa agctgctaaa   1740
tacggtgccg cggcgggtct ggtgccagga ggtccgggtt ttggtccggg agtggttggc   1800
gtgcctggcg caggcgttcc tggtgtgggc gttccaggtg cagggattcc tgttgtgcct   1860
ggtgccggta ttcccggcgc ggccgttccg gggtggtta gcccggaagc cgcagcgaag   1920
gctgcggcaa aggcagcaaa gtatggcgca cgcccaggag tcggcgtggg tggtatcccg   1980
acctatgggg tgggcgcagg gggttttcct ggtttcggcg taggtgtagg aggtataccg   2040
ggcgtggccg gtgtaccagg ggttggtggc gtccctggtg ttggcggtgt gccaggtgtt   2100
ggtatttcac cggaagcaca ggcagcagcc gcagctaagg cagcgaaata tggtgccgcc   2160
ggcgcaggag ttttaggtgg gctggttccg ggcccgcagg cagctgtgcc gggggttcca   2220
ggcaccggtg gtgtccctgg agtcggtacg ccggctgcag cggcagccaa agcggctgcg   2280
aaagcagcac agtttggctt agtaccgggt gtgggagttg cccccggcgt tggcgttgct   2340
ccaggggtgg gtgttgctcc tggcgtcggt ctggctcctg gagtgggcgt agcacccggt   2400
gtgggggtgg ccccgggtgt tggggttgca ccgggtatcg gtccgggcgg tgtcgcagca   2460
gcagctaaaa gcgcggcgaa agttgcggcc aaagcccaac tgcgcgccgc cgcgggcctc   2520
ggtgcaggta ttccggggct gggtgtcgga gttggagtcc cgggtttggg cgtgggcgcg   2580
ggagttccgg gactgggagt gggtgccgga gttcctggct ttggtgcagg cgcagatgaa   2640
ggtgttcgtc gtagcctgag tccggaactg cgtgaaggtg atccgagtag cagccagcat   2700
ctgccgagca ccccgagcag cccgcgtgtt ccgggtgcat tagctgcagc aaaagccgcc   2760
aagtatggtg cagccgtgcc gggcgtctta ggtggtctgg gcgccctggg tggtgtaggc   2820
attccgggag gtgttgtggg tgcaggaccg gccgccgcag ctgcggccgc caaagcagct   2880
gcaaaagcgg cccagtttgg tttagtgggc gccgcaggtt taggcggttt aggtgtgggt   2940
ggactgggtg tacctggcgt aggcggtctg ggtggaattc cgcccgcagc ggccgcgaaa   3000
gcggcaaaat atggcgcggc aggcctgggc ggcgtgctgg gtggggcagg tcagtttccg   3060
ctgggcgggg ttgccgcacg tccgggattt ggtctgagcc cgattttccc tggcggcgca   3120
tgtctgggta aagcatgtgg tcgtaaacgt aaacacccag aaacgctggt gaaagtaaaa   3180
gatgctgaag atcagttggg tgcacgagtg ggttacatcg aactggatct caacagcggt   3240
aagatccttg agagttttcg ccccgaagaa cgttttccaa tgatgagcac ttttaaagtt   3300
ctgctatgtg gcgcggtatt atcccgtatt gacgccgggc aagagcaact cggtcgccgc   3360
atacactatt ctcagaatga cttggttgag tactcaccag tcacagaaaa gcatcttacg   3420
gatggcatga cagtaagaga attatgcagt gctgccataa ccatgagtga taacactgcg   3480
gccaacttac ttctgacaac gatcggagga ccgaaggagc taaccgcttt tttgcacaac   3540
atgggggatc atgtaactcg ccttgatcgt tgggaaccgg agctgaatga agccatacca   3600
aacgacgagc gtgacaccac gatgcctgta gcaatggcaa caacgttgcg caaactatta   3660
actggcgaac tacttactct agcttcccgg caacaattaa tagactggat ggaggcggat   3720
aaagttgcag gaccacttct gcgctcggcc cttccggctg gctggtttat tgctgataaa   3780
tctggagccg gtgagcgtgg gtctcgcggt atcattgcag cactggggcc agatggtaag   3840
ccctcccgta tcgtagttat ctacacgacg gggagtcagg caactatgga tgaacgaaat   3900
agacagatcg ctgagatagg tgcctcactg attaagcatt ggtaa                   3945
```

<210> SEQ ID NO 28
<211> LENGTH: 1314

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 28

```
Met Lys Lys Ile Trp Leu Ala Leu Ala Gly Leu Val Leu Ala Phe Ser
1               5                   10                  15

Ala Ser Ala Ala Gln Tyr Glu Asp His His His His His His His His
            20                  25                  30

His Ser Gly Ser Ser Leu Val Pro Arg Gly Ser His Met Ser Gly Ser
        35                  40                  45

Ser Ser Lys Gly Glu Glu Leu Phe Thr Gly Val Val Pro Ile Leu Val
    50                  55                  60

Glu Leu Asp Gly Asp Val Asn Gly His Lys Phe Ser Val Arg Gly Glu
65                  70                  75                  80

Gly Glu Gly Asp Ala Thr Asn Gly Lys Leu Thr Leu Lys Phe Ile Cys
                85                  90                  95

Thr Thr Gly Lys Leu Pro Val Pro Trp Pro Thr Leu Val Thr Thr Leu
            100                 105                 110

Thr Tyr Gly Val Gln Cys Phe Ser Arg Tyr Pro Asp His Met Lys Gln
        115                 120                 125

His Asp Phe Phe Lys Ser Ala Met Pro Glu Gly Tyr Val Gln Glu Arg
    130                 135                 140

Thr Ile Ser Phe Lys Asp Asp Gly Thr Tyr Lys Thr Arg Ala Glu Val
145                 150                 155                 160

Lys Phe Glu Gly Asp Thr Leu Val Asn Arg Ile Glu Leu Lys Gly Ile
                165                 170                 175

Asp Phe Lys Glu Asp Gly Asn Ile Leu Gly His Lys Leu Glu Tyr Asn
            180                 185                 190

Phe Asn Ser His Asn Val Tyr Ile Thr Ala Asp Lys Gln Lys Asn Gly
        195                 200                 205

Ile Lys Ala Asn Phe Lys Ile Arg His Asn Val Glu Asp Gly Ser Val
    210                 215                 220

Gln Leu Ala Asp His Tyr Gln Gln Asn Thr Pro Ile Gly Asp Gly Pro
225                 230                 235                 240

Val Leu Leu Pro Asp Asn His Tyr Leu Ser Thr Gln Ser Lys Leu Ser
                245                 250                 255

Lys Asp Pro Asn Glu Lys Arg Asp His Met Val Leu Leu Glu Phe Val
            260                 265                 270

Thr Ala Ala Gly Ile Thr His Gly Met Asp Glu Leu Tyr Lys Ser Gly
        275                 280                 285

Ala Pro Gly Gly Gly Val Pro Gly Ala Ile Pro Gly Gly Val Pro Gly
    290                 295                 300

Gly Val Phe Tyr Pro Gly Ala Gly Leu Gly Ala Leu Gly Gly Gly Ala
305                 310                 315                 320

Leu Gly Pro Gly Gly Lys Pro Leu Lys Pro Val Pro Gly Gly Leu Ala
                325                 330                 335

Gly Ala Gly Leu Gly Ala Gly Leu Gly Ala Phe Pro Ala Val Thr Phe
            340                 345                 350

Pro Gly Ala Leu Val Pro Gly Gly Val Ala Asp Ala Ala Ala Ala Tyr
        355                 360                 365

Lys Ala Ala Lys Ala Gly Ala Gly Leu Gly Gly Val Pro Gly Val Gly
    370                 375                 380
```

-continued

Gly Leu Gly Val Ser Ala Gly Ala Val Val Pro Gln Pro Gly Ala Gly
385 390 395 400

Val Lys Pro Gly Lys Val Pro Gly Val Gly Leu Pro Gly Val Tyr Pro
405 410 415

Gly Gly Val Leu Pro Gly Ala Arg Phe Pro Gly Val Gly Val Leu Pro
420 425 430

Gly Val Pro Thr Gly Ala Gly Val Lys Pro Lys Ala Pro Gly Val Gly
435 440 445

Gly Ala Phe Ala Gly Ile Pro Gly Val Gly Pro Phe Gly Gly Pro Gln
450 455 460

Pro Gly Val Pro Leu Gly Tyr Pro Ile Lys Ala Pro Lys Leu Pro Gly
465 470 475 480

Gly Tyr Gly Leu Pro Tyr Thr Thr Gly Lys Leu Pro Tyr Gly Tyr Gly
485 490 495

Pro Gly Gly Val Ala Gly Ala Ala Gly Lys Ala Gly Tyr Pro Thr Gly
500 505 510

Thr Gly Val Gly Pro Gln Ala Ala Ala Ala Ala Ala Ala Lys Ala Ala
515 520 525

Ala Lys Phe Gly Ala Gly Ala Ala Gly Val Leu Pro Gly Val Gly Gly
530 535 540

Ala Gly Val Pro Gly Val Pro Gly Ala Ile Pro Gly Ile Gly Gly Ile
545 550 555 560

Ala Gly Val Gly Thr Pro Ala Ala Ala Ala Ala Ala Ala Ala Ala Ala
565 570 575

Lys Ala Ala Lys Tyr Gly Ala Ala Ala Gly Leu Val Pro Gly Gly Pro
580 585 590

Gly Phe Gly Pro Gly Val Val Gly Val Pro Gly Ala Gly Val Pro Gly
595 600 605

Val Gly Val Pro Gly Ala Gly Ile Pro Val Val Pro Gly Ala Gly Ile
610 615 620

Pro Gly Ala Ala Val Pro Gly Val Val Ser Pro Glu Ala Ala Ala Lys
625 630 635 640

Ala Ala Ala Lys Ala Ala Lys Tyr Gly Ala Arg Pro Gly Val Gly Val
645 650 655

Gly Gly Ile Pro Thr Tyr Gly Val Gly Ala Gly Gly Phe Pro Gly Phe
660 665 670

Gly Val Gly Val Gly Gly Ile Pro Gly Val Ala Gly Val Pro Gly Val
675 680 685

Gly Gly Val Pro Gly Val Gly Gly Val Pro Gly Val Gly Ile Ser Pro
690 695 700

Glu Ala Gln Ala Ala Ala Ala Ala Lys Ala Ala Lys Tyr Gly Ala Ala
705 710 715 720

Gly Ala Gly Val Leu Gly Gly Leu Val Pro Gly Pro Gln Ala Ala Val
725 730 735

Pro Gly Val Pro Gly Thr Gly Gly Val Pro Gly Val Gly Thr Pro Ala
740 745 750

Ala Ala Ala Ala Lys Ala Ala Ala Lys Ala Ala Gln Phe Gly Leu Val
755 760 765

Pro Gly Val Gly Val Ala Pro Gly Val Gly Val Ala Pro Gly Val Gly
770 775 780

Val Ala Pro Gly Val Gly Leu Ala Pro Gly Val Gly Val Ala Pro Gly
785 790 795 800

-continued

```
Val Gly Val Ala Pro Gly Val Gly Val Ala Pro Gly Ile Gly Pro Gly
                805                 810                 815

Gly Val Ala Ala Ala Ala Lys Ser Ala Ala Lys Val Ala Ala Lys Ala
            820                 825                 830

Gln Leu Arg Ala Ala Ala Gly Leu Gly Ala Gly Ile Pro Gly Leu Gly
        835                 840                 845

Val Gly Val Gly Val Pro Gly Leu Gly Val Gly Ala Gly Val Pro Gly
    850                 855                 860

Leu Gly Val Gly Ala Gly Val Pro Gly Phe Gly Ala Gly Ala Asp Glu
865                 870                 875                 880

Gly Val Arg Arg Ser Leu Ser Pro Glu Leu Arg Glu Gly Asp Pro Ser
                885                 890                 895

Ser Ser Gln His Leu Pro Ser Thr Pro Ser Ser Pro Arg Val Pro Gly
            900                 905                 910

Ala Leu Ala Ala Ala Lys Ala Ala Lys Tyr Gly Ala Ala Val Pro Gly
        915                 920                 925

Val Leu Gly Gly Leu Gly Ala Leu Gly Gly Val Gly Ile Pro Gly Gly
    930                 935                 940

Val Val Gly Ala Gly Pro Ala Ala Ala Ala Ala Ala Ala Lys Ala Ala
945                 950                 955                 960

Ala Lys Ala Ala Gln Phe Gly Leu Val Gly Ala Ala Gly Leu Gly Gly
                965                 970                 975

Leu Gly Val Gly Gly Leu Gly Val Pro Gly Val Gly Gly Leu Gly Gly
            980                 985                 990

Ile Pro Pro Ala Ala Ala Ala Lys  Ala Ala Lys Tyr Gly  Ala Ala Gly
        995                 1000                 1005

Leu Gly  Gly Val Leu Gly Gly  Ala Gly Gln Phe Pro  Leu Gly Gly
    1010                 1015                 1020

Val Ala  Ala Arg Pro Gly Phe  Gly Leu Ser Pro Ile  Phe Pro Gly
    1025                 1030                 1035

Gly Ala  Cys Leu Gly Lys Ala  Cys Gly Arg Lys Arg  Lys His Pro
    1040                 1045                 1050

Glu Thr  Leu Val Lys Val Lys  Asp Ala Glu Asp Gln  Leu Gly Ala
    1055                 1060                 1065

Arg Val  Gly Tyr Ile Glu Leu  Asp Leu Asn Ser Gly  Lys Ile Leu
    1070                 1075                 1080

Glu Ser  Phe Arg Pro Glu Glu  Arg Phe Pro Met Met  Ser Thr Phe
    1085                 1090                 1095

Lys Val  Leu Leu Cys Gly Ala  Val Leu Ser Arg Ile  Asp Ala Gly
    1100                 1105                 1110

Gln Glu  Gln Leu Gly Arg Arg  Ile His Tyr Ser Gln  Asn Asp Leu
    1115                 1120                 1125

Val Glu  Tyr Ser Pro Val Thr  Glu Lys His Leu Thr  Asp Gly Met
    1130                 1135                 1140

Thr Val  Arg Glu Leu Cys Ser  Ala Ala Ile Thr Met  Ser Asp Asn
    1145                 1150                 1155

Thr Ala  Ala Asn Leu Leu Leu  Thr Thr Ile Gly Gly  Pro Lys Glu
    1160                 1165                 1170

Leu Thr  Ala Phe Leu His Asn  Met Gly Asp His Val  Thr Arg Leu
    1175                 1180                 1185

Asp Arg  Trp Glu Pro Glu Leu  Asn Glu Ala Ile Pro  Asn Asp Glu
    1190                 1195                 1200

Arg Asp  Thr Thr Met Pro Val  Ala Met Ala Thr Thr  Leu Arg Lys
```

```
    1205                1210                1215

Leu Leu  Thr Gly Glu Leu Leu  Thr Leu Ala Ser Arg  Gln Gln Leu
    1220                1225                1230

Ile Asp  Trp Met Glu Ala Asp  Lys Val Ala Gly Pro  Leu Leu Arg
    1235                1240                1245

Ser Ala  Leu Pro Ala Gly Trp  Phe Ile Ala Asp Lys  Ser Gly Ala
    1250                1255                1260

Gly Glu  Arg Gly Ser Arg Gly  Ile Ile Ala Ala Leu  Gly Pro Asp
    1265                1270                1275

Gly Lys  Pro Ser Arg Ile Val  Val Ile Tyr Thr Thr  Gly Ser Gln
    1280                1285                1290

Ala Thr  Met Asp Glu Arg Asn  Arg Gln Ile Ala Glu  Ile Gly Ala
    1295                1300                1305

Ser Leu  Ile Lys His Trp
    1310


<210> SEQ ID NO 29
<211> LENGTH: 760
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gly Gly Val Pro Gly Ala Ile Pro Gly Gly Val Pro Gly Gly Val Phe
1               5                   10                  15

Tyr Pro Gly Ala Gly Leu Gly Ala Leu Gly Gly Gly Ala Leu Gly Pro
            20                  25                  30

Gly Gly Lys Pro Leu Lys Pro Val Pro Gly Gly Leu Ala Gly Ala Gly
        35                  40                  45

Leu Gly Ala Gly Leu Gly Ala Phe Pro Ala Val Thr Phe Pro Gly Ala
    50                  55                  60

Leu Val Pro Gly Gly Val Ala Asp Ala Ala Ala Ala Tyr Lys Ala Ala
65                  70                  75                  80

Lys Ala Gly Ala Gly Leu Gly Gly Val Pro Gly Val Gly Gly Leu Gly
                85                  90                  95

Val Ser Ala Gly Ala Val Val Pro Gln Pro Gly Ala Gly Val Lys Pro
            100                 105                 110

Gly Lys Val Pro Gly Val Gly Leu Pro Gly Val Tyr Pro Gly Gly Val
        115                 120                 125

Leu Pro Gly Ala Arg Phe Pro Gly Val Gly Val Leu Pro Gly Val Pro
    130                 135                 140

Thr Gly Ala Gly Val Lys Pro Lys Ala Pro Gly Val Gly Gly Ala Phe
145                 150                 155                 160

Ala Gly Ile Pro Gly Val Gly Pro Phe Gly Gly Pro Gln Pro Gly Val
                165                 170                 175

Pro Leu Gly Tyr Pro Ile Lys Ala Pro Lys Leu Pro Gly Gly Tyr Gly
            180                 185                 190

Leu Pro Tyr Thr Thr Gly Lys Leu Pro Tyr Gly Tyr Gly Pro Gly Gly
        195                 200                 205

Val Ala Gly Ala Ala Gly Lys Ala Gly Tyr Pro Thr Gly Thr Gly Val
    210                 215                 220

Gly Pro Gln Ala Ala Ala Ala Ala Ala Ala Lys Ala Ala Ala Lys Phe
225                 230                 235                 240
```

```
Gly Ala Gly Ala Ala Gly Val Leu Pro Gly Val Gly Gly Ala Gly Val
                245                 250                 255

Pro Gly Val Pro Gly Ala Ile Pro Gly Ile Gly Gly Ile Ala Gly Val
            260                 265                 270

Gly Thr Pro Ala Ala Ala Ala Ala Ala Ala Ala Ala Ala Lys Ala Ala
        275                 280                 285

Lys Tyr Gly Ala Ala Ala Gly Leu Val Pro Gly Gly Pro Gly Phe Gly
    290                 295                 300

Pro Gly Val Val Gly Val Pro Gly Ala Gly Val Pro Gly Val Gly Val
305                 310                 315                 320

Pro Gly Ala Gly Ile Pro Val Val Pro Gly Ala Gly Ile Pro Gly Ala
                325                 330                 335

Ala Val Pro Gly Val Val Ser Pro Glu Ala Ala Ala Lys Ala Ala Ala
            340                 345                 350

Lys Ala Ala Lys Tyr Gly Ala Arg Pro Gly Val Gly Val Gly Gly Ile
        355                 360                 365

Pro Thr Tyr Gly Val Gly Ala Gly Gly Phe Pro Gly Phe Gly Val Gly
    370                 375                 380

Val Gly Gly Ile Pro Gly Val Ala Gly Val Pro Gly Val Gly Gly Val
385                 390                 395                 400

Pro Gly Val Gly Gly Val Pro Gly Val Gly Ile Ser Pro Glu Ala Gln
                405                 410                 415

Ala Ala Ala Ala Ala Lys Ala Ala Lys Tyr Gly Ala Ala Gly Ala Gly
            420                 425                 430

Val Leu Gly Gly Leu Val Pro Gly Pro Gln Ala Ala Val Pro Gly Val
        435                 440                 445

Pro Gly Thr Gly Gly Val Pro Gly Val Gly Thr Pro Ala Ala Ala Ala
    450                 455                 460

Ala Lys Ala Ala Ala Lys Ala Ala Gln Phe Gly Leu Val Pro Gly Val
465                 470                 475                 480

Gly Val Ala Pro Gly Val Gly Val Ala Pro Gly Val Gly Val Ala Pro
                485                 490                 495

Gly Val Gly Leu Ala Pro Gly Val Gly Val Ala Pro Gly Val Gly Val
            500                 505                 510

Ala Pro Gly Val Gly Val Ala Pro Gly Ile Gly Pro Gly Gly Val Ala
        515                 520                 525

Ala Ala Ala Lys Ser Ala Ala Lys Val Ala Ala Lys Ala Gln Leu Arg
    530                 535                 540

Ala Ala Ala Gly Leu Gly Ala Gly Ile Pro Gly Leu Gly Val Gly Val
545                 550                 555                 560

Gly Val Pro Gly Leu Gly Val Gly Ala Gly Val Pro Gly Leu Gly Val
                565                 570                 575

Gly Ala Gly Val Pro Gly Phe Gly Ala Gly Ala Asp Glu Gly Val Arg
            580                 585                 590

Arg Ser Leu Ser Pro Glu Leu Arg Glu Gly Asp Pro Ser Ser Ser Gln
        595                 600                 605

His Leu Pro Ser Thr Pro Ser Ser Pro Arg Val Pro Gly Ala Leu Ala
    610                 615                 620

Ala Ala Lys Ala Ala Lys Tyr Gly Ala Ala Val Pro Gly Val Leu Gly
625                 630                 635                 640

Gly Leu Gly Ala Leu Gly Gly Val Gly Ile Pro Gly Gly Val Val Gly
                645                 650                 655

Ala Gly Pro Ala Ala Ala Ala Ala Ala Ala Lys Ala Ala Ala Lys Ala
```

-continued

```
            660                 665                 670

Ala Gln Phe Gly Leu Val Gly Ala Ala Gly Leu Gly Gly Leu Gly Val
        675                 680                 685

Gly Gly Leu Gly Val Pro Gly Val Gly Gly Leu Gly Gly Ile Pro Pro
    690                 695                 700

Ala Ala Ala Ala Lys Ala Ala Lys Tyr Gly Ala Ala Gly Leu Gly Gly
705                 710                 715                 720

Val Leu Gly Gly Ala Gly Gln Phe Pro Leu Gly Gly Val Ala Ala Arg
                725                 730                 735

Pro Gly Phe Gly Leu Ser Pro Ile Phe Pro Gly Gly Ala Cys Leu Gly
            740                 745                 750

Lys Ala Cys Gly Arg Lys Arg Lys
        755                 760
```

<210> SEQ ID NO 30
<211> LENGTH: 2115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

```
ggtggcgtac caggcgcaat tcctgggggt gtcccaggcg gtgtttttta tccgggcgcc     60

ggtcttggcg cactgggtgg cggtgcactg ggcccgggcg gcaaaccgct gaaaccggta    120

ccaggtggtt tagcaggcgc cggcttaggc gcaggtctgg gagcatttcc ggcagttacc    180

tttccagggg cactggttcc tggaggtgtg gccgatgcag ccgcggcata taaagccgct    240

aaagccggtg cgggtttagg aggcgtccca ggtgtcggtg gcctgggtgt tagcgccggt    300

gcagttgttc cgcagccggg agcagggggtt aaacctggta aagtgccggg agtaggtctg    360

ccaggcgttt atcctggtgg tgttttgccg ggtgcccgtt ttccgggcgt tggtgttctt    420

ccaggcgtgc cgaccggagc cggtgttaaa ccgaaagccc ccggtgttgg aggtgcattt    480

gcaggcatcc cgggagttgg cccgtttggt ggtccgcaac ctggggttcc gttaggttat    540

ccgattaaag caccgaaact gcccggcggt tatggtctgc cgtacacaac cggtaaactg    600

ccgtatggtt atggcccggg tggagttgcg ggtgcagcag gtaaagcggg ttatcctacc    660

ggaaccggtg taggtccgca ggccgctgct gccgccgccg caaaagcagc ggctaaattt    720

ggcgccggag cagcgggtgt tctgcctgga gttggtggtg cgggcgtgcc aggggtacct    780

ggtgcaattc cgggtattgg tggtattgcc ggtgtcggca ccccggccgc ggcagctgcg    840

gcagcggcgg ctgccaaagc tgctaaatac ggtgccgcgg cgggtctggt gccaggaggt    900

ccgggttttg gtccgggagt ggttggcgtg cctggcgcag gcgttcctgg tgtgggcgtt    960

ccaggtgcag ggattcctgt tgtgcctggt gccggtattc ccggcgcggc cgttccgggg   1020

gtggttagcc cggaagccgc agcgaaggct gcggcaaagg cagcaaagta tggcgcacgc   1080

ccaggagtcg gcgtgggtgg tatcccgacc tatggggtgg gcgcaggggg ttttcctggt   1140

ttcggcgtag gtgtaggagg tataccgggc gtggccggtg taccaggggt tggtggcgtc   1200

cctggtgttg gcggtgtgcc aggtgttggt atttcaccgg aagcacaggc agcagccgca   1260

gctaaggcag cgaaatatgg tgccgccggc gcaggagttt taggtgggct ggttccgggc   1320

ccgcaggcag ctgtgccggg ggttccaggc accggtggtg tccctggagt cggtacgccg   1380

gctgcagcgg cagccaaagc ggctgcgaaa gcagcacagt ttggcttagt accgggtgtg   1440
```

-continued

```
ggagttgccc ccggcgttgg cgttgctcca ggggtgggtg ttgctcctgg cgtcggtctg   1500

gctcctggag tgggcgtagc acccggtgtg ggggtggccc cgggtgttgg ggttgcaccg   1560

ggtatcggtc cgggcggtgt cgcagcagca gctaaaagcg cggcgaaagt tgcggccaaa   1620

gcccaactgc gcgccgccgc gggcctcggt gcaggtattc cggggctggg tgtcggagtt   1680

ggagtcccgg gtttgggcgt gggcgcggga gttccgggac tgggagtggg tgccggagtt   1740

cctggctttg gtgcaggcgc agatgaaggt gttcgtcgta gcctgagtcc ggaactgcgt   1800

gaaggtgatc cgagtagcag ccagcatctg ccgagcaccc cgagcagccc gcgtgttccg   1860

ggtgcattag ctgcagcaaa agccgccaag tatggtgcag ccgtgccggg cgtcttaggt   1920

ggtctgggcg ccctgggtgg tgtaggcatt ccgggaggtg ttgtgggtgc aggaccggcc   1980

gccgcagctg cggccgccaa agcagctgca aaagcggccc agtttggttt agtgggcgcc   2040

gcaggtttag gcggtttagg tgtgggtgga ctgggtgtac ctggcgtagg cggtctgggt   2100

ggaattccgc cctaa                                                    2115


<210> SEQ ID NO 31
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gly Gly Val Pro Gly Ala Ile Pro Gly Gly Val Pro Gly Gly Val Phe
1               5                   10                  15

Tyr Pro Gly Ala Gly Leu Gly Ala Leu Gly Gly Gly Ala Leu Gly Pro
            20                  25                  30

Gly Gly Lys Pro Leu Lys Pro Val Pro Gly Gly Leu Ala Gly Ala Gly
        35                  40                  45

Leu Gly Ala Gly Leu Gly Ala Phe Pro Ala Val Thr Phe Pro Gly Ala
    50                  55                  60

Leu Val Pro Gly Gly Val Ala Asp Ala Ala Ala Ala Tyr Lys Ala Ala
65                  70                  75                  80

Lys Ala Gly Ala Gly Leu Gly Gly Val Pro Gly Val Gly Gly Leu Gly
                85                  90                  95

Val Ser Ala Gly Ala Val Val Pro Gln Pro Gly Ala Gly Val Lys Pro
            100                 105                 110

Gly Lys Val Pro Gly Val Gly Leu Pro Gly Val Tyr Pro Gly Gly Val
        115                 120                 125

Leu Pro Gly Ala Arg Phe Pro Gly Val Gly Val Leu Pro Gly Val Pro
    130                 135                 140

Thr Gly Ala Gly Val Lys Pro Lys Ala Pro Gly Val Gly Gly Ala Phe
145                 150                 155                 160

Ala Gly Ile Pro Gly Val Gly Pro Phe Gly Gly Pro Gln Pro Gly Val
                165                 170                 175

Pro Leu Gly Tyr Pro Ile Lys Ala Pro Lys Leu Pro Gly Gly Tyr Gly
            180                 185                 190

Leu Pro Tyr Thr Thr Gly Lys Leu Pro Tyr Gly Tyr Gly Pro Gly Gly
        195                 200                 205

Val Ala Gly Ala Ala Gly Lys Ala Gly Tyr Pro Thr Gly Thr Gly Val
    210                 215                 220

Gly Pro Gln Ala Ala Ala Ala Ala Ala Ala Lys Ala Ala Ala Lys Phe
225                 230                 235                 240
```

```
Gly Ala Gly Ala Ala Gly Val Leu Pro Gly Val Gly Gly Ala Gly Val
                245                 250                 255

Pro Gly Val Pro Gly Ala Ile Pro Gly Ile Gly Gly Ile Ala Gly Val
            260                 265                 270

Gly Thr Pro Ala Ala Ala Ala Ala Ala Ala Ala Ala Ala Lys Ala Ala
        275                 280                 285

Lys Tyr Gly Ala Ala Ala Gly Leu Val Pro Gly Gly Pro Gly Phe Gly
    290                 295                 300

Pro Gly Val Val Gly Val Pro Gly Ala Gly Val Pro Gly Val Gly Val
305                 310                 315                 320

Pro Gly Ala Gly Ile Pro Val Val Pro Gly Ala Gly Ile Pro Gly Ala
                325                 330                 335

Ala Val Pro Gly Val Val Ser Pro Glu Ala Ala Ala Lys Ala Ala Ala
            340                 345                 350

Lys Ala Ala Lys Tyr Gly Ala Arg Pro Gly Val Gly Val Gly Gly Ile
        355                 360                 365

Pro Thr Tyr Gly Val Gly Ala Gly Gly Phe Pro Gly Phe Gly Val Gly
    370                 375                 380

Val Gly Gly Ile Pro Gly Val Ala Gly Val Pro Gly Val Gly Gly Val
385                 390                 395                 400

Pro Gly Val Gly Gly Val Pro Gly Val Gly Ile Ser Pro Glu Ala Gln
                405                 410                 415

Ala Ala Ala Ala Ala Lys Ala Ala Lys Tyr Gly Ala Ala Gly Ala Gly
            420                 425                 430

Val Leu Gly Gly Leu Val Pro Gly Pro Gln Ala Ala Val Pro Gly Val
        435                 440                 445

Pro Gly Thr Gly Gly Val Pro Gly Val Gly Thr Pro Ala Ala Ala Ala
    450                 455                 460

Ala Lys Ala Ala Ala Lys Ala Ala Gln Phe Gly Leu Val Pro Gly Val
465                 470                 475                 480

Gly Val Ala Pro Gly Val Gly Val Ala Pro Gly Val Gly Val Ala Pro
                485                 490                 495

Gly Val Gly Leu Ala Pro Gly Val Gly Val Ala Pro Gly Val Gly Val
            500                 505                 510

Ala Pro Gly Val Gly Val Ala Pro Gly Ile Gly Pro Gly Gly Val Ala
        515                 520                 525

Ala Ala Ala Lys Ser Ala Ala Lys Val Ala Ala Lys Ala Gln Leu Arg
    530                 535                 540

Ala Ala Ala Gly Leu Gly Ala Gly Ile Pro Gly Leu Gly Val Gly Val
545                 550                 555                 560

Gly Val Pro Gly Leu Gly Val Gly Ala Gly Val Pro Gly Leu Gly Val
                565                 570                 575

Gly Ala Gly Val Pro Gly Phe Gly Ala Gly Ala Asp Glu Gly Val Arg
            580                 585                 590

Arg Ser Leu Ser Pro Glu Leu Arg Glu Gly Asp Pro Ser Ser Ser Gln
        595                 600                 605

His Leu Pro Ser Thr Pro Ser Ser Pro Arg Val Pro Gly Ala Leu Ala
    610                 615                 620

Ala Ala Lys Ala Ala Lys Tyr Gly Ala Ala Val Pro Gly Val Leu Gly
625                 630                 635                 640

Gly Leu Gly Ala Leu Gly Gly Val Gly Ile Pro Gly Gly Val Val Gly
                645                 650                 655
```

```
Ala Gly Pro Ala Ala Ala Ala Ala Ala Ala Lys Ala Ala Ala Lys Ala
            660                 665                 670

Ala Gln Phe Gly Leu Val Gly Ala Ala Gly Leu Gly Gly Leu Gly Val
        675                 680                 685

Gly Gly Leu Gly Val Pro Gly Val Gly Gly Leu Gly Gly Ile Pro Pro
    690                 695                 700
```

<210> SEQ ID NO 32
<211> LENGTH: 2115
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32

```
ggtggcgtac caggcgcaat tcctgggggt gtcccaggcg gtgtttttta tccgggcgcc     60

ggtcttggcg cactgggtgg cggtgcactg ggcccgggcg gcaaaccgct gaaaccggta    120

ccaggtggtt tagcaggcgc cggcttaggc gcaggtctgg gagcatttcc ggcagttacc    180

tttccagggg cactggttcc tggaggtgtg gccgatgcag ccgcggcata taaagccgct    240

aaagccggtg cgggtttagg aggcgtccca ggtgtcggtg gcctgggtgt tagcgccggt    300

gcagttgttc cgcagccggg agcagggggtt aaacctggta aagtgccggg agtaggtctg    360

ccaggcgttt atcctggtgg tgttttgccg ggtgcccgtt ttccgggcgt tggtgttctt    420

ccaggcgtgc cgaccggagc cggtgttaaa ccgaaagccc ccggtgttgg aggtgcattt    480

gcaggcatcc cgggagttgg cccgtttggt ggtccgcaac ctggggttcc gttaggttat    540

ccgattaaag caccgaaact gcccggcggt tatggtctgc cgtacacaac cggtaaactg    600

ccgtatggtt atggcccggg tggagttgcg ggtgcagcag gtaaagcggg ttatcctacc    660

ggaaccggtg taggtccgca ggccgctgct gccgccgccg caaaagcagc ggctaaattt    720

ggcgccggag cagcgggtgt tctgcctgga gttggtggtg cgggcgtgcc aggggtacct    780

ggtgcaattc cgggtattgg tggtattgcc ggtgtcggca ccccggccgc ggcagctgcg    840

gcagcggcgg ctgccaaagc tgctaaatac ggtgccgcgg cgggtctggt gccaggaggt    900

ccgggttttg gtccgggagt ggttggcgtg cctggcgcag gcgttcctgg tgtgggcgtt    960

ccaggtgcag ggattcctgt tgtgcctggt gccggtattc ccggcgcggc cgttccgggg   1020

gtggttagcc cggaagccgc agcgaaggct gcggcaaagg cagcaaagta tggcgcacgc   1080

ccaggagtcg gcgtgggtgg tatcccgacc tatggggtgg gcgcaggggg ttttcctggt   1140

ttcggcgtag gtgtaggagg tataccgggc gtggccggtg taccaggggt tggtggcgtc   1200

cctggtgttg gcggtgtgcc aggtgttggt atttcaccgg aagcacaggc agcagccgca   1260

gctaaggcag cgaaatatgg tgccgccggc gcaggagttt taggtgggct ggttccgggc   1320

ccgcaggcag ctgtgccggg ggttccaggc accggtggtg tccctggagt cggtacgccg   1380

gctgcagcgg cagccaaagc ggctgcgaaa gcagcacagt ttggcttagt accgggtgtg   1440

ggagttgccc ccggcgttgg cgttgctcca ggggtgggtg ttgctcctgg cgtcggtctg   1500

gctcctggag tgggcgtagc acccggtgtg ggggtggccc cgggtgttgg ggttgcaccg   1560

ggtatcggtc cgggcggtgt cgcagcagca gctaaaagcg cggcgaaagt tgcggccaaa   1620

gcccaactgc gcgccgccgc gggcctcggt gcaggtattc cggggctggg tgtcggagtt   1680

ggagtcccgg gtttgggcgt gggcgcggga gttccgggac tgggagtggg tgccggagtt   1740

cctggctttg gtgcaggcgc agatgaaggt gttcgtcgta gcctgagtcc ggaactgcgt   1800
```

```
gaaggtgatc cgagtagcag ccagcatctg ccgagcaccc cgagcagccc gcgtgttccg   1860

ggtgcattag ctgcagcaaa agccgccaag tatggtgcag ccgtgccggg cgtcttaggt   1920

ggtctgggcg ccctgggtgg tgtaggcatt ccgggaggtg ttgtgggtgc aggaccggcc   1980

gccgcagctg cggccgccaa agcagctgca aaagcggccc agtttggttt agtgggcgcc   2040

gcaggtttag gcggtttagg tgtgggtgga ctgggtgtac ctggcgtagg cggtctgggt   2100

ggaattccgc cctaa                                                    2115
```

```
<210> SEQ ID NO 33
<211> LENGTH: 676
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gly Leu Gly Gly Val Pro Gly Val Gly Gly Leu Gly Val Ser Ala Gly
1               5                   10                  15

Ala Val Val Pro Gln Pro Gly Ala Gly Val Lys Pro Gly Lys Val Pro
            20                  25                  30

Gly Val Gly Leu Pro Gly Val Tyr Pro Gly Gly Val Leu Pro Gly Ala
        35                  40                  45

Arg Phe Pro Gly Val Gly Val Leu Pro Gly Val Pro Thr Gly Ala Gly
    50                  55                  60

Val Lys Pro Lys Ala Pro Gly Val Gly Gly Ala Phe Ala Gly Ile Pro
65                  70                  75                  80

Gly Val Gly Pro Phe Gly Gly Pro Gln Pro Gly Val Pro Leu Gly Tyr
                85                  90                  95

Pro Ile Lys Ala Pro Lys Leu Pro Gly Gly Tyr Gly Leu Pro Tyr Thr
            100                 105                 110

Thr Gly Lys Leu Pro Tyr Gly Tyr Gly Pro Gly Gly Val Ala Gly Ala
        115                 120                 125

Ala Gly Lys Ala Gly Tyr Pro Thr Gly Thr Gly Val Gly Pro Gln Ala
    130                 135                 140

Ala Ala Ala Ala Ala Ala Lys Ala Ala Ala Lys Phe Gly Ala Gly Ala
145                 150                 155                 160

Ala Gly Val Leu Pro Gly Val Gly Gly Ala Gly Val Pro Gly Val Pro
                165                 170                 175

Gly Ala Ile Pro Gly Ile Gly Gly Ile Ala Gly Val Gly Thr Pro Ala
            180                 185                 190

Ala Ala Ala Ala Ala Ala Ala Ala Ala Lys Ala Ala Lys Tyr Gly Ala
        195                 200                 205

Ala Ala Gly Leu Val Pro Gly Gly Pro Gly Phe Gly Pro Gly Val Val
    210                 215                 220

Gly Val Pro Gly Ala Gly Val Pro Gly Val Gly Val Pro Gly Ala Gly
225                 230                 235                 240

Ile Pro Val Val Pro Gly Ala Gly Ile Pro Gly Ala Ala Val Pro Gly
                245                 250                 255

Val Val Ser Pro Glu Ala Ala Ala Lys Ala Ala Ala Lys Ala Ala Lys
            260                 265                 270

Tyr Gly Ala Arg Pro Gly Val Gly Val Gly Gly Ile Pro Thr Tyr Gly
        275                 280                 285

Val Gly Ala Gly Gly Phe Pro Gly Phe Gly Val Gly Val Gly Gly Ile
```

```
    290                 295                 300

Pro Gly Val Ala Gly Val Pro Gly Val Gly Gly Val Pro Gly Val Gly
305                 310                 315                 320

Gly Val Pro Gly Val Gly Ile Ser Pro Glu Ala Gln Ala Ala Ala Ala
                325                 330                 335

Ala Lys Ala Ala Lys Tyr Gly Ala Ala Gly Ala Gly Val Leu Gly Gly
            340                 345                 350

Leu Val Pro Gly Pro Gln Ala Ala Val Pro Gly Val Pro Gly Thr Gly
        355                 360                 365

Gly Val Pro Gly Val Gly Thr Pro Ala Ala Ala Ala Ala Lys Ala Ala
    370                 375                 380

Ala Lys Ala Ala Gln Phe Gly Leu Val Pro Gly Val Gly Val Ala Pro
385                 390                 395                 400

Gly Val Gly Val Ala Pro Gly Val Gly Val Ala Pro Gly Val Gly Leu
                405                 410                 415

Ala Pro Gly Val Gly Val Ala Pro Gly Val Gly Val Ala Pro Gly Val
            420                 425                 430

Gly Val Ala Pro Gly Ile Gly Pro Gly Gly Val Ala Ala Ala Ala Lys
        435                 440                 445

Ser Ala Ala Lys Val Ala Ala Lys Ala Gln Leu Arg Ala Ala Ala Gly
    450                 455                 460

Leu Gly Ala Gly Ile Pro Gly Leu Gly Val Gly Val Gly Val Pro Gly
465                 470                 475                 480

Leu Gly Val Gly Ala Gly Val Pro Gly Leu Gly Val Gly Ala Gly Val
                485                 490                 495

Pro Gly Phe Gly Ala Gly Ala Asp Glu Gly Val Arg Arg Ser Leu Ser
            500                 505                 510

Pro Glu Leu Arg Glu Gly Asp Pro Ser Ser Ser Gln His Leu Pro Ser
        515                 520                 525

Thr Pro Ser Ser Pro Arg Val Pro Gly Ala Leu Ala Ala Ala Lys Ala
    530                 535                 540

Ala Lys Tyr Gly Ala Ala Val Pro Gly Val Leu Gly Gly Leu Gly Ala
545                 550                 555                 560

Leu Gly Gly Val Gly Ile Pro Gly Gly Val Val Gly Ala Gly Pro Ala
                565                 570                 575

Ala Ala Ala Ala Ala Ala Lys Ala Ala Ala Lys Ala Ala Gln Phe Gly
            580                 585                 590

Leu Val Gly Ala Ala Gly Leu Gly Gly Leu Gly Val Gly Gly Leu Gly
        595                 600                 605

Val Pro Gly Val Gly Gly Leu Gly Gly Ile Pro Pro Ala Ala Ala Ala
    610                 615                 620

Lys Ala Ala Lys Tyr Gly Ala Ala Gly Leu Gly Gly Val Leu Gly Gly
625                 630                 635                 640

Ala Gly Gln Phe Pro Leu Gly Gly Val Ala Ala Arg Pro Gly Phe Gly
                645                 650                 655

Leu Ser Pro Ile Phe Pro Gly Gly Ala Cys Leu Gly Lys Ala Cys Gly
            660                 665                 670

Arg Lys Arg Lys
        675


<210> SEQ ID NO 34
<211> LENGTH: 2031
<212> TYPE: DNA
<213> ORGANISM: Artificial Sequence
```

<220> FEATURE:
<223> OTHER INFORMATION: Description of Artificial Sequence: Synthetic
polynucleotide

<400> SEQUENCE: 34
ggtttaggag gcgtcccagg tgtcggtggc ctgggtgtta gcgccggtgc agttgttccg 60
cagccgggag caggggttaa acctggtaaa gtgccgggag taggtctgcc aggcgtttat 120
cctggtggtg ttttgccggg tgcccgtttt ccgggcgttg gtgttcttcc aggcgtgccg 180
accggagccg gtgttaaacc gaaagccccc ggtgttggag gtgcatttgc aggcatcccg 240
ggagttggcc cgtttggtgg tccgcaacct ggggttccgt taggttatcc gattaaagca 300
ccgaaactgc ccggcggtta tggtctgccg tacacaaccg gtaaactgcc gtatggttat 360
ggcccgggtg gagttgcggg tgcagcaggt aaagcgggtt atcctaccgg aaccggtgta 420
ggtccgcagg ccgctgctgc cgccgccgca aaagcagcgg ctaaatttgg cgccggagca 480
gcgggtgttc tgcctggagt tggtggtgcg ggcgtgccag ggtacctggt tgcaattccg 540
ggtattggtg gtattgccgg tgtcggcacc ccggccgcgg cagctgcggc agcggcggct 600
gccaaagctg ctaaatacgg tgccgcggcg ggtctggtgc caggaggtcc gggttttggt 660
ccgggagtgg ttggcgtgcc tggcgcaggc gttcctggtg tgggcgttcc aggtgcaggg 720
attcctgttg tgcctggtgc cggtattccc ggcgcggccg ttccgggggt ggttagcccg 780
gaagccgcag cgaaggctgc ggcaaaggca gcaaagtatg gcgcacgccc aggagtcggc 840
gtgggtggta tcccgaccta tggggtgggc gcagggggtt ttcctggttt cggcgtaggt 900
gtaggaggta taccgggcgt ggccggtgta ccaggggttg gtggcgtccc tggtgttggc 960
ggtgtgccag gtgttggtat ttcaccggaa gcacaggcag cagccgcagc taaggcagcg 1020
aaatatggtg ccgccggcgc aggagtttta ggtgggctgg ttccgggccc gcaggcagct 1080
gtgccggggg ttccaggcac cggtggtgtc cctggagtcg gtacgccggc tgcagcggca 1140
gccaaagcgg ctgcgaaagc agcacagttt ggcttagtac cgggtgtggg agttgccccc 1200
ggcgttggcg ttgctccagg ggtgggtgtt gctcctggcg tcggtctggc tcctggagtg 1260
ggcgtagcac ccggtgtggg ggtggccccg ggtgttgggg ttgcaccggg tatcggtccg 1320
ggcggtgtcg cagcagcagc taaaagcgcg gcgaaagttg cggccaaagc ccaactgcgc 1380
gccgccgcgg gcctcggtgc aggtattccg gggctgggtg tcggagttgg agtcccgggt 1440
ttgggcgtgg gcgcgggagt tccgggactg ggagtgggtg ccggagttcc tggctttggt 1500
gcaggcgcag atgaaggtgt tcgtcgtagc ctgagtccgg aactgcgtga aggtgatccg 1560
agtagcagcc agcatctgcc gagcaccccg agcagcccgc gtgttccggg tgcattagct 1620
gcagcaaaag ccgccaagta tggtgcagcc gtgccgggcg tcttaggtgg tctgggcgcc 1680
ctgggtggtg taggcattcc gggaggtgtt gtgggtgcag gaccggccgc cgcagctgcg 1740
gccgccaaag cagctgcaaa agcggcccag tttggtttag tgggcgccgc aggtttaggc 1800
ggtttaggtg tgggtggact gggtgtacct ggcgtaggcg gtctgggtgg aattccgccc 1860
gcagcggccg cgaaagcggc aaaatatggc gcggcaggcc tgggcggcgt gctgggtggg 1920
gcaggtcagt ttccgctggg cggggttgcc gcacgtccgg gatttggtct gagcccgatt 1980
ttccctggcg gcgcatgtct gggtaaagca tgtggtcgta aacgtaaata a 2031

<210> SEQ ID NO 35
<211> LENGTH: 659
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 35

```
Gly Gly Val Pro Gly Ala Ile Pro Gly Gly Val Pro Gly Gly Val Phe
1               5                   10                  15

Tyr Pro Gly Ala Gly Leu Gly Ala Leu Gly Gly Gly Ala Leu Gly Pro
            20                  25                  30

Gly Gly Lys Pro Leu Lys Pro Val Pro Gly Gly Leu Ala Gly Ala Gly
        35                  40                  45

Leu Gly Ala Gly Leu Gly Ala Phe Pro Ala Val Thr Phe Pro Gly Ala
    50                  55                  60

Leu Val Pro Gly Gly Val Ala Asp Ala Ala Ala Ala Tyr Lys Ala Ala
65                  70                  75                  80

Lys Ala Gly Ala Gly Leu Gly Gly Val Pro Gly Val Gly Gly Leu Gly
                85                  90                  95

Val Ser Ala Gly Ala Val Val Pro Gln Pro Gly Ala Gly Val Lys Pro
            100                 105                 110

Gly Lys Val Pro Gly Val Gly Leu Pro Gly Val Tyr Pro Gly Gly Val
        115                 120                 125

Leu Pro Gly Ala Arg Phe Pro Gly Val Gly Val Leu Pro Gly Val Pro
    130                 135                 140

Thr Gly Ala Gly Val Lys Pro Lys Ala Pro Gly Val Gly Gly Ala Phe
145                 150                 155                 160

Ala Gly Ile Pro Gly Val Gly Pro Phe Gly Gly Pro Gln Pro Gly Val
                165                 170                 175

Pro Leu Gly Tyr Pro Ile Lys Ala Pro Lys Leu Pro Gly Gly Tyr Gly
            180                 185                 190

Leu Pro Tyr Thr Thr Gly Lys Leu Pro Tyr Gly Tyr Gly Pro Gly Gly
        195                 200                 205

Val Ala Gly Ala Ala Gly Lys Ala Gly Tyr Pro Thr Gly Thr Gly Val
    210                 215                 220

Gly Pro Gln Ala Ala Ala Ala Ala Ala Ala Lys Ala Ala Ala Lys Phe
225                 230                 235                 240

Gly Ala Gly Ala Ala Gly Val Leu Pro Gly Val Gly Gly Ala Gly Val
                245                 250                 255

Pro Gly Val Pro Gly Ala Ile Pro Gly Ile Gly Gly Ile Ala Gly Val
            260                 265                 270

Gly Thr Pro Ala Ala Ala Ala Ala Ala Ala Ala Ala Ala Lys Ala Ala
        275                 280                 285

Lys Tyr Gly Ala Ala Ala Gly Leu Val Pro Gly Gly Pro Gly Phe Gly
    290                 295                 300

Pro Gly Val Val Gly Val Pro Gly Ala Gly Val Pro Gly Val Gly Val
305                 310                 315                 320

Pro Gly Ala Gly Ile Pro Val Val Pro Gly Ala Gly Ile Pro Gly Ala
                325                 330                 335

Ala Val Pro Gly Val Val Ser Pro Glu Ala Ala Ala Lys Ala Ala Ala
            340                 345                 350

Lys Ala Ala Lys Tyr Gly Ala Arg Pro Gly Val Gly Val Gly Gly Ile
        355                 360                 365

Pro Thr Tyr Gly Val Gly Ala Gly Gly Phe Pro Gly Phe Gly Val Gly
    370                 375                 380

Val Gly Gly Ile Pro Gly Val Ala Gly Val Pro Gly Val Gly Gly Val
```

```
385                 390                 395                 400

Pro Gly Val Gly Gly Val Pro Gly Val Gly Ile Ser Pro Glu Ala Gln
                405                 410                 415

Ala Ala Ala Ala Ala Lys Ala Ala Lys Tyr Gly Ala Ala Gly Ala Gly
            420                 425                 430

Val Leu Gly Gly Leu Val Pro Gly Pro Gln Ala Ala Val Pro Gly Val
        435                 440                 445

Pro Gly Thr Gly Gly Val Pro Gly Val Gly Thr Pro Ala Ala Ala Ala
    450                 455                 460

Ala Lys Ala Ala Ala Lys Ala Ala Gln Phe Gly Leu Val Pro Gly Val
465                 470                 475                 480

Gly Val Ala Pro Gly Val Gly Val Ala Pro Gly Val Gly Val Ala Pro
                485                 490                 495

Gly Val Gly Leu Ala Pro Gly Val Gly Val Ala Pro Gly Val Gly Val
            500                 505                 510

Ala Pro Gly Val Gly Val Ala Pro Gly Ile Gly Pro Gly Gly Val Ala
        515                 520                 525

Ala Ala Ala Lys Ser Ala Ala Lys Val Ala Ala Lys Ala Gln Leu Arg
    530                 535                 540

Ala Ala Ala Gly Leu Gly Ala Gly Ile Pro Gly Leu Gly Val Gly Val
545                 550                 555                 560

Gly Val Pro Gly Leu Gly Val Gly Ala Gly Val Pro Gly Leu Gly Val
                565                 570                 575

Gly Ala Gly Val Pro Gly Phe Gly Ala Gly Ala Asp Glu Gly Val Arg
            580                 585                 590

Arg Ser Leu Ser Pro Glu Leu Arg Glu Gly Asp Pro Ser Ser Ser Gln
        595                 600                 605

His Leu Pro Ser Thr Pro Ser Ser Pro Arg Val Pro Gly Ala Leu Ala
    610                 615                 620

Ala Ala Lys Ala Ala Lys Tyr Gly Ala Ala Val Pro Gly Val Leu Gly
625                 630                 635                 640

Gly Leu Gly Ala Leu Gly Gly Val Gly Ile Pro Gly Gly Val Val Gly
                645                 650                 655

Ala Gly Pro
```

```
<210> SEQ ID NO 36
<211> LENGTH: 1980
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

ggtggcgtac caggcgcaat tcctgggggt gtcccaggcg gtgtttttta tccgggcgcc     60

ggtcttggcg cactgggtgg cggtgcactg ggcccgggcg gcaaaccgct gaaaccggta    120

ccaggtggtt tagcaggcgc cggcttaggc gcaggtctgg gagcatttcc ggcagttacc    180

tttccagggg cactggttcc tggaggtgtg gccgatgcag ccgcggcata taaagccgct    240

aaagccggtg cgggtttagg aggcgtccca ggtgtcggtg gcctgggtgt tagcgccggt    300

gcagttgttc cgcagccggg agcagggggtt aaacctggta aagtgccggg agtaggtctg    360

ccaggcgttt atcctggtgg tgttttgccg ggtgcccgtt ttccgggcgt tggtgttctt    420

ccaggcgtgc cgaccggagc cggtgttaaa ccgaaagccc ccggtgttgg aggtgcattt    480
```

-continued

```
gcaggcatcc cgggagttgg cccgtttggt ggtccgcaac ctggggttcc gttaggttat    540

ccgattaaag caccgaaact gcccggcggt tatggtctgc cgtacacaac cggtaaactg    600

ccgtatggtt atggcccggg tggagttgcg ggtgcagcag gtaaagcggg ttatcctacc    660

ggaaccggtg taggtccgca ggccgctgct gccgccgccg caaaagcagc ggctaaattt    720

ggcgccggag cagcgggtgt tctgcctgga gttggtggtg cgggcgtgcc aggggtacct    780

ggtgcaattc cgggtattgg tggtattgcc ggtgtcggca ccccggccgc ggcagctgcg    840

gcagcggcgg ctgccaaagc tgctaaatac ggtgccgcgg cgggtctggt gccaggaggt    900

ccgggttttg gtccgggagt ggttggcgtg cctggcgcag gcgttcctgg tgtgggcgtt    960

ccaggtgcag ggattcctgt tgtgcctggt gccggtattc ccggcgcggc cgttccgggg   1020

gtggttagcc cggaagccgc agcgaaggct gcggcaaagg cagcaaagta tggcgcacgc   1080

ccaggagtcg gcgtgggtgg tatcccgacc tatggggtgg gcgcaggggg ttttcctggt   1140

ttcggcgtag gtgtaggagg tataccgggc gtggccggtg taccaggggt tggtggcgtc   1200

cctggtgttg gcggtgtgcc aggtgttggt atttcaccgg aagcacaggc agcagccgca   1260

gctaaggcag cgaaatatgg tgccgccggc gcaggagttt taggtgggct ggttccgggc   1320

ccgcaggcag ctgtgccggg ggttccaggc accggtggtg tccctggagt cggtacgccg   1380

gctgcagcgg cagccaaagc ggctgcgaaa gcagcacagt ttggcttagt accgggtgtg   1440

ggagttgccc ccggcgttgg cgttgctcca ggggtgggtg ttgctcctgg cgtcggtctg   1500

gctcctggag tgggcgtagc acccggtgtg gggtggccc cgggtgttgg ggttgcaccg   1560

ggtatcggtc cgggcggtgt cgcagcagca gctaaaagcg cggcgaaagt tgcggccaaa   1620

gcccaactgc gcgccgccgc gggcctcggt gcaggtattc cggggctggg tgtcggagtt   1680

ggagtcccgg gtttgggcgt gggcgcggga gttccgggac tgggagtggg tgccggagtt   1740

cctggctttg gtgcaggcgc agatgaaggt gttcgtcgta gcctgagtcc ggaactgcgt   1800

gaaggtgatc cgagtagcag ccagcatctg ccgagcaccc cgagcagccc gcgtgttccg   1860

ggtgcattag ctgcagcaaa agccgccaag tatggtgcag ccgtgccggg cgtcttaggt   1920

ggtctgggcg ccctgggtgg tgtaggcatt ccgggaggtg ttgtgggtgc aggaccgtaa   1980
```

```
<210> SEQ ID NO 37
<211> LENGTH: 622
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gly Gly Val Pro Gly Ala Ile Pro Gly Gly Val Pro Gly Gly Val Phe
1               5                   10                  15

Tyr Pro Gly Ala Gly Leu Gly Ala Leu Gly Gly Gly Ala Leu Gly Pro
            20                  25                  30

Gly Gly Lys Pro Leu Lys Pro Val Pro Gly Gly Leu Ala Gly Ala Gly
        35                  40                  45

Leu Gly Ala Gly Leu Gly Ala Phe Pro Ala Val Thr Phe Pro Gly Ala
    50                  55                  60

Leu Val Pro Gly Gly Val Ala Asp Ala Ala Ala Ala Tyr Lys Ala Ala
65                  70                  75                  80

Lys Ala Gly Ala Gly Leu Gly Gly Val Pro Gly Val Gly Gly Leu Gly
                85                  90                  95
```

-continued

```
Val Ser Ala Gly Ala Val Val Pro Gln Pro Gly Ala Gly Val Lys Pro
            100                 105                 110

Gly Lys Val Pro Gly Val Gly Leu Pro Gly Val Tyr Pro Gly Gly Val
        115                 120                 125

Leu Pro Gly Ala Arg Phe Pro Gly Val Gly Val Leu Pro Gly Val Pro
    130                 135                 140

Thr Gly Ala Gly Val Lys Pro Lys Ala Pro Gly Val Gly Gly Ala Phe
145                 150                 155                 160

Ala Gly Ile Pro Gly Val Gly Pro Phe Gly Gly Pro Gln Pro Gly Val
                165                 170                 175

Pro Leu Gly Tyr Pro Ile Lys Ala Pro Lys Leu Pro Gly Gly Tyr Gly
            180                 185                 190

Leu Pro Tyr Thr Thr Gly Lys Leu Pro Tyr Gly Tyr Gly Pro Gly Gly
        195                 200                 205

Val Ala Gly Ala Ala Gly Lys Ala Gly Tyr Pro Thr Gly Thr Gly Val
    210                 215                 220

Gly Pro Gln Ala Ala Ala Ala Ala Ala Ala Lys Ala Ala Ala Lys Phe
225                 230                 235                 240

Gly Ala Gly Ala Ala Gly Val Leu Pro Gly Val Gly Gly Ala Gly Val
                245                 250                 255

Pro Gly Val Pro Gly Ala Ile Pro Gly Ile Gly Gly Ile Ala Gly Val
            260                 265                 270

Gly Thr Pro Ala Ala Ala Ala Ala Ala Ala Ala Ala Ala Lys Ala Ala
        275                 280                 285

Lys Tyr Gly Ala Ala Ala Gly Leu Val Pro Gly Gly Pro Gly Phe Gly
    290                 295                 300

Pro Gly Val Val Gly Val Pro Gly Ala Gly Val Pro Gly Val Gly Val
305                 310                 315                 320

Pro Gly Ala Gly Ile Pro Val Val Pro Gly Ala Gly Ile Pro Gly Ala
                325                 330                 335

Ala Val Pro Gly Val Val Ser Pro Glu Ala Ala Ala Lys Ala Ala Ala
            340                 345                 350

Lys Ala Ala Lys Tyr Gly Ala Arg Pro Gly Val Gly Val Gly Gly Ile
        355                 360                 365

Pro Thr Tyr Gly Val Gly Ala Gly Gly Phe Pro Gly Phe Gly Val Gly
    370                 375                 380

Val Gly Gly Ile Pro Gly Val Ala Gly Val Pro Gly Val Gly Gly Val
385                 390                 395                 400

Pro Gly Val Gly Gly Val Pro Gly Val Gly Ile Ser Pro Glu Ala Gln
                405                 410                 415

Ala Ala Ala Ala Ala Lys Ala Ala Lys Tyr Gly Ala Ala Gly Ala Gly
            420                 425                 430

Val Leu Gly Gly Leu Val Pro Gly Pro Gln Ala Ala Val Pro Gly Val
        435                 440                 445

Pro Gly Thr Gly Gly Val Pro Gly Val Gly Thr Pro Ala Ala Ala Ala
    450                 455                 460

Ala Lys Ala Ala Ala Lys Ala Ala Gln Phe Gly Leu Val Pro Gly Val
465                 470                 475                 480

Gly Val Ala Pro Gly Val Gly Val Ala Pro Gly Val Gly Val Ala Pro
                485                 490                 495

Gly Val Gly Leu Ala Pro Gly Val Gly Val Ala Pro Gly Val Gly Val
            500                 505                 510

Ala Pro Gly Val Gly Val Ala Pro Gly Ile Gly Pro Gly Gly Val Ala
```

```
        515                 520                 525

Ala Ala Ala Lys Ser Ala Ala Lys Val Ala Ala Lys Ala Gln Leu Arg
    530                 535                 540

Ala Ala Ala Gly Leu Gly Ala Gly Ile Pro Gly Leu Gly Val Gly Val
545                 550                 555                 560

Gly Val Pro Gly Leu Gly Val Gly Ala Gly Val Pro Gly Leu Gly Val
                565                 570                 575

Gly Ala Gly Val Pro Gly Phe Gly Ala Gly Ala Asp Glu Gly Val Arg
            580                 585                 590

Arg Ser Leu Ser Pro Glu Leu Arg Glu Gly Asp Pro Ser Ser Ser Gln
        595                 600                 605

His Leu Pro Ser Thr Pro Ser Ser Pro Arg Val Pro Gly Ala
    610                 615                 620


<210> SEQ ID NO 38
<211> LENGTH: 1869
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

ggtggcgtac caggcgcaat tcctgggggt gtcccaggcg gtgtttttta tccgggcgcc     60

ggtcttggcg cactgggtgg cggtgcactg ggcccgggcg gcaaaccgct gaaaccggta    120

ccaggtggtt tagcaggcgc cggcttaggc gcaggtctgg gagcatttcc ggcagttacc    180

tttccagggg cactggttcc tggaggtgtg gccgatgcag ccgcggcata taaagccgct    240

aaagccggtg cgggtttagg aggcgtccca ggtgtcggtg gcctgggtgt tagcgccggt    300

gcagttgttc cgcagccggg agcagggggtt aaacctggta aagtgccggg agtaggtctg    360

ccaggcgttt atcctggtgg tgttttgccg ggtgcccgtt ttccgggcgt tggtgttctt    420

ccaggcgtgc cgaccggagc cggtgttaaa ccgaaagccc ccggtgttgg aggtgcattt    480

gcaggcatcc cgggagttgg cccgtttggt ggtccgcaac ctggggttcc gttaggttat    540

ccgattaaag caccgaaact gcccggcggt tatggtctgc cgtacacaac cggtaaactg    600

ccgtatggtt atggcccggg tggagttgcg ggtgcagcag gtaaagcggg ttatcctacc    660

ggaaccggtg taggtccgca ggccgctgct gccgccgccg caaaagcagc ggctaaattt    720

ggcgccggag cagcgggtgt tctgcctgga gttggtggtg cgggcgtgcc aggggtacct    780

ggtgcaattc cgggtattgg tggtattgcc ggtgtcggca ccccggccgc ggcagctgcg    840

gcagcggcgg ctgccaaagc tgctaaatac ggtgccgcgg cgggtctggt gccaggaggt    900

ccgggttttg gtccgggagt ggttggcgtg cctggcgcag gcgttcctgg tgtgggcgtt    960

ccaggtgcag ggattcctgt tgtgcctggt gccggtattc ccggcgcggc cgttccgggg   1020

gtggttagcc cggaagccgc agcgaaggct gcggcaaagg cagcaaagta tggcgcacgc   1080

ccaggagtcg gcgtgggtgg tatcccgacc tatggggtgg gcgcaggggg ttttcctggt   1140

ttcggcgtag gtgtaggagg tataccgggc gtggccggtg taccaggggt tggtggcgtc   1200

cctggtgttg gcggtgtgcc aggtgttggt atttcaccgg aagcacaggc agcagccgca   1260

gctaaggcag cgaaatatgg tgccgccggc gcaggagttt taggtgggct ggttccgggc   1320

ccgcaggcag ctgtgccggg ggttccaggc accggtggtg tccctggagt cggtacgccg   1380

gctgcagcgg cagccaaagc ggctgcgaaa gcagcacagt ttggcttagt accgggtgtg   1440
```

-continued

```
ggagttgccc ccggcgttgg cgttgctcca ggggtgggtg ttgctcctgg cgtcggtctg   1500

gctcctggag tgggcgtagc acccggtgtg ggggtggccc cgggtgttgg ggttgcaccg   1560

ggtatcggtc cgggcggtgt cgcagcagca gctaaaagcg cggcgaaagt tgcggccaaa   1620

gcccaactgc gcgccgccgc gggcctcggt gcaggtattc cggggctggg tgtcggagtt   1680

ggagtcccgg gtttgggcgt gggcgcggga gttccgggac tgggagtggg tgccggagtt   1740

cctggctttg gtgcaggcgc agatgaaggt gttcgtcgta gcctgagtcc ggaactgcgt   1800

gaaggtgatc cgagtagcag ccagcatctg ccgagcaccc cgagcagccc gcgtgttccg   1860

ggtgcataa                                                           1869


<210> SEQ ID NO 39
<211> LENGTH: 527
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gly Gly Val Pro Gly Ala Ile Pro Gly Gly Val Pro Gly Gly Val Phe
1               5                   10                  15

Tyr Pro Gly Ala Gly Leu Gly Ala Leu Gly Gly Gly Ala Leu Gly Pro
            20                  25                  30

Gly Gly Lys Pro Leu Lys Pro Val Pro Gly Gly Leu Ala Gly Ala Gly
        35                  40                  45

Leu Gly Ala Gly Leu Gly Ala Phe Pro Ala Val Thr Phe Pro Gly Ala
    50                  55                  60

Leu Val Pro Gly Gly Val Ala Asp Ala Ala Ala Ala Tyr Lys Ala Ala
65                  70                  75                  80

Lys Ala Gly Ala Gly Leu Gly Gly Val Pro Gly Val Gly Gly Leu Gly
                85                  90                  95

Val Ser Ala Gly Ala Val Val Pro Gln Pro Gly Ala Gly Val Lys Pro
            100                 105                 110

Gly Lys Val Pro Gly Val Gly Leu Pro Gly Val Tyr Pro Gly Gly Val
        115                 120                 125

Leu Pro Gly Ala Arg Phe Pro Gly Val Gly Val Leu Pro Gly Val Pro
    130                 135                 140

Thr Gly Ala Gly Val Lys Pro Lys Ala Pro Gly Val Gly Gly Ala Phe
145                 150                 155                 160

Ala Gly Ile Pro Gly Val Gly Pro Phe Gly Gly Pro Gln Pro Gly Val
                165                 170                 175

Pro Leu Gly Tyr Pro Ile Lys Ala Pro Lys Leu Pro Gly Gly Tyr Gly
            180                 185                 190

Leu Pro Tyr Thr Thr Gly Lys Leu Pro Tyr Gly Tyr Gly Pro Gly Gly
        195                 200                 205

Val Ala Gly Ala Ala Gly Lys Ala Gly Tyr Pro Thr Gly Thr Gly Val
    210                 215                 220

Gly Pro Gln Ala Ala Ala Ala Ala Ala Ala Lys Ala Ala Ala Lys Phe
225                 230                 235                 240

Gly Ala Gly Ala Ala Gly Val Leu Pro Gly Val Gly Gly Ala Gly Val
                245                 250                 255

Pro Gly Val Pro Gly Ala Ile Pro Gly Ile Gly Gly Ile Ala Gly Val
            260                 265                 270

Gly Thr Pro Ala Ala Ala Ala Ala Ala Ala Ala Ala Ala Lys Ala Ala
```

-continued

```
        275                 280                 285

Lys Tyr Gly Ala Ala Ala Gly Leu Val Pro Gly Gly Pro Gly Phe Gly
    290                 295                 300

Pro Gly Val Val Gly Val Pro Gly Ala Gly Val Pro Gly Val Gly Val
305                 310                 315                 320

Pro Gly Ala Gly Ile Pro Val Val Pro Gly Ala Gly Ile Pro Gly Ala
                325                 330                 335

Ala Val Pro Gly Val Val Ser Pro Glu Ala Ala Ala Lys Ala Ala Ala
            340                 345                 350

Lys Ala Ala Lys Tyr Gly Ala Arg Pro Gly Val Gly Val Gly Gly Ile
        355                 360                 365

Pro Thr Tyr Gly Val Gly Ala Gly Gly Phe Pro Gly Phe Gly Val Gly
    370                 375                 380

Val Gly Gly Ile Pro Gly Val Ala Gly Val Pro Gly Val Gly Gly Val
385                 390                 395                 400

Pro Gly Val Gly Gly Val Pro Gly Val Gly Ile Ser Pro Glu Ala Gln
                405                 410                 415

Ala Ala Ala Ala Ala Lys Ala Ala Lys Tyr Gly Ala Ala Gly Ala Gly
            420                 425                 430

Val Leu Gly Gly Leu Val Pro Gly Pro Gln Ala Ala Val Pro Gly Val
        435                 440                 445

Pro Gly Thr Gly Gly Val Pro Gly Val Gly Thr Pro Ala Ala Ala Ala
    450                 455                 460

Ala Lys Ala Ala Ala Lys Ala Ala Gln Phe Gly Leu Val Pro Gly Val
465                 470                 475                 480

Gly Val Ala Pro Gly Val Gly Val Ala Pro Gly Val Gly Val Ala Pro
                485                 490                 495

Gly Val Gly Leu Ala Pro Gly Val Gly Val Ala Pro Gly Val Gly Val
            500                 505                 510

Ala Pro Gly Val Gly Val Ala Pro Gly Ile Gly Pro Gly Gly Val
        515                 520                 525
```

<210> SEQ ID NO 40
<211> LENGTH: 1584
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 40

```
ggtggcgtac caggcgcaat tcctgggggt gtcccaggcg gtgtttttta tccgggcgcc      60

ggtcttggcg cactgggtgg cggtgcactg ggcccgggcg gcaaaccgct gaaaccggta     120

ccaggtggtt tagcaggcgc cggcttaggc gcaggtctgg gagcatttcc ggcagttacc     180

tttccagggg cactggttcc tggaggtgtg gccgatgcag ccgcggcata taaagccgct     240

aaagccggtg cgggtttagg aggcgtccca ggtgtcggtg gcctgggtgt tagcgccggt     300

gcagttgttc cgcagccggg agcagggggtt aaacctggta aagtgccggg agtaggtctg     360

ccaggcgttt atcctggtgg tgttttgccg ggtgcccgtt ttccgggcgt tggtgttctt     420

ccaggcgtgc cgaccggagc cggtgttaaa ccgaaagccc ccggtgttgg aggtgcattt     480

gcaggcatcc cgggagttgg cccgtttggt ggtccgcaac ctggggttcc gttaggttat     540

ccgattaaag caccgaaact gcccggcggt tatggtctgc cgtacacaac cggtaaactg     600

ccgtatggtt atggcccggg tggagttgcg ggtgcagcag gtaaagcggg ttatcctacc     660
```

-continued

```
ggaaccggtg taggtccgca ggccgctgct gccgccgccg caaaagcagc ggctaaattt    720

ggcgccggag cagcgggtgt tctgcctgga gttggtggtg cgggcgtgcc aggggtacct    780

ggtgcaattc cgggtattgg tggtattgcc ggtgtcggca ccccggccgc ggcagctgcg    840

gcagcggcgg ctgccaaagc tgctaaatac ggtgccgcgg cgggtctggt gccaggaggt    900

ccgggttttg gtccgggagt ggttggcgtg cctggcgcag gcgttcctgg tgtgggcgtt    960

ccaggtgcag ggattcctgt tgtgcctggt gccggtattc ccggcgcggc cgttccgggg   1020

gtggttagcc cggaagccgc agcgaaggct gcggcaaagg cagcaaagta tggcgcacgc   1080

ccaggagtcg gcgtgggtgg tatcccgacc tatggggtgg gcgcaggggg ttttcctggt   1140

ttcggcgtag gtgtaggagg tataccgggc gtggccggtg taccaggggt tggtggcgtc   1200

cctggtgttg gcggtgtgcc aggtgttggt atttcaccgg aagcacaggc agcagccgca   1260

gctaaggcag cgaaatatgg tgccgccggc gcaggagttt taggtgggct ggttccgggc   1320

ccgcaggcag ctgtgccggg ggttccaggc accggtggtg tccctggagt cggtacgccg   1380

gctgcagcgg cagccaaagc ggctgcgaaa gcagcacagt ttggcttagt accgggtgtg   1440

ggagttgccc ccggcgttgg cgttgctcca ggggtgggtg ttgctcctgg cgtcggtctg   1500

gctcctggag tgggcgtagc acccggtgtg gggtggcccc cggtgttgg ggttgcaccg    1560

ggtatcggtc cgggcggtgt ctaa                                          1584


<210> SEQ ID NO 41
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gly Val Leu Pro Gly Val Gly Gly Ala Gly Val Pro Gly Val Pro Gly
1               5                   10                  15

Ala Ile Pro Gly Ile Gly Gly Ile Ala Gly Val Gly Thr Pro Ala Ala
            20                  25                  30

Ala Ala Ala Ala Ala Ala Ala Ala Lys Ala Ala Lys Tyr Gly Ala Ala
        35                  40                  45

Ala Gly Leu Val Pro Gly Gly Pro Gly Phe Gly Pro Gly Val Val Gly
    50                  55                  60

Val Pro Gly Ala Gly Val Pro Gly Val Gly Val Pro Gly Ala Gly Ile
65                  70                  75                  80

Pro Val Val Pro Gly Ala Gly Ile Pro Gly Ala Ala Val Pro Gly Val
                85                  90                  95

Val Ser Pro Glu Ala Ala Ala Lys Ala Ala Ala Lys Ala Ala Lys Tyr
            100                 105                 110

Gly Ala Arg Pro Gly Val Gly Val Gly Gly Ile Pro Thr Tyr Gly Val
        115                 120                 125

Gly Ala Gly Gly Phe Pro Gly Phe Gly Val Gly Val Gly Gly Ile Pro
    130                 135                 140

Gly Val Ala Gly Val Pro Gly Val Gly Gly Val Pro Gly Val Gly Gly
145                 150                 155                 160

Val Pro Gly Val Gly Ile Ser Pro Glu Ala Gln Ala Ala Ala Ala Ala
                165                 170                 175

Lys Ala Ala Lys Tyr Gly Ala Ala Gly Ala Gly Val Leu Gly Gly Leu
            180                 185                 190
```

```
Val Pro Gly Pro Gln Ala Ala Val Pro Gly Val Pro Gly Thr Gly Gly
        195                 200                 205

Val Pro Gly Val Gly Thr Pro Ala Ala Ala Ala Ala Lys Ala Ala Ala
    210                 215                 220

Lys Ala Ala Gln Phe Gly Leu Val Pro Gly Val Gly Val Ala Pro Gly
225                 230                 235                 240

Val Gly Val Ala Pro Gly Val Gly Val Ala Pro Gly Val Gly Leu Ala
                245                 250                 255

Pro Gly Val Gly Val Ala Pro Gly Val Gly Val Ala Pro Gly Val Gly
            260                 265                 270

Val Ala Pro Gly Ile Gly Pro Gly Gly Val Ala Ala Ala Ala Lys Ser
        275                 280                 285

Ala Ala Lys Val Ala Ala Lys Ala Gln Leu Arg Ala Ala Ala Gly Leu
    290                 295                 300

Gly Ala Gly Ile Pro Gly Leu Gly Val Gly Val Gly Val Pro Gly Leu
305                 310                 315                 320

Gly Val Gly Ala Gly Val Pro Gly Leu Gly Val Gly Ala Gly Val Pro
                325                 330                 335

Gly Phe Gly Ala Gly Ala Asp Glu Gly Val Arg Arg Ser Leu Ser Pro
            340                 345                 350

Glu Leu Arg Glu Gly Asp Pro Ser Ser Ser Gln His Leu Pro Ser Thr
        355                 360                 365

Pro Ser Ser Pro Arg Val Pro Gly Ala Leu Ala Ala Ala Lys Ala Ala
    370                 375                 380

Lys Tyr Gly Ala Ala Val Pro Gly Val Leu Gly Gly Leu Gly Ala Leu
385                 390                 395                 400

Gly Gly Val Gly Ile Pro Gly Gly Val Val Gly Ala Gly Pro Ala Ala
                405                 410                 415

Ala Ala Ala Ala Ala Lys Ala Ala Ala Lys Ala Ala Gln Phe Gly Leu
            420                 425                 430

Val Gly Ala Ala Gly Leu Gly Gly Leu Gly Val Gly Gly Leu Gly Val
        435                 440                 445

Pro Gly Val Gly Gly Leu Gly Gly Ile Pro Pro Ala Ala Ala Ala Lys
    450                 455                 460

Ala Ala Lys Tyr Gly Ala Ala Gly Leu Gly Gly Val Leu Gly Gly Ala
465                 470                 475                 480

Gly Gln Phe Pro Leu Gly Gly Val Ala Ala Arg Pro Gly Phe Gly Leu
                485                 490                 495

Ser Pro Ile Phe Pro Gly Gly Ala Cys Leu Gly Lys Ala Cys Gly Arg
            500                 505                 510

Lys Arg Lys
        515
```

<210> SEQ ID NO 42
<211> LENGTH: 1548
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 42

```
ggtgttctgc ctggagttgg tggtgcgggc gtgccagggg tacctggtgc aattccgggt      60

attggtggta ttgccggtgt cggcaccccg gccgcggcag ctgcggcagc ggcggctgcc     120
```

```
aaagctgcta aatacggtgc cgcggcgggt ctggtgccag gaggtccggg ttttggtccg    180
ggagtggttg gcgtgcctgg cgcaggcgtt cctggtgtgg gcgttccagg tgcagggatt    240
cctgttgtgc ctggtgccgg tattcccggc gcggccgttc cgggggtggt tagcccggaa    300
gccgcagcga aggctgcggc aaaggcagca aagtatggcg cacgcccagg agtcggcgtg    360
ggtggtatcc cgacctatgg ggtgggcgca gggggttttc ctggtttcgg cgtaggtgta    420
ggaggtatac cgggcgtggc cggtgtacca ggggttggtg gcgtccctgg tgttggcggt    480
gtgccaggtg ttggtatttc accggaagca caggcagcag ccgcagctaa ggcagcgaaa    540
tatggtgccg ccggcgcagg agttttaggt gggctggttc cgggcccgca ggcagctgtg    600
ccgggggttc caggcaccgg tggtgtccct ggagtcggta cgccggctgc agcggcagcc    660
aaagcggctg cgaaagcagc acagtttggc ttagtaccgg gtgtgggagt tgccccccggc    720
gttggcgttg ctccaggggt gggtgttgct cctggcgtcg gtctggctcc tggagtgggc    780
gtagcacccg gtgtgggggt ggccccgggt gttggggttg caccgggtat cggtccgggc    840
ggtgtcgcag cagcagctaa aagcgcggcg aaagttgcgg ccaaagccca actgcgcgcc    900
gccgcgggcc tcggtgcagg tattccgggg ctgggtgtcg gagttggagt cccgggtttg    960
ggcgtgggcg cgggagttcc gggactggga gtgggtgccg gagttcctgg ctttggtgca   1020
ggcgcagatg aaggtgttcg tcgtagcctg agtccggaac tgcgtgaagg tgatccgagt   1080
agcagccagc atctgccgag caccccgagc agcccgcgtg ttccgggtgc attagctgca   1140
gcaaaagccg ccaagtatgg tgcagccgtg ccgggcgtct taggtggtct gggcgccctg   1200
ggtggtgtag gcattccggg aggtgttgtg ggtgcaggac cggccgccgc agctgcggcc   1260
gccaaagcag ctgcaaaagc ggcccagttt ggtttagtgg gcgccgcagg tttaggcggt   1320
ttaggtgtgg gtggactggg tgtacctggc gtaggcggtc tgggtggaat tccgcccgca   1380
gcggccgcga aagcggcaaa atatggcgcg gcaggcctgg gcggcgtgct gggtggggca   1440
ggtcagtttc cgctgggcgg ggttgccgca cgtccgggat ttggtctgag cccgattttc   1500
cctggcggcg catgtctggg taaagcatgt ggtcgtaaac gtaaataa                1548
```

<210> SEQ ID NO 43
<211> LENGTH: 466
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 43

```
Gly Leu Val Pro Gly Gly Pro Gly Phe Gly Pro Gly Val Val Gly Val
1               5                   10                  15

Pro Gly Ala Gly Val Pro Gly Val Gly Val Pro Gly Ala Gly Ile Pro
            20                  25                  30

Val Val Pro Gly Ala Gly Ile Pro Gly Ala Ala Val Pro Gly Val Val
        35                  40                  45

Ser Pro Glu Ala Ala Ala Lys Ala Ala Ala Lys Ala Ala Lys Tyr Gly
    50                  55                  60

Ala Arg Pro Gly Val Gly Val Gly Gly Ile Pro Thr Tyr Gly Val Gly
65                  70                  75                  80

Ala Gly Gly Phe Pro Gly Phe Gly Val Gly Val Gly Gly Ile Pro Gly
                85                  90                  95

Val Ala Gly Val Pro Gly Val Gly Gly Val Pro Gly Val Gly Gly Val
            100                 105                 110
```

-continued

```
Pro Gly Val Gly Ile Ser Pro Glu Ala Gln Ala Ala Ala Ala Ala Lys
        115                 120                 125

Ala Ala Lys Tyr Gly Ala Ala Gly Ala Gly Val Leu Gly Gly Leu Val
    130                 135                 140

Pro Gly Pro Gln Ala Ala Val Pro Gly Val Pro Gly Thr Gly Gly Val
145                 150                 155                 160

Pro Gly Val Gly Thr Pro Ala Ala Ala Ala Ala Lys Ala Ala Ala Lys
                165                 170                 175

Ala Ala Gln Phe Gly Leu Val Pro Gly Val Gly Val Ala Pro Gly Val
            180                 185                 190

Gly Val Ala Pro Gly Val Gly Val Ala Pro Gly Val Gly Leu Ala Pro
        195                 200                 205

Gly Val Gly Val Ala Pro Gly Val Gly Val Ala Pro Gly Val Gly Val
    210                 215                 220

Ala Pro Gly Ile Gly Pro Gly Gly Val Ala Ala Ala Ala Lys Ser Ala
225                 230                 235                 240

Ala Lys Val Ala Ala Lys Ala Gln Leu Arg Ala Ala Ala Gly Leu Gly
                245                 250                 255

Ala Gly Ile Pro Gly Leu Gly Val Gly Val Gly Val Pro Gly Leu Gly
            260                 265                 270

Val Gly Ala Gly Val Pro Gly Leu Gly Val Gly Ala Gly Val Pro Gly
        275                 280                 285

Phe Gly Ala Gly Ala Asp Glu Gly Val Arg Arg Ser Leu Ser Pro Glu
    290                 295                 300

Leu Arg Glu Gly Asp Pro Ser Ser Ser Gln His Leu Pro Ser Thr Pro
305                 310                 315                 320

Ser Ser Pro Arg Val Pro Gly Ala Leu Ala Ala Ala Lys Ala Ala Lys
                325                 330                 335

Tyr Gly Ala Ala Val Pro Gly Val Leu Gly Gly Leu Gly Ala Leu Gly
            340                 345                 350

Gly Val Gly Ile Pro Gly Gly Val Val Gly Ala Gly Pro Ala Ala Ala
        355                 360                 365

Ala Ala Ala Ala Lys Ala Ala Ala Lys Ala Ala Gln Phe Gly Leu Val
    370                 375                 380

Gly Ala Ala Gly Leu Gly Gly Leu Gly Val Gly Gly Leu Gly Val Pro
385                 390                 395                 400

Gly Val Gly Gly Leu Gly Gly Ile Pro Pro Ala Ala Ala Ala Lys Ala
                405                 410                 415

Ala Lys Tyr Gly Ala Ala Gly Leu Gly Gly Val Leu Gly Gly Ala Gly
            420                 425                 430

Gln Phe Pro Leu Gly Gly Val Ala Ala Arg Pro Gly Phe Gly Leu Ser
        435                 440                 445

Pro Ile Phe Pro Gly Gly Ala Cys Leu Gly Lys Ala Cys Gly Arg Lys
    450                 455                 460

Arg Lys
465
```

<210> SEQ ID NO 44
<211> LENGTH: 1401
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 44
ggtctggtgc caggaggtcc gggttttggt ccgggagtgg ttggcgtgcc tggcgcaggc 60
gttcctggtg tgggcgttcc aggtgcaggg attcctgttg tgcctggtgc cggtattccc 120
ggcgcggccg ttccgggggt ggttagcccg gaagccgcag cgaaggctgc ggcaaaggca 180
gcaaagtatg gcgcacgccc aggagtcggc gtgggtggta tcccgaccta tggggtgggc 240
gcagggggtt ttcctggttt cggcgtaggt gtaggaggta taccgggcgt ggccggtgta 300
ccaggggttg gtggcgtccc tggtgttggc ggtgtgccag gtgttggtat ttcaccggaa 360
gcacaggcag cagccgcagc taaggcagcg aaatatggtg ccgccggcgc aggagtttta 420
ggtgggctgg ttccgggccc gcaggcagct gtgccggggg ttccaggcac cggtggtgtc 480
cctggagtcg gtacgccggc tgcagcggca gccaaagcgg ctgcgaaagc agcacagttt 540
ggcttagtac cgggtgtggg agttgccccc ggcgttggcg ttgctccagg ggtgggtgtt 600
gctcctggcg tcggtctggc tcctggagtg ggcgtagcac ccggtgtggg ggtggccccg 660
ggtgttgggg ttgcaccggg tatcggtccg ggcggtgtcg cagcagcagc taaaagcgcg 720
gcgaaagttg cggccaaagc ccaactgcgc gccgccgcgg gcctcggtgc aggtattccg 780
gggctgggtg tcggagttgg agtcccgggt ttgggcgtgg gcgcgggagt tccgggactg 840
ggagtgggtg ccggagttcc tggctttggt gcaggcgcag atgaaggtgt tcgtcgtagc 900
ctgagtccgg aactgcgtga aggtgatccg agtagcagcc agcatctgcc gagcaccccg 960
agcagcccgc gtgttccggg tgcattagct gcagcaaaag ccgccaagta tggtgcagcc 1020
gtgccgggcg tcttaggtgg tctgggcgcc ctgggtggtg taggcattcc gggaggtgtt 1080
gtgggtgcag gaccggccgc cgcagctgcg gccgccaaag cagctgcaaa agcggcccag 1140
tttggtttag tgggcgccgc aggtttaggc ggtttaggtg tgggtggact gggtgtacct 1200
ggcgtaggcg gtctgggtgg aattccgccc gcagcggccg cgaaagcggc aaaatatggc 1260
gcggcaggcc tgggcggcgt gctgggtggg gcaggtcagt ttccgctggg cggggttgcc 1320
gcacgtccgg gatttggtct gagcccgatt ttccctggcg gcgcatgtct gggtaaagca 1380
tgtggtcgta aacgtaaata a 1401

<210> SEQ ID NO 45
<211> LENGTH: 460
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

Gly Gly Val Pro Gly Ala Ile Pro Gly Gly Val Pro Gly Gly Val Phe
1 5 10 15

Tyr Pro Gly Ala Gly Leu Gly Ala Leu Gly Gly Gly Ala Leu Gly Pro
20 25 30

Gly Gly Lys Pro Leu Lys Pro Val Pro Gly Gly Leu Ala Gly Ala Gly
35 40 45

Leu Gly Ala Gly Leu Gly Ala Phe Pro Ala Val Thr Phe Pro Gly Ala
50 55 60

Leu Val Pro Gly Gly Val Ala Asp Ala Ala Ala Ala Tyr Lys Ala Ala
65 70 75 80

Lys Ala Gly Ala Gly Leu Gly Gly Val Pro Gly Val Gly Gly Leu Gly
85 90 95

```
Val Ser Ala Gly Ala Val Val Pro Gln Pro Gly Ala Gly Val Lys Pro
            100                 105                 110

Gly Lys Val Pro Gly Val Gly Leu Pro Gly Val Tyr Pro Gly Gly Val
        115                 120                 125

Leu Pro Gly Ala Arg Phe Pro Gly Val Gly Val Leu Pro Gly Val Pro
    130                 135                 140

Thr Gly Ala Gly Val Lys Pro Lys Ala Pro Gly Val Gly Gly Ala Phe
145                 150                 155                 160

Ala Gly Ile Pro Gly Val Gly Pro Phe Gly Gly Pro Gln Pro Gly Val
                165                 170                 175

Pro Leu Gly Tyr Pro Ile Lys Ala Pro Lys Leu Pro Gly Gly Tyr Gly
            180                 185                 190

Leu Pro Tyr Thr Thr Gly Lys Leu Pro Tyr Gly Tyr Gly Pro Gly Gly
        195                 200                 205

Val Ala Gly Ala Ala Gly Lys Ala Gly Tyr Pro Thr Gly Thr Gly Val
    210                 215                 220

Gly Pro Gln Ala Ala Ala Ala Ala Ala Ala Lys Ala Ala Ala Lys Phe
225                 230                 235                 240

Gly Ala Gly Ala Ala Gly Val Leu Pro Gly Val Gly Gly Ala Gly Val
                245                 250                 255

Pro Gly Val Pro Gly Ala Ile Pro Gly Ile Gly Gly Ile Ala Gly Val
            260                 265                 270

Gly Thr Pro Ala Ala Ala Ala Ala Ala Ala Ala Ala Ala Lys Ala Ala
        275                 280                 285

Lys Tyr Gly Ala Ala Ala Gly Leu Val Pro Gly Gly Pro Gly Phe Gly
    290                 295                 300

Pro Gly Val Val Gly Val Pro Gly Ala Gly Val Pro Gly Val Gly Val
305                 310                 315                 320

Pro Gly Ala Gly Ile Pro Val Val Pro Gly Ala Gly Ile Pro Gly Ala
                325                 330                 335

Ala Val Pro Gly Val Val Ser Pro Glu Ala Ala Ala Lys Ala Ala Ala
            340                 345                 350

Lys Ala Ala Lys Tyr Gly Ala Arg Pro Gly Val Gly Val Gly Gly Ile
        355                 360                 365

Pro Thr Tyr Gly Val Gly Ala Gly Gly Phe Pro Gly Phe Gly Val Gly
    370                 375                 380

Val Gly Gly Ile Pro Gly Val Ala Gly Val Pro Gly Val Gly Gly Val
385                 390                 395                 400

Pro Gly Val Gly Gly Val Pro Gly Val Gly Ile Ser Pro Glu Ala Gln
                405                 410                 415

Ala Ala Ala Ala Ala Lys Ala Ala Lys Tyr Gly Ala Ala Gly Ala Gly
            420                 425                 430

Val Leu Gly Gly Leu Val Pro Gly Pro Gln Ala Ala Val Pro Gly Val
        435                 440                 445

Pro Gly Thr Gly Gly Val Pro Gly Val Gly Thr Pro
    450                 455                 460
```

<210> SEQ ID NO 46
<211> LENGTH: 1383
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 46

```
ggtggcgtac caggcgcaat tcctgggggt gtcccaggcg gtgtttttta tccgggcgcc     60

ggtcttggcg cactgggtgg cggtgcactg ggcccgggcg gcaaaccgct gaaaccggta    120

ccaggtggtt tagcaggcgc cggcttaggc gcaggtctgg gagcatttcc ggcagttacc    180

tttccagggg cactggttcc tggaggtgtg gccgatgcag ccgcggcata taaagccgct    240

aaagccggtg cgggtttagg aggcgtccca ggtgtcggtg gcctgggtgt tagcgccggt    300

gcagttgttc cgcagccggg agcaggggtt aaacctggta aagtgccggg agtaggtctg    360

ccaggcgttt atcctggtgg tgttttgccg ggtgcccgtt ttccgggcgt tggtgttctt    420

ccaggcgtgc cgaccggagc cggtgttaaa ccgaaagccc ccggtgttgg aggtgcattt    480

gcaggcatcc cgggagttgg cccgtttggt ggtccgcaac ctggggttcc gttaggttat    540

ccgattaaag caccgaaact gcccggcggt tatggtctgc cgtacacaac cggtaaactg    600

ccgtatggtt atggcccggg tggagttgcg ggtgcagcag gtaaagcggg ttatcctacc    660

ggaaccggtg taggtccgca ggccgctgct gccgccgccg caaaagcagc ggctaaattt    720

ggcgccggag cagcgggtgt tctgcctgga gttggtggtg cgggcgtgcc aggggtacct    780

ggtgcaattc cgggtattgg tggtattgcc ggtgtcggca ccccggccgc ggcagctgcg    840

gcagcggcgg ctgccaaagc tgctaaatac ggtgccgcgg cgggtctggt gccaggaggt    900

ccgggttttg gtccgggagt ggttggcgtg cctggcgcag gcgttcctgg tgtgggcgtt    960

ccaggtgcag ggattcctgt tgtgcctggt gccggtattc ccggcgcggc cgttccgggg   1020

gtggttagcc cggaagccgc agcgaaggct gcggcaaagg cagcaaagta tggcgcacgc   1080

ccaggagtcg gcgtgggtgg tatcccgacc tatggggtgg gcgcaggggg ttttcctggt   1140

ttcggcgtag gtgtaggagg tataccgggc gtggccggtg taccaggggt tggtggcgtc   1200

cctggtgttg gcggtgtgcc aggtgttggt atttcaccgg aagcacaggc agcagccgca   1260

gctaaggcag cgaaatatgg tgccgccggc gcaggagttt taggtgggct ggttccgggc   1320

ccgcaggcag ctgtgccggg ggttccaggc accggtggtg tccctggagt cggtacgccg   1380

taa                                                                 1383
```

<210> SEQ ID NO 47
<211> LENGTH: 416
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Gly Gly Val Pro Gly Ala Ile Pro Gly Gly Val Pro Gly Gly Val Phe
1               5                   10                  15

Tyr Pro Gly Ala Gly Leu Gly Ala Leu Gly Gly Gly Ala Leu Gly Pro
            20                  25                  30

Gly Gly Lys Pro Leu Lys Pro Val Pro Gly Gly Leu Ala Gly Ala Gly
        35                  40                  45

Leu Gly Ala Gly Leu Gly Ala Phe Pro Ala Val Thr Phe Pro Gly Ala
    50                  55                  60

Leu Val Pro Gly Gly Val Ala Asp Ala Ala Ala Ala Tyr Lys Ala Ala
65                  70                  75                  80

Lys Ala Gly Ala Gly Leu Gly Gly Val Pro Gly Val Gly Gly Leu Gly
                85                  90                  95

Val Ser Ala Gly Ala Val Val Pro Gln Pro Gly Ala Gly Val Lys Pro
```

```
            100                 105                 110

Gly Lys Val Pro Gly Val Gly Leu Pro Gly Val Tyr Pro Gly Gly Val
        115                 120                 125

Leu Pro Gly Ala Arg Phe Pro Gly Val Gly Val Leu Pro Gly Val Pro
    130                 135                 140

Thr Gly Ala Gly Val Lys Pro Lys Ala Pro Gly Val Gly Gly Ala Phe
145                 150                 155                 160

Ala Gly Ile Pro Gly Val Gly Pro Phe Gly Gly Pro Gln Pro Gly Val
                165                 170                 175

Pro Leu Gly Tyr Pro Ile Lys Ala Pro Lys Leu Pro Gly Gly Tyr Gly
            180                 185                 190

Leu Pro Tyr Thr Thr Gly Lys Leu Pro Tyr Gly Tyr Gly Pro Gly Gly
        195                 200                 205

Val Ala Gly Ala Ala Gly Lys Ala Gly Tyr Pro Thr Gly Thr Gly Val
    210                 215                 220

Gly Pro Gln Ala Ala Ala Ala Ala Ala Ala Lys Ala Ala Ala Lys Phe
225                 230                 235                 240

Gly Ala Gly Ala Ala Gly Val Leu Pro Gly Val Gly Gly Ala Gly Val
                245                 250                 255

Pro Gly Val Pro Gly Ala Ile Pro Gly Ile Gly Gly Ile Ala Gly Val
            260                 265                 270

Gly Thr Pro Ala Ala Ala Ala Ala Ala Ala Ala Ala Ala Lys Ala Ala
        275                 280                 285

Lys Tyr Gly Ala Ala Ala Gly Leu Val Pro Gly Gly Pro Gly Phe Gly
    290                 295                 300

Pro Gly Val Val Gly Val Pro Gly Ala Gly Val Pro Gly Val Gly Val
305                 310                 315                 320

Pro Gly Ala Gly Ile Pro Val Val Pro Gly Ala Gly Ile Pro Gly Ala
                325                 330                 335

Ala Val Pro Gly Val Val Ser Pro Glu Ala Ala Ala Lys Ala Ala Ala
            340                 345                 350

Lys Ala Ala Lys Tyr Gly Ala Arg Pro Gly Val Gly Val Gly Gly Ile
        355                 360                 365

Pro Thr Tyr Gly Val Gly Ala Gly Gly Phe Pro Gly Phe Gly Val Gly
    370                 375                 380

Val Gly Gly Ile Pro Gly Val Ala Gly Val Pro Gly Val Gly Gly Val
385                 390                 395                 400

Pro Gly Val Gly Gly Val Pro Gly Val Gly Ile Ser Pro Glu Ala Gln
                405                 410                 415
```

<210> SEQ ID NO 48
<211> LENGTH: 1251
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48

```
ggtggcgtac caggcgcaat tcctgggggt gtcccaggcg gtgtttttta tccgggcgcc      60

ggtcttggcg cactgggtgg cggtgcactg ggcccgggcg gcaaaccgct gaaaccggta     120

ccaggtggtt tagcaggcgc cggcttaggc gcaggtctgg gagcatttcc ggcagttacc     180

tttccagggg cactggttcc tggaggtgtg gccgatgcag ccgcggcata taaagccgct     240

aaagccggtg cgggtttagg aggcgtccca ggtgtcggtg gcctgggtgt tagcgccggt     300
```

-continued

```
gcagttgttc cgcagccggg agcaggggtt aaacctggta aagtgccggg agtaggtctg    360

ccaggcgttt atcctggtgg tgttttgccg ggtgcccgtt ttccgggcgt tggtgttctt    420

ccaggcgtgc cgaccggagc cggtgttaaa ccgaaagccc ccggtgttgg aggtgcattt    480

gcaggcatcc cgggagttgg cccgtttggt ggtccgcaac ctggggttcc gttaggttat    540

ccgattaaag caccgaaact gcccggcggt tatggtctgc cgtacacaac cggtaaactg    600

ccgtatggtt atggcccggg tggagttgcg ggtgcagcag gtaaagcggg ttatcctacc    660

ggaaccggtg taggtccgca ggccgctgct gccgccgccg caaaagcagc ggctaaattt    720

ggcgccggag cagcgggtgt tctgcctgga gttggtggtg cgggcgtgcc aggggtacct    780

ggtgcaattc cgggtattgg tggtattgcc ggtgtcggca ccccggccgc ggcagctgcg    840

gcagcggcgg ctgccaaagc tgctaaatac ggtgccgcgg cgggtctggt gccaggaggt    900

ccgggttttg gtccgggagt ggttggcgtg cctggcgcag gcgttcctgg tgtgggcgtt    960

ccaggtgcag ggattcctgt tgtgcctggt gccggtattc ccggcgcggc cgttccgggg   1020

gtggttagcc cggaagccgc agcgaaggct gcggcaaagg cagcaaagta tggcgcacgc   1080

ccaggagtcg gcgtgggtgg tatcccgacc tatggggtgg gcgcaggggg ttttcctggt   1140

ttcggcgtag gtgtaggagg tataccgggc gtggccggtg taccaggggt tggtggcgtc   1200

cctggtgttg gcggtgtgcc aggtgttggt atttcaccgg aagcacagta a            1251
```

```
<210> SEQ ID NO 49
<211> LENGTH: 401
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Arg Pro Gly Val Gly Val Gly Gly Ile Pro Thr Tyr Gly Val Gly Ala
1               5                   10                  15

Gly Gly Phe Pro Gly Phe Gly Val Gly Val Gly Gly Ile Pro Gly Val
            20                  25                  30

Ala Gly Val Pro Gly Val Gly Gly Val Pro Gly Val Gly Gly Val Pro
        35                  40                  45

Gly Val Gly Ile Ser Pro Glu Ala Gln Ala Ala Ala Ala Ala Lys Ala
    50                  55                  60

Ala Lys Tyr Gly Ala Ala Gly Ala Gly Val Leu Gly Gly Leu Val Pro
65                  70                  75                  80

Gly Pro Gln Ala Ala Val Pro Gly Val Pro Gly Thr Gly Gly Val Pro
                85                  90                  95

Gly Val Gly Thr Pro Ala Ala Ala Ala Ala Lys Ala Ala Ala Lys Ala
            100                 105                 110

Ala Gln Phe Gly Leu Val Pro Gly Val Gly Val Ala Pro Gly Val Gly
        115                 120                 125

Val Ala Pro Gly Val Gly Val Ala Pro Gly Val Gly Leu Ala Pro Gly
    130                 135                 140

Val Gly Val Ala Pro Gly Val Gly Val Ala Pro Gly Val Gly Val Ala
145                 150                 155                 160

Pro Gly Ile Gly Pro Gly Gly Val Ala Ala Ala Lys Ser Ala Ala
                165                 170                 175

Lys Val Ala Ala Lys Ala Gln Leu Arg Ala Ala Ala Gly Leu Gly Ala
            180                 185                 190
```

```
Gly Ile Pro Gly Leu Gly Val Gly Val Gly Val Pro Gly Leu Gly Val
        195                 200                 205

Gly Ala Gly Val Pro Gly Leu Gly Val Gly Ala Gly Val Pro Gly Phe
    210                 215                 220

Gly Ala Gly Ala Asp Glu Gly Val Arg Arg Ser Leu Ser Pro Glu Leu
225                 230                 235                 240

Arg Glu Gly Asp Pro Ser Ser Ser Gln His Leu Pro Ser Thr Pro Ser
                245                 250                 255

Ser Pro Arg Val Pro Gly Ala Leu Ala Ala Ala Lys Ala Ala Lys Tyr
            260                 265                 270

Gly Ala Ala Val Pro Gly Val Leu Gly Gly Leu Gly Ala Leu Gly Gly
        275                 280                 285

Val Gly Ile Pro Gly Gly Val Val Gly Ala Gly Pro Ala Ala Ala Ala
    290                 295                 300

Ala Ala Ala Lys Ala Ala Ala Lys Ala Ala Gln Phe Gly Leu Val Gly
305                 310                 315                 320

Ala Ala Gly Leu Gly Gly Leu Gly Val Gly Gly Leu Gly Val Pro Gly
                325                 330                 335

Val Gly Gly Leu Gly Gly Ile Pro Pro Ala Ala Ala Ala Lys Ala Ala
            340                 345                 350

Lys Tyr Gly Ala Ala Gly Leu Gly Gly Val Leu Gly Gly Ala Gly Gln
        355                 360                 365

Phe Pro Leu Gly Gly Val Ala Ala Arg Pro Gly Phe Gly Leu Ser Pro
    370                 375                 380

Ile Phe Pro Gly Gly Ala Cys Leu Gly Lys Ala Cys Gly Arg Lys Arg
385                 390                 395                 400

Lys
```

<210> SEQ ID NO 50
<211> LENGTH: 1206
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50

```
cgcccaggag tcggcgtggg tggtatcccg acctatgggg tgggcgcagg gggttttcct     60

ggtttcggcg taggtgtagg aggtataccg ggcgtggccg gtgtaccagg ggttggtggc    120

gtccctggtg ttggcggtgt gccaggtgtt ggtatttcac cggaagcaca ggcagcagcc    180

gcagctaagg cagcgaaata tggtgccgcc ggcgcaggag ttttaggtgg gctggttccg    240

ggcccgcagg cagctgtgcc gggggttcca ggcaccggtg gtgtccctgg agtcggtacg    300

ccggctgcag cggcagccaa agcggctgcg aaagcagcac agtttggctt agtaccgggt    360

gtgggagttg cccccggcgt tggcgttgct ccaggggtgg gtgttgctcc tggcgtcggt    420

ctggctcctg gagtgggcgt agcacccggt gtgggggtgg ccccgggtgt tggggttgca    480

ccgggtatcg gtccgggcgg tgtcgcagca gcagctaaaa gcgcggcgaa agttgcggcc    540

aaagcccaac tgcgcgccgc cgcgggcctc ggtgcaggta ttccggggct gggtgtcgga    600

gttggagtcc cgggtttggg cgtgggcgcg ggagttccgg gactgggagt gggtgccgga    660

gttcctggct ttggtgcagg cgcagatgaa ggtgttcgtc gtagcctgag tccggaactg    720

cgtgaaggtg atccgagtag cagccagcat ctgccgagca ccccgagcag cccgcgtgtt    780
```

-continued

```
ccgggtgcat tagctgcagc aaaagccgcc aagtatggtg cagccgtgcc gggcgtctta    840

ggtggtctgg gcgccctggg tggtgtaggc attccgggag gtgttgtggg tgcaggaccg    900

gccgccgcag ctgcggccgc caaagcagct gcaaaagcgg cccagtttgg tttagtgggc    960

gccgcaggtt taggcggttt aggtgtgggt ggactgggtg tacctggcgt aggcggtctg   1020

ggtggaattc cgcccgcagc ggccgcgaaa gcggcaaaat atggcgcggc aggcctgggc   1080

ggcgtgctgg gtggggcagg tcagtttccg ctgggcgggg ttgccgcacg tccgggattt   1140

ggtctgagcc cgattttccc tggcggcgca tgtctgggta aagcatgtgg tcgtaaacgt   1200

aaataa                                                              1206


<210> SEQ ID NO 51
<211> LENGTH: 371
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gly Gly Val Pro Gly Ala Ile Pro Gly Gly Val Pro Gly Gly Val Phe
1               5                   10                  15

Tyr Pro Gly Ala Gly Leu Gly Ala Leu Gly Gly Gly Ala Leu Gly Pro
            20                  25                  30

Gly Gly Lys Pro Leu Lys Pro Val Pro Gly Gly Leu Ala Gly Ala Gly
        35                  40                  45

Leu Gly Ala Gly Leu Gly Ala Phe Pro Ala Val Thr Phe Pro Gly Ala
    50                  55                  60

Leu Val Pro Gly Gly Val Ala Asp Ala Ala Ala Ala Tyr Lys Ala Ala
65                  70                  75                  80

Lys Ala Gly Ala Gly Leu Gly Gly Val Pro Gly Val Gly Gly Leu Gly
                85                  90                  95

Val Ser Ala Gly Ala Val Val Pro Gln Pro Gly Ala Gly Val Lys Pro
            100                 105                 110

Gly Lys Val Pro Gly Val Gly Leu Pro Gly Val Tyr Pro Gly Gly Val
        115                 120                 125

Leu Pro Gly Ala Arg Phe Pro Gly Val Gly Val Leu Pro Gly Val Pro
    130                 135                 140

Thr Gly Ala Gly Val Lys Pro Lys Ala Pro Gly Val Gly Gly Ala Phe
145                 150                 155                 160

Ala Gly Ile Pro Gly Val Gly Pro Phe Gly Gly Pro Gln Pro Gly Val
                165                 170                 175

Pro Leu Gly Tyr Pro Ile Lys Ala Pro Lys Leu Pro Gly Gly Tyr Gly
            180                 185                 190

Leu Pro Tyr Thr Thr Gly Lys Leu Pro Tyr Gly Tyr Gly Pro Gly Gly
        195                 200                 205

Val Ala Gly Ala Ala Gly Lys Ala Gly Tyr Pro Thr Gly Thr Gly Val
    210                 215                 220

Gly Pro Gln Ala Ala Ala Ala Ala Ala Ala Lys Ala Ala Ala Lys Phe
225                 230                 235                 240

Gly Ala Gly Ala Ala Gly Val Leu Pro Gly Val Gly Gly Ala Gly Val
                245                 250                 255

Pro Gly Val Pro Gly Ala Ile Pro Gly Ile Gly Gly Ile Ala Gly Val
            260                 265                 270

Gly Thr Pro Ala Ala Ala Ala Ala Ala Ala Ala Ala Ala Lys Ala Ala
```

-continued

```
        275                 280                 285

Lys Tyr Gly Ala Ala Ala Gly Leu Val Pro Gly Gly Pro Gly Phe Gly
    290                 295                 300

Pro Gly Val Val Gly Val Pro Gly Ala Gly Val Pro Gly Val Gly Val
305                 310                 315                 320

Pro Gly Ala Gly Ile Pro Val Val Pro Gly Ala Gly Ile Pro Gly Ala
                325                 330                 335

Ala Val Pro Gly Val Val Ser Pro Glu Ala Ala Ala Lys Ala Ala Ala
            340                 345                 350

Lys Ala Ala Lys Tyr Gly Ala Arg Pro Gly Val Gly Val Gly Gly Ile
        355                 360                 365

Pro Thr Tyr
    370


<210> SEQ ID NO 52
<211> LENGTH: 1116
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

ggtggcgtac caggcgcaat tcctgggggt gtcccaggcg gtgtttttta tccgggcgcc     60

ggtcttggcg cactgggtgg cggtgcactg ggcccgggcg gcaaaccgct gaaaccggta    120

ccaggtggtt tagcaggcgc cggcttaggc gcaggtctgg gagcatttcc ggcagttacc    180

tttccagggg cactggttcc tggaggtgtg gccgatgcag ccgcggcata taaagccgct    240

aaagccggtg cgggtttagg aggcgtccca ggtgtcggtg gcctgggtgt tagcgccggt    300

gcagttgttc cgcagccggg agcagggggtt aaacctggta aagtgccggg agtaggtctg    360

ccaggcgttt atcctggtgg tgttttgccg ggtgcccgtt ttccgggcgt tggtgttctt    420

ccaggcgtgc cgaccggagc cggtgttaaa ccgaaagccc ccggtgttgg aggtgcattt    480

gcaggcatcc cgggagttgg cccgtttggt ggtccgcaac ctggggttcc gttaggttat    540

ccgattaaag caccgaaact gcccggcggt tatggtctgc cgtacacaac cggtaaactg    600

ccgtatggtt atggcccggg tggagttgcg ggtgcagcag gtaaagcggg ttatcctacc    660

ggaaccggtg taggtccgca ggccgctgct gccgccgccg caaaagcagc ggctaaattt    720

ggcgccggag cagcgggtgt tctgcctgga gttggtggtg cgggcgtgcc aggggtacct    780

ggtgcaattc cgggtattgg tggtattgcc ggtgtcggca ccccggccgc ggcagctgcg    840

gcagcggcgg ctgccaaagc tgctaaatac ggtgccgcgg cgggtctggt gccaggaggt    900

ccgggttttg gtccgggagt ggttggcgtg cctggcgcag gcgttcctgg tgtgggcgtt    960

ccaggtgcag ggattcctgt tgtgcctggt gccggtattc ccggcgcggc cgttccgggg   1020

gtggttagcc cggaagccgc agcgaaggct gcggcaaagg cagcaaagta tggcgcacgc   1080

ccaggagtcg gcgtgggtgg tatcccgacc tattaa                             1116


<210> SEQ ID NO 53
<211> LENGTH: 345
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53
```

```
Gly Gly Val Pro Gly Ala Ile Pro Gly Gly Val Pro Gly Gly Val Phe
1               5                   10                  15

Tyr Pro Gly Ala Gly Leu Gly Ala Leu Gly Gly Gly Ala Leu Gly Pro
            20                  25                  30

Gly Gly Lys Pro Leu Lys Pro Val Pro Gly Gly Leu Ala Gly Ala Gly
        35                  40                  45

Leu Gly Ala Gly Leu Gly Ala Phe Pro Ala Val Thr Phe Pro Gly Ala
    50                  55                  60

Leu Val Pro Gly Gly Val Ala Asp Ala Ala Ala Ala Tyr Lys Ala Ala
65                  70                  75                  80

Lys Ala Gly Ala Gly Leu Gly Gly Val Pro Gly Val Gly Gly Leu Gly
                85                  90                  95

Val Ser Ala Gly Ala Val Val Pro Gln Pro Gly Ala Gly Val Lys Pro
            100                 105                 110

Gly Lys Val Pro Gly Val Gly Leu Pro Gly Val Tyr Pro Gly Gly Val
        115                 120                 125

Leu Pro Gly Ala Arg Phe Pro Gly Val Gly Val Leu Pro Gly Val Pro
    130                 135                 140

Thr Gly Ala Gly Val Lys Pro Lys Ala Pro Gly Val Gly Gly Ala Phe
145                 150                 155                 160

Ala Gly Ile Pro Gly Val Gly Pro Phe Gly Gly Pro Gln Pro Gly Val
                165                 170                 175

Pro Leu Gly Tyr Pro Ile Lys Ala Pro Lys Leu Pro Gly Gly Tyr Gly
            180                 185                 190

Leu Pro Tyr Thr Thr Gly Lys Leu Pro Tyr Gly Tyr Gly Pro Gly Gly
        195                 200                 205

Val Ala Gly Ala Ala Gly Lys Ala Gly Tyr Pro Thr Gly Thr Gly Val
    210                 215                 220

Gly Pro Gln Ala Ala Ala Ala Ala Ala Ala Lys Ala Ala Ala Lys Phe
225                 230                 235                 240

Gly Ala Gly Ala Ala Gly Val Leu Pro Gly Val Gly Gly Ala Gly Val
                245                 250                 255

Pro Gly Val Pro Gly Ala Ile Pro Gly Ile Gly Gly Ile Ala Gly Val
            260                 265                 270

Gly Thr Pro Ala Ala Ala Ala Ala Ala Ala Ala Ala Ala Lys Ala Ala
        275                 280                 285

Lys Tyr Gly Ala Ala Ala Gly Leu Val Pro Gly Gly Pro Gly Phe Gly
    290                 295                 300

Pro Gly Val Val Gly Val Pro Gly Ala Gly Val Pro Gly Val Gly Val
305                 310                 315                 320

Pro Gly Ala Gly Ile Pro Val Val Pro Gly Ala Gly Ile Pro Gly Ala
                325                 330                 335

Ala Val Pro Gly Val Val Ser Pro Glu
            340                 345
```

<210> SEQ ID NO 54
<211> LENGTH: 1038
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54

```
ggtggcgtac caggcgcaat tcctgggggt gtcccaggcg gtgtttttta tccgggcgcc     60
```

```
ggtcttggcg cactgggtgg cggtgcactg ggcccgggcg gcaaaccgct gaaaccggta    120

ccaggtggtt tagcaggcgc cggcttaggc gcaggtctgg gagcatttcc ggcagttacc    180

tttccagggg cactggttcc tggaggtgtg gccgatgcag ccgcggcata taaagccgct    240

aaagccggtg cgggtttagg aggcgtccca ggtgtcggtg gcctgggtgt tagcgccggt    300

gcagttgttc cgcagccggg agcaggggtt aaacctggta aagtgccggg agtaggtctg    360

ccaggcgttt atcctggtgg tgttttgccg ggtgcccgtt ttccgggcgt tggtgttctt    420

ccaggcgtgc cgaccggagc cggtgttaaa ccgaaagccc ccggtgttgg aggtgcattt    480

gcaggcatcc cgggagttgg cccgtttggt ggtccgcaac ctggggttcc gttaggttat    540

ccgattaaag caccgaaact gcccggcggt tatggtctgc cgtacacaac cggtaaactg    600

ccgtatggtt atggcccggg tggagttgcg ggtgcagcag gtaaagcggg ttatcctacc    660

ggaaccggtg taggtccgca ggccgctgct gccgccgccg caaaagcagc ggctaaattt    720

ggcgccggag cagcgggtgt tctgcctgga gttggtggtg cgggcgtgcc aggggtacct    780

ggtgcaattc cgggtattgg tggtattgcc ggtgtcggca ccccggccgc ggcagctgcg    840

gcagcggcgg ctgccaaagc tgctaaatac ggtgccgcgg cgggtctggt gccaggaggt    900

ccgggttttg gtccgggagt ggttggcgtg cctggcgcag gcgttcctgg tgtgggcgtt    960

ccaggtgcag ggattcctgt tgtgcctggt gccggtattc ccggcgcggc cgttccgggg   1020

gtggttagcc cggaataa                                                 1038
```

<210> SEQ ID NO 55
<211> LENGTH: 336
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

```
Lys Tyr Gly Ala Ala Gly Ala Gly Val Leu Gly Gly Leu Val Pro Gly
1               5                   10                  15

Pro Gln Ala Ala Val Pro Gly Val Pro Gly Thr Gly Gly Val Pro Gly
            20                  25                  30

Val Gly Thr Pro Ala Ala Ala Ala Ala Lys Ala Ala Ala Lys Ala Ala
        35                  40                  45

Gln Phe Gly Leu Val Pro Gly Val Gly Val Ala Pro Gly Val Gly Val
    50                  55                  60

Ala Pro Gly Val Gly Val Ala Pro Gly Val Gly Leu Ala Pro Gly Val
65                  70                  75                  80

Gly Val Ala Pro Gly Val Gly Val Ala Pro Gly Val Gly Val Ala Pro
                85                  90                  95

Gly Ile Gly Pro Gly Gly Val Ala Ala Ala Ala Lys Ser Ala Ala Lys
            100                 105                 110

Val Ala Ala Lys Ala Gln Leu Arg Ala Ala Ala Gly Leu Gly Ala Gly
        115                 120                 125

Ile Pro Gly Leu Gly Val Gly Val Gly Val Pro Gly Leu Gly Val Gly
    130                 135                 140

Ala Gly Val Pro Gly Leu Gly Val Gly Ala Gly Val Pro Gly Phe Gly
145                 150                 155                 160

Ala Gly Ala Asp Glu Gly Val Arg Arg Ser Leu Ser Pro Glu Leu Arg
                165                 170                 175
```

-continued

```
Glu Gly Asp Pro Ser Ser Ser Gln His Leu Pro Ser Thr Pro Ser Ser
            180                 185                 190

Pro Arg Val Pro Gly Ala Leu Ala Ala Ala Lys Ala Ala Lys Tyr Gly
        195                 200                 205

Ala Ala Val Pro Gly Val Leu Gly Gly Leu Gly Ala Leu Gly Gly Val
    210                 215                 220

Gly Ile Pro Gly Gly Val Val Gly Ala Gly Pro Ala Ala Ala Ala Ala
225                 230                 235                 240

Ala Ala Lys Ala Ala Ala Lys Ala Ala Gln Phe Gly Leu Val Gly Ala
                245                 250                 255

Ala Gly Leu Gly Gly Leu Gly Val Gly Gly Leu Gly Val Pro Gly Val
            260                 265                 270

Gly Gly Leu Gly Gly Ile Pro Pro Ala Ala Ala Ala Lys Ala Ala Lys
        275                 280                 285

Tyr Gly Ala Ala Gly Leu Gly Gly Val Leu Gly Gly Ala Gly Gln Phe
    290                 295                 300

Pro Leu Gly Gly Val Ala Ala Arg Pro Gly Phe Gly Leu Ser Pro Ile
305                 310                 315                 320

Phe Pro Gly Gly Ala Cys Leu Gly Lys Ala Cys Gly Arg Lys Arg Lys
                325                 330                 335
```

<210> SEQ ID NO 56
<211> LENGTH: 1011
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 56

```
aaatatggtg ccgccggcgc aggagtttta ggtgggctgg ttccgggccc gcaggcagct     60

gtgccggggg ttccaggcac cggtggtgtc cctggagtcg gtacgccggc tgcagcggca    120

gccaaagcgg ctgcgaaagc agcacagttt ggcttagtac cgggtgtggg agttgccccc    180

ggcgttggcg ttgctccagg ggtgggtgtt gctcctggcg tcggtctggc tcctggagtg    240

ggcgtagcac ccggtgtggg ggtggccccg ggtgttgggg ttgcaccggg tatcggtccg    300

ggcggtgtcg cagcagcagc taaaagcgcg gcgaaagttg cggccaaagc ccaactgcgc    360

gccgccgcgg gcctcggtgc aggtattccg gggctgggtg tcggagttgg agtcccgggt    420

ttgggcgtgg gcgcgggagt tccgggactg ggagtgggtg ccggagttcc tggctttggt    480

gcaggcgcag atgaaggtgt tcgtcgtagc ctgagtccgg aactgcgtga aggtgatccg    540

agtagcagcc agcatctgcc gagcaccccg agcagcccgc gtgttccggg tgcattagct    600

gcagcaaaag ccgccaagta tggtgcagcc gtgccgggcg tcttaggtgg tctgggcgcc    660

ctgggtggtg taggcattcc gggaggtgtt gtgggtgcag gaccggccgc cgcagctgcg    720

gccgccaaag cagctgcaaa agcggcccag tttggtttag tgggcgccgc aggtttaggc    780

ggtttaggtg tgggtggact gggtgtacct ggcgtaggcg gtctgggtgg aattccgccc    840

gcagcggccg cgaaagcggc aaaatatggc gcggcaggcc tgggcggcgt gctgggtggg    900

gcaggtcagt ttccgctggg cggggttgcc gcacgtccgg gatttggtct gagcccgatt    960

ttccctggcg gcgcatgtct gggtaaagca tgtggtcgta aacgtaaata a            1011
```

<210> SEQ ID NO 57
<211> LENGTH: 288
<212> TYPE: PRT

<213> ORGANISM: Artificial Sequence
<220> FEATURE:
<223> OTHER INFORMATION: Description of Artificial Sequence: Synthetic
polypeptide

<400> SEQUENCE: 57

```
Gln Phe Gly Leu Val Pro Gly Val Gly Val Ala Pro Gly Val Gly Val
1               5                   10                  15

Ala Pro Gly Val Gly Val Ala Pro Gly Val Gly Leu Ala Pro Gly Val
            20                  25                  30

Gly Val Ala Pro Gly Val Gly Val Ala Pro Gly Val Gly Val Ala Pro
        35                  40                  45

Gly Ile Gly Pro Gly Gly Val Ala Ala Ala Ala Lys Ser Ala Ala Lys
    50                  55                  60

Val Ala Ala Lys Ala Gln Leu Arg Ala Ala Ala Gly Leu Gly Ala Gly
65                  70                  75                  80

Ile Pro Gly Leu Gly Val Gly Val Gly Val Pro Gly Leu Gly Val Gly
                85                  90                  95

Ala Gly Val Pro Gly Leu Gly Val Gly Ala Gly Val Pro Gly Phe Gly
            100                 105                 110

Ala Gly Ala Asp Glu Gly Val Arg Arg Ser Leu Ser Pro Glu Leu Arg
        115                 120                 125

Glu Gly Asp Pro Ser Ser Ser Gln His Leu Pro Ser Thr Pro Ser Ser
    130                 135                 140

Pro Arg Val Pro Gly Ala Leu Ala Ala Ala Lys Ala Ala Lys Tyr Gly
145                 150                 155                 160

Ala Ala Val Pro Gly Val Leu Gly Gly Leu Gly Ala Leu Gly Gly Val
                165                 170                 175

Gly Ile Pro Gly Gly Val Val Gly Ala Gly Pro Ala Ala Ala Ala Ala
            180                 185                 190

Ala Ala Lys Ala Ala Ala Lys Ala Ala Gln Phe Gly Leu Val Gly Ala
        195                 200                 205

Ala Gly Leu Gly Gly Leu Gly Val Gly Gly Leu Gly Val Pro Gly Val
    210                 215                 220

Gly Gly Leu Gly Gly Ile Pro Pro Ala Ala Ala Ala Lys Ala Ala Lys
225                 230                 235                 240

Tyr Gly Ala Ala Gly Leu Gly Gly Val Leu Gly Gly Ala Gly Gln Phe
                245                 250                 255

Pro Leu Gly Gly Val Ala Ala Arg Pro Gly Phe Gly Leu Ser Pro Ile
            260                 265                 270

Phe Pro Gly Gly Ala Cys Leu Gly Lys Ala Cys Gly Arg Lys Arg Lys
        275                 280                 285
```

<210> SEQ ID NO 58
<211> LENGTH: 867
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 58

```
cagtttggct tagtaccggg tgtgggagtt gccccggcg ttggcgttgc tccaggggtg     60

ggtgttgctc ctggcgtcgg tctggctcct ggagtgggcg tagcacccgg tgtgggggtg    120

gccccgggtg ttggggttgc accgggtatc ggtccgggcg gtgtcgcagc agcagctaaa    180

agcgcggcga aagttgcggc caaagcccaa ctgcgcgccg ccgcgggcct cggtgcaggt    240
```

```
attccggggc tgggtgtcgg agttggagtc ccgggtttgg gcgtgggcgc gggagttccg    300

ggactgggag tgggtgccgg agttcctggc tttggtgcag gcgcagatga aggtgttcgt    360

cgtagcctga gtccggaact gcgtgaaggt gatccgagta gcagccagca tctgccgagc    420

accccgagca gcccgcgtgt tccgggtgca ttagctgcag caaaagccgc caagtatggt    480

gcagccgtgc cgggcgtctt aggtggtctg ggcgccctgg gtggtgtagg cattccggga    540

ggtgttgtgg gtgcaggacc ggccgccgca gctgcggccg ccaaagcagc tgcaaaagcg    600

gcccagtttg gtttagtggg cgccgcaggt ttaggcggtt taggtgtggg tggactgggt    660

gtacctggcg taggcggtct gggtggaatt ccgcccgcag cggccgcgaa agcggcaaaa    720

tatggcgcgg caggcctggg cggcgtgctg ggtggggcag gtcagtttcc gctgggcggg    780

gttgccgcac gtccgggatt tggtctgagc ccgattttcc ctggcggcgc atgtctgggt    840

aaagcatgtg gtcgtaaacg taaataa                                        867


<210> SEQ ID NO 59
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gly Gly Val Pro Gly Ala Ile Pro Gly Gly Val Pro Gly Gly Val Phe
1               5                   10                  15

Tyr Pro Gly Ala Gly Leu Gly Ala Leu Gly Gly Gly Ala Leu Gly Pro
            20                  25                  30

Gly Gly Lys Pro Leu Lys Pro Val Pro Gly Gly Leu Ala Gly Ala Gly
        35                  40                  45

Leu Gly Ala Gly Leu Gly Ala Phe Pro Ala Val Thr Phe Pro Gly Ala
    50                  55                  60

Leu Val Pro Gly Gly Val Ala Asp Ala Ala Ala Ala Tyr Lys Ala Ala
65                  70                  75                  80

Lys Ala Gly Ala Gly Leu Gly Gly Val Pro Gly Val Gly Gly Leu Gly
                85                  90                  95

Val Ser Ala Gly Ala Val Val Pro Gln Pro Gly Ala Gly Val Lys Pro
            100                 105                 110

Gly Lys Val Pro Gly Val Gly Leu Pro Gly Val Tyr Pro Gly Gly Val
        115                 120                 125

Leu Pro Gly Ala Arg Phe Pro Gly Val Gly Val Leu Pro Gly Val Pro
    130                 135                 140

Thr Gly Ala Gly Val Lys Pro Lys Ala Pro Gly Val Gly Gly Ala Phe
145                 150                 155                 160

Ala Gly Ile Pro Gly Val Gly Pro Phe Gly Gly Pro Gln Pro Gly Val
                165                 170                 175

Pro Leu Gly Tyr Pro Ile Lys Ala Pro Lys Leu Pro Gly Gly Tyr Gly
            180                 185                 190

Leu Pro Tyr Thr Thr Gly Lys Leu Pro Tyr Gly Tyr Gly Pro Gly Gly
        195                 200                 205

Val Ala Gly Ala Ala Gly Lys Ala Gly Tyr Pro Thr Gly Thr Gly Val
    210                 215                 220

Gly Pro Gln Ala Ala Ala Ala Ala Ala Ala Lys Ala Ala Ala Lys Phe
225                 230                 235                 240
```

```
Gly Ala Gly Ala Ala Gly Val Leu Pro Gly Val Gly Gly Ala Gly Val
                245                 250                 255

Pro Gly Val Pro Gly Ala Ile Pro Gly Ile Gly Gly Ile Ala Gly Val
            260                 265                 270

Gly Thr Pro
        275
```

<210> SEQ ID NO 60
<211> LENGTH: 828
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 60

```
ggtggcgtac caggcgcaat tcctgggggt gtcccaggcg gtgtttttta tccgggcgcc      60

ggtcttggcg cactgggtgg cggtgcactg ggcccgggcg gcaaaccgct gaaaccggta     120

ccaggtggtt tagcaggcgc cggcttaggc gcaggtctgg gagcatttcc ggcagttacc     180

tttccagggg cactggttcc tggaggtgtg gccgatgcag ccgcggcata taaagccgct     240

aaagccggtg cgggtttagg aggcgtccca ggtgtcggtg gcctgggtgt tagcgccggt     300

gcagttgttc cgcagccggg agcaggggtt aaacctggta aagtgccggg agtaggtctg     360

ccaggcgttt atcctggtgg tgttttgccg ggtgcccgtt ttccgggcgt tggtgttctt     420

ccaggcgtgc cgaccggagc cggtgttaaa ccgaaagccc ccggtgttgg aggtgcattt     480

gcaggcatcc cgggagttgg cccgtttggt ggtccgcaac ctggggttcc gttaggttat     540

ccgattaaag caccgaaact gcccggcggt tatggtctgc cgtacacaac cggtaaactg     600

ccgtatggtt atggcccggg tggagttgcg ggtgcagcag gtaaagcggg ttatcctacc     660

ggaaccggtg taggtccgca ggccgctgct gccgccgccg caaaagcagc ggctaaattt     720

ggcgccggag cagcgggtgt tctgcctgga gttggtggtg cgggcgtgcc aggggtacct     780

ggtgcaattc cgggtattgg tggtattgcc ggtgtcggca ccccgtaa                  828
```

<210> SEQ ID NO 61
<211> LENGTH: 227
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 61

```
Gly Gly Val Pro Gly Ala Ile Pro Gly Gly Val Pro Gly Gly Val Phe
1               5                   10                  15

Tyr Pro Gly Ala Gly Leu Gly Ala Leu Gly Gly Gly Ala Leu Gly Pro
            20                  25                  30

Gly Gly Lys Pro Leu Lys Pro Val Pro Gly Gly Leu Ala Gly Ala Gly
        35                  40                  45

Leu Gly Ala Gly Leu Gly Ala Phe Pro Ala Val Thr Phe Pro Gly Ala
    50                  55                  60

Leu Val Pro Gly Gly Val Ala Asp Ala Ala Ala Ala Tyr Lys Ala Ala
65                  70                  75                  80

Lys Ala Gly Ala Gly Leu Gly Gly Val Pro Gly Val Gly Gly Leu Gly
                85                  90                  95

Val Ser Ala Gly Ala Val Val Pro Gln Pro Gly Ala Gly Val Lys Pro
            100                 105                 110
```

-continued

Gly Lys Val Pro Gly Val Gly Leu Pro Gly Val Tyr Pro Gly Gly Val
115 120 125

Leu Pro Gly Ala Arg Phe Pro Gly Val Gly Val Leu Pro Gly Val Pro
130 135 140

Thr Gly Ala Gly Val Lys Pro Lys Ala Pro Gly Val Gly Gly Ala Phe
145 150 155 160

Ala Gly Ile Pro Gly Val Gly Pro Phe Gly Gly Pro Gln Pro Gly Val
165 170 175

Pro Leu Gly Tyr Pro Ile Lys Ala Pro Lys Leu Pro Gly Gly Tyr Gly
180 185 190

Leu Pro Tyr Thr Thr Gly Lys Leu Pro Tyr Gly Tyr Gly Pro Gly Gly
195 200 205

Val Ala Gly Ala Ala Gly Lys Ala Gly Tyr Pro Thr Gly Thr Gly Val
210 215 220

Gly Pro Gln
225

<210> SEQ ID NO 62
<211> LENGTH: 684
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 62
ggtggcgtac caggcgcaat tcctgggggt gtcccaggcg gtgtttttta tccgggcgcc 60
ggtcttggcg cactgggtgg cggtgcactg ggcccgggcg gcaaaccgct gaaaccggta 120
ccaggtggtt tagcaggcgc cggcttaggc gcaggtctgg gagcatttcc ggcagttacc 180
tttccagggg cactggttcc tggaggtgtg gccgatgcag ccgcggcata taaagccgct 240
aaagccggtg cgggtttagg aggcgtccca ggtgtcggtg gcctgggtgt tagcgccggt 300
gcagttgttc cgcagccggg agcagggggtt aaacctggta aagtgccggg agtaggtctg 360
ccaggcgttt atcctggtgg tgttttgccg ggtgcccgtt ttccgggcgt tggtgttctt 420
ccaggcgtgc cgaccggagc cggtgttaaa ccgaaagccc ccggtgttgg aggtgcattt 480
gcaggcatcc cgggagttgg cccgtttggt ggtccgcaac ctggggttcc gttaggttat 540
ccgattaaag caccgaaact gcccggcggt tatggtctgc cgtacacaac cggtaaactg 600
ccgtatggtt atggcccggg tggagttgcg ggtgcagcag gtaaagcggg ttatcctacc 660
ggaaccggtg taggtccgca gtaa 684

<210> SEQ ID NO 63
<211> LENGTH: 219
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 63

Gln Leu Arg Ala Ala Ala Gly Leu Gly Ala Gly Ile Pro Gly Leu Gly
1 5 10 15

Val Gly Val Gly Val Pro Gly Leu Gly Val Gly Ala Gly Val Pro Gly
20 25 30

Leu Gly Val Gly Ala Gly Val Pro Gly Phe Gly Ala Gly Ala Asp Glu
35 40 45

-continued

```
Gly Val Arg Arg Ser Leu Ser Pro Glu Leu Arg Glu Gly Asp Pro Ser
    50                  55                  60

Ser Ser Gln His Leu Pro Ser Thr Pro Ser Ser Pro Arg Val Pro Gly
65                  70                  75                  80

Ala Leu Ala Ala Ala Lys Ala Ala Lys Tyr Gly Ala Ala Val Pro Gly
                85                  90                  95

Val Leu Gly Gly Leu Gly Ala Leu Gly Gly Val Gly Ile Pro Gly Gly
            100                 105                 110

Val Val Gly Ala Gly Pro Ala Ala Ala Ala Ala Ala Ala Lys Ala Ala
        115                 120                 125

Ala Lys Ala Ala Gln Phe Gly Leu Val Gly Ala Ala Gly Leu Gly Gly
    130                 135                 140

Leu Gly Val Gly Gly Leu Gly Val Pro Gly Val Gly Gly Leu Gly Gly
145                 150                 155                 160

Ile Pro Pro Ala Ala Ala Ala Lys Ala Ala Lys Tyr Gly Ala Ala Gly
                165                 170                 175

Leu Gly Gly Val Leu Gly Gly Ala Gly Gln Phe Pro Leu Gly Gly Val
            180                 185                 190

Ala Ala Arg Pro Gly Phe Gly Leu Ser Pro Ile Phe Pro Gly Gly Ala
        195                 200                 205

Cys Leu Gly Lys Ala Cys Gly Arg Lys Arg Lys
    210                 215
```

<210> SEQ ID NO 64
<211> LENGTH: 660
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 64

```
caactgcgcg ccgccgcggg cctcggtgca ggtattccgg ggctgggtgt cggagttgga      60

gtcccgggtt tgggcgtggg cgcgggagtt ccgggactgg gagtgggtgc cggagttcct     120

ggctttggtg caggcgcaga tgaaggtgtt cgtcgtagcc tgagtccgga actgcgtgaa     180

ggtgatccga gtagcagcca gcatctgccg agcaccccga gcagcccgcg tgttccgggt     240

gcattagctg cagcaaaagc cgccaagtat ggtgcagccg tgccgggcgt cttaggtggt     300

ctgggcgccc tgggtggtgt aggcattccg ggaggtgttg tgggtgcagg accggccgcc     360

gcagctgcgg ccgccaaagc agctgcaaaa gcggcccagt ttggtttagt gggcgccgca     420

ggtttaggcg gtttaggtgt gggtggactg ggtgtacctg gcgtaggcgg tctgggtgga     480

attccgcccg cagcggccgc gaaagcggca aaatatggcg cggcaggcct gggcggcgtg     540

ctgggtgggg caggtcagtt tccgctgggc ggggttgccg cacgtccggg atttggtctg     600

agcccgattt tccctggcgg cgcatgtctg ggtaaagcat gtggtcgtaa acgtaaataa     660
```

<210> SEQ ID NO 65
<211> LENGTH: 126
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 65

```
Val Pro Gly Val Leu Gly Gly Leu Gly Ala Leu Gly Gly Val Gly Ile
```

-continued

```
1               5                   10                  15

Pro Gly Gly Val Val Gly Ala Gly Pro Ala Ala Ala Ala Ala Ala Ala
            20                  25                  30

Lys Ala Ala Ala Lys Ala Ala Gln Phe Gly Leu Val Gly Ala Ala Gly
        35                  40                  45

Leu Gly Gly Leu Gly Val Gly Gly Leu Gly Val Pro Gly Val Gly Gly
    50                  55                  60

Leu Gly Gly Ile Pro Pro Ala Ala Ala Ala Lys Ala Ala Lys Tyr Gly
65                  70                  75                  80

Ala Ala Gly Leu Gly Gly Val Leu Gly Gly Ala Gly Gln Phe Pro Leu
                85                  90                  95

Gly Gly Val Ala Ala Arg Pro Gly Phe Gly Leu Ser Pro Ile Phe Pro
            100                 105                 110

Gly Gly Ala Cys Leu Gly Lys Ala Cys Gly Arg Lys Arg Lys
        115                 120                 125
```

<210> SEQ ID NO 66
<211> LENGTH: 381
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 66

```
gtgccgggcg tcttaggtgg tctgggcgcc ctgggtggtg taggcattcc gggaggtgtt      60

gtgggtgcag gaccggccgc cgcagctgcg gccgccaaag cagctgcaaa agcggcccag     120

tttggtttag tgggcgccgc aggtttaggc ggtttaggtg tgggtggact gggtgtacct     180

ggcgtaggcg gtctgggtgg aattccgccc gcagcggccg cgaaagcggc aaaatatggc     240

gcggcaggcc tgggcggcgt gctgggtggg gcaggtcagt ttccgctggg cggggttgcc     300

gcacgtccgg gatttggtct gagcccgatt ttccctggcg gcgcatgtct gggtaaagca     360

tgtggtcgta aacgtaaata a                                               381
```

<210> SEQ ID NO 67
<211> LENGTH: 87
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

```
Gln Phe Gly Leu Val Gly Ala Ala Gly Leu Gly Gly Leu Gly Val Gly
1               5                   10                  15

Gly Leu Gly Val Pro Gly Val Gly Gly Leu Gly Gly Ile Pro Pro Ala
            20                  25                  30

Ala Ala Ala Lys Ala Ala Lys Tyr Gly Ala Ala Gly Leu Gly Gly Val
        35                  40                  45

Leu Gly Gly Ala Gly Gln Phe Pro Leu Gly Gly Val Ala Ala Arg Pro
    50                  55                  60

Gly Phe Gly Leu Ser Pro Ile Phe Pro Gly Gly Ala Cys Leu Gly Lys
65                  70                  75                  80

Ala Cys Gly Arg Lys Arg Lys
                85
```

<210> SEQ ID NO 68

<211> LENGTH: 264
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 68
cagtttggtt tagtgggcgc cgcaggttta ggcggtttag gtgtgggtgg actgggtgta 60
cctggcgtag gcggtctggg tggaattccg cccgcagcgg ccgcgaaagc ggcaaaatat 120
ggcgcggcag gcctgggcgg cgtgctgggt ggggcaggtc agtttccgct gggcggggtt 180
gccgcacgtc cgggatttgg tctgagcccg attttccctg gcggcgcatg tctgggtaaa 240
gcatgtggtc gtaaacgtaa ataa 264

<210> SEQ ID NO 69
<211> LENGTH: 72
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 69

Gly Gly Val Pro Gly Ala Ile Pro Gly Gly Val Pro Gly Gly Val Phe
1 5 10 15

Tyr Pro Gly Ala Gly Leu Gly Ala Leu Gly Gly Gly Ala Leu Gly Pro
20 25 30

Gly Gly Lys Pro Leu Lys Pro Val Pro Gly Gly Leu Ala Gly Ala Gly
35 40 45

Leu Gly Ala Gly Leu Gly Ala Phe Pro Ala Val Thr Phe Pro Gly Ala
50 55 60

Leu Val Pro Gly Gly Val Ala Asp
65 70

<210> SEQ ID NO 70
<211> LENGTH: 219
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 70
ggtggcgtac caggcgcaat tcctgggggt gtcccaggcg gtgtttttta tccgggcgcc 60
ggtcttggcg cactgggtgg cggtgcactg ggcccgggcg gcaaaccgct gaaaccggta 120
ccaggtggtt tagcaggcgc cggcttaggc gcaggtctgg gagcatttcc ggcagttacc 180
tttccagggg cactggttcc tggaggtgtg gccgattaa 219

<210> SEQ ID NO 71
<211> LENGTH: 44
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 71

Gly Leu Gly Gly Val Leu Gly Gly Ala Gly Gln Phe Pro Leu Gly Gly
1 5 10 15

Val Ala Ala Arg Pro Gly Phe Gly Leu Ser Pro Ile Phe Pro Gly Gly 20 25 30

Ala Cys Leu Gly Lys Ala Cys Gly Arg Lys Arg Lys
35 40

<210> SEQ ID NO 72
<211> LENGTH: 135
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 72
ggcctgggcg gcgtgctggg tggggcaggt cagtttccgc tgggcggggt tgccgcacgt 60
ccgggatttg gtctgagccc gattttccct ggcggcgcat gtctgggtaa agcatgtggt 120
cgtaaacgta aataa 135

<210> SEQ ID NO 73
<211> LENGTH: 636
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 73
atgaaaaaga tttggctggc gctggctggt ttagttttag cgtttagcgc atcggcggcg 60
cagtatgaag atgcaggttt tccgggtctg cctggtccgg caggcgaacc gggtcgtcat 120
ggtaaagatg gtctgatggg tagtccgggt tttaaaggtg aagcaggttc accgggtgca 180
cctggtcagg atggcacccg tggtgaaccg ggtattccgg gatttccggg taatcgtggc 240
ctgatgggtc agaaaggtga aattggtccg cctggtcagc agggtaaaaa aggcgcaccg 300
ggtatgccag gactgatggg ttcaaatggc agtccgggtc agccaggcac accgggttca 360
aaaggtagca aaggcgaacc tggtattcag ggtatgcctg gtgcaagcgg tctgaaaggc 420
gagccaggtg ccaccggttc tccgggtgaa ccaggttata tgggtctgcc aggtatccaa 480
ggcaaaaaag gtgataaagg taatcagggc gaaaaaggca ttcagggcca gaaaggcgaa 540
aatggccgtc agggtattcc aggccagcag ggcatccagg gtcatcatgg tgcaaaaggt 600
gaacgtggtg aaaagggcga accaggtgtt cgttaa 636

<210> SEQ ID NO 74
<211> LENGTH: 211
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

Met Lys Lys Ile Trp Leu Ala Leu Ala Gly Leu Val Leu Ala Phe Ser
1 5 10 15

Ala Ser Ala Ala Gln Tyr Glu Asp Ala Gly Phe Pro Gly Leu Pro Gly
20 25 30

Pro Ala Gly Glu Pro Gly Arg His Gly Lys Asp Gly Leu Met Gly Ser
35 40 45

Pro Gly Phe Lys Gly Glu Ala Gly Ser Pro Gly Ala Pro Gly Gln Asp
50 55 60

Gly Thr Arg Gly Glu Pro Gly Ile Pro Gly Phe Pro Gly Asn Arg Gly

-continued

```
65                  70                  75                  80

Leu Met Gly Gln Lys Gly Glu Ile Gly Pro Pro Gly Gln Gln Gly Lys
                85                  90                  95

Lys Gly Ala Pro Gly Met Pro Gly Leu Met Gly Ser Asn Gly Ser Pro
            100                 105                 110

Gly Gln Pro Gly Thr Pro Gly Ser Lys Gly Ser Lys Gly Glu Pro Gly
        115                 120                 125

Ile Gln Gly Met Pro Gly Ala Ser Gly Leu Lys Gly Glu Pro Gly Ala
    130                 135                 140

Thr Gly Ser Pro Gly Glu Pro Gly Tyr Met Gly Leu Pro Gly Ile Gln
145                 150                 155                 160

Gly Lys Lys Gly Asp Lys Gly Asn Gln Gly Glu Lys Gly Ile Gln Gly
                165                 170                 175

Gln Lys Gly Glu Asn Gly Arg Gln Gly Ile Pro Gly Gln Gln Gly Ile
            180                 185                 190

Gln Gly His His Gly Ala Lys Gly Glu Arg Gly Glu Lys Gly Glu Pro
        195                 200                 205

Gly Val Arg
    210
```

<210> SEQ ID NO 75
<211> LENGTH: 565
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 75

```
tgcaggtttt ccgggtctgc ctggtccggc aggcgaaccg ggtcgtcatg gtaaagatgg     60

tctgatgggt agtccgggtt ttaaaggtga agcaggttca ccgggtgcac ctggtcagga    120

tggcacccgt ggtgaaccgg gtattccggg atttccgggt aatcgtggcc tgatgggtca    180

gaaaggtgaa attggtccgc ctggtcagca gggtaaaaaa ggcgcaccgg gtatgccagg    240

actgatgggt tcaaatggca gtccgggtca gccaggcaca ccgggttcaa aaggtagcaa    300

aggcgaacct ggtattcagg gtatgcctgg tgcaagcggt ctgaaaggcg agccaggtgc    360

caccggttct ccgggtgaac caggttatat gggtctgcca ggtatccaag gcaaaaaagg    420

tgataaaggt aatcagggcg aaaaaggcat tcagggccag aaaggcgaaa atggccgtca    480

gggtattcca ggccagcagg gcatccaggg tcatcatggt gcaaaaggtg aacgtggtga    540

aaagggcgaa ccaggtgttc gttaa                                          565
```

<210> SEQ ID NO 76
<211> LENGTH: 187
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 76

```
Ala Gly Phe Pro Gly Leu Pro Gly Pro Ala Gly Glu Pro Gly Arg His
1               5                   10                  15

Gly Lys Asp Gly Leu Met Gly Ser Pro Gly Phe Lys Gly Glu Ala Gly
            20                  25                  30

Ser Pro Gly Ala Pro Gly Gln Asp Gly Thr Arg Gly Glu Pro Gly Ile
        35                  40                  45
```

```
Pro Gly Phe Pro Gly Asn Arg Gly Leu Met Gly Gln Lys Gly Glu Ile
    50                  55                  60

Gly Pro Pro Gly Gln Gln Gly Lys Lys Gly Ala Pro Gly Met Pro Gly
65                  70                  75                  80

Leu Met Gly Ser Asn Gly Ser Pro Gly Gln Pro Gly Thr Pro Gly Ser
                85                  90                  95

Lys Gly Ser Lys Gly Glu Pro Gly Ile Gln Gly Met Pro Gly Ala Ser
            100                 105                 110

Gly Leu Lys Gly Glu Pro Gly Ala Thr Gly Ser Pro Gly Glu Pro Gly
        115                 120                 125

Tyr Met Gly Leu Pro Gly Ile Gln Gly Lys Lys Gly Asp Lys Gly Asn
    130                 135                 140

Gln Gly Glu Lys Gly Ile Gln Gly Gln Lys Gly Glu Asn Gly Arg Gln
145                 150                 155                 160

Gly Ile Pro Gly Gln Gln Gly Ile Gln Gly His His Gly Ala Lys Gly
                165                 170                 175

Glu Arg Gly Glu Lys Gly Glu Pro Gly Val Arg
            180                 185


<210> SEQ ID NO 77
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

atgaaaaaga tttggctggc gctggctggt ttagttttag cgtttagcgc atcggcggcg     60

cagtatgaag atatgggtcc gcctggtagc cgtggtgcaa gtggtccggc aggcgttcgt    120

ggtccgaatg gtgatgcagg tcgtccgggt gaaccgggtc tgatgggtcc tcgtggtctg    180

cctggttcac cgggtaatat tggtcctgca ggtaaagaag gtccggttgg tctgccaggt    240

attgatggcc gtccgggtcc gattggtcca gccggtgcac gtggtgaacc tggcaatatt    300

ggttttccgg gtcctaaagg tccgaccggt gatccgggta aaaatggtga taaaggtcat    360

gcaggtctgg caggcgcacg cggtgcacct ggtccggatg gtaataatgg tgcacagggt    420

ccaccgggtc cgcagggtgt tcaaggtggt aaaggcgaac agggtcctgc cggtcctccg    480

ggttttcagg gactgcctgg tccgagcggt cctgcgggtg aagttggtaa acctggtgaa    540

cgcggtctgc atggtgaatt tggcctgcct gggcctgcag gtccgcgtgg cgaacgtggt    600

ccgccaggtg aaagcggtgc agcaggtccg acaggttaa                           639


<210> SEQ ID NO 78
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Met Lys Lys Ile Trp Leu Ala Leu Ala Gly Leu Val Leu Ala Phe Ser
1               5                   10                  15

Ala Ser Ala Ala Gln Tyr Glu Asp Met Gly Pro Pro Gly Ser Arg Gly
            20                  25                  30

Ala Ser Gly Pro Ala Gly Val Arg Gly Pro Asn Gly Asp Ala Gly Arg
```

```
        35                  40                  45

Pro Gly Glu Pro Gly Leu Met Gly Pro Arg Gly Leu Pro Gly Ser Pro
    50                  55                  60

Gly Asn Ile Gly Pro Ala Gly Lys Glu Gly Pro Val Gly Leu Pro Gly
65                  70                  75                  80

Ile Asp Gly Arg Pro Gly Pro Ile Gly Pro Ala Gly Ala Arg Gly Glu
                85                  90                  95

Pro Gly Asn Ile Gly Phe Pro Gly Pro Lys Gly Pro Thr Gly Asp Pro
            100                 105                 110

Gly Lys Asn Gly Asp Lys Gly His Ala Gly Leu Ala Gly Ala Arg Gly
        115                 120                 125

Ala Pro Gly Pro Asp Gly Asn Asn Gly Ala Gln Gly Pro Pro Gly Pro
    130                 135                 140

Gln Gly Val Gln Gly Gly Lys Gly Glu Gln Gly Pro Ala Gly Pro Pro
145                 150                 155                 160

Gly Phe Gln Gly Leu Pro Gly Pro Ser Gly Pro Ala Gly Glu Val Gly
                165                 170                 175

Lys Pro Gly Glu Arg Gly Leu His Gly Glu Phe Gly Leu Pro Gly Pro
            180                 185                 190

Ala Gly Pro Arg Gly Glu Arg Gly Pro Pro Gly Glu Ser Gly Ala Ala
        195                 200                 205

Gly Pro Thr Gly
    210
```

<210> SEQ ID NO 79
<211> LENGTH: 567
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 79

```
atgggtccgc ctggtagccg tggtgcaagt ggtccggcag gcgttcgtgg tccgaatggt      60

gatgcaggtc gtccgggtga accgggtctg atgggtcctc gtggtctgcc tggttcaccg     120

ggtaatattg gtcctgcagg taaagaaggt ccggttggtc tgccaggtat tgatggccgt     180

ccgggtccga ttggtccagc cggtgcacgt ggtgaacctg gcaatattgg ttttccgggt     240

cctaaaggtc cgaccggtga tccgggtaaa aatggtgata aaggtcatgc aggtctggca     300

ggcgcacgcg gtgcacctgg tccggatggt aataatggtg cacagggtcc accgggtccg     360

cagggtgttc aaggtggtaa aggcgaacag ggtcctgccg gtcctccggg ttttcaggga     420

ctgcctggtc cgagcggtcc tgcgggtgaa gttggtaaac ctggtgaacg cggtctgcat     480

ggtgaatttg gcctgcctgg gcctgcaggt ccgcgtggcg aacgtggtcc gccaggtgaa     540

agcggtgcag caggtccgac aggttaa                                          567
```

<210> SEQ ID NO 80
<211> LENGTH: 188
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 80

```
Met Gly Pro Pro Gly Ser Arg Gly Ala Ser Gly Pro Ala Gly Val Arg
1               5                   10                  15
```

```
Gly Pro Asn Gly Asp Ala Gly Arg Pro Gly Glu Pro Gly Leu Met Gly
            20                  25                  30

Pro Arg Gly Leu Pro Gly Ser Pro Gly Asn Ile Gly Pro Ala Gly Lys
        35                  40                  45

Glu Gly Pro Val Gly Leu Pro Gly Ile Asp Gly Arg Pro Gly Pro Ile
    50                  55                  60

Gly Pro Ala Gly Ala Arg Gly Glu Pro Gly Asn Ile Gly Phe Pro Gly
65                  70                  75                  80

Pro Lys Gly Pro Thr Gly Asp Pro Gly Lys Asn Gly Asp Lys Gly His
                85                  90                  95

Ala Gly Leu Ala Gly Ala Arg Gly Ala Pro Gly Pro Asp Gly Asn Asn
            100                 105                 110

Gly Ala Gln Gly Pro Pro Gly Pro Gln Gly Val Gln Gly Gly Lys Gly
        115                 120                 125

Glu Gln Gly Pro Ala Gly Pro Pro Gly Phe Gln Gly Leu Pro Gly Pro
    130                 135                 140

Ser Gly Pro Ala Gly Glu Val Gly Lys Pro Gly Glu Arg Gly Leu His
145                 150                 155                 160

Gly Glu Phe Gly Leu Pro Gly Pro Ala Gly Pro Arg Gly Glu Arg Gly
                165                 170                 175

Pro Pro Gly Glu Ser Gly Ala Ala Gly Pro Thr Gly
            180                 185
```

<210> SEQ ID NO 81
<211> LENGTH: 612
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 81

```
atgaaaaaga tttggctggc gctggctggt ttagttttag cgtttagcgc atcggcggcg      60

cagtatgaag atggttttca gggtcctgcc ggtgaaccgg gtgaacctgg tcagacaggt     120

ccggcaggcg cacgtggtcc tgcaggtcct cctggtaaag ccggtgaaga tggtcatccg     180

ggtaaaccgg gtcgtcctgg tgaacgtggt gttgttggtc cgcagggtgc ccgtggtttt     240

ccgggtactc cgggtctgcc aggttttaaa ggtattcgtg gtcataatgg tctggatggt     300

ctgaaaggtc agcctggtgc accgggtgtt aaaggtgaac caggtgctcc gggtgaaaat     360

ggcacaccgg gtcagaccgg tgcgcgtggt ctgcctggcg aacgcggtcg tgttggtgca     420

cctggtccag ccggtgcacg cggtagtgat ggtagcgttg gtccggttgg tccagcgggt     480

ccgattggta gcgcaggtcc accgggtttt ccaggcgcac cgggtccgaa aggtgaaatt     540

ggtgcagttg gtaatgcagg ccctgccggt ccagcaggac cgcgtggtga agttggcctg     600

cctggtctgt aa                                                         612
```

<210> SEQ ID NO 82
<211> LENGTH: 203
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

```
Met Lys Lys Ile Trp Leu Ala Leu Ala Gly Leu Val Leu Ala Phe Ser
```

```
1               5                   10                  15

Ala Ser Ala Ala Gln Tyr Glu Asp Gly Phe Gln Gly Pro Ala Gly Glu
            20                  25                  30

Pro Gly Glu Pro Gly Gln Thr Gly Pro Ala Gly Ala Arg Gly Pro Ala
        35                  40                  45

Gly Pro Pro Gly Lys Ala Gly Glu Asp Gly His Pro Gly Lys Pro Gly
    50                  55                  60

Arg Pro Gly Glu Arg Gly Val Val Gly Pro Gln Gly Ala Arg Gly Phe
65                  70                  75                  80

Pro Gly Thr Pro Gly Leu Pro Gly Phe Lys Gly Ile Arg Gly His Asn
                85                  90                  95

Gly Leu Asp Gly Leu Lys Gly Gln Pro Gly Ala Pro Gly Val Lys Gly
            100                 105                 110

Glu Pro Gly Ala Pro Gly Glu Asn Gly Thr Pro Gly Gln Thr Gly Ala
        115                 120                 125

Arg Gly Leu Pro Gly Glu Arg Gly Arg Val Gly Ala Pro Gly Pro Ala
    130                 135                 140

Gly Ala Arg Gly Ser Asp Gly Ser Val Gly Pro Val Gly Pro Ala Gly
145                 150                 155                 160

Pro Ile Gly Ser Ala Gly Pro Pro Gly Phe Pro Gly Ala Pro Gly Pro
                165                 170                 175

Lys Gly Glu Ile Gly Ala Val Gly Asn Ala Gly Pro Ala Gly Pro Ala
            180                 185                 190

Gly Pro Arg Gly Glu Val Gly Leu Pro Gly Leu
        195                 200


<210> SEQ ID NO 83
<211> LENGTH: 540
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83

ggttttcagg gtcctgccgg tgaaccgggt gaacctggtc agacaggtcc ggcaggcgca     60

cgtggtcctg caggtcctcc tggtaaagcc ggtgaagatg gtcatccggg taaaccgggt    120

cgtcctggtg aacgtggtgt tgttggtccg cagggtgccc gtggttttcc gggtactccg    180

ggtctgccag gttttaaagg tattcgtggt cataatggtc tggatggtct gaaaggtcag    240

cctggtgcac cgggtgttaa aggtgaacca ggtgctccgg gtgaaaatgg cacaccgggt    300

cagaccggtg cgcgtggtct gcctggcgaa cgcggtcgtg ttggtgcacc tggtccagcc    360

ggtgcacgcg gtagtgatgg tagcgttggt ccggttggtc cagcgggtcc gattggtagc    420

gcaggtccac cgggttttcc aggcgcaccg ggtccgaaag gtgaaattgg tgcagttggt    480

aatgcaggcc ctgccggtcc agcaggaccg cgtggtgaag ttggcctgcc tggtctgtaa    540


<210> SEQ ID NO 84
<211> LENGTH: 179
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gly Phe Gln Gly Pro Ala Gly Glu Pro Gly Glu Pro Gly Gln Thr Gly
```

-continued 1 5 10 15

Pro Ala Gly Ala Arg Gly Pro Ala Gly Pro Pro Gly Lys Ala Gly Glu
20 25 30

Asp Gly His Pro Gly Lys Pro Gly Arg Pro Gly Glu Arg Gly Val Val
35 40 45

Gly Pro Gln Gly Ala Arg Gly Phe Pro Gly Thr Pro Gly Leu Pro Gly
50 55 60

Phe Lys Gly Ile Arg Gly His Asn Gly Leu Asp Gly Leu Lys Gly Gln
65 70 75 80

Pro Gly Ala Pro Gly Val Lys Gly Glu Pro Gly Ala Pro Gly Glu Asn
85 90 95

Gly Thr Pro Gly Gln Thr Gly Ala Arg Gly Leu Pro Gly Glu Arg Gly
100 105 110

Arg Val Gly Ala Pro Gly Pro Ala Gly Ala Arg Gly Ser Asp Gly Ser
115 120 125

Val Gly Pro Val Gly Pro Ala Gly Pro Ile Gly Ser Ala Gly Pro Pro
130 135 140

Gly Phe Pro Gly Ala Pro Gly Pro Lys Gly Glu Ile Gly Ala Val Gly
145 150 155 160

Asn Ala Gly Pro Ala Gly Pro Ala Gly Pro Arg Gly Glu Val Gly Leu
165 170 175

Pro Gly Leu

<210> SEQ ID NO 85
<211> LENGTH: 689
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 85
gtccgcaggg tgttgttggt gcagatggta aagacggtac cccgggtgaa aaaggagaac 60
agggacgtac aggtgcagca ggtaaacagg gcagcccggg tgccgatggt gcccgtggcc 120
cgctgggtag cattggtcag cagggtgcaa gaggcgaacc gggcgatccg ggtagtccgg 180
gcctgcgtgg tgatacgggt ctggccggtg ttaaaggcgt tgcaggtcct tcaggtcgtc 240
caggtcaacc gggtgcaaat ggtctgccgg gtgttaatgg tcgtggcggt ctggaacgtg 300
gtctggcagg accgccgggt cctgatggtc gccgcggtga aacgggttca ccgggtattg 360
ccggtgccct gggtaaacca ggtctggaag gtccgaaagg ttatcctggt ctgcgcggtc 420
gtgatggtac caatggcaaa cgtggcgaac agggcgaaac cggtccagat ggtgttcgtg 480
gtattccggg taacgatggt cagagcggta aaccgggcat tgatggtatt gatggcacca 540
atggtcagcc tggcgaagca ggttatcagg gtggtcgcgg tacccgtggt cagctgggtg 600
aaacaggtga tgttggtcag aatggtgatc gcggcgcacc gggtccggat ggtagcaaag 660
gtagcgccgg tcgtccgggt ttacgttaa 689

<210> SEQ ID NO 86
<211> LENGTH: 229
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 86

Gly Pro Gln Gly Val Val Gly Ala Asp Gly Lys Asp Gly Thr Pro Gly
1 5 10 15

Glu Lys Gly Glu Gln Gly Arg Thr Gly Ala Ala Gly Lys Gln Gly Ser
20 25 30

Pro Gly Ala Asp Gly Ala Arg Gly Pro Leu Gly Ser Ile Gly Gln Gln
35 40 45

Gly Ala Arg Gly Glu Pro Gly Asp Pro Gly Ser Pro Gly Leu Arg Gly
50 55 60

Asp Thr Gly Leu Ala Gly Val Lys Gly Val Ala Gly Pro Ser Gly Arg
65 70 75 80

Pro Gly Gln Pro Gly Ala Asn Gly Leu Pro Gly Val Asn Gly Arg Gly
85 90 95

Gly Leu Glu Arg Gly Leu Ala Gly Pro Pro Gly Pro Asp Gly Arg Arg
100 105 110

Gly Glu Thr Gly Ser Pro Gly Ile Ala Gly Ala Leu Gly Lys Pro Gly
115 120 125

Leu Glu Gly Pro Lys Gly Tyr Pro Gly Leu Arg Gly Arg Asp Gly Thr
130 135 140

Asn Gly Lys Arg Gly Glu Gln Gly Glu Thr Gly Pro Asp Gly Val Arg
145 150 155 160

Gly Ile Pro Gly Asn Asp Gly Gln Ser Gly Lys Pro Gly Ile Asp Gly
165 170 175

Ile Asp Gly Thr Asn Gly Gln Pro Gly Glu Ala Gly Tyr Gln Gly Gly
180 185 190

Arg Gly Thr Arg Gly Gln Leu Gly Glu Thr Gly Asp Val Gly Gln Asn
195 200 205

Gly Asp Arg Gly Ala Pro Gly Pro Asp Gly Ser Lys Gly Ser Ala Gly
210 215 220

Arg Pro Gly Leu Arg
225

<210> SEQ ID NO 87
<211> LENGTH: 2283
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 87
ggtggcgtac caggcgcaat tcctgggggt gtcccaggcg gtgtttttta tccgggcgcc 60
ggtcttggcg cactgggtgg cggtgcactg ggcccgggcg gcaaaccgct gaaaccggta 120
ccaggtggtt tagcaggcgc cggcttaggc gcaggtctgg gagcatttcc ggcagttacc 180
tttccagggg cactggttcc tggaggtgtg gccgatgcag ccgcggcata taaagccgct 240
aaagccggtg cgggtttagg aggcgtccca ggtgtcggtg gcctgggtgt tagcgccggt 300
gcagttgttc cgcagccggg agcagggggtt aaacctggta aagtgccggg agtaggtctg 360
ccaggcgttt atcctggtgg tgttttgccg ggtgcccgtt ttccgggcgt tggtgttctt 420
ccaggcgtgc cgaccggagc cggtgttaaa ccgaaagccc ccggtgttgg aggtgcattt 480
gcaggcatcc cgggagttgg cccgtttggt ggtccgcaac ctggggttcc gttaggttat 540
ccgattaaag caccgaaact gcccggcggt tatggtctgc cgtacacaac cggtaaactg 600
ccgtatggtt atggcccggg tggagttgcg ggtgcagcag gtaaagcggg ttatcctacc 660

-continued ggaaccggtg taggtccgca ggccgctgct gccgccgccg caaaagcagc ggctaaattt 720
ggcgccggag cagcgggtgt tctgcctgga gttggtggtg cgggcgtgcc aggggtacct 780
ggtgcaattc cgggtattgg tggtattgcc ggtgtcggca ccccggccgc ggcagctgcg 840
gcagcggcgg ctgccaaagc tgctaaatac ggtgccgcgg cgggtctggt gccaggaggt 900
ccgggttttg gtccgggagt ggttggcgtg cctggcgcag gcgttcctgg tgtgggcgtt 960
ccaggtgcag ggattcctgt tgtgcctggt gccggtattc ccggcgcggc cgttccgggg 1020
gtggttagcc cggaagccgc agcgaaggct gcggcaaagg cagcaaagta tggcgcacgc 1080
ccaggagtcg gcgtgggtgg tatcccgacc tatggggtgg gcgcaggggg ttttcctggt 1140
ttcggcgtag gtgtaggagg tataccgggc gtggccggtg taccaggggt tggtggcgtc 1200
cctggtgttg gcggtgtgcc aggtgttggt atttcaccgg aagcacaggc agcagccgca 1260
gctaaggcag cgaaatatgg tgccgccggc gcaggagttt taggtgggct ggttccgggc 1320
ccgcaggcag ctgtgccggg ggttccaggc accggtggtg tccctggagt cggtacgccg 1380
gctgcagcgg cagccaaagc ggctgcgaaa gcagcacagt ttggcttagt accgggtgtg 1440
ggagttgccc ccggcgttgg cgttgctcca ggggtgggtg ttgctcctgg cgtcggtctg 1500
gctcctggag tgggcgtagc acccggtgtg ggggtggccc cgggtgttgg ggttgcaccg 1560
ggtatcggtc cgggcggtgt cgcagcagca gctaaaagcg cggcgaaagt tgcggccaaa 1620
gcccaactgc gcgccgccgc gggcctcggt gcaggtattc cggggctggg tgtcggagtt 1680
ggagtcccgg gtttgggcgt gggcgcggga gttccgggac tgggagtggg tgccggagtt 1740
cctggctttg gtgcaggcgc agatgaaggt gttcgtcgta gcctgagtcc ggaactgcgt 1800
gaaggtgatc cgagtagcag ccagcatctg ccgagcaccc cgagcagccc gcgtgttccg 1860
ggtgcattag ctgcagcaaa agccgccaag tatggtgcag ccgtgccggg cgtcttaggt 1920
ggtctgggcg ccctgggtgg tgtaggcatt ccgggaggtg ttgtgggtgc aggaccggcc 1980
gccgcagctg cggccgccaa agcagctgca aaagcggccc agtttggttt agtgggcgcc 2040
gcaggtttag gcggtttagg tgtgggtgga ctgggtgtac ctggcgtagg cggtctgggt 2100
ggaattccgc ccgcagcggc cgcgaaagcg gcaaaatatg gcgcggcagg cctgggcggc 2160
gtgctgggtg gggcaggtca gtttccgctg ggcggggttg ccgcacgtcc gggatttggt 2220
ctgagcccga ttttccctgg cggcgcatgt ctgggtaaag catgtggtcg taaacgtaaa 2280
taa 2283

<210> SEQ ID NO 88
<211> LENGTH: 760
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 88

Gly Gly Val Pro Gly Ala Ile Pro Gly Gly Val Pro Gly Gly Val Phe
1 5 10 15

Tyr Pro Gly Ala Gly Leu Gly Ala Leu Gly Gly Gly Ala Leu Gly Pro
20 25 30

Gly Gly Lys Pro Leu Lys Pro Val Pro Gly Gly Leu Ala Gly Ala Gly
35 40 45

Leu Gly Ala Gly Leu Gly Ala Phe Pro Ala Val Thr Phe Pro Gly Ala
50 55 60

-continued

```
Leu Val Pro Gly Gly Val Ala Asp Ala Ala Ala Ala Tyr Lys Ala Ala
65                  70                  75                  80

Lys Ala Gly Ala Gly Leu Gly Gly Val Pro Gly Val Gly Gly Leu Gly
                85                  90                  95

Val Ser Ala Gly Ala Val Val Pro Gln Pro Gly Ala Gly Val Lys Pro
            100                 105                 110

Gly Lys Val Pro Gly Val Gly Leu Pro Gly Val Tyr Pro Gly Gly Val
        115                 120                 125

Leu Pro Gly Ala Arg Phe Pro Gly Val Gly Val Leu Pro Gly Val Pro
    130                 135                 140

Thr Gly Ala Gly Val Lys Pro Lys Ala Pro Gly Val Gly Gly Ala Phe
145                 150                 155                 160

Ala Gly Ile Pro Gly Val Gly Pro Phe Gly Gly Pro Gln Pro Gly Val
                165                 170                 175

Pro Leu Gly Tyr Pro Ile Lys Ala Pro Lys Leu Pro Gly Gly Tyr Gly
            180                 185                 190

Leu Pro Tyr Thr Thr Gly Lys Leu Pro Tyr Gly Tyr Gly Pro Gly Gly
        195                 200                 205

Val Ala Gly Ala Ala Gly Lys Ala Gly Tyr Pro Thr Gly Thr Gly Val
    210                 215                 220

Gly Pro Gln Ala Ala Ala Ala Ala Ala Ala Lys Ala Ala Ala Lys Phe
225                 230                 235                 240

Gly Ala Gly Ala Ala Gly Val Leu Pro Gly Val Gly Gly Ala Gly Val
                245                 250                 255

Pro Gly Val Pro Gly Ala Ile Pro Gly Ile Gly Gly Ile Ala Gly Val
            260                 265                 270

Gly Thr Pro Ala Ala Ala Ala Ala Ala Ala Ala Ala Ala Lys Ala Ala
        275                 280                 285

Lys Tyr Gly Ala Ala Ala Gly Leu Val Pro Gly Gly Pro Gly Phe Gly
    290                 295                 300

Pro Gly Val Val Gly Val Pro Gly Ala Gly Val Pro Gly Val Gly Val
305                 310                 315                 320

Pro Gly Ala Gly Ile Pro Val Val Pro Gly Ala Gly Ile Pro Gly Ala
                325                 330                 335

Ala Val Pro Gly Val Val Ser Pro Glu Ala Ala Ala Lys Ala Ala Ala
            340                 345                 350

Lys Ala Ala Lys Tyr Gly Ala Arg Pro Gly Val Gly Val Gly Gly Ile
        355                 360                 365

Pro Thr Tyr Gly Val Gly Ala Gly Gly Phe Pro Gly Phe Gly Val Gly
    370                 375                 380

Val Gly Gly Ile Pro Gly Val Ala Gly Val Pro Gly Val Gly Gly Val
385                 390                 395                 400

Pro Gly Val Gly Gly Val Pro Gly Val Gly Ile Ser Pro Glu Ala Gln
                405                 410                 415

Ala Ala Ala Ala Ala Lys Ala Ala Lys Tyr Gly Ala Ala Gly Ala Gly
            420                 425                 430

Val Leu Gly Gly Leu Val Pro Gly Pro Gln Ala Ala Val Pro Gly Val
        435                 440                 445

Pro Gly Thr Gly Gly Val Pro Gly Val Gly Thr Pro Ala Ala Ala Ala
    450                 455                 460

Ala Lys Ala Ala Ala Lys Ala Ala Gln Phe Gly Leu Val Pro Gly Val
465                 470                 475                 480

Gly Val Ala Pro Gly Val Gly Val Ala Pro Gly Val Gly Val Ala Pro
```

-continued

```
                485                 490                 495

Gly Val Gly Leu Ala Pro Gly Val Gly Val Ala Pro Gly Val Gly Val
            500                 505                 510

Ala Pro Gly Val Gly Val Ala Pro Gly Ile Gly Pro Gly Gly Val Ala
        515                 520                 525

Ala Ala Ala Lys Ser Ala Ala Lys Val Ala Ala Lys Ala Gln Leu Arg
    530                 535                 540

Ala Ala Ala Gly Leu Gly Ala Gly Ile Pro Gly Leu Gly Val Gly Val
545                 550                 555                 560

Gly Val Pro Gly Leu Gly Val Gly Ala Gly Val Pro Gly Leu Gly Val
                565                 570                 575

Gly Ala Gly Val Pro Gly Phe Gly Ala Gly Ala Asp Glu Gly Val Arg
            580                 585                 590

Arg Ser Leu Ser Pro Glu Leu Arg Glu Gly Asp Pro Ser Ser Ser Gln
        595                 600                 605

His Leu Pro Ser Thr Pro Ser Ser Pro Arg Val Pro Gly Ala Leu Ala
    610                 615                 620

Ala Ala Lys Ala Ala Lys Tyr Gly Ala Ala Val Pro Gly Val Leu Gly
625                 630                 635                 640

Gly Leu Gly Ala Leu Gly Gly Val Gly Ile Pro Gly Gly Val Val Gly
                645                 650                 655

Ala Gly Pro Ala Ala Ala Ala Ala Ala Ala Lys Ala Ala Ala Lys Ala
            660                 665                 670

Ala Gln Phe Gly Leu Val Gly Ala Ala Gly Leu Gly Gly Leu Gly Val
        675                 680                 685

Gly Gly Leu Gly Val Pro Gly Val Gly Gly Leu Gly Gly Ile Pro Pro
    690                 695                 700

Ala Ala Ala Ala Lys Ala Ala Lys Tyr Gly Ala Ala Gly Leu Gly Gly
705                 710                 715                 720

Val Leu Gly Gly Ala Gly Gln Phe Pro Leu Gly Gly Val Ala Ala Arg
                725                 730                 735

Pro Gly Phe Gly Leu Ser Pro Ile Phe Pro Gly Gly Ala Cys Leu Gly
            740                 745                 750

Lys Ala Cys Gly Arg Lys Arg Lys
        755                 760


<210> SEQ ID NO 89
<211> LENGTH: 429
<212> TYPE: PRT
<213> ORGANISM: Podocoryna carnea

<400> SEQUENCE: 89

Gly Pro Gln Gly Val Val Gly Ala Asp Gly Lys Asp Gly Thr Pro Gly
1               5                   10                  15

Glu Lys Gly Glu Gln Gly Arg Thr Gly Ala Ala Gly Lys Gln Gly Ser
            20                  25                  30

Pro Gly Ala Asp Gly Ala Arg Gly Pro Leu Gly Ser Ile Gly Gln Gln
        35                  40                  45

Gly Ala Arg Gly Glu Pro Gly Asp Pro Gly Ser Pro Gly Leu Arg Gly
    50                  55                  60

Asp Thr Gly Leu Ala Gly Val Lys Gly Val Ala Gly Pro Ser Gly Arg
65                  70                  75                  80

Pro Gly Gln Pro Gly Ala Asn Gly Leu Pro Gly Val Asn Gly Arg Gly
                85                  90                  95
```

```
Gly Leu Arg Gly Lys Pro Gly Ala Lys Gly Ile Ala Gly Ser Asp Gly
            100                 105                 110

Glu Ala Gly Glu Ser Gly Ala Pro Gly Gln Ser Gly Pro Thr Gly Pro
        115                 120                 125

Arg Gly Gln Arg Gly Pro Ser Gly Glu Asp Gly Asn Pro Gly Leu Gln
    130                 135                 140

Gly Leu Pro Gly Ser Asp Gly Glu Pro Gly Glu Glu Gly Gln Pro Gly
145                 150                 155                 160

Arg Ser Gly Gln Pro Gly Gln Gln Gly Pro Arg Gly Ser Pro Gly Glu
                165                 170                 175

Val Gly Pro Arg Gly Ser Lys Gly Pro Ser Gly Asp Arg Gly Asp Arg
            180                 185                 190

Gly Glu Arg Gly Val Pro Gly Gln Thr Gly Ser Ala Gly Asn Val Gly
        195                 200                 205

Glu Asp Gly Glu Gln Gly Gly Lys Gly Val Asp Gly Ala Ser Gly Pro
    210                 215                 220

Ser Gly Ala Leu Gly Ala Arg Gly Pro Pro Gly Ser Arg Gly Asp Thr
225                 230                 235                 240

Gly Ala Val Gly Pro Pro Gly Pro Thr Gly Arg Ser Gly Leu Pro Gly
                245                 250                 255

Asn Ala Gly Gln Lys Gly Pro Ser Gly Glu Pro Gly Ser Pro Gly Lys
            260                 265                 270

Ala Gly Ser Ala Gly Glu Gln Gly Pro Pro Gly Lys Asp Gly Ser Asn
        275                 280                 285

Gly Glu Pro Gly Ser Pro Gly Lys Glu Gly Glu Arg Gly Leu Ala Gly
    290                 295                 300

Pro Pro Gly Pro Asp Gly Arg Arg Gly Glu Thr Gly Ser Pro Gly Ile
305                 310                 315                 320

Ala Gly Ala Leu Gly Lys Pro Gly Leu Glu Gly Pro Lys Gly Tyr Pro
                325                 330                 335

Gly Leu Arg Gly Arg Asp Gly Thr Asn Gly Lys Arg Gly Glu Gln Gly
            340                 345                 350

Glu Thr Gly Pro Asp Gly Val Arg Gly Ile Pro Gly Asn Asp Gly Gln
        355                 360                 365

Ser Gly Lys Pro Gly Ile Asp Gly Ile Asp Gly Thr Asn Gly Gln Pro
    370                 375                 380

Gly Glu Ala Gly Tyr Gln Gly Gly Arg Gly Thr Arg Gly Gln Leu Gly
385                 390                 395                 400

Glu Thr Gly Asp Val Gly Gln Asn Gly Asp Arg Gly Ala Pro Gly Pro
                405                 410                 415

Asp Gly Ser Lys Gly Ser Ala Gly Arg Pro Gly Leu Arg
            420                 425
```

<210> SEQ ID NO 90
<211> LENGTH: 570
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90

```
ggtccgcagg gtgttgttgg tgcagatggt aaagacggta ccccgggtaa tgcaggtcag      60

aaaggtccgt caggtgaacc tggcagccct ggtaaagcag gtagtgccgg tgagcagggt     120

ccgccgggca aagatggtag taatggtgag ccgggtagcc ctggcaaaga aggtgaacgt     180
```

-continued

```
ggtctggcag gaccgccggg tcctgatggt cgccgcggtg aaacgggttc accgggtatt    240

gccggtgccc tgggtaaacc aggtctggaa ggtccgaaag gttatcctgg tctgcgcggt    300

cgtgatggta ccaatggcaa acgtggcgaa cagggcgaaa ccggtccaga tggtgttcgt    360

ggtattccgg gtaacgatgg tcagagcggt aaaccgggca ttgatggtat tgatggcacc    420

aatggtcagc ctggcgaagc aggttatcag ggtggtcgcg gtacccgtgg tcagctgggt    480

gaaacaggtg atgttggtca gaatggtgat cgcggcgcac cgggtccgga tggtagcaaa    540

ggtagcgccg gtcgtccggg tttacgttaa                                     570
```

```
<210> SEQ ID NO 91
<211> LENGTH: 189
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gly Pro Gln Gly Val Val Gly Ala Asp Gly Lys Asp Gly Thr Pro Gly
1               5                   10                  15

Asn Ala Gly Gln Lys Gly Pro Ser Gly Glu Pro Gly Ser Pro Gly Lys
            20                  25                  30

Ala Gly Ser Ala Gly Glu Gln Gly Pro Pro Gly Lys Asp Gly Ser Asn
        35                  40                  45

Gly Glu Pro Gly Ser Pro Gly Lys Glu Gly Glu Arg Gly Leu Ala Gly
    50                  55                  60

Pro Pro Gly Pro Asp Gly Arg Arg Gly Glu Thr Gly Ser Pro Gly Ile
65                  70                  75                  80

Ala Gly Ala Leu Gly Lys Pro Gly Leu Glu Gly Pro Lys Gly Tyr Pro
                85                  90                  95

Gly Leu Arg Gly Arg Asp Gly Thr Asn Gly Lys Arg Gly Glu Gln Gly
            100                 105                 110

Glu Thr Gly Pro Asp Gly Val Arg Gly Ile Pro Gly Asn Asp Gly Gln
        115                 120                 125

Ser Gly Lys Pro Gly Ile Asp Gly Ile Asp Gly Thr Asn Gly Gln Pro
    130                 135                 140

Gly Glu Ala Gly Tyr Gln Gly Gly Arg Gly Thr Arg Gly Gln Leu Gly
145                 150                 155                 160

Glu Thr Gly Asp Val Gly Gln Asn Gly Asp Arg Gly Ala Pro Gly Pro
                165                 170                 175

Asp Gly Ser Lys Gly Ser Ala Gly Arg Pro Gly Leu Arg
            180                 185


<210> SEQ ID NO 92
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Met Lys Lys Ile Trp Leu Ala Leu Ala Gly Leu Val Leu Ala Phe Ser
1               5                   10                  15

Ala Ser Ala Gly Asp Gln Gly Pro Val Gly Arg Thr Gly Glu Val Gly
            20                  25                  30
```

```
Ala Val Gly Pro Pro Gly Phe Ala Gly Glu Lys Gly Pro Ser Gly Glu
        35                  40                  45

Ala Gly Thr Ala Gly Pro Pro Gly Thr Pro Gly Pro Gln Gly Leu Leu
    50                  55                  60

Gly Ala Pro Gly Ile Leu Gly Leu Pro Gly Ser Arg Gly Glu Arg Gly
65                  70                  75                  80

Leu Pro Gly Val Ala Gly Ala Val Gly Glu Pro Gly Pro Leu Gly Ile
                85                  90                  95

Ala Gly Pro Pro Gly Ala Arg Gly Pro Pro Gly Ala Val Gly Ser Pro
            100                 105                 110

Gly Val Asn Gly Ala Pro Gly Glu Ala Gly Arg Asp Gly Asn Pro Gly
        115                 120                 125

Asn Asp Gly Pro Pro Gly Arg Asp Gly Gln Pro Gly His Lys Gly Glu
    130                 135                 140

Arg Gly Tyr Pro Gly Asn Ile Gly Pro Val Gly Ala Ala Gly Ala Pro
145                 150                 155                 160

Gly Pro His Gly Pro Val Gly Pro Ala Gly Lys His Gly Asn Arg Gly
                165                 170                 175

Glu Thr Gly Pro Ser Gly Pro Val Gly Pro Ala Gly Ala Val Gly Pro
            180                 185                 190

Arg Gly Pro Ser Gly Pro Gln Gly Ile Arg Gly Asp Lys Gly Glu Pro
        195                 200                 205

Gly Glu Lys Gly Pro Arg Gly Leu Pro Gly Leu Gly Asp Tyr Lys Asp
    210                 215                 220

Asp Asp Asp Lys
225
```

<210> SEQ ID NO 93
<211> LENGTH: 687
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 93

```
atgaaaaaga tttggctggc gctggctggt ttagttttag cgtttagcgc atcggcgggt     60

gatcagggtc cggttggtcg taccggtgaa gttggtgcag tcgggccgcc gggttttgcg    120

ggtgaaaaag gcccgtcagg tgaagcaggc accgctggcc ctcctggcac gcctggccca    180

cagggtttac tgggcgcacc tggaattctg ggactgccgg gcagccgtgg agaacgcggt    240

ttaccaggtg ttgccggtgc cgttggtgaa cctggtccac tgggcattgc agggccgcct    300

ggcgcacggg gaccgcctgg tgctgttggt agtccgggtg tgaatggtgc tccgggtgaa    360

gccggtcgtg acggtaatcc gggaaatgac ggcccgccag gccgcgatgg tcagccgggt    420

cataaaggtg agcgtggtta cccaggtaat attggtccag tcggtgccgc cggtgcgccg    480

ggtcctcatg gccctgtcgg tccagccggt aaacatggta atcgcggtga gacaggtccg    540

tcaggaccag tgggccctgc tggcgcagtc ggtccgcgcg ggccgagtgg ccctcagggt    600

attcgtggcg ataaagggga accgggcgaa aaagggccgc ggggtctgcc aggcctgggt    660

gactacaaag acgacgacga caaataa                                        687
```

<210> SEQ ID NO 94
<211> LENGTH: 228
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 94

```
Met Lys Lys Ile Trp Leu Ala Leu Ala Gly Leu Val Leu Ala Phe Ser
1               5                   10                  15

Ala Ser Ala Lys Gly His Asn Gly Leu Gln Gly Leu Pro Gly Ile Ala
            20                  25                  30

Gly His His Gly Asp Gln Gly Ala Pro Gly Ser Val Gly Pro Ala Gly
        35                  40                  45

Pro Arg Gly Pro Ala Gly Pro Ser Gly Pro Ala Gly Lys Asp Gly Arg
    50                  55                  60

Thr Gly His Pro Gly Thr Val Gly Pro Ala Gly Ile Arg Gly Pro Gln
65                  70                  75                  80

Gly His Gln Gly Pro Ala Gly Pro Pro Gly Pro Pro Gly Pro Pro Gly
                85                  90                  95

Pro Pro Gly Val Ser Gly Gly Gly Tyr Asp Phe Gly Tyr Asp Gly Asp
            100                 105                 110

Phe Tyr Arg Ala Asp Gln Pro Arg Ser Ala Pro Ser Leu Arg Pro Lys
        115                 120                 125

Asp Tyr Glu Val Asp Ala Thr Leu Lys Ser Leu Asn Asn Gln Ile Glu
    130                 135                 140

Thr Leu Leu Thr Pro Glu Gly Ser Arg Lys Asn Pro Ala Arg Thr Cys
145                 150                 155                 160

Arg Asp Leu Arg Leu Ser His Pro Glu Trp Ser Ser Gly Tyr Tyr Trp
                165                 170                 175

Ile Asp Pro Asn Gln Gly Cys Thr Met Asp Ala Ile Lys Val Tyr Cys
            180                 185                 190

Asp Phe Ser Thr Gly Glu Thr Cys Ile Arg Ala Gln Pro Glu Asn Ile
        195                 200                 205

Pro Ala Lys Asn Trp Tyr Arg Ser Ser Lys Asp Gly Asp Tyr Lys Asp
    210                 215                 220

Asp Asp Asp Lys
225
```

<210> SEQ ID NO 95
<211> LENGTH: 687
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 95

```
atgaaaaaga tttggctggc gctggctggt ttagttttag cgtttagcgc atcggcgaaa     60

ggtcacaatg gactgcaagg cctgccaggt attgcaggtc atcatggtga tcaaggtgcc    120

ccgggaagcg ttggtccggc ggggccgaga ggccctgcgg gaccttcagg tccggcaggc    180

aaagatggtc ggacaggcca tccgggcacc gttggccctg caggaattcg tggaccgcag    240

ggtcatcagg gacctgctgg tccgccaggt cccccgggcc ctccgggacc accgggtgtt    300

agtggtggtg gttatgattt tggctatgat ggtgattttt atcgtgcaga tcagccgcgt    360

agcgcaccga gcctgcgtcc taaagattat gaagttgatg caaccctgaa aagcctgaat    420

aatcagattg aaacactgct gacaccggaa ggtagccgta aaaatccggc ccgtacctgt    480

cgtgatctgc gtctgagcca cccggaatgg agcagcggtt attattggat tgatccgaat    540
```

```
caaggttgta ccatggatgc aattaaagtt tattgtgatt ttagcacagg tgaaacatgt    600

atccgtgcac agccggaaaa tattccggcc aaaaattggt atcgtagtag caaagatggt    660

gactacaaag acgacgacga caaataa                                        687
```

<210> SEQ ID NO 96
<211> LENGTH: 262
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 96

```
Met Lys Lys Ile Trp Leu Ala Leu Ala Gly Leu Val Leu Ala Phe Ser
1               5                   10                  15

Ala Ser Ala Tyr Glu Val Asp Ala Thr Leu Lys Ser Leu Asn Asn Gln
            20                  25                  30

Ile Glu Thr Leu Leu Thr Pro Glu Gly Ser Arg Lys Asn Pro Ala Arg
        35                  40                  45

Thr Cys Arg Asp Leu Arg Leu Ser His Pro Glu Trp Ser Ser Gly Tyr
    50                  55                  60

Tyr Trp Ile Asp Pro Asn Gln Gly Cys Thr Met Asp Ala Ile Lys Val
65                  70                  75                  80

Tyr Cys Asp Phe Ser Thr Gly Glu Thr Cys Ile Arg Ala Gln Pro Glu
                85                  90                  95

Asn Ile Pro Ala Lys Asn Trp Tyr Arg Ser Ser Lys Asp Lys Lys His
            100                 105                 110

Val Trp Leu Gly Glu Thr Ile Asn Ala Gly Ser Gln Phe Glu Tyr Asn
        115                 120                 125

Val Glu Gly Val Thr Ser Lys Glu Met Ala Thr Gln Leu Ala Phe Met
    130                 135                 140

Arg Leu Leu Ala Asn Tyr Ala Ser Gln Asn Ile Thr Tyr His Cys Lys
145                 150                 155                 160

Asn Ser Ile Ala Tyr Met Asp Glu Glu Thr Gly Asn Leu Lys Lys Ala
                165                 170                 175

Val Ile Leu Gln Gly Ser Asn Asp Val Glu Leu Val Ala Glu Gly Asn
            180                 185                 190

Ser Arg Phe Thr Tyr Thr Val Leu Val Asp Gly Cys Ser Lys Lys Thr
        195                 200                 205

Asn Glu Trp Gly Lys Thr Ile Ile Glu Tyr Lys Thr Asn Lys Pro Ser
    210                 215                 220

Arg Leu Pro Phe Leu Asp Ile Ala Pro Leu Asp Ile Gly Gly Ala Asp
225                 230                 235                 240

Gln Glu Phe Phe Val Asp Ile Gly Pro Val Cys Phe Lys Gly Asp Tyr
                245                 250                 255

Lys Asp Asp Asp Asp Lys
            260
```

<210> SEQ ID NO 97
<211> LENGTH: 788
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 97

-continued

```
tgaaaaagat ttggctggcg ctggctggtt tagttttagc gtttagcgca tcggcgtatg     60

aagttgatgc aaccctgaaa agcctgaata atcagattga aacactgctg acaccggaag    120

gtagccgtaa aaatccggcc cgtacctgtc gtgatctgcg tctgagccac ccggaatgga    180

gcagcggtta ttattggatt gatccgaatc aaggttgtac catggatgca attaaagttt    240

attgtgattt tagcacaggt gaaacatgta tccgtgcaca gccggaaaat attccggcca    300

aaaattggta tcgtagtagc aaagataaaa aacatgtgtg gctgggtgaa accattaatg    360

caggtagcca gtttgaatac aatgttgaag gtgttaccag caaagaaatg gcaacacagc    420

tggcatttat gcgtctgctg gcaaattatg caagccagaa tattacatat cattgtaaaa    480

atagcattgc atatatggat gaagaaaccg gtaatctgaa aaaagcagtt attctgcagg    540

gtagcaatga tgttgaactg gttgccgaag gtaatagccg ttttacatat accgttctgg    600

ttgatggttg tagcaaaaaa accaatgaat ggggtaaaac catcattgaa tataaaacca    660

acaaaccgag ccgtctgccg tttctggata tcgctccgct ggatattggt ggtgccgatc    720

aggaattttt tgtcgatatc ggtcctgtgt gttttaaagg tgactacaaa gacgacgacg    780

acaaataa                                                              788
```

<210> SEQ ID NO 98
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

```
Met Lys Lys Ile Trp Leu Ala Leu Ala Gly Leu Val Leu Ala Phe Ser
1               5                   10                  15

Ala Ser Ala Gly Gly Val Pro Gly Ala Ile Pro Gly Gly Val Pro Gly
            20                  25                  30

Gly Val Phe Tyr Pro Gly Ala Gly Leu Gly Ala Leu Gly Gly Gly Ala
        35                  40                  45

Leu Gly Pro Gly Gly Lys Pro Leu Lys Pro Val Pro Gly Gly Leu Ala
    50                  55                  60

Gly Ala Gly Leu Gly Ala Gly Leu Gly Ala Phe Pro Ala Val Thr Phe
65                  70                  75                  80

Pro Gly Ala Leu Val Pro Gly Gly Val Ala Asp Ala Ala Ala Ala Tyr
                85                  90                  95

Lys Ala Ala Lys Ala Gly Ala Gly Leu Gly Gly Val Pro Gly Val Gly
            100                 105                 110

Gly Leu Gly Val Ser Ala Gly Ala Val Val Pro Gln Pro Gly Ala Gly
        115                 120                 125

Val Lys Pro Gly Lys Val Pro Gly Val Gly Leu Pro Gly Val Tyr Pro
    130                 135                 140

Gly Gly Val Leu Pro Gly Ala Arg Phe Pro Gly Val Gly Val Leu Pro
145                 150                 155                 160

Gly Val Pro Thr Gly Ala Gly Val Lys Pro Lys Ala Pro Gly Val Gly
                165                 170                 175

Gly Ala Phe Ala Gly Ile Pro Gly Val Gly Pro Phe Gly Gly Pro Gln
            180                 185                 190

Pro Gly Val Pro Leu Gly Tyr Pro Ile Lys Ala Pro Lys Leu Pro Gly
        195                 200                 205
```

-continued

```
Gly Tyr Gly Leu Pro Tyr Thr Thr Gly Lys Leu Gly Asp Tyr Lys Asp
    210                 215                 220

Asp Asp Asp Lys
225


<210> SEQ ID NO 99
<211> LENGTH: 687
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99

atgaaaaaga tttggctggc gctggctggt ttagttttag cgtttagcgc atcggcgggt      60

ggcgtaccag gcgcaattcc tgggggtgtc ccaggcggtg ttttttatcc gggcgccggt     120

cttggcgcac tgggtggcgg tgcactgggc ccgggcggca aaccgctgaa accggtacca     180

ggtggtttag caggcgccgg cttaggcgca ggtctgggag catttccggc agttaccttt     240

ccaggggcac tggttcctgg aggtgtggcc gatgcagccg cggcatataa agccgctaaa     300

gccggtgcgg gtttaggagg cgtcccaggt gtcggtggcc tgggtgttag cgccggtgca     360

gttgttccgc agccgggagc aggggttaaa cctggtaaag tgccgggagt aggtctgcca     420

ggcgtttatc ctggtggtgt tttgccgggt gcccgttttc cgggcgttgg tgttcttcca     480

ggcgtgccga ccggagccgg tgttaaaccg aaagcccccg gtgttggagg tgcatttgca     540

ggcatcccgg gagttggccc gtttggtggt ccgcaacctg ggttccgtt aggttatccg      600

attaaagcac cgaaactgcc cggcggttat ggtctgccgt acacaaccgg taaactgggt     660

gactacaaag acgacgacga caaataa                                         687


<210> SEQ ID NO 100
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Met Lys Lys Ile Trp Leu Ala Leu Ala Gly Leu Val Leu Ala Phe Ser
1               5                   10                  15

Ala Ser Ala Pro Tyr Gly Tyr Gly Pro Gly Gly Val Ala Gly Ala Ala
            20                  25                  30

Gly Lys Ala Gly Tyr Pro Thr Gly Thr Gly Val Gly Pro Gln Ala Ala
        35                  40                  45

Ala Ala Ala Ala Ala Lys Ala Ala Ala Lys Phe Gly Ala Gly Ala Ala
    50                  55                  60

Gly Val Leu Pro Gly Val Gly Gly Ala Gly Val Pro Gly Val Pro Gly
65                  70                  75                  80

Ala Ile Pro Gly Ile Gly Gly Ile Ala Gly Val Gly Thr Pro Ala Ala
                85                  90                  95

Ala Ala Ala Ala Ala Ala Ala Ala Lys Ala Ala Lys Tyr Gly Ala Ala
            100                 105                 110

Ala Gly Leu Val Pro Gly Gly Pro Gly Phe Gly Pro Gly Val Val Gly
        115                 120                 125

Val Pro Gly Ala Gly Val Pro Gly Val Gly Val Pro Gly Ala Gly Ile
    130                 135                 140
```

```
Pro Val Val Pro Gly Ala Gly Ile Pro Gly Ala Ala Val Pro Gly Val
145                 150                 155                 160

Val Ser Pro Glu Ala Ala Ala Lys Ala Ala Ala Lys Ala Ala Lys Tyr
                165                 170                 175

Gly Ala Arg Pro Gly Val Gly Val Gly Gly Ile Pro Thr Tyr Gly Val
            180                 185                 190

Gly Ala Gly Gly Phe Pro Gly Phe Gly Val Gly Val Gly Gly Ile Pro
        195                 200                 205

Gly Val Ala Gly Val Pro Gly Val Gly Gly Val Gly Asp Tyr Lys Asp
    210                 215                 220

Asp Asp Asp Lys
225
```

<210> SEQ ID NO 101
<211> LENGTH: 687
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 101

```
atgaaaaaga tttggctggc gctggctggt ttagttttag cgtttagcgc atcggcgccg     60

tatggttatg gcccgggtgg agttgcgggt gcagcaggta aagcgggtta tcctaccgga    120

accggtgtag gtccgcaggc cgctgctgcc gccgccgcaa aagcagcggc taaatttggc    180

gccggagcag cgggtgttct gcctggagtt ggtggtgcgg gcgtgccagg ggtacctggt    240

gcaattccgg gtattggtgg tattgccggt gtcggcaccc cggccgcggc agctgcggca    300

gcggcggctg ccaaagctgc taaatacggt gccgcggcgg gtctggtgcc aggaggtccg    360

ggttttggtc cgggagtggt tggcgtgcct ggcgcaggcg ttcctggtgt gggcgttcca    420

ggtgcaggga ttcctgttgt gcctggtgcc ggtattcccg gcgcggccgt tccgggggtg    480

gttagcccgg aagccgcagc gaaggctgcg gcaaaggcag caaagtatgg cgcacgccca    540

ggagtcggcg tgggtggtat cccgacctat ggggtgggcg caggggggttt tcctggtttc    600

ggcgtaggtg taggaggtat accgggcgtg gccggtgtac caggggttgg tggcgtcggt    660

gactacaaag acgacgacga caaataa                                        687
```

<210> SEQ ID NO 102
<211> LENGTH: 273
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 102

```
Met Lys Lys Ile Trp Leu Ala Leu Ala Gly Leu Val Leu Ala Phe Ser
1               5                   10                  15

Ala Ser Ala Pro Val Gly Arg Arg Gly Pro Lys Gly Ser Arg Gly Asp
            20                  25                  30

Pro Gly Asp Gly Gly Ala Ala Gly Pro Lys Gly Pro Glu Gly Val Asp
        35                  40                  45

Gly Leu Ile Gly Glu Pro Gly Gln Pro Gly Pro Ile Gly Ala Glu Gly
    50                  55                  60

Ser Ser Gly Leu Glu Gly Phe Leu Gly Asp Lys Gly Ser Lys Gly Ala
65                  70                  75                  80
```

```
Arg Gly Gly Pro Gly Asn Arg Gly Arg Pro Gly Gln Asp Gly Val Pro
                85                  90                  95

Gly Gln Asp Gly Arg Ala Gly Glu Lys Gly Glu Gly Gly Glu Thr Gly
            100                 105                 110

Asp Arg Gly Gln Gln Gly Leu Arg Gly Lys Val Gly Asp Pro Gly Leu
        115                 120                 125

Val Gly Asp Leu Gly Ala Gln Gly Pro Gln Gly Ser Gln Gly Leu Val
    130                 135                 140

Gly Pro Pro Gly Ile Pro Gly Glu Pro Gly Ser Gly Gly Glu Pro Gly
145                 150                 155                 160

Asp Gln Gly Pro Arg Gly Pro Glu Gly Pro Gln Gly Ser Pro Gly Val
                165                 170                 175

Arg Gly Gly Arg Gly Glu Arg Gly Thr Pro Gly Ala Val Gly Pro Lys
            180                 185                 190

Gly Pro Pro Gly Lys Asn Gly Ala Asp Gly Pro Arg Gly Leu Pro Gly
        195                 200                 205

Ala Ser Gly Pro Pro Gly Ser Pro Gly Asn Gln Gly Pro Glu Gly Ser
    210                 215                 220

Arg Gly Ala Asp Gly Asn Asn Gly Phe Pro Gly Asp Asp Gly Glu Asn
225                 230                 235                 240

Gly Leu Val Gly Ile Pro Gly Glu Pro Gly Pro Lys Gly Ala Arg Gly
                245                 250                 255

Thr Arg Gly Glu Leu Gly Lys Thr Gly Asp Tyr Lys Asp Asp Asp Asp
            260                 265                 270

Lys
```

```
<210> SEQ ID NO 103
<211> LENGTH: 822
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103

atgaaaaaga tttggctggc gctggctggt ttagttttag cgtttagcgc atcggcgccg      60

gttggtcgtc gtggtccgaa aggtagccgt ggtgatcctg gtgatggtgg tgcagcaggt     120

cctaaaggtc cggaaggtgt tgatggtctg attggtgaac cgggtcagcc tggtccgatt     180

ggcgcagaag gtagcagcgg tctggaaggt tttctgggtg ataaaggtag caaaggtgca     240

cgtggtggtc cgggtaatcg cggtcgtcct ggtcaggatg gtgttccggg tcaagatggt     300

cgtgccggtg aaaaaggtga aggtggtgaa accggtgatc gcggtcagca gggtctgcgt     360

ggtaaagttg gtgatccagg tctggtgggt gatctgggtg cacagggtcc gcagggtagc     420

caaggtctgg ttggtccgcc tggtattccg ggtgaacctg gtagcggtgg cgaaccgggt     480

gatcagggtc ctcgcggtcc agaaggtcct cagggttcac cgggtgttcg cggtggtcgt     540

ggtgaacgtg gtacaccggg tgcagttgga ccgaaaggtc cgccaggtaa aaatggtgca     600

gatggtccgc gtggtctgcc tggtgcaagc ggtcctccgg gtagtcctgg taaccagggt     660

cctgaaggtt ctcgtggtgc cgatggtaat aatggttttc caggtgatga tggtgaaaat     720

ggcctggttg gtatccctgg cgaaccaggt ccaaaaggcg cacgcggtac acgcggtgaa     780

ctgggtaaaa ccggtgacta caaagacgac gacgacaaat aa                        822

<210> SEQ ID NO 104
```

<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Met Lys Lys Ile Trp Leu Ala Leu Ala Gly Leu Val Leu Ala Phe Ser
1               5                   10                  15

Ala Ser Ala Gly Arg Gly Gly Pro Ala Gly Leu Gln Gly Ala Ala Gly
            20                  25                  30

Asn Pro Gly Asp Pro Gly Asp Arg Gly Gln Ala Gly Glu Ile Gly Leu
        35                  40                  45

Pro Gly Thr Glu Gly Gln Arg Gly Gln Gly Gly Ser Arg Gly Asp Asp
    50                  55                  60

Gly Ile Gly Gly Gln Ser Gly Thr Asp Gly Asp Pro Gly Asn Asp Gly
65                  70                  75                  80

Val Ala Gly Ile Arg Gly Ala Arg Gly Glu Pro Gly Ala Thr Gly Pro
                85                  90                  95

Glu Gly Ala Ala Gly Gln Lys Gly Asp Arg Gly Arg Phe Gly Glu Gln
            100                 105                 110

Gly Arg Pro Gly Asn Asp Gly Pro Pro Gly Arg Arg Gly Arg Val Gly
        115                 120                 125

Asn Leu Gly Glu Thr Gly Ala Glu Gly Asp Glu Gly Thr Arg Gly Tyr
    130                 135                 140

Thr Gly Asp Arg Gly Pro Glu Gly Ala Ile Gly Ile Ser Gly Val Thr
145                 150                 155                 160

Gly Asn Pro Gly Pro Gln Gly Ile Lys Gly Pro Pro Gly Asp Thr Gly
                165                 170                 175

His Pro Gly Arg Gln Gly Pro Ser Gly Pro Gln Gly Pro Pro Gly Ile
            180                 185                 190

Pro Gly Thr Asp Gly Leu Thr Ile His Asn Leu Ile Lys Pro Pro Ser
        195                 200                 205

Gln Phe Phe Asp Ala Thr Ser Ser Ser Asp Pro Leu Thr Asp Ala Val
    210                 215                 220

Val Glu Ser Ile Leu Lys Ser Phe Gln Tyr Ala Glu Leu Glu Ile Asp
225                 230                 235                 240

Leu Thr Lys Lys Pro Asp Gly Thr Met Lys Tyr Pro Ala Ile Ser Cys
                245                 250                 255

Asp Asp Leu His Lys Asp Tyr Pro Gln Leu Pro Ser Gly Asn Tyr Thr
            260                 265                 270

Leu Asp Pro Asn Gly Gly Cys Lys Asn Asp Ala Phe Glu Thr Tyr Cys
        275                 280                 285

Glu Phe Asn Asn Ser Val Lys Met Cys Leu Thr Pro Lys Ile Pro Thr
    290                 295                 300

Leu Leu Pro Met Gly Thr Tyr Lys Tyr Tyr Val Asn Ser Glu Gly Tyr
305                 310                 315                 320

Tyr Ser Pro Asn Asp Phe Gly Leu Asn Leu Arg Phe Phe Glu Tyr Tyr
                325                 330                 335

Gly Ser Val Thr Gln Leu Lys Phe Leu Gln Thr Lys Ala Thr Arg Val
            340                 345                 350

Thr Gln Thr Ile Arg Val Leu Cys Lys Asn Tyr Asp Pro Leu His Lys
        355                 360                 365

Gln Pro Val Phe Ile Gly Met Asn Asp Glu Thr Val Met Asp Glu Pro

```
    370                 375                 380

Arg Met Glu Glu Asn Gln Cys Gln Tyr Phe Asn Gly Leu Ser Ala His
385                 390                 395                 400

Val Glu Leu Glu Leu Ser Ser Asn Asp Pro Ser Tyr Leu Pro Ile Tyr
                405                 410                 415

Glu Met Arg Leu Tyr Leu Gly Arg Lys Thr Asn Glu Glu Leu Gly Ile
            420                 425                 430

Glu Leu Gly Asp Leu Cys Phe Glu Tyr Gly Asp Tyr Lys Asp Asp Asp
        435                 440                 445

Asp Lys
    450
```

<210> SEQ ID NO 105
<211> LENGTH: 1353
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 105

```
atgaaaaaga tttggctggc gctggctggt ttagttttag cgtttagcgc atcggcgggt     60

cgtggcggtc cggcaggtct gcagggtgct gcaggtaatc ctggcgaccc tggcgatcgt    120

ggtcaggcag gcgaaattgg tctgccaggc accgaaggtc agcgtggtca aggtggttca    180

cgtggtgatg acggtattgg tggtcagagc ggcaccgatg gcgatccggg taacgatggt    240

gttgcaggta ttcgtggtgc acgcggagaa cctggtgcca ccggacctga aggtgcagcc    300

ggtcagaaag gtgatcgtgg ccgttttggc gaacagggtc gtccgggaaa tgatggtcca    360

ccgggtcgcc gtggccgtgt gggcaatctg ggtgaaacag gtgccgaagg tgatgaaggc    420

acccgtggtt atacaggtga ccgtggaccg gaaggcgcaa ttggtattag cggtgtgacc    480

ggtaatccgg gtccacaggg cattaaaggc cctccgggtg atacgggtca tccgggtcgt    540

cagggaccga gcggtccgca aggaccaccg ggtattccag gtacagatgg cctgaccatt    600

cataatctga ttaaaccgcc tagccagttt tttgatgcaa ccagcagcag cgatccgctg    660

accgatgcag ttgttgaaag cattctgaaa tcttttcagt atgccgagct ggaaattgac    720

ctgaccaaaa aaccggatgg caccatgaaa tatccggcaa ttagctgtga tgatctgcac    780

aaagattatc cgcagctgcc gagcggtaat tataccctgg atccgaatgg tggttgtaaa    840

aatgatgcct ttgaaaccta ttgcgagttc aacaatagcg tgaaaatgtg tctgaccccg    900

aaaattccga cactgctgcc gatgggcacc tataaatact atgttaatag cgagggttac    960

tacagcccga atgatttggg tctgaatctg cgctttttg agtattatgg tagcgttacc    1020

cagctgaaat ttctgcagac caaagcaacc cgtgttaccc agaccattcg tgttctgtgt   1080

aaaaactatg atccgctgca taaacagccg gtttttattg gtatgaatga cgaaaccgtt   1140

atggatgaac cgcgtatgga agaaaatcag tgccagtatt ttaacggtct gagcgcacat   1200

gttgaactgg aactgagcag caatgatccg agctatctgc cgatttatga aatgcgtctg   1260

tatctgggtc gtaaaaccaa tgaagaactg ggcattgaac tgggcgatct gtgttttgaa   1320

tatggtgact acaaagacga cgacgacaaa taa                                1353
```

<210> SEQ ID NO 106
<211> LENGTH: 286
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 106

Met Lys Lys Ile Trp Leu Ala Leu Ala Gly Leu Val Leu Ala Phe Ser
1               5                   10                  15

Ala Ser Ala Glu Lys Thr Ser Ser Lys Val Ala Leu Met Thr Val Leu
            20                  25                  30

Val Val Ile Thr Gly Ala Leu Ile Ile Glu Gly Thr Ser Ile Thr Arg
        35                  40                  45

Gly Ser Thr His Val Asn Arg Gly Leu Arg Lys Arg Gln Thr Ser Glu
    50                  55                  60

Asp Asn Cys Glu Ala Val Lys Val Gly Leu Pro Gly Arg Asp Gly Arg
65                  70                  75                  80

Glu Gly Pro Pro Gly Pro Pro Gly Pro Ala Gly Arg Asp Gly Arg Asp
                85                  90                  95

Ala Val Cys Ser Asn Gln Thr Thr Gly Leu Gly Ala Lys Gly Asp Arg
            100                 105                 110

Gly Pro Pro Gly Thr Pro Gly Phe Pro Gly Glu Val Gly Arg Pro Gly
        115                 120                 125

Pro Pro Gly Ala Asp Gly Ile Pro Gly Pro Gln Gly Glu Arg Gly Ala
    130                 135                 140

Val Gly Pro Gly Gly Lys Pro Gly Pro Arg Gly Glu Val Gly Thr Pro
145                 150                 155                 160

Gly Ala Asp Gly Ala Asp Gly Ala Thr Gly Ala Thr Gly Val Gln Gly
                165                 170                 175

Pro Asp Gly Ala Lys Gly Glu Lys Gly Ala Ser Gly Thr Ala Gly Leu
            180                 185                 190

Lys Gly Glu Lys Gly Asp Thr Cys Ile Pro Asp Ser Asn Ser Thr Leu
        195                 200                 205

Gly Met Pro Gly Thr Pro Gly Ala Gly Gly Ser Lys Gly Gln Lys Gly
    210                 215                 220

Glu Ser Gly Ile Val Gly Pro Lys Gly Glu Arg Gly Glu Ile Gly Thr
225                 230                 235                 240

Pro Gly His Pro Gly Phe Arg Gly Ala Asp Gly Glu Pro Gly His Lys
                245                 250                 255

Gly Val Pro Gly Arg Ala Gly Ala Gln Gly Asp Arg Gly Asp Pro Gly
            260                 265                 270

Asp Asp Gly Leu Thr Gly Asp Tyr Lys Asp Asp Asp Asp Lys
        275                 280                 285


<210> SEQ ID NO 107
<211> LENGTH: 861
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107

atgaaaaaga tttggctggc gctggctggt ttagttttag cgtttagcgc atcggcggaa      60

aaaaccagca gcaaagttgc actgatgacc gttctggttg ttattaccgg tgcactgatt     120

attgaaggca ccagcattac ccgtggtagc acccatgtta atcgtggtct gcgtaaacgt     180

cagaccagcg aagataattg tgaagcagtt aaagttggtc tgccaggtcg tgatggtcgt     240
```

```
gaaggtcctc cgggtccgcc tggtccggct ggcagagatg gccgtgatgc agtttgtagc    300

aatcagacca ccggtctggg tgcaaaaggt gatcgtggtc cgccaggtac accgggtttt    360

ccgggtgaag ttggccgtcc gggtccaccg ggtgcagatg gtattccggg tcctcagggt    420

gaacgtggtg cagttggtcc tggtggtaaa cctggtccgc gtggtgaagt gggcacccct    480

ggtgccgatg gcgcagatgg tgcaaccggt gcgaccggtg ttcagggtcc tgatggtgcc    540

aaaggcgaaa aaggtgcaag cggcaccgca ggtctgaaag gtgagaaagg cgatacctgt    600

attccggata gcaatagcac cctgggtatg cctggtacac caggtgccgg tggtagcaaa    660

ggccagaaag gtgaaagtgg tattgttggt ccgaaaggcg aacgcggtga aattggcaca    720

ccgggtcatc ctggttttcg tggtgcggat ggtgaaccag gtcataaagg tgttccgggt    780

cgtgccggtg cgcagggtga tcgcggtgat ccgggtgatg atggtctgac cggtgactac    840

aaagacgacg acgacaaata a                                              861
```

<210> SEQ ID NO 108
<211> LENGTH: 512
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

```
Met Lys Lys Ile Trp Leu Ala Leu Ala Gly Leu Val Leu Ala Phe Ser
1               5                   10                  15

Ala Ser Ala Gly Phe Pro Gly Ala Pro Gly Ala Asp Gly Ala Pro Gly
            20                  25                  30

Gln Lys Gly Glu Leu Gly Ala Val Gly Pro Gln Gly Thr Pro Gly Leu
        35                  40                  45

Ser Gly Pro Ser Gly Pro Thr Gly Pro Pro Gly Pro Lys Gly Val Arg
    50                  55                  60

Gly Ala Pro Gly Ser Ser Gly Ala Lys Gly Asp Ala Gly Asn Pro Gly
65                  70                  75                  80

Asp Asp Gly Pro Val Gly Pro Gln Gly Val Pro Gly Val Asp Gly Ser
                85                  90                  95

Pro Gly Gln Lys Gly Glu Thr Gly Arg Val Gly Pro Arg Gly His Asp
            100                 105                 110

Gly Ile Asn Gly Thr Pro Gly Glu Asp Gly Ala Thr Gly Phe Pro Gly
        115                 120                 125

Pro Asp Gly Ala Lys Gly Glu Lys Gly Thr Ser Gly Thr Ala Gly Leu
    130                 135                 140

Lys Gly Glu Lys Gly Asp Thr Cys Ile Pro Asp Ser Asn Ser Thr Leu
145                 150                 155                 160

Gly Met Pro Gly Thr Pro Gly Ala Gly Trp Ser Lys Gly Gln Lys Gly
                165                 170                 175

Glu Ser Gly Ile Val Gly Pro Lys Gly Glu Lys Gly Glu Ile Gly Thr
            180                 185                 190

Pro Gly Pro Pro Gly Phe Arg Gly Ala Asp Gly Glu Pro Gly Gln Arg
        195                 200                 205

Gly Glu Pro Gly Arg Ala Gly Ala Gln Gly Glu Arg Gly Ala Pro Gly
    210                 215                 220

Asn Asn Gly Arg Asp Gly Phe Pro Gly Asp Pro Gly Ala Asp Gly Ala
225                 230                 235                 240

Pro Gly Gln Lys Gly Glu Leu Gly Ala Ile Gly His Pro Gly Phe Ser
```

```
                245                 250                 255

Gly Pro Ser Gly Pro Ser Gly Pro Thr Gly Pro Pro Gly Pro Lys Gly
            260                 265                 270

Val Arg Gly Ala Gln Gly Arg Pro Gly Asp Arg Gly Ser Pro Gly Asp
        275                 280                 285

Val Gly Pro Ile Gly Ala Pro Gly Pro Pro Gly Ala Asp Gly Val Pro
    290                 295                 300

Gly Leu Thr Gly Val Gln Gly Arg Asp Gly Pro Lys Gly Glu Ser Ala
305                 310                 315                 320

Ser Ser Gly Ala Val Tyr Val Arg Trp Gly Arg Thr Thr Cys Pro Ser
                325                 330                 335

Gly Ala Asp Val Val Tyr Ser Gly Arg Ala Ala Gly Ala Lys Tyr Asp
            340                 345                 350

His Ser Gly Gly Thr Ser Asp His His Cys Leu Pro Asn Asn Pro Gln
        355                 360                 365

Tyr Leu Ser Glu Asp Asp Thr Asn Ala Leu Gly Ala Gln Leu Tyr Gly
    370                 375                 380

Val Glu Tyr Glu Ile Arg Asp Arg Ser Ser Pro Tyr Asn Ser Leu Asp
385                 390                 395                 400

Gln Ser Asp Met Pro Cys Val Val Cys Asn Ala Asn Gly Arg Ser Gln
                405                 410                 415

Leu Leu Met Val Pro Ala Arg Tyr Thr Cys Pro Thr Gly Trp Ser Arg
            420                 425                 430

Glu Tyr Tyr Gly Tyr Met Met Ser Glu Gly Lys Ala Lys Asn Arg Glu
        435                 440                 445

Gly Arg Lys Thr Thr Ile Cys Met Asp Phe Ser Ala Glu Ala Val Pro
    450                 455                 460

Gly Ser Gly Ala Asn Thr Asn Pro Ser Pro Gly Ile Met Met Arg Ala
465                 470                 475                 480

Asn Cys Asn Gly Leu Ala Cys Pro Pro Tyr Gln Ser Asn Thr Pro Leu
                485                 490                 495

Thr Cys Ala Val Cys Thr Lys Gly Asp Tyr Lys Asp Asp Asp Asp Lys
            500                 505                 510


<210> SEQ ID NO 109
<211> LENGTH: 1539
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109

atgaaaaaga tttggctggc gctggctggt ttagttttag cgtttagcgc atcggcgggt      60

tttcctggcg ctccgggtgc cgacggtgct ccgggtcaaa aaggtgaact gggtgccgtg     120

ggtccgcagg gcactccggg tctgagtggt cctagtggtc cgaccggtcc accaggtcca     180

aaaggcgtgc gtggtgcacc gggtagcagc ggagccaaag gtgatgcagg taaccctggt     240

gatgacggtc cggttggtcc acagggcgtt ccaggtgttg atggtagccc tggccaaaag     300

ggtgaaaccg gtcgtgtggg tcctcgtggt catgatggta ttaatggcac cccaggtgaa     360

gatggtgcga caggctttcc aggtccggat ggcgcaaagg gtgagaaggg caccagcggt     420

acagctggcc tgaagggcga aaagggcgat acatgcatcc cggattcaaa ttcaacactg     480

ggcatgccag gtacgcctgg cgcaggttgg agtaaaggac aaaaaggcga atcaggcatt     540
```

```
gtgggaccta aaggcgagaa gggtgagatt ggtactccgg gaccgccagg ctttcgcggt    600

gcagacggcg aaccgggtca gcgtggcgaa cctggtcgtg caggcgcaca aggtgaacgc    660

ggagcccctg gtaataatgg acgtgatggc tttcctggtg atccaggtgc agatggcgca    720

cctggccaga aaggcgaact gggagcaatt ggtcatccgg gatttagcgg tccgtcaggt    780

ccgagcggac cgacaggtcc tcctggaccg aaaggtgtac gtggcgcaca gggtcgtcct    840

ggcgatcgtg gcagtccagg tgatgtgggt ccgattggtg cacctggtcc tccaggtgcg    900

gacggcgtgc ctggtttaac aggtgtgcag ggtcgcgacg gtcctaaagg tgaatcagca    960

agcagcggtg cagtttatgt tcgttggggt cgtaccacct gtcctagcgg agcagatgtt   1020

gtttatagcg gtcgcgcagc cggtgcaaaa tatgatcatt caggtggcac ctcagatcat   1080

cattgtctgc cgaataatcc gcagtatctg agcgaagatg ataccaatgc actgggtgca   1140

cagctgtatg gtgtggaata tgaaattcgt gatcgtagca gcccgtataa tagcctggat   1200

cagagcgata tgccgtgtgt tgtttgtaat gcaaatggtc gtagccagct gctgatggtt   1260

ccggcacgtt atacatgccc gaccggttgg agccgtgaat attatggtta tatgatgagc   1320

gaaggcaaag ccaaaaatcg cgaaggtcgt aaaaccacca tttgtatgga ttttagcgca   1380

gaagcagttc ctggtagcgg tgcaaatacc aatccgagtc cgggtattat gatgcgtgca   1440

aattgtaatg gtctggcatg tccgccttat cagagcaata caccgctgac ctgtgccgtt   1500

tgtaccaaag gtgactacaa agacgacgac gacaaataa                          1539
```

```
<210> SEQ ID NO 110
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Met Lys Lys Ile Trp Leu Ala Leu Ala Gly Leu Val Leu Ala Phe Ser
1               5                   10                  15

Ala Ser Ala Gly Pro Ala Gly Ala Lys Gly Pro Ser Gly Asp Ile Gly
            20                  25                  30

Arg Pro Gly Glu Ser Gly Ser Pro Gly Ala Arg Gly His Ser Gly Gln
        35                  40                  45

Pro Gly Arg Thr Gly Ile Ala Gly Asn Gln Gly Leu Pro Gly Thr Ala
    50                  55                  60

Gly Glu Glu Gly Arg Thr Gly Pro Pro Gly Pro Ala Gly Leu Arg Gly
65                  70                  75                  80

Gln Ala Gly Met Met Gly Phe Pro Gly Pro Lys Gly Ala Ala Gly Leu
                85                  90                  95

Pro Gly Lys Pro Gly Asp Arg Gly Asn Val Gly Leu Ala Gly Pro Arg
            100                 105                 110

Gly Ala Pro Gly Lys Asp Gly Glu Val Gly Ala Gln Gly Pro Pro Gly
        115                 120                 125

Val Ala Gly Pro Thr Gly Pro Arg Gly Glu Thr Gly Leu Ala Gly Ser
    130                 135                 140

Val Gly Phe Gln Gly Met Pro Gly Pro Ser Gly Ala Ala Gly Glu Pro
145                 150                 155                 160

Gly Lys Pro Gly Asn Gln Gly Leu Arg Gly Asp Ala Gly Ser Pro Gly
                165                 170                 175

Met Ile Gly Pro Arg Gly Glu Arg Gly Leu Pro Gly Glu Arg Gly Ala
```

```
            180                 185                 190

Ser Gly Ala Gln Gly Leu Leu Gly Pro Arg Gly Thr Ser Gly Ala Pro
        195                 200                 205

Gly Leu Gly Asp Tyr Lys Asp Asp Asp Asp Lys
    210                 215
```

<210> SEQ ID NO 111
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 111

```
atgaaaaaga tttggctggc gctggctggt ttagttttag cgtttagcgc atcggcgggt     60

ccggcaggcg caaaaggtcc gagcggtgat attggtcgtc cgggtgaaag cggtagtccg    120

ggtgcacgtg gtcatagcgg tcagcctggt cgtaccggta ttgcaggtaa tcagggtctg    180

cctggtacag ccggtgaaga aggtcgcacc ggtccgccag gtcctgcagg tctgcgtggt    240

caggcaggta tgatgggttt tccgggtccg aaaggtgcag cgggtctgcc aggcaaaccg    300

ggtgatcgtg gtaatgttgg tctggctggt ccgcgtggtg caccgggtaa agatggtgaa    360

gttggtgcac agggtcctcc gggtgttgca ggtccgaccg gtcctcgtgg tgaaaccggt    420

ctggcaggta gcgttggttt tcagggtatg ccaggtccgt caggtgcagc aggcgaacct    480

ggtaaaccgg gtaaccaggg cctgcgtggt gatgccggtt caccgggtat gattggtcca    540

cgcggtgaac gtggcctgcc tggcgaacgt ggtgcaagcg gtgcacaagg tctgctgggt    600

ccacgtggca cctcaggcgc accaggtctg ggtgactaca aagacgacga cgacaaataa    660
```

<210> SEQ ID NO 112
<211> LENGTH: 237
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 112

```
Met Lys Lys Ile Trp Leu Ala Leu Ala Gly Leu Val Leu Ala Phe Ser
1               5                   10                  15

Ala Ser Ala Gln Gly Ile Pro Gly Ser Ala Gly Lys Glu Gly Gly Lys
            20                  25                  30

Gly Asp Pro Gly Pro Leu Gly Ser Pro Gly Lys Pro Gly Pro Asp Gly
        35                  40                  45

Leu Arg Gly Phe Ala Gly Ala Arg Gly Leu Pro Gly Ala Ala Gly Pro
    50                  55                  60

Pro Gly Leu Lys Gly Ala Glu Gly Pro Met Gly Ala Pro Gly Leu Thr
65                  70                  75                  80

Gly Ser Thr Gly Glu Arg Gly Pro Asn Gly Pro Ala Gly Ala Ile Gly
                85                  90                  95

Leu Pro Gly Arg Pro Gly Gly Pro Gly Pro Pro Gly Pro Val Gly Glu
            100                 105                 110

Lys Gly Asp Pro Gly Asp Lys Gly Leu Pro Gly Pro Ala Gly Asp Asp
        115                 120                 125

Gly Val Gln Gly Ala Met Gly Leu Pro Gly Pro Ile Gly Ser Gln Gly
    130                 135                 140
```

```
Pro Pro Gly Asp Tyr Gly Asp Lys Gly Glu Leu Gly Lys Pro Gly Gln
145                 150                 155                 160

Lys Gly Ser Lys Gly Asp Lys Gly Glu Ser Gly Pro Pro Gly Pro Ile
                165                 170                 175

Gly Ile Gln Gly Pro Ile Gly His Pro Gly Pro Ile Gly Ser Asp Gly
            180                 185                 190

Ser Pro Gly Leu Arg Gly Tyr Leu Gly Met Arg Gly Gln Lys Gly Asp
        195                 200                 205

Asp Gly Ile Arg Gly Leu Pro Gly Ser Ala Gly Pro Val Gly Leu Gln
    210                 215                 220

Gly Leu Pro Gly Gly Asp Tyr Lys Asp Asp Asp Asp Lys
225                 230                 235


<210> SEQ ID NO 113
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113

atgaaaaaga tttggctggc gctggctggt ttagttttag cgtttagcgc atcggcgcag      60

ggtattccgg gtagcgcagg taaagaaggt ggtaaaggcg atccgggtcc gctgggttca     120

ccgggtaaac cgggtcctga tggtctgcgt ggttttgccg gtgcacgtgg tctgcctggt     180

gcagcaggtc cgcctggtct gaaaggtgcc gaaggtccga tgggtgctcc gggtctgacc     240

ggtagcaccg gtgaacgcgg tccgaatggt ccggcaggcg caattggtct gccaggtcgt     300

cctggtggtc cgggtcctcc tggtccggtt ggtgaaaaag gtgatcctgg tgataaaggc     360

ctgcctggtc ctgccggtga tgatggtgtt cagggtgcca tgggcttacc gggtccgatt     420

ggtagccagg gtcctccggg tgattatggc gataaaggtg aactgggtaa acctggccag     480

aaaggtagca aaggtgacaa aggcgaaagc ggtccgccag gtccgatcgg cattcagggt     540

cctattggtc atccaggtcc aattggttca gatggctcac cgggactgcg tggctatctg     600

ggtatgcgtg gacagaaagg tgatgacggt attcgtggcc tgccaggtag tgcaggtccg     660

gtgggtctgc agggactgcc tggtggtgac tacaaagacg acgacgacaa ataa           714


<210> SEQ ID NO 114
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Met Lys Lys Ile Trp Leu Ala Leu Ala Gly Leu Val Leu Ala Phe Ser
1               5                   10                  15

Ala Ser Ala Lys Gly Glu Thr Gly Glu Ala Gly Asp Pro Gly Thr Pro
            20                  25                  30

Gly Glu Pro Gly Ile Ala Gly Pro Lys Gly Asp Val Gly Asp Lys Gly
        35                  40                  45

Asp Ala Gly Pro Pro Gly Ala Ala Gly Pro Ala Gly Val Lys Gly Pro
    50                  55                  60

Pro Gly Glu Asp Gly Ala Lys Gly Asp Val Gly Pro Ala Gly Phe Pro
65                  70                  75                  80
```

```
Gly Asp Pro Gly Pro Thr Gly Glu Pro Gly Val Pro Gly Met Asp Gly
                85                  90                  95

Gly Val Gly Glu Lys Gly Ser Leu Gly Asp Pro Gly Leu Thr Gly Pro
            100                 105                 110

Arg Gly Ala Ser Gly Glu Pro Gly Pro Pro Gly Ser Pro Gly Lys Arg
        115                 120                 125

Gly Pro Pro Gly Pro Ala Gly Pro Glu Gly Arg Glu Gly Leu Lys Gly
    130                 135                 140

Ser Lys Gly Ser Pro Gly Gln Glu Gly Pro Val Gly Arg Thr Gly Pro
145                 150                 155                 160

Ile Gly Pro Gln Gly Ser Pro Gly Asn Val Gly Pro Lys Gly Leu Arg
                165                 170                 175

Gly Ile Pro Gly Pro Thr Gly Glu Gln Gly Leu Leu Gly Pro Pro Gly
            180                 185                 190

Gln Ala Gly Pro Pro Gly Pro Met Gly Pro Pro Gly Met Pro Gly Leu
        195                 200                 205

Arg Gly Ala Gln Gly Leu Lys Gly Asp Lys Gly His Val Gly Leu Ile
    210                 215                 220

Gly Leu Ile Gly Pro Pro Gly Glu Met Gly Glu Lys Gly Asp Gln Gly
225                 230                 235                 240

Leu Pro Gly Ile Gln Gly Asp Tyr Lys Asp Asp Asp Asp Lys
                245                 250
```

<210> SEQ ID NO 115
<211> LENGTH: 765
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115

```
atgaaaaaga tttggctggc gctggctggt ttagttttag cgtttagcgc atcggcgaaa      60

ggtgaaaccg gtgaagcggg tgatccgggt acaccgggtg aacctggtat tgcaggtccg     120

aaaggtgatg ttggtgataa aggtgacgca ggtccgcctg gtgcagcagg tccggcaggc     180

gttaaaggtc ctccgggtga agatggtgca aaaggcgacg ttggtcctgc aggttttcct     240

ggcgatccgg gtccgactgg tgaaccgggt gtgccaggta tggatggtgg tgtgggtgaa     300

aaaggtagcc tgggtgatcc tggtctgacc ggtccgcgtg gcgcaagtgg tgaaccaggt     360

ccaccgggta gtccgggtaa acgtggtcct cctggaccgg ctggtccgga aggtcgtgaa     420

ggtctgaaag gtagcaaagg ttcaccgggt caagaaggtc cggttggtcg taccggtccg     480

attggtccgc agggctcacc gggtaatgtt ggtcctaaag gtctgcgtgg tattccgggt     540

cctacaggcg aacagggtct gctgggtccg ccaggccaag caggtcctcc aggtcctatg     600

ggtccacctg gtatgcctgg cctgcgtggt gcccagggcc tgaaaggcga taaaggccat     660

gttggtctga ttggcctgat tggtccacca ggtgaaatgg gagaaaaagg cgatcagggc     720

ctgcctggta ttcagggtga ctacaaagac gacgacgaca aataa                     765
```

<210> SEQ ID NO 116
<211> LENGTH: 30
<212> TYPE: PRT
<213> ORGANISM: Artificial Sequence
<220> FEATURE:
<223> OTHER INFORMATION: Description of Artificial Sequence: Synthetic
      His tag
<220> FEATURE:

<221> NAME/KEY: MISC_FEATURE
<222> LOCATION: (1)..(30)
<223> OTHER INFORMATION: This sequence may encompass 2-30 residues

<400> SEQUENCE: 116

His His His His His His His His His His His His His His His His
1 5 10 15

His His His His His His His His His His His His His His
20 25 30

<210> SEQ ID NO 117
<211> LENGTH: 20
<212> TYPE: PRT
<213> ORGANISM: Artificial Sequence
<220> FEATURE:
<223> OTHER INFORMATION: Description of Artificial Sequence: Synthetic
His tag
<220> FEATURE:
<221> NAME/KEY: MISC_FEATURE
<222> LOCATION: (1)..(20)
<223> OTHER INFORMATION: This sequence may encompass 2-20 residues

<400> SEQUENCE: 117

His His His His His His His His His His His His His His His His
1 5 10 15

His His His His
20

<210> SEQ ID NO 118
<211> LENGTH: 15
<212> TYPE: PRT
<213> ORGANISM: Artificial Sequence
<220> FEATURE:
<223> OTHER INFORMATION: Description of Artificial Sequence: Synthetic
His tag
<220> FEATURE:
<221> NAME/KEY: MISC_FEATURE
<222> LOCATION: (1)..(15)
<223> OTHER INFORMATION: This sequence may encompass 5-15 residues

<400> SEQUENCE: 118

His His His His His His His His His His His His His His His
1 5 10 15

<210> SEQ ID NO 119
<211> LENGTH: 18
<212> TYPE: PRT
<213> ORGANISM: Artificial Sequence
<220> FEATURE:
<223> OTHER INFORMATION: Description of Artificial Sequence: Synthetic
His tag
<220> FEATURE:
<221> NAME/KEY: MISC_FEATURE
<222> LOCATION: (1)..(18)
<223> OTHER INFORMATION: This sequence may encompass 5-18 residues

<400> SEQUENCE: 119

His His His His His His His His His His His His His His His His
1 5 10 15

His His

<210> SEQ ID NO 120
<211> LENGTH: 16
<212> TYPE: PRT
<213> ORGANISM: Artificial Sequence
<220> FEATURE:
<223> OTHER INFORMATION: Description of Artificial Sequence: Synthetic
His tag

```
<220> FEATURE:
<221> NAME/KEY: MISC_FEATURE
<222> LOCATION: (1)..(16)
<223> OTHER INFORMATION: This sequence may encompass 5-16 residues

<400> SEQUENCE: 120

His His His His His His His His His His His His His His His His
1               5                   10                  15


<210> SEQ ID NO 121
<211> LENGTH: 14
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: MISC_FEATURE
<222> LOCATION: (1)..(14)
<223> OTHER INFORMATION: This sequence may encompass 5-14 residues

<400> SEQUENCE: 121

His His His His His His His His His His His His His His
1               5                   10


<210> SEQ ID NO 122
<211> LENGTH: 13
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: MISC_FEATURE
<222> LOCATION: (1)..(13)
<223> OTHER INFORMATION: This sequence may encompass 5-13 residues

<400> SEQUENCE: 122

His His His His His His His His His His His His His
1               5                   10


<210> SEQ ID NO 123
<211> LENGTH: 12
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: MISC_FEATURE
<222> LOCATION: (1)..(12)
<223> OTHER INFORMATION: This sequence may encompass 5-12 residues

<400> SEQUENCE: 123

His His His His His His His His His His His His
1               5                   10


<210> SEQ ID NO 124
<211> LENGTH: 11
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: MISC_FEATURE
<222> LOCATION: (1)..(11)
<223> OTHER INFORMATION: This sequence may encompass 5-11 residues

<400> SEQUENCE: 124
```

His His His His His His His His His His His
1 5 10

<210> SEQ ID NO 125
<211> LENGTH: 10
<212> TYPE: PRT
<213> ORGANISM: Artificial Sequence
<220> FEATURE:
<223> OTHER INFORMATION: Description of Artificial Sequence: Synthetic
His tag
<220> FEATURE:
<221> NAME/KEY: MISC_FEATURE
<222> LOCATION: (1)..(10)
<223> OTHER INFORMATION: This sequence may encompass 5-10 residues

<400> SEQUENCE: 125

His His His His His His His His His His
1 5 10

<210> SEQ ID NO 126
<211> LENGTH: 12
<212> TYPE: PRT
<213> ORGANISM: Artificial Sequence
<220> FEATURE:
<223> OTHER INFORMATION: Description of Artificial Sequence: Synthetic
His tag
<220> FEATURE:
<221> NAME/KEY: MISC_FEATURE
<222> LOCATION: (1)..(12)
<223> OTHER INFORMATION: This sequence may encompass 6-12 residues

<400> SEQUENCE: 126

His His His His His His His His His His His His
1 5 10

<210> SEQ ID NO 127
<211> LENGTH: 11
<212> TYPE: PRT
<213> ORGANISM: Artificial Sequence
<220> FEATURE:
<223> OTHER INFORMATION: Description of Artificial Sequence: Synthetic
His tag
<220> FEATURE:
<221> NAME/KEY: MISC_FEATURE
<222> LOCATION: (1)..(11)
<223> OTHER INFORMATION: This sequence may encompass 6-11 residues

<400> SEQUENCE: 127

His His His His His His His His His His His
1 5 10

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Synthetic
His tag
<220> FEATURE:
<221> NAME/KEY: MISC_FEATURE
<222> LOCATION: (1)..(10)
<223> OTHER INFORMATION: This sequence may encompass 7-10 residues

<400> SEQUENCE: 128

His His His His His His His His His His
1 5 10

<210> SEQ ID NO 129
<211> LENGTH: 9
<212> TYPE: PRT

<213> ORGANISM: Artificial Sequence
<220> FEATURE:
<223> OTHER INFORMATION: Description of Artificial Sequence: Synthetic
9xHis tag

<400> SEQUENCE: 129

His His His His His His His His His
1 5

<210> SEQ ID NO 130
<211> LENGTH: 150
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MISC_FEATURE
<222> LOCATION: (1)..(150)
<223> OTHER INFORMATION: This sequence may encompass 2-50 "Gly Glu Lys"
repeating units

<400> SEQUENCE: 130

Gly Glu Lys Gly Glu Lys Gly Glu Lys Gly Glu Lys Gly Glu Lys Gly
1 5 10 15

Glu Lys Gly Glu Lys Gly Glu Lys Gly Glu Lys Gly Glu Lys Gly Glu
20 25 30

Lys Gly Glu Lys Gly Glu Lys Gly Glu Lys Gly Glu Lys Gly Glu Lys
35 40 45

Gly Glu Lys Gly Glu Lys Gly Glu Lys Gly Glu Lys Gly Glu Lys Gly
50 55 60

Glu Lys Gly Glu Lys Gly Glu Lys Gly Glu Lys Gly Glu Lys Gly Glu
65 70 75 80

Lys Gly Glu Lys Gly Glu Lys Gly Glu Lys Gly Glu Lys Gly Glu Lys
85 90 95

Gly Glu Lys Gly Glu Lys Gly Glu Lys Gly Glu Lys Gly Glu Lys Gly
100 105 110

Glu Lys Gly Glu Lys Gly Glu Lys Gly Glu Lys Gly Glu Lys Gly Glu
115 120 125

Lys Gly Glu Lys Gly Glu Lys Gly Glu Lys Gly Glu Lys Gly Glu Lys
130 135 140

Gly Glu Lys Gly Glu Lys
145 150

<210> SEQ ID NO 131
<211> LENGTH: 150
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MISC_FEATURE
<222> LOCATION: (1)..(150)
<223> OTHER INFORMATION: This sequence may encompass 2-50 "Gly Asp Lys"
repeating units

<400> SEQUENCE: 131

Gly Asp Lys Gly Asp Lys Gly Asp Lys Gly Asp Lys Gly Asp Lys Gly
1 5 10 15

Asp Lys Gly Asp Lys Gly Asp Lys Gly Asp Lys Gly Asp Lys Gly Asp
20 25 30

Lys Gly Asp Lys Gly Asp Lys Gly Asp Lys Gly Asp Lys Gly Asp Lys

```
        35                  40                  45

Gly Asp Lys Gly Asp Lys Gly Asp Lys Gly Asp Lys Gly Asp Lys Gly
    50                  55                  60

Asp Lys Gly Asp Lys Gly Asp Lys Gly Asp Lys Gly Asp Lys Gly Asp
65                  70                  75                  80

Lys Gly Asp Lys Gly Asp Lys Gly Asp Lys Gly Asp Lys Gly Asp Lys
                85                  90                  95

Gly Asp Lys Gly Asp Lys Gly Asp Lys Gly Asp Lys Gly Asp Lys Gly
            100                 105                 110

Asp Lys Gly Asp Lys Gly Asp Lys Gly Asp Lys Gly Asp Lys Gly Asp
        115                 120                 125

Lys Gly Asp Lys Gly Asp Lys Gly Asp Lys Gly Asp Lys Gly Asp Lys
    130                 135                 140

Gly Asp Lys Gly Asp Lys
145                 150
```

<210> SEQ ID NO 132
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(120)
<223> OTHER INFORMATION: This sequence may encompass 2-40 “Gly Glu Lys” repeating units

<400> SEQUENCE: 132

```
Gly Glu Lys Gly Glu Lys Gly Glu Lys Gly Glu Lys Gly Glu Lys Gly
1               5                   10                  15

Glu Lys Gly Glu Lys Gly Glu Lys Gly Glu Lys Gly Glu Lys Gly Glu
            20                  25                  30

Lys Gly Glu Lys Gly Glu Lys Gly Glu Lys Gly Glu Lys Gly Glu Lys
        35                  40                  45

Gly Glu Lys Gly Glu Lys Gly Glu Lys Gly Glu Lys Gly Glu Lys Gly
    50                  55                  60

Glu Lys Gly Glu Lys Gly Glu Lys Gly Glu Lys Gly Glu Lys Gly Glu
65                  70                  75                  80

Lys Gly Glu Lys Gly Glu Lys Gly Glu Lys Gly Glu Lys Gly Glu Lys
                85                  90                  95

Gly Glu Lys Gly Glu Lys Gly Glu Lys Gly Glu Lys Gly Glu Lys Gly
            100                 105                 110

Glu Lys Gly Glu Lys Gly Glu Lys
        115                 120
```

<210> SEQ ID NO 133
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(120)
<223> OTHER INFORMATION: This sequence may encompass 2-40 “Gly Asp Lys” repeating units

<400> SEQUENCE: 133

-continued

```
Gly Asp Lys Gly Asp Lys Gly Asp Lys Gly Asp Lys Gly Asp Lys Gly
1               5                   10                  15

Asp Lys Gly Asp Lys Gly Asp Lys Gly Asp Lys Gly Asp Lys Gly Asp
            20                  25                  30

Lys Gly Asp Lys Gly Asp Lys Gly Asp Lys Gly Asp Lys Gly Asp Lys
        35                  40                  45

Gly Asp Lys Gly Asp Lys Gly Asp Lys Gly Asp Lys Gly Asp Lys Gly
    50                  55                  60

Asp Lys Gly Asp Lys Gly Asp Lys Gly Asp Lys Gly Asp Lys Gly Asp
65                  70                  75                  80

Lys Gly Asp Lys Gly Asp Lys Gly Asp Lys Gly Asp Lys Gly Asp Lys
                85                  90                  95

Gly Asp Lys Gly Asp Lys Gly Asp Lys Gly Asp Lys Gly Asp Lys Gly
            100                 105                 110

Asp Lys Gly Asp Lys Gly Asp Lys
        115                 120


<210> SEQ ID NO 134
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(90)
<223> OTHER INFORMATION: This sequence may encompass 2-30 "Gly Glu Lys"
      repeating units

<400> SEQUENCE: 134

Gly Glu Lys Gly Glu Lys Gly Glu Lys Gly Glu Lys Gly Glu Lys Gly
1               5                   10                  15

Glu Lys Gly Glu Lys Gly Glu Lys Gly Glu Lys Gly Glu Lys Gly Glu
            20                  25                  30

Lys Gly Glu Lys Gly Glu Lys Gly Glu Lys Gly Glu Lys Gly Glu Lys
        35                  40                  45

Gly Glu Lys Gly Glu Lys Gly Glu Lys Gly Glu Lys Gly Glu Lys Gly
    50                  55                  60

Glu Lys Gly Glu Lys Gly Glu Lys Gly Glu Lys Gly Glu Lys Gly Glu
65                  70                  75                  80

Lys Gly Glu Lys Gly Glu Lys Gly Glu Lys
                85                  90


<210> SEQ ID NO 135
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(90)
<223> OTHER INFORMATION: This sequence may encompass 2-30 "Gly Asp Lys"
      repeating units

<400> SEQUENCE: 135

Gly Asp Lys Gly Asp Lys Gly Asp Lys Gly Asp Lys Gly Asp Lys Gly
1               5                   10                  15

Asp Lys Gly Asp Lys Gly Asp Lys Gly Asp Lys Gly Asp Lys Gly Asp
            20                  25                  30
```

Lys Gly Asp Lys Gly Asp Lys Gly Asp Lys Gly Asp Lys Gly Asp Lys
35 40 45

Gly Asp Lys Gly Asp Lys Gly Asp Lys Gly Asp Lys Gly Asp Lys Gly
50 55 60

Asp Lys Gly Asp Lys Gly Asp Lys Gly Asp Lys Gly Asp Lys Gly Asp
65 70 75 80

Lys Gly Asp Lys Gly Asp Lys Gly Asp Lys
85 90

<210> SEQ ID NO 136
<211> LENGTH: 60
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(60)
<223> OTHER INFORMATION: This sequence may encompass 2-20 "Gly Glu Lys" repeating units

<400> SEQUENCE: 136

Gly Glu Lys Gly Glu Lys Gly Glu Lys Gly Glu Lys Gly Glu Lys Gly
1 5 10 15

Glu Lys Gly Glu Lys Gly Glu Lys Gly Glu Lys Gly Glu Lys Gly Glu
20 25 30

Lys Gly Glu Lys Gly Glu Lys Gly Glu Lys Gly Glu Lys Gly Glu Lys
35 40 45

Gly Glu Lys Gly Glu Lys Gly Glu Lys Gly Glu Lys
50 55 60

<210> SEQ ID NO 137
<211> LENGTH: 60
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(60)
<223> OTHER INFORMATION: This sequence may encompass 2-20 "Gly Asp Lys" repeating units

<400> SEQUENCE: 137

Gly Asp Lys Gly Asp Lys Gly Asp Lys Gly Asp Lys Gly Asp Lys Gly
1 5 10 15

Asp Lys Gly Asp Lys Gly Asp Lys Gly Asp Lys Gly Asp Lys Gly Asp
20 25 30

Lys Gly Asp Lys Gly Asp Lys Gly Asp Lys Gly Asp Lys Gly Asp Lys
35 40 45

Gly Asp Lys Gly Asp Lys Gly Asp Lys Gly Asp Lys
50 55 60

<210> SEQ ID NO 138
<211> LENGTH: 45
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE

```
<222> LOCATION: (1)..(45)
<223> OTHER INFORMATION: This sequence may encompass 2-15 "Gly Glu Lys"
      repeating units

<400> SEQUENCE: 138

Gly Glu Lys Gly Glu Lys Gly Glu Lys Gly Glu Lys Gly Glu Lys Gly
1               5                   10                  15

Glu Lys Gly Glu Lys Gly Glu Lys Gly Glu Lys Gly Glu Lys Gly Glu
            20                  25                  30

Lys Gly Glu Lys Gly Glu Lys Gly Glu Lys Gly Glu Lys
        35                  40                  45


<210> SEQ ID NO 139
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(45)
<223> OTHER INFORMATION: This sequence may encompass 2-15 "Gly Asp Lys"
      repeating units

<400> SEQUENCE: 139

Gly Asp Lys Gly Asp Lys Gly Asp Lys Gly Asp Lys Gly Asp Lys Gly
1               5                   10                  15

Asp Lys Gly Asp Lys Gly Asp Lys Gly Asp Lys Gly Asp Lys Gly Asp
            20                  25                  30

Lys Gly Asp Lys Gly Asp Lys Gly Asp Lys Gly Asp Lys
        35                  40                  45


<210> SEQ ID NO 140
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(30)
<223> OTHER INFORMATION: This sequence may encompass 2-10 "Gly Glu Lys"
      repeating units

<400> SEQUENCE: 140

Gly Glu Lys Gly Glu Lys Gly Glu Lys Gly Glu Lys Gly Glu Lys Gly
1               5                   10                  15

Glu Lys Gly Glu Lys Gly Glu Lys Gly Glu Lys Gly Glu Lys
            20                  25                  30


<210> SEQ ID NO 141
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(30)
<223> OTHER INFORMATION: This sequence may encompass 2-10 "Gly Asp Lys"
      repeating units

<400> SEQUENCE: 141

Gly Asp Lys Gly Asp Lys Gly Asp Lys Gly Asp Lys Gly Asp Lys Gly
```

```
1               5                   10                  15

Asp Lys Gly Asp Lys Gly Asp Lys Gly Asp Lys Gly Asp Lys
            20                  25                  30


<210> SEQ ID NO 142
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(27)
<223> OTHER INFORMATION: This sequence may encompass 2-9 "Gly Glu Lys"
      repeating units

<400> SEQUENCE: 142

Gly Glu Lys Gly Glu Lys Gly Glu Lys Gly Glu Lys Gly Glu Lys Gly
1               5                   10                  15

Glu Lys Gly Glu Lys Gly Glu Lys Gly Glu Lys
            20                  25


<210> SEQ ID NO 143
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(27)
<223> OTHER INFORMATION: This sequence may encompass 2-9 "Gly Asp Lys"
      repeating units

<400> SEQUENCE: 143

Gly Asp Lys Gly Asp Lys Gly Asp Lys Gly Asp Lys Gly Asp Lys Gly
1               5                   10                  15

Asp Lys Gly Asp Lys Gly Asp Lys Gly Asp Lys
            20                  25


<210> SEQ ID NO 144
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(24)
<223> OTHER INFORMATION: This sequence may encompass 2-8 "Gly Glu Lys"
      repeating units

<400> SEQUENCE: 144

Gly Glu Lys Gly Glu Lys Gly Glu Lys Gly Glu Lys Gly Glu Lys Gly
1               5                   10                  15

Glu Lys Gly Glu Lys Gly Glu Lys
            20


<210> SEQ ID NO 145
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
```

<220> FEATURE:
<221> NAME/KEY: MISC_FEATURE
<222> LOCATION: (1)..(24)
<223> OTHER INFORMATION: This sequence may encompass 2-8 “Gly Asp Lys” repeating units

<400> SEQUENCE: 145

```
Gly Asp Lys Gly Asp Lys Gly Asp Lys Gly Asp Lys Gly Asp Lys Gly
1               5                   10                  15

Asp Lys Gly Asp Lys Gly Asp Lys
            20
```

<210> SEQ ID NO 146
<211> LENGTH: 21
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (1)..(21)
<223> OTHER INFORMATION: This sequence may encompass 2-7 “Gly Glu Lys” repeating units

<400> SEQUENCE: 146

```
Gly Glu Lys Gly Glu Lys Gly Glu Lys Gly Glu Lys Gly Glu Lys Gly
1               5                   10                  15

Glu Lys Gly Glu Lys
            20
```

<210> SEQ ID NO 147
<211> LENGTH: 21
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (1)..(21)
<223> OTHER INFORMATION: This sequence may encompass 2-7 “Gly Asp Lys” repeating units

<400> SEQUENCE: 147

```
Gly Asp Lys Gly Asp Lys Gly Asp Lys Gly Asp Lys Gly Asp Lys Gly
1               5                   10                  15

Asp Lys Gly Asp Lys
            20
```

<210> SEQ ID NO 148
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (1)..(18)
<223> OTHER INFORMATION: This sequence may encompass 2-6 “Gly Glu Lys” repeating units

<400> SEQUENCE: 148

```
Gly Glu Lys Gly Glu Lys Gly Glu Lys Gly Glu Lys Gly Glu Lys Gly
1               5                   10                  15

Glu Lys
```

<210> SEQ ID NO 149
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (1)..(18)
<223> OTHER INFORMATION: This sequence may encompass 2-6 "Gly Asp Lys" repeating units

<400> SEQUENCE: 149

Gly Asp Lys Gly Asp Lys Gly Asp Lys Gly Asp Lys Gly Asp Lys Gly
1 5 10 15

Asp Lys

<210> SEQ ID NO 150
<211> LENGTH: 15
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (1)..(15)
<223> OTHER INFORMATION: This sequence may encompass 2-5 "Gly Glu Lys" repeating units

<400> SEQUENCE: 150

Gly Glu Lys Gly Glu Lys Gly Glu Lys Gly Glu Lys Gly Glu Lys
1 5 10 15

<210> SEQ ID NO 151
<211> LENGTH: 15
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (1)..(15)
<223> OTHER INFORMATION: This sequence may encompass 2-5 "Gly Asp Lys" repeating units

<400> SEQUENCE: 151

Gly Asp Lys Gly Asp Lys Gly Asp Lys Gly Asp Lys Gly Asp Lys
1 5 10 15

<210> SEQ ID NO 152
<211> LENGTH: 12
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (1)..(12)
<223> OTHER INFORMATION: This sequence may encompass 2-4 "Gly Glu Lys" repeating units

<400> SEQUENCE: 152

Gly Glu Lys Gly Glu Lys Gly Glu Lys Gly Glu Lys
1 5 10

-continued

```
<210> SEQ ID NO 153
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(12)
<223> OTHER INFORMATION: This sequence may encompass 2-4 "Gly Asp Lys"
      repeating units

<400> SEQUENCE: 153

Gly Asp Lys Gly Asp Lys Gly Asp Lys Gly Asp Lys
1               5                   10
```